US008324457B2

(12) United States Patent
Guida, Jr. et al.

(10) Patent No.: US 8,324,457 B2
(45) Date of Patent: *Dec. 4, 2012

(54) SOYBEAN EVENT 3560.4.3.5 AND COMPOSITIONS AND METHODS FOR THE IDENTIFICATION AND/OR DETECTION THEREOF

(75) Inventors: Anthony D. Guida, Jr., Newark, DE (US); Christine B. Hazel, Port Deposit, MD (US); Jeffrey M. Hegstad, Ankeny, IA (US); Zhongsen Li, Hockessin, DE (US); Mark D. Vogt, Ankeny, IA (US); Aiqiu Xing, Wilmington, DE (US)

(73) Assignees: Pioneer Hi-Bred International, Inc., Johnston, IA (US); E.I. duPont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/109,797

(22) Filed: May 17, 2011

(65) Prior Publication Data

US 2011/0224082 A1    Sep. 15, 2011

Related U.S. Application Data

(63) Continuation of application No. 12/156,182, filed on May 30, 2008, now Pat. No. 7,968,770, which is a continuation-in-part of application No. 11/765,940, filed on Jun. 20, 2007, now Pat. No. 7,951,995.

(60) Provisional application No. 60/817,011, filed on Jun. 28, 2006, provisional application No. 60/847,154, filed on Sep. 26, 2006.

(51) Int. Cl.
    *C12N 15/82* (2006.01)
(52) U.S. Cl. .................................... 800/300
(58) Field of Classification Search .................. None
    See application file for complete search history.

(56) References Cited

U.S. PATENT DOCUMENTS

| 5,633,435 | A | 5/1997 | Barry et al. |
| 7,217,858 | B2 | 5/2007 | Falco et al. |
| 7,405,074 | B2 | 7/2008 | Castle et al. |
| 7,462,481 | B2 | 12/2008 | Castle et al. |
| 7,687,434 | B2 | 3/2010 | DeBillot et al. |
| 7,968,770 | B2 * | 6/2011 | Guida et al. .................. 800/300 |
| 2004/0031072 | A1 | 2/2004 | La Rosa et al. |
| 2004/0107457 | A1 | 6/2004 | Kuvshinov et al. |
| 2008/0051288 | A1 | 2/2008 | Cressman, Jr. et al. |
| 2010/0184079 | A1 | 7/2010 | Cressman, Jr. et al. |

FOREIGN PATENT DOCUMENTS

| WO | WO 98/39419 | 9/1998 |
| WO | WO 02/36782 A2 | 5/2002 |
| WO | WO 03/052073 A2 | 6/2003 |
| WO | WO 03/092360 A2 | 11/2003 |
| WO | WO 2005/012515 A2 | 2/2005 |
| WO | WO 2006/039376 A2 | 4/2006 |
| WO | WO 2007/024782 A2 | 3/2007 |

OTHER PUBLICATIONS

Lowe, T., et al., "A computer program for selection of oligonucleotide primers for polymerase chain reactions," *Nucleic Acids Research*, 1990, vol. 18(7), pp. 1757-1761.
Nucleic acid search report, AC ADP64406, 2004, 4 pages.
Nucleic acid search report, AC AFP10027, 2007, 3 pages.
Devine, Malcolm D., "Why are there not more herbicide-tolerant crops?," *Pest Manag Sci*, 2005, vol. 61, pp. 312-317.
McElroy, David, "Moving agbiotech downstream—Companies must turn to effective process development as a competitive weapon in agricultural biotechnology," *Nature Biotechnology*, 1999, vol. 17, pp. 1071-1074.
Mumm, R., et al., "Perspectives—Quality Control in the Development of Transgenic Crop Seed Products," *Crop Sci.*, 2001, vol. 41, pp. 1381-1389.
Castle, L.A., et al., "Discovery and Directed Evolution of a Glyphosate Tolerance Gene", *Science*, vol. 304, No. 21, May 21, 2004, pp. 1151-1154.
Green, J.M., "Review of Glyphosate and ALS-Inhibiting Herbicide Crop Resistance and Resistant Weed Management", *Weed Technology*, 2007, vol. 21, pp. 547-558.
Hegstad, Jeff, "Herbicide Efficacy and Yield Evaluations", CSB Meeting, Feb. 22, 2007.
Hegstad, Jeff, "Herbicide Efficacy and Yield Evaluations", ASA/CSSA/SSSA 2007 International Annual Meetings.
Rood, T.A., et al.., "Petition for the Determination of Nonregulated Status for Herbicide Tolerant 356043 Soybean", Sep. 2006.
Terry, C.F. and Harris, N., "Event-Specific Detection of Roundup Ready Soya using two Different Real Time PCR Detection Chemistries", *Eur. Food Res Technol.*, vol. 213, 2001, pp. 425-431.
Windels, P., et al., "Characterization of the Roundup Ready Soybean Insert", *Eur Food Res Technol.*, vol. 213, 2001, pp. 107-112.
Windels, P., et al., "Development of a Line Specific GMO Detection Method: A Case Study", *Med. Fac. Landbouww. Univ. Gent.*, vol. 64, No. 5B, Sep. 22, 1999, pp. 459-462.

\* cited by examiner

*Primary Examiner* — David H Kruse
(74) *Attorney, Agent, or Firm* — Alston & Bird LLP

(57) ABSTRACT

Compositions and methods related to transgenic glyphosate/ALS inhibitor-tolerant soybean plants are provided. Specifically, soybean plants having a 3560.4.3.5 event which imparts tolerance to glyphosate and at least one ALS-inhibiting herbicide are provided. The soybean plant harboring the 3560.4.3.5 event at the recited chromosomal location comprises genomic/transgene junctions having at least the polynucleotide sequence of SEQ ID NO:10 and/or 11. The characterization of the genomic insertion site of the 3560.4.3.5 event provides for an enhanced breeding efficiency and enables the use of molecular markers to track the transgene insert in the breeding populations and progeny thereof. Various methods and compositions for the identification, detection, and use of the soybean 3560.4.3.5 events are provided. Methods and compositions for increasing yield are also provided.

10 Claims, 24 Drawing Sheets

Figure 4A

```
   1  AGCAATTGTT TTGTGCATTT CCAAATTTCA ATCTGATTTA TTAAATAAAA
  51  AAATTTTAAT TCGGGTTGAT TGTAAATCAG CTAAAGACAT TTTACAGAAA
 101  GACGTCAAAA ATCTTGGCTC CAAACAAATT TTTGCAAGAT GGCAAGCAAT
 151  ATTAAGTGTT TTTGATTTTG ACAGAATATA TCAAGGGCAC TTTAAACTCT
 201  CTACCTAACT ATCTTACACG TGAATTCTTA TAGACAAATT CTCATGCCAC
 251  CTAAGGCATC AGGCACCCCT CTCAGGGGTA GACGAAGCAC GAGTAAAGGA
 301  TTCAAGTTGG CCCTACCAGA GCCAACTATC AAAAGAGTT CTTCCGCATC
 351  CTCTGGGTCA TCTACCCAAA AACCTAAAAT AAAAGGGTCA TCAACCCAAA
 401  TAGTCACCAT CAAACCTGAG TCATCCACTC AGGAATCCCC AAAACCTTCA
 451  ACCTCAAAAC AAACAAGGC CGACTATACC TTCTCAGTAC AACACTCCAG
 501  GCCCTACAAG AAATTGGTCT AACCAAACTC CCAAAACTCG CCAAAAAGAC
 551  TTGGGCAGAC ATTGCCTCAG AATCTAATGA TGAATTTGAA ACTGATTTAC
 601  AAATCATGAT TCAAAACTCC AAACAATCCA AAACGATTGT CAATCCAAAA
 651  GGAAAACAGA CCTTATCCCA ACAAAGACA CCATTACCAA AACCTACTAA
 701  CAGTTATATT TACAAAAATA AATTTCCAAC TGTTTTGTAG ATGGAGCCAA
 751  AATTTTGGGA CAAAAATCCC TTCAAGGCTA CAGCCAAGGC ATTTCCACCG
 801  GGCTTCCATT TCAAACCTAT TTCCACCAAT AAAACAAGAA TCTTTTACGA
 851  ATTCATACTG ATAGACACAA ACTCAGTGTC TATTAAACAC TTCAAAGACC
 901  CAAATGACAT AAATTTAAAC ACTCATTCAA CCATCCAGAT TTTAAAGTTC
 951  ATACAACCTC GACAATGTGG AACAAATATA AATCAAGCCA AACAATTCTT
1001  TGTACCCTTT GATCCTATAG GTTACACTAT TGGGATTATG TAGATGCATG
1051  GACCAATGTA TTCTGGCATC AAAATAACAA ATTCAAACAT TCTTGGCTTA
1101  TTTATTTCAA AACTAACACC GTCTATAATT TTCCAAATTG GTTCCTCCAA
1151  CGGTGGGACT TTTTTGGACC AAACTTTGAT ATCTACCCGG AGCAAGTCCA
1201  ACAAGGGTTT GATCAGTTCA AAAAAATGTT CAATTCTCAG GAATCACGAA
1251  TCCCTGTAGA CCTAAAATAC TTTTCCAATT TTGCATTGTC GTGGATATTT
1301  TCATGGCAAT ACAGATATGG GAAAACTGAA AACAACAAGC AGTTTCCATC
1351  ACTGCAACAT CATGCATTTA TCAAGTGGTG GAATTAGTTT GATACATCAA
1401  AAGCAGCACC AGATCAAGTG AGAATCTGGT TTCAAGCCCA TCCAGAATTT
1451  TTGAAAGTTG CTAATCCTGA GACTTCTTTA TTCCTCAATC AGAAGTCTCA
1501  ATTAGCTGCT TTCCTTTCTA GTTCCAAGTC AAAAGAAATT CTGGCACAAA
1551  ATCTAAAAGA AGTCCTACAG CTTCTCCAAC AAGAAGAAGA TAAAGGCTCT
1601  TCCTCAAAGA AGGAAGATAA CAATTCTTCA AAAGAAGATG ACGACCCTTT
1651  CTACCAAAAT GAAAATGATT GTTTTGGTAT TTCTCTAAAT GATGATTAAT
1701  TAAAAAATTA CATGTACTAT GTAAATAGTT TCGGTCACGA AACTGGCACT
1751  GTAGCTACAG TAAATTTTAT GGCTATTTAA GGAGTTCTCG GCCCATTTGT
1801  GAGGTACCTT TTCAGGTAGT CAGATCTCTA TTTTTAGAGA GAGAAACTCT
1851  AGGAAACAAT CTTTGTAAGT TTTTCTTTCG ATTTCAATAA ATTCAAAGTT
1901  TTCTCTTCAT ATCTCTTCTC CCTCTTGACC GGTCCTGTGC GGTTCTGCCA
1951  TCGCTTCAGT TTCTTCTCTT CTCTCCCCTT ATCGATATTG TGTGGCTCTA
2001  TTGCCACTTC GATTTCTTTT ATGTTGCTTT CATTTTAATT TGTTTTACCA
2051  TTTTCTTTTG ATATTATAAT TTCTATTTAA CTCTTGGTCA TACTGCATAT
2101  ATTCATAATA TATTCTTACA TCCTATCTAT CCGTTTGATC TCTTTTCACT
2151  GTTATATATA TATATATATA TATATATATC GTTAACTTC ATGTTAGTAA
2201  TAAGATTAGA GTAAAAAATA TATATATAAC GAAGTTATTT TAACAAAAGG
2251  TATTTTTGTA AAAAAAAATT ATATGCTAAA AAAGTTTTAC TATATCTAAG
2301  CATGATTTTT TTTAATTCCC AAAACACGTG TAAATATTTT TAGGAATATT
2351  TTGTAAAAAA TCAAACATTT TTTTAATTAT TCGTATAAAA CATCAATCTT
2401  TAAGAATCAT AATTTTTAGA AATCATGATT TCTGGATATA AAAATACTTT
```

FIGURE 4B

```
2451  TTCTTGCAGC CAAACGTCTT CTAAAGCCAC ATGTTAATGG GTGTACAAAT
2501  TATAAAGTTT TTATAAACAT ATCACTTTTT AAAGTTAAAA ATATCACTAA
2551  TACGTTTCTA AATGCATTTT TTTTAGAAAT TATAAGTTTC TAGCACTCCA
2601  TTGGAGTTGT ATAGAACTAC TACTAATCTA CTATTAATAA CAATTTATCT
2651  CCTCCAAATA TTTAAGTAAA CTGCATATTT AGAGAATGTT GGACAGTAAA
2701  GCTAGCCACT CAATATTTAG GTGCTCCCCG AAAGAGGAAA GCAAACAAGC
2751  CACCAGCACT TCAATCAGTA AAGCTAGCCA CTCAACTCGC TCTCTTCAAA
2801  TTCCCTTTTA CATTTTATTT CAGATCCTCC ACCTAGCCAA GTAGGTCTCA
2851  AAAGGTTTAC CCCGCATATG CTTAGTCGCC GCAAGCTCCA TATAGGTTAC
2901  TTTGCGGGCT ACTGAATAGA ATCTTCGGTG AAAGGCGTCT ACCATATCGG
2951  CGCAACTATT GATCGAGTGC GTGTATACCA CGTGAATGCG ACACCCGAAA
3001  GACTAGCAGA AAAGTGCTTC AGCAACAAAC TCTCATCGTG AGCAGTGTCT
3051  CTGCTGGCAA TTTCGAAATT ACTAATATGC TGCTCTCGAG ATCTCCACTT
3101  CCATCATACA ACCGAAACCA GCTAAGGAAG GAGCGATCCA TAAGAATCGC
3151  CTCGAATAGC CATAACCTCA TCTCGCCTTC CACCGCACCA GCAAGAGGAA
3201  ACCGAATTAG AGCTGAAAGA ATACTAGAGC CATCGTAGGA GAACCGGATT
3251  CTTGACCGAT CGACTTTTGC CCGAGGTCGT TAGGTCGAAT AGGCTAGGTT
3301  TACGAAAAAG AGACTAAGGC CGCTCTAGAG ATCCGTCAAC ATGGTGGAGC
3351  ACGACACTCT CGTCTACTCC AAGAATATCA AAGATACAGT CTCAGAAGAC
3401  CAAAGGGCTA TTGAGACTTT TCAACAAAGG GTAATATCGG GAAACCTCCT
3451  CGGATTCCAT TGCCCAGCTA TCTGTCACTT CATCAAAAGG ACAGTAGAAA
3501  AGGAAGGTGG CACCTACAAA TGCCATCATT GCGATAAAGG AAAGGCTATC
3551  GTTCAAGATG CCTCTGCCGA CAGTGGTCCC AAAGATGGAC CCCCACCCAC
3601  GAGGAGCATC GTGGAAAAAG AAGACGTTCC AACCACGTCT TCAAAGCAAG
3651  TGGATTGATG TGATGATCCT ATGCGTATGG TATGACGTGT GTTCAAGATG
3701  ATGACTTCAA ACCTACCTAT GACGTATGGT ATGACGTGTG TCGACTGATG
3751  ACTTAGATCC ACTCGAGCGG CTATAAATAC GTACCTACGC ACCCTGCGCT
3801  ACCATCCCTA GAGCTGCAGC TTATTTTTAC AACAATTACC AACAACAACA
3851  AACAACAAAC AACATTACAA TTACTATTTA CAATTACAGT CGACCCGGGA
3901  TCCACACGAC ACCATGATAG AGGTGAAACC GATTAACGCA GAGGATACCT
3951  ATGAACTAAG GCATAGAATA CTCAGACCAA ACCAGCCGAT AGAAGCGTGT
4001  ATGTTTGAAA GCGATTTACT TCGTGGTGCA TTTCACTTAG GCGGCTTTTA
4051  CAGGGGCAAA CTGATTTCCA TAGCTTCATT CCACCAGGCC GAGCACTCGG
4101  AACTCCAAGG CCAGAAACAG TACCAGCTCC GAGGTATGGC TACCTTGGAA
4151  GGTTATCGTG AGCAGAAAGC GGGATCAACT CTAGTTAAAC ACGCTGAAGA
4201  AATCCTTCGT AAGAGGGGGG CGGACATGCT TTGGTGTAAT GCGAGGACAT
4251  CCGCCTCAGG CTACTACAAA AAGTTAGGCT TCAGCGAGCA GGGAGAGATA
4301  TTTGACACGC CGCCAGTAGG ACCTCACATC CTGATGTATA AAAGGATCAC
4351  ATAACTAGCT AGTCAGTTAA CCTAGACTTG TCCATCTTCT GGATTGGCCA
4401  ACTTAATTAA TGTATGAAAT AAAAGGATGC ACACATAGTG ACATGCTAAT
4451  CACTATAATG TGGGCATCAA AGTTGTGTGT TATGTGTAAT TACTAGTTAT
4501  CTGAATAAAA GAGAAAGAGA TCATCCATAT TTCTTATCCT AAATGAATGT
4551  CACGTGTCTT TATAATTCTT TGATGAACCA GATGCATTTC ATTAACCAAA
4601  TCCATATACA TATAAATATT AATCATATAT AATTAATATC AATTGGGTTA
4651  GCAAAACAAA TCTAGTCTAG GTGTGTTTTG CGAATTCGAT ATCAAGCTTT
4701  GCTCTAGATC AAACTCACAT CCAAACATAA CATGGATATC TTCCTTACCA
4751  ATCATACTAA TTATTTTGGG TTAAATATTA ATCATTATTT TTAAGATATT
4801  AATTAAGAAA TTAAAGATT TTTTAAAAAA ATGTATAAAA TTATATTATT
4851  CATGATTTTT CATACATTTG ATTTTGATAA TAAATATATT TTTTTTAATT
```

FIGURE 4C

```
4901    TCTTAAAAAA TGTTGCAAGA CACTTATTAG ACATAGTCTT GTTCTGTTTA
4951    CAAAAGCATT CATCATTTAA TACATTAAAA AATATTTAAT ACTAACAGTA
5001    GAATCTTCTT GTGAGTGGTG TGGGAGTAGG CAACCTGGCA TTGAAACGAG
5051    AGAAAGAGAG TCAGAACCAG AAGACAAATA AAAGTATGC AACAAACAAA
5101    TCAAAATCAA AGGGCAAAGG CTGGGGTTGG CTCAATTGGT TGCTACATTC
5151    AATTTTCAAC TCAGTCAACG GTTGAGATTC ACTCTGACTT CCCCAATCTA
5201    AGCCGCGGAT GCAAACGGTT GAATCTAACC CACAATCCAA TCTCGTTACT
5251    TAGGGGCTTT TCCGTCATTA ACTCACCCCT GCCACCCGGT TTCCCTATAA
5301    ATTGGAACTC AATGCTCCCC TCTAAACTCG TATCGCTTCA GAGTTGAGAC
5351    CAAGACACAC TCGTTCATAT ATCTCTCTGC TCTTCTCTTC TCTTCTACCT
5401    CTCAAGGTAC TTTTCTTCTC CCTCTACCAA ATCCTAGATT CCGTGGTTCA
5451    ATTTCGGATC TTGCACTTCT GGTTTGCTTT GCCTTGCTTT TTCCTCAACT
5501    GGGTCCATCT AGGATCCATG TGAAACTCTA CTCTTTCTTT AATATCTGCG
5551    GAATACGCGT TTGACTTTCA GATCTAGTCG AAATCATTTC ATAATTGCCT
5601    TTCTTTCTTT TAGCTTATGA GAAATAAAAT CACTTTTTTT TTATTTCAAA
5651    ATAAACCTTG GGCCTTGTGC TGACTGAGAT GGGGTTTGGT GATTACAGAA
5701    TTTTAGCGAA TTTTGTAATT GTACTTGTTT GTCTGTAGTT TTGTTTTGTT
5751    TTCTTGTTTC TCATACATTC CTTAGGCTTC AATTTTATTC GAGTATAGGT
5801    CACAATAGGA ATTCAAACTT TGAGCAGGGG AATTAATCCC TTCCTTCAAA
5851    TCCAGTTTGT TTGTATATAT GTTTAAAAAA TGAAACTTTT GCTTTAAATT
5901    CTATTATAAC TTTTTTTATG GCTGAAATTT TTGCATGTGT CTTTGCTCTC
5951    TGTTGTAAAT TTACTGTTTA GGTACTAACT CTAGGCTTGT TGTGCAGTTT
6001    TTGAAGTATA ACCATGCCAC ACAACACAAT GGCGGCCACC GCTTCCAGAA
6051    CCACCCGATT CTCTTCTTCC TCTTCACACC CCACCTTCCC CAAACGCATT
6101    ACTAGATCCA CCCTCCCTCT CTCTCATCAA ACCCTCACCA AACCCAACCA
6151    CGCTCTCAAA ATCAAATGTT CCATCTCCAA ACCCCCCACG GCGGCGCCCT
6201    TCACCAAGGA AGCGCCGACC ACGGAGCCCT TCGTGTCACG GTTCGCCTCC
6251    GGCGAACCTC GCAAGGGCGC GGACATCCTT GTGGAGGCGC TGGAGAGGCA
6301    GGGCGTGACG ACGGTGTTCG CGTACCCCGG CGGTGCGTCG ATGGAGATCC
6351    ACCAGGCGCT CACGCGCTCC GCCGCCATCC GCAACGTGCT CCCGCGCCAC
6401    GAGCAGGGCG GCGTCTTCGC CGCCGAAGGC TACGCGCGTT CCTCCGGCCT
6451    CCCCGGCGTC TGCATTGCCA CCTCCGGCCC CGGCGCCACC AACCTCGTGA
6501    GCGGCCTCGC CGACGCTTTA ATGGACAGCG TCCCAGTCGT CGCCATCACC
6551    GGCCAGGTCG CCCGCCGGAT GATCGGCACC GACGCCTTCC AAGAAACCCC
6601    GATCGTGGAG GTGAGCAGAT CCATCACGAA GCACAACTAC CTCATCCTCG
6651    ACGTCGACGA CATCCCCCGC GTCGTCGCCG AGGCTTTCTT CGTCGCCACC
6701    TCCGGCCGCC CCGGTCCGGT CCTCATCGAC ATTCCCAAAG ACGTTCAGCA
6751    GCAACTCGCC GTGCCTAATT GGGACGAGCC CGTTAACCTC CCCGGTTACC
6801    TCGCCAGGCT GCCCAGGCCC CCGCCGAGG CCCAATTGGA ACACATTGTC
6851    AGACTCATCA TGGAGGCCCA AAAGCCCGTT CTCTACGTCG GCGGTGGCAG
6901    TTTGAATTCC AGTGCTGAAT TGAGGCGCTT TGTTGAACTC ACTGGTATTC
6951    CCGTTGCTAG CACTTAATG GGTCTTGGAA CTTTTCCTAT TGGTGATGAA
7001    TATTCCCTTC AGATGCTGGG TATGCATGGT ACTGTTTATG CTAACTATGC
7051    TGTTGACAAT AGTGATTTGT TGCTTGCCTT TGGGGTAAGG TTTGATGACC
7101    GTGTTACTGG GAAGCTTGAG GCTTTTGCTA GTAGGGCTAA GATTGTTCAC
7151    ATTGATATTG ATTCTGCCGA GATTGGGAAG AACAAGCAGG CGCACGTGTC
7201    GGTTTGCGCG GATTTGAAGT TGGCCTTGAA GGGAATTAAT ATGATTTTGG
7251    AGGAGAAAGG AGTGGAGGGT AAGTTTGATC TTGGAGGTTG GAGAGAAGAG
7301    ATTAATGTGC AGAAACACAA GTTTCCATTG GGTTACAAGA CATTCCAGGA
```

FIGURE 4D

```
7351  CGCGATTTCT CCGCAGCATG CTATCGAGGT TCTTGATGAG TTGACTAATG
7401  GAGATGCTAT TGTTAGTACT GGGGTTGGGC AGCATCAAAT GTGGGCTGCG
7451  CAGTTTTACA AGTACAAGAG ACCGAGGCAG TGGTTGACCT CAGGGGGTCT
7501  TGGAGCCATG GGTTTTGGAT TGCCTGCGGC TATTGGTGCT GCTGTTGCTA
7551  ACCCTGGGGC TGTTGTGGTT GACATTGATG GGGATGGTAG TTTCATCATG
7601  AATGTTCAGG AGTTGGCCAC TATAAGAGTG GAGAATCTCC CAGTTAAGAT
7651  ATTGTTGTTG AACAATCAGC ATTTGGGTAT GGTGGTTCAG TTGGAGGATA
7701  GGTTCTACAA GTCCAATAGA GCTCACACCT ATCTTGGAGA TCCGTCTAGC
7751  GAGAGCGAGA TATTCCCAAA CATGCTCAAG TTTGCTGATG CTTGTGGGAT
7801  ACCGGCAGCG CGAGTGACGA AGAAGGAAGA GCTTAGAGCG GCAATTCAGA
7851  GAATGTTGGA CACCCCTGGC CCCTACCTTC TTGATGTCAT TGTGCCCCAT
7901  CAGGAGCATG TGTTGCCGAT GATTCCCAGT AATGGATCCT TCAAGGATGT
7951  GATAACTGAG GGTGATGGTA GAACGAGGTA CTGATTGCCT AGACCAAATG
8001  TTCCTTGATG CTTGTTTTGT ACAATATATA TAAGATAATG CTGTCCTAGT
8051  TGCAGGATTT GGCCTGTGGT GAGCATCATA GTCTGTAGTA GTTTTGGTAG
8101  CAAGACATTT TATTTTCCTT TTATTTAACT TACTACATGC AGTAGCATCT
8151  ATCTATCTCT GTAGTCTGAT ATCTCCTGTT GTCTGTATTG TGCCGTTGGA
8201  TTTTTTGCTG TAGTGAGACT GAAAATGATG TGCTAGTAAT AATATTTCTG
8251  TTAGAAATCT AAGTAGAGAA TCTGTTGAAG AAGTCAAAAG CTAATGGAAT
8301  CAGGTTACAT ATTCAATGTT TTTCTTTTTT TAGCGGTTGG TAGACGTGTA
8351  GATTCAACTT CTCTTGGAGC TCACCTAGGC AATCAGTAAA ATGCATATTC
8401  CTTTTTTAAC TTGCCATTTA TTTACTTTTA GTGGAAATTG TGACCAATTT
8451  GTTCATGTAG AACGGATTTG GACCATTGCG TCCACAAAAC GTCTCTTTTG
8501  CTCGATCTTC ACAAAGCGAT ACCGAAATCC AGAGATAGTT TTCAAAAGTC
8551  AGAAATGGCA AAGTTATAAA TAGTAAAACA GAATAGATGC TGTAATCGAC
8601  TTCAATAACA AGTGGCATCA CGTTTCTAGT TCTAGACCCA TCAGCTGGGC
8651  CGGCCACTAG TGAGCTCGGT ACCCGGGGGC GCGTAATATC ATCATTAGGA
8701  AGACACTGCC CATCTTGAAT AGGATTTTAG CTACTAAATA TGTTGATGGT
8751  CTTTATGAAA AACTATTAAC TAGGAATATT ATGCTACCCA TATGGAAAGA
8801  AGACGCTAGG GGAATAGAAA GACCATCAAA TAAACGAAGT CAACACCAGG
8851  TCTTCCGAAG CATTAACAAT TACCTATTTA ATATGTACTC AGTCCGGGTG
8901  GATATCTCAC TACATTGACG CAGTTTGTTC AAAGACGAAC GCCCTGAATT
8951  ATGCCATCTG CTTAGGCTTT CAAATATGGT ACGCTCTAAT GCCAAGCCTT
9001  ATGCTGGTCT TAGGGTATTA TCATCAAATC TTTAAGCCAG AGGTAGTTAA
9051  ATACATCAAG GACACCATAG GAGTATGGCA CAACGATATT GTCAAGATCG
9101  CATCAGATCT AATAGGCAAT AATGAATTCT TCATGCAGCC CGACGTGGGA
9151  ACGCTCGAAA GCAGTGGGGC CTCTGGGACA GGGACCAGAC CTGAGTCGCT
9201  AACATTTGGG AATAAGAGAA GTAGATATAC CCAATTTTTT AACTAGCCAA
9251  GGAAGGAAAG CGGGAAAGGT CCGATACAAA GGAAAGGGTT GCGAGGCTTA
9301  ACGATTTAGA ATATAGCTGT TGAGGTGGCA CTTGTTCCCC CGGGGCGGGG
9351  GTATATGCCC GTAGCTTTAT TCTGTCACTT CTTTCAGATC AATGAAGTTG
9401  AAAAGTTATA GAGTAAGGGA CCCTTGTTTA CAAAGCTGTC ACTCCAAGAA
9451  CTCGAAGTCA AGCATCTTCG GGAATATCCA GATTAGTCTT CAACTAGAGA
9501  AAGGATAGGA ATCTCCTTTG CAGAGTTTTC TTCTCCTGCT GATGTAGCGG
9551  TAAAGTCAAA AGTTGGATGC CCTTTTTTCT TTATTTAATT AATTCCGTTG
9601  ATAGAGCTTT TGAGCGGATG CAAGCACTAG ATTCTTCAAC GAGTACCAAT
9651  AATAAATGAA TTCACCAGAC TAAGAGAAGA AAACAGAACA AAAAGATTAA
9701  GCCCAGCCGC CTTCGGGAAG ACCTATCTTC GTCGGGAGGA AGAGCCCTCT
9751  TTACACCATT GTGATTAGAA AAAACCGAAA AGTGGACCGG CCTAGTAACC
```

FIGURE 4E

```
 9801   AATAGAGCGG GGCTTGATCC CCACTTTAAA TCTATTGGAT AGAGCCCTCA
 9851   GCCCAGGGCA AGCGATTGAA TTCTATTTGA TTATGGGTTA GGTGGAACCT
 9901   GAAACTAGCA CTTACAAATG AGTTAGCAAA AGGAAAAAGA CAATTCTCAA
 9951   ATGCGTACAA GACTTTCTTC CTTCTTTGTT TAAGAGGCCA GTCTGCGATG
10001   GATGCTCGTG CATGAAAAAG GGCTTTGATC TATTCACCAC TTATATAATA
10051   GAGCCAATCT CTGCAGGACA AGATATCTAT TTTGTCATTG GGAAGTAAGG
10101   CTTAAGTCGA CGAAAAAGTT AGGAAAGGGG ATCATATGGC TAGGGTTGCC
10151   CTCGGGGCTC AAGGGTTTAG CGATGAAGAG TGCCAAGCAA AAGGTCAATA
10201   CCGGTACGCC GATCAAAGAA GTCCAGTGGC AAGGCCCTTT CAGCCAAGCT
10251   AGCGTGCTGA ACAGAAAGTC GTAGAGTGAT GACAGCTTCT TCTTCTTGAG
10301   TCATTCGTGT GACAACATCA GGATCTCGTC GAAAGACCTC CTCTGCCTAT
10351   CTCTCCCGCA AGAGAGGACT CGTTATGGCG CACCTCTTTT TAGCAGTCTC
10401   GTCAATAAGA TAAGATTGCC CCTCCCTTCT TATTGATTTG ATAAAGGGCT
10451   TTGTCCACTC CCTCTCTTCT TAGCCGAGCG GAGTGACGGT TTAGTTTAGG
10501   CTTTAGATGC CACTGCGAAA GACTCTAGAG ATCCACTCTC ACAGCGTATA
10551   CGCGACATCC CTATGTATAC ACAATCCTTT CAAGCAGCTA GGACAGCTAG
10601   CAAGCAAGTT ATCTGTTCGC GGACAAGCTC TCTGGATGAC AAAAAACATG
10651   CTCTTTCATG CGGAAAAAAC ACGGTCTTTC GTGGAAGTTG GTCGATTTGA
10701   AGTCGCTTTA TGAGTGAAAA TGGGTCGATG ACGAAAAAGA CGGGGAAAAT
10751   GATCAACTGT CACATTTTGA TGCCAGTTTA GGGCTAAAAT GAACTTTCAT
10801   CCAAAAAGAC CGAGAAAACG CTCCACTGGC AGGATCCGAT CGGAAATAA
```

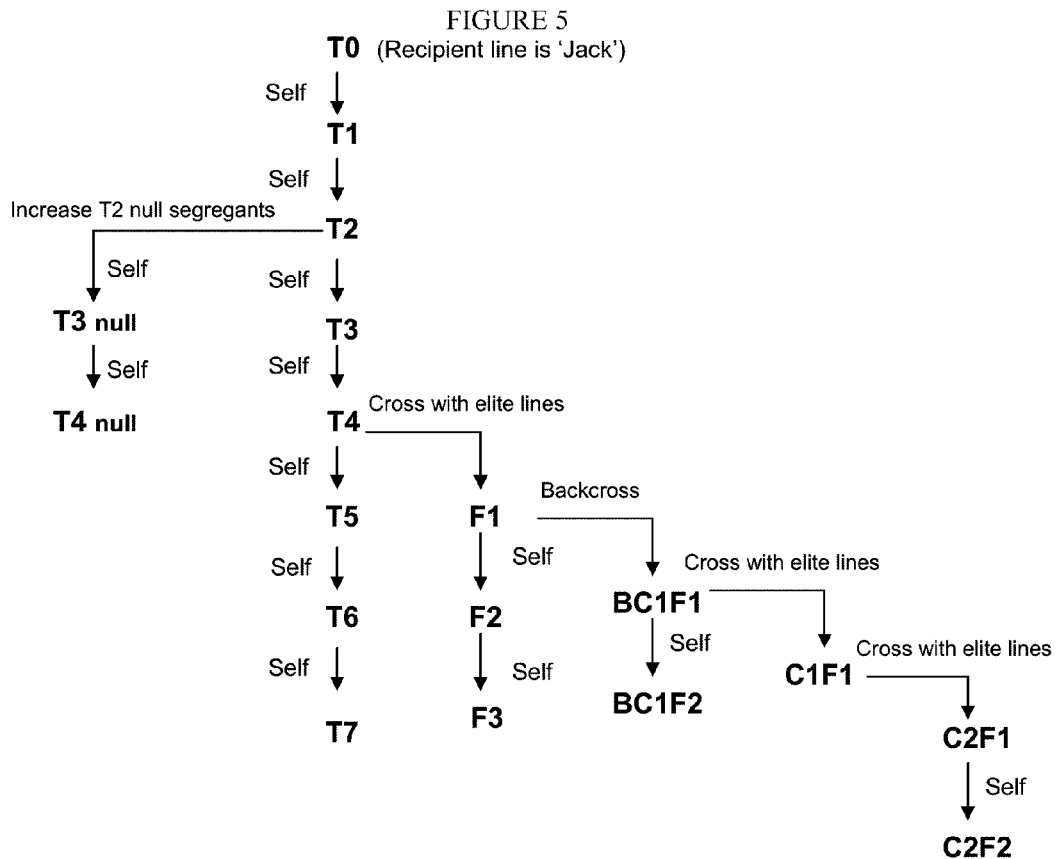

FIGURE 5

| Analysis | GLYAT 3560.4.3.5 Soybean Generation Used | Control Used |
|---|---|---|
| Molecular | T4, T5 and F3 | Jack and Elite 1* |
| Inheritance | T1, F2, F3, BC1F2 and C2F2 | Not applicable |
| Levels of transgenic proteins | T5 | Jack |
| Germination / dormancy | T7 | Jack |
| Field agronomics | T3 | T3 null segregants |
| | T4 | T4 null segregants |
| | T5 | Jack |
| Compositional assessment | T5 | Jack and four commercial soybean varieties |
| Poultry study | T7 | Jack and three commercial soybean varieties |

*Elite 1 is one of several elite soybean lines crossed with T4 plants to yield F1 plants.

| Number | Probe Identification |
|---|---|
| 1 | SCP1 promoter probe |
| 2 | glyat 4601 probe |
| 3 | pinII terminator probe |
| 4 | SAMS probe |
| 5 | gm-hra probe |
| 6 | gm-als terminator probe |

| Letter | Backbone Probe Identification |
|---|---|
| A | backbone 20163 probe |
| B | hyg 20163 probe |

Figure 10A

```
   1 AGCAATTGTT TTGTGCATTT CCAAATTTCA ATCTGATTTA TTAAATAAAA AAATTTTAAT TCGGGTTGAT TGTAAATCAG CTAAAGACAT TTTACAGAAA
     TCGTTAACAA AACACGTAAA GGTTTAAAGT TAGACTAAAT AATTTATTTT TTTAAAATTA AGCCCAACTA ACATTTAGTC GATTTCTGTA AAATGTCTTT

101 GACGTCAAAA ATCTTGGCTC CAAACAAATT TTTGCAAGAT GGCAAGCAAT CCGTTCGTTA ATTAAGTGTT TTTGATTTTG ACAGAATATA TCAAGGGCAC TTTAAACTCT
     CTGCAGTTTT TAGAACCGAG GTTTGTTTAA AAACGTTCTA GGCAAGCAAT TAATTCAACAA AAACTAAAAC TGTCTATAT AGTTCCCGTG AAATTTGAGA

201 CTACCTAACT ATCTTACACG TGAATTCTTA TAGACAAATT CTCCATGCCAC CTAAGGCATC AGGCACCCCT CTCAGGGGTA GACGAAGCAC GAGTAAAGGA
     GATGGATTGA TAGAATGTGC ACTTAAGAAT ATCTGTTTAA CAGTACCGTG GATTCCGTAG TCCGTGGGGA GAGTCCCCAT CTGCTTCGTG CTCATTTCCT

301 TTCAAGTTGG CCCTACCAGA GCCAACTATC AAAAAGAGTT CTTCCGCATC CTCTGGGTCA TCTACCCAAA AACCTAAAAT AAAAGGGTCA TCAACCCAAA
     AAGTTCAACC GGGATGGTCT CGGTTGATAG TTTTTCTCAA GAAGGCGTAG GAGACCCAGT AGATGGGTTT TTGGATTTTA TTTTCCCAGT AGTTGGGTTT

401 TAGTCACCAT CAAACCTCAG TCATCCACTC AGCAATCCCC AAAACCTTCA ACCTCAAAAC AAACAAAGCC CCACTATACC TTCTCACTAC AACACTCCAG
     ATCAGTGGTA GTTTGGACTC AGTAGGTGAG TCCTTAGGGG TTTTGGAAGT TGGAGTTTTG TTTGTTTCCG GCTGATATGG AAGAGTCATG TTGTGAGGTC

501 GCCCTACAAG AAATTGGTCT AACCAAACTC CCAAAAACTG TTGGGCAGAC ATTGCCTCAG AATCTAATGA TGAATTTGAA ACTGATTTAC
     CGGGATGTTC TTTAACCAGA TTGGTTTGAG GGTTTTTGAC AACCCGCTG TAACGGAGTC TTAGATTACT ACTTAAACTT TGACTAAATG

601 AAATCATGAT TCAAAACTCC AAACAATCCA AAACGATTGT CAATCCAAAA GGAAAACAGA CCTTATCCCA CCATTACCAA AACCTACTAA
     TTTAGTACTA AGTTTTGAGG TTTGTTAGGT TTTGCTAACA GTTAGGTTTT CCTTTTGTCT GGAATAGGGT TGTTTTCGT GGTAATGGTT TTGGATGATT

701 CAGTTATATT TACAAAAAATA AATTTCCAAC TGTTTTGTAG ATGGAGCCAA AATTTTGGGA CAAAAATCCC TTCAAGGCTA CAGCCAAGGC ATTTCCACCG
     GTCAATATAA ATGTTTTAT ACAAAACATC TACCTCGGTT TTAAACCCT GTTTTTAGGG AAGTTCCGAT GTCGGTTCCG TAAAGGTGGC

801 GCTTTCCATT TCAAACCTAT TTCCACCAAT AAAACAAGAA TCTTTTACGA ATTCATACTG ATAGACACAA ACTCAGTGTC TATTAAACAC TTCAAAGACC
     CGAAGGTAA AGTTTGGATA AAGGTGGTTA TTTTGTTCTT AGAAAATGCT TAAGTATGAC TATCTGTGTT TGAGTCACAG ATAATTGTG AAGTTTCTGG

901 CAAAATGACAT AAATTTAAAC ACTCATTCAA CCATCCAATC TTTAAAGTTC ATACACCCTC GACAATGTGG AACCAAATATA AATCAAGCCA AACAATTCTT
     GTTTACTGTA TTTAAATTTG TGAGTAAGTT GGTAGTCTA AAATTTCAAG TATGTTGGAG CTGTTACACC TTGTTTATAT TTAGTTCGGT TTGTTAAGAA

1001 TGTACCCTTT GATCCTATAG GTTACACTAT TGGGATTATG TAGATGCATG GACCAATGTA TTCTGGCATC CGGTGGGACT TTTTTGGACC AAACTTTGAT TCTTGGCTTA
     ACATGGCAAA CTAGGATATC CAATCTGATA ACCCTAATAC ATCTACCTAC CTGGTTACAT AAGACCCGTAG TTTTATTGTT TAAGTTTGTA ACAACCGAAT

1101 TTTATTTCAA AACTAACACC GTCTATAATT TTCCAAATTG CAATTCTCAG GTTCCCTCCA CGGTGGGACT TTTTTGGACC AAAAAACCTG TTTGAAACTA ATCTACCCGG AGCAAGTCCA
     AAATAAAGTT TTGATTGTGG CAGATATTAA AAGGTTTAAC CAAGGAGTTC CTTAGTAGTC AGGGACATCT GGATTTTATG AAAAGGTTAA AACGTAACTA TGCGTTCAGT TCGTTCAGT

1201 ACAAGGCTTT GATCAGTTCA AAAAAATGTT CAATTCTCAG CAATCACGAA TCCCTCGAGA CCTAAAATAC TTTTCCAATT ATCTACCCGG AGCAAGTCCA
     TGTTCCCAAA CTAGTCAAGT TTGATTGTGG CAGATATTAA AAGGTTTAAC CTTAGTAGTC AGGGACATCT GGATTTTATG AAAAGGTAAA TAGATGGCC TCGTTCAGT

1301 TCATGGCAAT ACAGATATGG GAAAACTGAA AACAACAAGC AGTTCCATC ACTGCAACAT CATGCATTTA TCAAGTGGTG GAATTAGTTT GATACATCAA
     AGTACCGTTA TGTCTATACC CTTTTGACTT TTGTTGTTCG TCAAGGTAG TGACGTTGTA GTACGTAAAT AGTTCACCAC CTTAATCAAA CTATGTAGTT
```

```
2801 TTCCCTTTTA CATTTTATTT CAGATCCTCC ACCTAGCCAA GTAGGTCTCA AAAGGTTTAC CCCGCATATG CTTAGTCGCC GCAAGCTCCA TATAGGTTAC
     AAGGGAAAAT GTAAAATAAA GTCTAGGAGG TGGATCGGTT CATCCAGAGT TTTCCAAATG GGGCGTATAC GAATCAGCGG CGTTCGAGGT ATATCCAATG
                                           1679 (SEQ ID NO 23) 100.0%

2901 TTTGCGGGCT ACTGAATAGA ATCTTCGGTG AAAGGCGTCT ACCATATCGG CGCAACTATT GATCGAGTGC GTGTATACCA CGTGAATGCG ACACCCGAAA
     AAACGCCCGA TGACTTATCT TAGAAGCCAC TTTCCGCAGA TGGTATAGCC GCGTTGATAA CTAGCTCACG CACATATGGT GCACTTACGC TGTGGGCTTT

3001 GACTAGCAGA AAAGTGCTTC AGCAACAAAC TCTCATCGTG AGCAGTGTCT CTGCTGGCAA TTTCGAAATT ACTAATATGC TGCTCTCGAG ATCTCCACTT
     CTGATCGTCT TTTCACGAAG TCGTTGTTTG AGAGTAGCAC TCGTCACAGA GACGACCGTT AAAGCTTTAA TGATTATACG ACGAGAGCTC TAGAGGTGAA

3101 CCATCATACA ACCGAAACCA GCTAAGGAAG GAGCGATCCA TAAGAATCGC CATAACCTCA TCTCGCCTTC CACCGCACCA GCAAGAGGAA
     GGTAGTATGT TGGCTTTGGT CGATTCCTTC CTCGCTAGGT ATTCTTAGCG GTATTGGAGT AGAGCGGAAG GTGGCGTGGT CGTTCTCCTT
                                                          1297 (SEQ ID NO 16) 100.0%
                                                                                    7 100.0%

3201 ACCGAATTAG AGCTGAAAGA ATATACTAGAGC CATCGTAGAA GAACCGGATT CTTGACCGAT CGACTTTTGC TAGGTCGAAT AGGCTAGGTT
     TGGCTTAATC TCGACTTTCT TATGATCTCG GTAGCATCTT CTTGGCCTAA GAACTGGCTA GCTGAAAACG GGCTCCAGCA ATCCAGCTTA TCCGATCCAA
                                         1514 (SEQ ID NO 44) 100.0%

3301 TACGAAAAAG AGACTAAGGC CGCTCTAGAG ATCCGTCAAC ATGGTGGAGC ACGACACTCT CGTCTACTCC AAGAATATCA AAGATACAGT CTCAGAAGAC
     ATGCTTTTTC TCTGATTCCG GCGAGATCTC TAGGCAGTTG TACCACCTCG TGCTGTGAGA GCAGATGAGG TTCTTATAGT TTCTATGTCA GAGTCTTCTG
     7 100.0%                                                                                              1658 (SEQ ID NO 20) 100.0%
                                                              8 100.0%
              9 100.0%
```

Figure 10D

```
      125323 (SEQ ID NO 46) 100.0%
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
3401  CAAAGGGCTA TTGAGACTTT TCAACAAAGG GTAATATCGG GAAACCTCCT CGGATTCCAT TGCCCAGCTA TCTGTCACTT CATCAAAAGG ACAGTAGAAA
      GTTTCCCGAT AACTCTGAAA AGTTGTTTCC CATTATAGCC CTTTGGAGGA GCCTAAGGTA ACGGGTCGAT AGACAGTGAA GTAGTTTCC TGTCATCTTT
      ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
      1658 (SEQ ID NO 20) 100.0%                                       104314 (SEQ ID NO 45) 100.0%

3501  AGCAAGCTGC CACCTACAAA TGCCATCATT CCGATAAACC AAAGCCTATC CTTCAAGATG CCTCTCCCCA CACTCCTCCC AAAGATGGAC CCCCACCCAC
      TCCTTCCACC GTGGATGTTT ACGGTAGTAA GGCTATTTGG TTTCCGATAG CAAGTTCTAC GGAGACGGCT GTCACCAGGG TTTCTACCTG GGGGTGGGTG

3601  GAGGAGCATC GTGGAAAAAG AAGACGTTCC TCAAAGCAAG TGGATTGATG TGATGATCCT ATGCGTATGG TATGACGTGT GTTCAAGATG
      CTCCTCGTAG CACCTTTTTC TTCTGCAAGG AGTTTCGTTC ACCTACTAC ACTACTAGGA TACGCATACC ATACTGCACA CAAGTTCTAC

3701  ATGACTTCAA ACCTACCTAT GACGTATGGT TCGACTGTGT ACTTAGATCC ACTCGAGCGG GTACCTACGC ACCCTGCGCT
      TACTGAAGTT TGGATGGATA CTGCATACCA AGCTGACTAC TGAATCTAGG TGAGCTCGCC CATGGATGCG TGGGACGCGA

3801  ACCATCCCTA GAGCTGCAGC TTATTTTTAC AACAATTACC AACAACAACA TTACTATTTA CAATTACAGT CGACCCGGGA
      TGGTAGGGAT CTCGACGTCG AATAAAAATG TTGTTAATGG TTGTTGTTGT AATGATAAAT GTTAATGTCA GCTGGGCCCT

3901  TCCACACGAC ACCATGATAG AGTTGAAACC GAGGATACCT ATGAACTAAG CTCAGACCAA ACCAGCCGAT AGAAGCGTGT
      AGGTGTGCTG TGGTACTATC TCCACTTTGG CTCCTATGGA TACTTGATTC GAGTCTGGTT TGGTCGGCTA TCTTCGCACA

4001  ATGTTTGAAA GCGATTACT TCGTGGTGCA TTTCACTTAG CAGGGCAAA GCATAGAATA CTGATTTCCA TAGCTTCATT CCACCAGGCC GAGCACTCGG
      TACAAACTTT CGCTAATGA AGCACCACGT AAAGTGAATC CGCCGAAAT GTCCCCGTT GACTAAAGGT ATCGAAGTAA GGTGGTCCGG CTCGTGAGCC

4101  AACTCCAAGC CCAGAAACAG TACCAGCTCC GAGGTATGGC GGTTATCGTG AGCAGAAAGC GGGATCAACT CTAGTTAAAC ACGCTGAAGA
      TTGAGGTTCC GGTCTTTGTC ATGGTCGAGG CTCCATACCG CCAATGACAC TCGTCTTTCG CCCTAGTTGA GATCAATTTG TGCGACTTCT

4201  AATCCTTCGT AAGAGGGGGG CGGACATGCT TTGGTGTAAT GCGAGGACAT CCGCCTCAGG AAGTTAGGCT TCAGCGAGCA GGGAGAGATA
      TTAGGAAGCA TTCTCCCCCC GCCTGTACGA AACCACATTA CGCTCCTGTA GGCGGAGTCC TTCAATCCGA AGTCGCTCGT CCCTCTCTAT

4301  TTTGACACGC CGCCAGTAGG ACCTCACATC AAAGGATCAA ATAACTAGCT AGTCAGTTAA CCTAGACTTG TCCATCTTCT GGATTGGCCA
      AAACTGTGCG GCGGTCATCC TGGAGTGTAG TTTCCTAGTT TATTGATCGA TCAGTCAATT GGATCTGAAC AGGTAGAAGA CCTAACCGGT

4401  ACTTAATTAA TGTATGAAAT AAAAGGATGC ACATGTAATG CACTATAAGT TGGGCATCAA AGTTGTGT TATGTGTAAT TACTAGTTAT
      TGAATTAATT ACATACTTTA TTTTCCTACG TGTGTATCAC GTGATATTAC ACCCGTAGTT TCAACACACA ATACACATTA ATGATCAATA

4501  CTGAATAAAA GAGAAAGAGA TCATCCATAT AAATGAATGT CACGTCTCTT TATAATTCTT TGATGAACCA GATGCATTTC ATTAACCAAA
      GACTTATTTT CTCTTTCTCT AGTAGGTATA TTTACTTACA AGAATAGGA ACTGCAGAA ATATTAAGAA ACTACTTGGT CTACGTAAAG TAATTGTTT
```

Figure 10E

```
4601  TCCATATACA TATAAATATT AATCATATAT AATTAATATC AATTGGGTTA GCAAAACAAA TCTAGTCTAG GTGTGTTTTG CGAATTCGAT ATCAAGCTTT
      AGTATATATGT ATATTTATAA TTAGTATATA TTAATTATAG TTAACCCAAT CGTTTTGTTT AGATCAGATC CACACAAAAC GCTTAAGCTA TAGTTCGAAA
4701  GCTCTAGATC AAACTCACAT CCAAACATAA CATGGATATC TTCCTTACCA ATCATACTAA TTATTTTGGG TTAAATATTA ATCATTATTT TTAAGATATT
      CGAGATCTAG TTTGAGTGTA GGTTTGTATT GTACCTATAG AAGGAATGGT TAGTATGATT AATAAAACCC AATTATAAT TAGTAATAAT AATTCTATAA
4801  AATTAAGAAA TTTAAAAGAT ATGTATAAAA TTATATATATT CATGATTTTT CATACATTTG ATTTTGATAA TAAATATATT TTTTTTAATT
      TTAATTCTTT AATTTCTAA AAAATTTTTT TACATATTT AATATAATAA GTACTAAAAA GTATGTAAAC TAAAACTATT ATTTATATAA AAAAAATTAA
4901  TCTTAAAAAA TGTTGCAAGA CACTTATTAG ACATAGTCTT GTTCTGTTTA CAAAAGCATT CATCATTTAA TACATTAAAA AATATTTAAT ACTAACAGTA
      AGAATTTTTT ACAACGTTCT GTGAATAATC TGTATCAGAA CAAGACAAAT GTTTTCGTAA GTAGTAAATT ATGTAATTTT TTATAAATTA TGATTGTCAT
5001  GAATCTTCTT GTGAGTGGTG TGGGAGTAGG CAACCTGGCA TTGAAACGAG AGAAAGAGAG TCAGAACCAG AAGACAAATA AAAAGTATGC AACAAACAAA
      CTTAGAAGAA CACTCACCAC ACCCTCATCC GTTGGACCGT AACTTTGCTC TCTTTCTCTC AGTCTTGGTC AGTCAGTTAT TTCTGTTTAT TTTTCATACG TTGTTTGTTT
5101  TCAAAATCAA AGGGCAAAGG CTGGGGTTGG CTCAATTGGT TGCTACATTC AATTTTCAAC TCAGTCAACG GTTGAGATTC ACTCTGACTT CCCCAATCTA
      AGTTTTAGTT TCCCGTTTCC GACCCCAACC GAGTTAACCA ACGATGTAAG TTAAAAGTTG AGTCAGTTGC CAACTCTAAG TGAGACTGAA GGGGTTAGAT
5201  AGCCGCGGAT GCAAACGGTT GAATCTAACC CACCAATCCA TCTCGTTACT TAGGGGCTTT TCCGTCATTA ACTCACCCCT GCCACCCGGT TTCCTATAA
      TCGGCGCCTA CGTTTGCCAA CTTAGATTGG GTGTTAGGTT AGAGCAATGA ATCCCCGAAA AGGCAGTAAT TGAGTGGGGA CGGTGGGCCA AAGGGATATT
5301  ATTGGAACTC AATGCTCCCC TCTAAACTCG TATCGCTTCA GAGTTGAGAC CAAGACACAC TCGTTCATAT ATCTCTCTGC TCTTCTCTTC TCTTCTACCT
      TAACCTTGAG TTACGAGGGG AGATTTGAGC ATAGCGAAGT CTCAACTCTG GTTCGTGTG AGCAAGTATA TAGAGAGACG AGAAGAGAAG AGAAGATGAA
5401  CTCAAGGTAC TTTTCTTCTC CCTCTACCAA ATCCTAGATT CCGTGGTTCA ATTTCGGATC GGTTTGCTTT GCCTTGCTTT ATAATTGCCT
      GAGTTCCATG AAAAGAAGAG GGAGATGGTT TAGGATCTAA GGCACCAAGT TAAAGCCTAG AACGTGAAGA CCAAACGAAA CGGAACGAAA AAGGAGTTGA
5501  GGGTCCATCT AGGATCCATG TGAAACTCTA CTCTTTCTTT AATATCTGCG GAATACGCGT TTGACTTTCA GATCTAGTCG AAATCATTTC ATAATTAACGGA
      CCCAGGTAGA TCCTAGGTAC ACTTTGAGAT GAGAAAGAAA CTTATAGCGC CCTTATGCGCA AACTGAAAGT CTAGATCAGC TTTAGTAAAG TATTAACGGA
5601  TTCTTTTCTT TAGCTTATGA GAAATAAAAT CACTTTTTTT TTATTTCAAA ATAAACCTTG TTCTTGTTTC CTTAGGCTTC AATTTTATTC GAGTATAGGT
      AAGAAAAGAA ATCGAATACT CTTTATTTTA GTGAAAAAAA AATAAAAGTT TATTTGGAAC AAGAACAAAG GAATCGGAAG TTAAAATAAG CTCATATCCA
5701  TTTAGCGAA TTTTTGTAATT GTACTTGTTT GTCTGTAGTT CAGACATCAA TTGTTTTGTT AACAAAACAA TCCAGTTTGT AGTATGTAAG AGTATGTAAG GTTAAAAAAA AATTTTTT TTAAAATAAG CTCATATCCA
      AAAATCGCTT AAAACATTAA CATGAACAAA CAGACATCAA TTGTTTTGTT AACAAAACAA TCCAGTTTGT AGTATGTAAG GAATCCGAAG TTAAATAAG CTCATATCCA
5801  CACCAATAGGA ATCAAACTT TGAGCAGGGG AATTAATCCC TTCCTTCAAA TCCAGTTTGT AGGTCAAACA CAAATTTTTT ACTTTGAAAA CGAAATTTAA
      GTGTTATCCT TAAGTTTGAA ACTCGTCCCC TTAATTACGG AAGGAAGTTT AGGTCAAACA CAAATTTTT ACTTTGAAAA CGAAATTTAA
5901  CTATTATAAC TTTTTTTATG GCTGAAATTT TTGCATGTGT CTTTGCTCTC TGTTGTAAAT TTACTGTTTA GGTACTAACT CTAGGCTTGT TGTGCAGTTT
      GATAATAATTG AAAAAAATAC CGACTTTAAA AACGTACACA GAAACGAGAG ACAACATTTA AATGACAAAT CCATGATTGA GATCCGAACA ACACGTCAAA
```

Figure 10F

```
6001  TTGAGTATA ACCATGCCAC ACAACACAAT GGCGGCCACC GCTTCCAGAA CCACCCGATT CTCTTCTTCC TCTTCACACC CCACCTTCCC CAAACGGATT
      AACTTCATAT TGGTACGGTG TGTTGTGTTA CCGCCGGTGG CGAAGGTCTT GGTGGGCTAA GAGAGAAGG AGAAGTGTGG GGTGGAAGGG GTTTGCGTAA

6101  ACTAGATCCA CCCTCCCTCT CTCTCATCAA ACCCTCACCA AACCCAACCA CGTCTCTCAA ATCAAATGTT CCATCTCCAA ACCCCCACG GCGGCGCCCT
      TGATCTAGGT GGGAGCCACA CAGACTAGTT TGGGAGTGGT TTGGGTTGGT GCAGAGACTT TAGTTTACAA GGTAGAGGTT TGCGGGTGC CCCCCGGCA

6201  TCACCAAGGA AGCGCCGACC ACGGAGCCCT TCGTGTCACG GTTGCCTCC GCAAGGGCGC GGACATCCTT GTGGAGGGGC TGGAGAGGCA
      AGTGGTTCCT TCGCGGCTGG TGCCTCGGGA AGCACAGTGC CAAGCGGACG CGTTCCCGCG CCTGTAGGAA CACCTCCGG ACCTCTCCGT

6301  GGGCGTGACG ACGGTGTTCG CGTACCCCGG GGTGCGTCG ATGGAGATCC ACCAGGCGCT CACGCCATCC GCAACGTGCT CCCGCCGCAC
      CCCGCACTGC TGCCACAAGC GCATGGGGCC CCACGCCAGC TACCTCTAGG TGGTCCCCA GTGCGGGTAGG CGTTGCCACGA GGGCGGGTG

6401  GAGCAGGGCG GCTCTTCGC CGCCGAAGGC TACGCGCGTT CCTCCGGCCT CCCCGCCGTC CCCCGCCCT TGCATTGCCA CCTCCGGCCC CGGCGCCACC AACCTCGTGA
      CTCGTCCCGC CGACAAGCG GCGGCTTCCG ATGCGCCAA GGAGGCCGA GGGGCCCGAC ACGTAACGGT GGAGGCCGGG GCCGCGGTGG TTGGAGCACT

6501  GCGGCCTCGC CGACGCTTTA ATGGACAGCG TCCCAGTCGT CGCCATCACC ATCGGACACC GACGCCTTCC AAGAAACCC
      CGCCGGAGCG GCTGCGAAAT TACCTGTCGC AGGGTCAGCA GCGGTAGTGG CCGGTCCAGC CTAGCCGTGG CTGCGGAAGG TTCTTTGGG

6601  GATCGTGGAG GTGAGCAGAT CCATCACGAA CTCATCCTCG ACGTCGACGA GCCATCCCGC GTCGTCGCCG AGGCTTTCTT CGTCGCCACC
      CTAGCACCTC CACTCGTCTA GGTAGTGCTT CGTGTTGATG TGCAGCTGCT GTAGGGGGCG CAGCAGCGGC TCCGAAAGAA GCAGCGGTGG

6701  TCCGCCCGCC CCGGTCCGGT CCTCATCGAC ATTCCCAAAG ACGTTCAGCA GCAACTCGCC GGGACGAGCGC CGTTAACCTC CCCGGTACC
      AGGCCGGCGG GGCCAGGCCA GGAGTAGCTG TAAGGGTTC TGCAAGTCGT CGTTGAGCGG CCCTGCTCGG GCAATTGGAG GGGCAATGG

6801  TCGCCAGGCT GCCCAGGCCC CCCGCCGAGG CCCAATTGGA ACACATTGTC AGACTCATCA TGGAGGCCA AAAGCCCGTT CTCTACGTCG GCGGTGCCAG
      AGCGGTCCGA CGGGTCCGGG GGGCGGCTCC GGGTTAACCT TGTGTAACAG TCTGAGTAGT ACCTCCGGGT TTTCGGGCAA GAGATGCAGC CGCCACCGTC

6901  TTTGAATTCC ACTGCTCAAT TCAGGCGCTT TGTTCAACTC CCCTTCCTAG CACTTTAATC CGTCTTGAA CTTTTCCTAT TGCTCATGAA
      AAACTTAAGG TCACGAGTTA AGTCCCGCAA ACAACTTGAG TGACCATAAG GGCAACGATC GTGAAATTAC GAAAAGGATA ACCACTACTT

7001  TATTCCCTTC AGATGCTGGG TATGCATGCT CTAACTATGC TGTTGACAAT AGTGATTTGT TGCTTGCCTT TGGGGTAAGG TTTGATGACC
      ATAAGGGAAG TCTACGACCC ATACGACTA GATTGATACG ACAACTGTTA TCACTAAACA ACGAACGGAA ACCCCATTCC AAACTACTGG

7101  CTCTTACTGG GAAGCTTGAG CCTTTTTCCTA CTAGCCCCTAA GATTGTTCAC ATTGATATTG ATTTCTCCGA CATTGCCAAC AACAAGCAGG CCCACGTGTC
      CACAATGACC CTTCGAACTC CGAAAAGGAT CATCCCGATT CTAACAAGTG TAACTATAAC TAAGACGCT GTAACCCTTC TTGTTCGTCC GGTGCACAG

7201  GGTTTGCGCG GATTTGAAGT TGGCCTTGAA GGGAATTAAT ATGATTTTGG AGGAGAAAGG AGTGGAGGGT AAGTTTGATC TTGGAGGTTG GAGAGAGAG
      CCAAACGCGC CTAAACTTCA ACCGGAACTT CCCTTAATTA TACTAAAACC TCCTCTTTCC TCACCTCCCA TTCAAACTAG AACCTCCAAC CTCTCTCTC

7301  ATTAATGTGC AGAAACACAA GTTTCCATTG GGTTACAAGA CATTCCAAGA CGGCGATTTCT CCGCAGCATG CTATCGAGGT TCTTGATGAG TTGACTAATG
      TAATTACACG TCTTTGTGTT CAAAGGTAAC CCAATGTTCT GTAAGGTCCT GCGCTAAAGA GGCTCGTAC GATAGCTCCA AGAACTACTC AACTGATTAC
```

Figure 10G

```
7401 GAGATGCTAT TGTTAGTACT GGGGTTGGGC AGCATCAAAT GTGGGCTGCG CAGTTTTACA AGTACAAGAG ACCGAGGCAG TGGTTGACCT CAGGGGGTCT
     CTCTACGATA ACAATCATGA CCCCAACCCG TCGTAGTTTA CACCCGACGC GTCAAAATGT TCATGTTCTC TGGCTCCGTC ACCAACTGGA GTCCCCCAGA

7501 TGGAGCCATG GGTTTTGGAT TGCCTGCGCG TATTGGTGCT ACCCTGGGGC GCTGTTGTT GACATTGATG GGGATGGTAG TTTCATCATG
     ACCTCGGTAC CCAAAACCTA ACGGACGCGC ATAACCACGA CGACAACGAT TGGGACCCCG ACAACACCAA CTGTAACTAC CCCTACCATC AAAGTAGTAC

7601 AATGTTCAGG AGTTGGCCAC TATAAGAGTG GAGAATCTCC CAGTTAAGAT ATTGTGTTG AACAATCAGC ATTTGGGTAT GGTGGTTCAG TTGGAGAGTA
     TTACAAGTCC TCAACCGGTG ATATTCTCAC CTCTTAGAGG GTCAATTCTA TAACACAAC TGTTAGTCG TAAACCCATA CCACCAAGTC AACCTCCTAT

7701 GGTTCTACAA GTCCAATAGA GCTCACACCT ATCTTGGAGA TCCGTCTAGC CAGTTAAGAT TATTCCCAAA CATGCTCAAG TTTGCTGATG CTTGTGGGAT
     CCAAGATGTT CAGGTTATCT CGAGTGTGGA TAGAACCTCT AGGCAGATCG GTCAATTCTA ATAAGGGTTT GTACGAGTTC AAACGACTAC GAACACCTA

7801 ACCGGCAGCG CGAGTGACGA AGAAGGAAGA GCTTAGACGG GCAATTCAGA CACCCCTGGC GTGGGACCTA CCCTACCTTC TTGATGTCAT TGTGCCCCAT
     TGGCCGTCGC GCTCACTGCT TCTTCCTTCT CGAATCTCGC CGTTAAGTCT CTTAAGTCT GTGGGACCTA GGGATGGAAG AACTACAGTA ACACGGGTA 1439 (SEQ ID NO 18) 100.0%
                                                                    ~~~~~~~~~~~~~~~~~~~~~~~~~

7901 CAGGAGCATG TGTTGCCGAT AATGGATCCT TCAAGGATGT GATAACTGAG GGTGATGTA GAACGAGGTA CTGATTGCCT AGACCAAATG
     GTCCTCGTAC ACAACGGCTA TTACCTAGGA AGTTCCTACA CTATTGACTC CCACTACCAT CTTGCTCCAT GACTAACGGA TCTGGTTAC

8001 TTCCTTGATG CTTGTTTTGT ACAATATATA TAAGATAATG TAGACGTGTA CTGTCCTAGT TGCAGGATTT GGCCTGTGT GAGCATCATA GTCTGTAGTA GTTTTGGTAG
     AAGGAACTAC GAACAAAACA TGTTATATAT ATTCTATTAC ATCTGCACAT GACAGGATCA AGTGCCTAAA CCGGACACCA CTCGTAGTAT CAGACATCAT CAAAACCATC

8101 CAAGACATTT TATTTTCCTT TTATTTAACT TACTACATGC AGTAGCATCT CTGTCCTGAT ATCTCCTGTT GTCTGTATTG TGCCGTTGGA
     GTTCTGTAAA ATAAAATGAA AATAATTGA ATGATGTACG TCATCGTAGA GACAGGACTA TAGAGCACAA CAGACATAAC ACGGCAACCT

8201 TTTTTTGCTG TAGTGAGACT TGCTAGTAAT GAAAATGATG TTAGAAATCT AAGTAGAGAA TCTGTTGAAG AAGTCAAAAG CTAATGGAAT
     AAAAAACGAC ATCACTCTGA ACGATCATTA CTTTTACTAC ACCAATTTCTG AATCTTTAGA TTCATCTCTT AGACAACTTC TTCAGTTTTC GATTACCTTA

8301 CAGGTTACAT ATTCAATGTT TAGCCGGTTG TAGACGTGTA ATCGCCAACC CTCTTGGAGC TCACCTAGCC AATCAGTAAA ATGCATATTC
     GTCCAATGTA TAAGTTACAA AATCGGCCAAC ATCTGCACAT GAGAACCTCG AGTGGATCCG TTAGTCATTT TACGTATAAG

8401 CTTTTTAAC TTGCCATTTA TTTACTTTTA GTGGAAATTG TGACCATGTAG GTTCATGTAG AACCGATTTG GACCATTGCG TCCACAAAAC GTCTCTTTTG
     GAAAAAATTG AACGGTAAAT AAATGAAAAT CACCTTTAAC CAAGTACATC ACTGTACG TTGCCTAAAC CTGGTAACGC AGGTGTTTTG CAGAGAAAC

8501 CTCGATCTTC ACAAAGCGAT ACGAAATCC AGAGATAGTT TTCAAAAGTC AGAAATGGCA TAGTAAAACA AAGTTATAAA TAGTAATGAC
     GAGCTAGAAG TGTTTCGCTA TGGCTTTAGG TCTCTATCGA AGTTTTCAG TCTTTACCGT AGTAAACA AAGTTATAAA TAGTAATGAC
```

Figure 10H

```
                                                                                              1660 (SEQ ID NO 21) 100.0%
8601 TTCAATAACA AGTGGCATCA CGTTTCTAGT TCTAGACCCA TCAGCTGGGC CGGCCACTAG TGAGCTCGGT ACCCGGGGGC GCGTAATATC ATCATTAGGA
     AAGTTATTGT TCACCGTAGT GCAAAGATCA AGATCTGGGT AGTCGACCCG GCCGGTGATC ACTCGAGCCA TGGGCCCCCG CGCATTATAG TAGTAATCCT 1660 (SEQ ID NO 21) 100.0%
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~       1298 (SEQ ID NO 17) 100.0%
8701 AGACACTGCC CATCTTGAAT AGGATTTTAG CTACTAAATA TGTTGATGGT CTTTATGAAA AACTATTAAC TAGGAATATT ATGGTACCCA TATGGAAAGA
     TCTGTGACGG GTAGAACTTA TCCTAAAATC GATGATTTAT ACAACTACCA GAAATACTTT TTGATAATTG ATCCTTATAA TACCATGGGT ATACCTTTCT
     ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
     1298 (SEQ ID NO 17) 100.0%

8801 AGACGCTAGG GGAATAGAAA GACCATCAAA TAAAGAAGT TCTTCCGAAG CATTAACAAT TACCTATTTA ATATGTACTC AGTCCGGGTG
     TCTGCGATCC CCTTATCTTT CTGGTAGTTT ATTTGCTTCA GTGTGGTCC AGAAGGCTTC GTAATTGTTA ATGGATAAAT TATACATGAG TCAGGCCCAC

8901 GATATCTCAC TACATTGACG CAGTTTGTTC AAAGACGAAC GCCCTGAATT ATGCCATCRG CTTAGGCTTT CAAATATGGT ACGCTCTAAT GCCAAGCCTT
     CTATAGAGTG ATGTAACTGC GTCAAACAAG TTTCTGCTTG CGGGACTTAA TACGGTAGAC GAATCCGAAA GTTTATACCA TGCGAGATTA CGGTTCGGAA
                                                                 1666 (SEQ ID NO 22) 100.0%
9001 ATGCTGGTCT TAGGGTATTA TCATCAAATC TTTTAAGCCAG AGTAGTTAA ATACATCAAG GACACCATAG GAGTATGGCA CAACGATATT GTCAAGATCG
     TACGACCAGA ATCCCATAAT AGTAGTTTAG AAATTCCGTC TCCATCAATT TATGTAGTTC CTGTGGTATC CTCATACCGT GTTGCTATAA CAGTTCTAGC

9101 CATCAGATCT AATAGGCAAT AATCAATTCT TCATGCCAGCC CGACGTCGGCA ACGCTCGAAA ACGCCACGCG CTCTGGGACA GGGACCACAC CTCAGTCGCT
     GTAGTCTAGA TTATCCGTTA TTACTTAAGA AGTACGTCGG GCTGCACCCT TGCGAGCTTT CGTCACCCGT GAGACCCTGT CCCTGGTCTG GACTCAGCGA

9201 AACATTTGGG AATAAGAGAA GTAGATATAC CCAATTTTTT AACTAGCCAA GGAAGGAAAG CGGGAAAAGGT CCGATACAAA GGAAAGGGTT GCGAGCTTA
     TTGTAAACCC TTATTCTCTT CATCTATATG GGTTAAAAAA TTGATCGGTT CCTTCCTTTC GCCCTTTCCA GGCTATGTTT CCTTTCCAA CGCTCCGAAT

9301 ACGATTTAGA ATATAGCTGT TGAGGTGGCA CTTTGTTCCCC CGGGGCGGGG GTATATGCCC GTAGCTTTAT TCTGTCACTT CTTTCAGATC AATGAAGTTG
     TGCTAAATCT TATATCGACA ACTCCACCGT GAACAAGGGG GCCCCGCCCC CATATACGGG CATCGAAATA AGACAGTGAA GAAAGTCTAG TTACTTCAAC

9401 AAAAGTTATA GAGTAAGGGA CCCTTGTTTA CAAAGCTGTC ACTCCAAGAA CTCGAAGTCA AGCATCTTCG GGAATATCCA GATTAGTCTT CAACTAGAGA
     TTTTCAATAT CTCATTCCCT GGGAACAAAT GTTTCGACAG TGAGGTTCTT GAGCTTCAGT TCGTAGAAGC CCTTATAGGT CTAATCAGAA GTTGATCTCT

9501 AAGGATAGGA ATCTCCTTTG CAGAGTTTTC TTCTCCTTGCT GATGTAGCGG TAAAGTCAAA AGTTGGATGC CCTTTTTCT TTATTTAATT AATTCCGTTG
     TTCCTATCCT TAGAGGAAAC GTCTCAAAAG AAGAGGACGA CTACATTGCC ATTTCAGTTT TCAACCTACG GGAAAAAGA AATAAATTAA TTAAGGCAAC
```

Figure 10I

```
9501  ATAGAGCTTT TGAGCGGATG CAAGCACTAG ATTCCTCAAC GAGTACCAAT AATAAATGAA TTCACCAGAC TAAGAGAAGA AAACAGAACA AAAAGATTAA
      TATCTCGAAA ACTCGCCTAC GTTCGTGATC TAAGGAGTTG CTCATGGTTA TTATTTACTT AAGTGGTCTG ATTCTCTTCT TTTGTCTTGT TTTTCTTAATT

9701  GCCCAGCCGC CTTCGGGAAG ACCTATCTTC GTCGGGAGGA AGAGCCCTCT TTACACCATT GTGATTAGAA AAAACCGAAA AGTGGACCGG CCTAGTAACC
      CGGGTCGGCG GAAGCCCTTC TGGATAGAAG CAGCCCCTCCT TCTCGGGAGA AATGTGGTAA CACTAATCTT TTTTGGCTTT TCACCTGGCC GGATCATTGG

9801  AATAGAGCGG GGCTTGATCC CCACTTTAAA TCTATTGGAT AGAGCCCTCA GCCCAGGGCA AGCGATTGAA TTCTATTTGA TTATGGGTTA GGTGGAACCT
      TTATCTCGCC CCGAACTAGG GGTGAAATTT AGATAACCTA TCTCGGGAGT CGGGTCCCGT TCGCTAACTT AAGATAAACT AATACCCAAT CCACCTTGGA

9901  GAAACTAGCA CTTACAAATG AGTTAGCAAA AGGAAAAAGA CAATTCTCAA ATGCGTACAA GACTTTCTC CTTCTTTGTT TAAGAGGCCA GTCTGCGATG
      CTTTGATCGT GAATGTTTAC TCAATCGTTT TCCTTTTTCT GTTAAGAGTT TACGCATGTT CTGAAAGAAG GAAGAAACAA ATTCTCCGGT CAGAGCGTAC

10001 GATGCTCGTG CATGAAAAAG GGCTTTGATC TATTCACCAC TTTATATAATA GAGCCAATCT CTGCAGGACA AGATATCTAT TTTGTCATTG GGAAGTAAGG
      CTACGAGCAC GTACTTTTTC CCGAAACTAG ATAAGTGGTG AATATATATT CTCGGTTAGA GACGTCCTGT TCTATAGATA AAACAGTAAC CCTTCATTCC

10101 CTTAAGTCGA CGAAAAAGTT AGGAAAGGGG ATCATATGGC TAGGGTTGCC CTCGGGGCTC AAGGGTTTAG CGATGAAGAG TGCCAAGCAA AAGGTCAATA
      GAATTCAGCT GCTTTTTCAA TCCTTTCCCC TAGTATACCG ATCCCAACGG GAGCCCCGAG TTCCCAAATC GCTACTTCTC ACGGTTCGTT TTCCAGTTAT

10201 CCCGGTACGCC GATCAAAGAA GTCCAGTGGC AAGGCCCTTT CAGCCAAGCT AGCGTGCTGA ACAGAAAGTC GTAGAGTGAT GACAGCTTCT TCTTCTTTGAG
      GGCCATGCGG CTAGTTTCTT CAGGTCACCG TTCCGGGAAA GTCGGTTCGA TCGCACGACT CATCTCACTA CATCCACTGT CTGTCGAAGA AGAAGAACTC

10301 TCATTCGTGT GACAACATCA GGATCTCGTC CTTCCCTTCT TATTGATTTG ATAAAGGGCT TTGTCCACTC TAGCCCAGCG GAGTGACGGT TTAGTTTAGG
      AGTAAGCACA CTGTTGTAGT CCTAGAGCAG GAAGGGAAGA ATAACTAAAC TATTTCCCGA AACAGGTGAG ATCGGCTCGC CTCACTGCCA AATCAAATCC

10401 GTCAATAAGA TAAGATTGCC CCTTCCCTTCT TATTGATTTG ATAAAGGGCT TTGTCCACTC TAGCCCAGCG GAGTGACGGT TTAGTTTAGG
      CAGTTATTCT ATTCTAACGG GGAGGAAGA ATAACTAAAC TATTTCCCGA AACAGGTGAG ATCGGCTCGC CTCACTGCCA AATCAAATCC

10501 CTTTAGATGC CACTGCGAAA GACTCTAGAG ATCCACTCTC ACAGCGTATA CGCGACATCC CTATGTATAC ACAATCCTTT CAAGCAGCTA GGACAGCTAG
      GAAATCTACG GTGACGCTTT CTGAGATCTC TAGGTGAGAG TGTCGCATAT GCGCTGTAGG GATACATATG TGTTAGGAAA GTTCGTCGAT CCTGTCGATC

10601 CAAGCAAGTT ATCTGTTCGC GGACAAGCTC TCTGTTCGAG AGACCTACTG CTCTTTCATG GGAAAACATG CGGAAAAAAC ACGGTCTTTC GTGGAAGTTG GTCGATTTGA
      GTTCGTTCAA TAGACAAGCG CCTGTTCGAG AGACCTACTG CTCTTTCATG GGAAAACATG CGGAAAAAAC ACGGTCTTTC GTGGAAGTTG GTCGATTTGA

10701 AGTCCCTTTA TGACTGAAAA ACGAAAAAGA CGGAAAAAAGA CCCGGAAAAAA CCCGCAAATG GATCAACTGT GATCAACTGT CACATTTGA TCCCACGTTTA CCCCTAAAAT GAACTTTCAT
      TCAGCGAAAT ACTCACTTTT ACCCAGCTAC TGCTTTTTCT GCCCCTTTTA CTAGTTGACA GTGTAAAAAACT ACGGTCAAAT CCCGATTTTA CTTGAAAGTA

10801 CCAAAAAGAC CGAGAAAACG CTCACCACTG AGGATCCGAT CGGAAATAA
      GGTTTTTCTG GCTCTTTTGC GAGGTGACCG TCCTAGGCTA GCCTTTATT
```

SOYBEAN EVENT 3560.4.3.5 AND COMPOSITIONS AND METHODS FOR THE IDENTIFICATION AND/OR DETECTION THEREOF

CROSS-REFERENCE TO RELATED APPLICATION

This application is a continuation of U.S. Ser. No. 12/156,182, filed May 30, 2008, which is a Continuation-in-Part of U.S. Utility application Ser. No. 11/765,940, filed Jun. 20, 2007, which claims the benefit of U.S. Provisional Application No. 60/817,011 filed on Jun. 28, 2006 and U.S. Provisional Application No. 60/847,154 filed on Sep. 26, 2006, each of which is herein incorporated by reference in its entirety.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 405384seqlist.txt, a creation date of May 17, 2011, and a size of 84.9 KB. The sequence listing filed via EFS-Web is part of the specification and is hereby incorporated in its entirety by reference herein.

FIELD OF THE INVENTION

This invention is in the field of molecular biology. More specifically, this invention pertains to multiple herbicide tolerances conferred by expression of a sequence that confers tolerance to glyphosate in conjunction with the expression of sequence that confers tolerance to one or more ALS inhibitor chemistries.

BACKGROUND OF THE INVENTION

The expression of foreign genes in plants is known to be influenced by their location in the plant genome, perhaps due to chromatin structure (e.g., heterochromatin) or the proximity of transcriptional regulatory elements (e.g., enhancers) close to the integration site (Weising et al. (1988) *Ann. Rev. Genet* 22: 421-477). At the same time the presence of the transgene at different locations in the genome influences the overall phenotype of the plant in different ways. For this reason, it is often necessary to screen a large number of events in order to identify an event characterized by optimal expression of an introduced gene of interest. For example, it has been observed in plants and in other organisms that there may be a wide variation in levels of expression of an introduced gene among events. There may also be differences in spatial or temporal patterns of expression, for example, differences in the relative expression of a transgene in various plant tissues, that may not correspond to the patterns expected from transcriptional regulatory elements present in the introduced gene construct. It is also observed that the transgene insertion can affect the endogenous gene expression. For these reasons, it is common to produce hundreds to thousands of different events and screen those events for a single event that has desired transgene expression levels and patterns for commercial purposes. An event that has desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It would be advantageous to be able to detect the presence of a particular event in order to determine whether progeny of a sexual cross contain a transgene of interest. In addition, a method for detecting a particular event would be helpful for complying with regulations requiring the pre-market approval and labeling of foods derived from recombinant crop plants, or for use in environmental monitoring, monitoring traits in crops in the field, or monitoring products derived from a crop harvest, as well as, for use in ensuring compliance of parties subject to regulatory or contractual terms.

In the commercial production of crops, it is desirable to easily and quickly eliminate unwanted plants (i.e., "weeds") from a field of crop plants. An ideal treatment would be one which could be applied to an entire field but which would eliminate only the unwanted plants while leaving the crop plants unharmed. One such treatment system would involve the use of crop plants which are tolerant to a herbicide so that when the herbicide was sprayed on a field of herbicide-tolerant crop plants, the crop plants would continue to thrive while non-herbicide-tolerant weeds were killed or severely damaged. Ideally, such treatment systems would take advantage of varying herbicide properties so that weed control could provide the best possible combination of flexibility and economy. For example, individual herbicides have different longevities in the field, and some herbicides persist and are effective for a relatively long time after they are applied to a field while other herbicides are quickly broken down into other and/or non-active compounds. An ideal treatment system would allow the use of different herbicides so that growers could tailor the choice of herbicides for a particular situation.

Due to local and regional variation in dominant weed species as well as preferred crop species, a continuing need exists for customized systems of crop protection and weed management which can be adapted to the needs of a particular region, geography, and/or locality. Methods and compositions that allow for the rapid identification of events in plants that produce such qualities are needed. For example, a continuing need exists for methods of crop protection and weed management which can reduce: the number of herbicide applications necessary to control weeds in a field; the amount of herbicide necessary to control weeds in a field; the amount of tilling necessary to produce a crop; and/or programs which delay or prevent the development and/or appearance of herbicide-resistant weeds. A continuing need exists for methods and compositions of crop protection and weed management which allow the targeted use of particular herbicide combinations and for the efficient detection of such an event.

BRIEF SUMMARY OF THE INVENTION

Compositions and methods related to transgenic glyphosate/ALS inhibitor-tolerant soybean plants are provided. Compositions comprise soybean plants containing a 3560.4.3.5 event which imparts tolerance to glyphosate and at least one ALS-inhibiting herbicide. The soybean plant harboring the 3560.4.3.5 event at the recited chromosomal location comprises genomic/transgene junctions having at least the polynucleotide sequence of SEQ ID NO:10 and/or 11. Further provided are the seeds deposited as Patent Deposit No. PTA-8287 and plants, plant cells, plant parts, grain and plant products derived therefrom. The characterization of the genomic insertion site of event 3560.4.3.5 provides for an enhanced breeding efficiency and enables the use of molecular markers to track the transgene insert in the breeding populations and progeny thereof. Various methods and compositions for the identification, detection, and use of the soybean event 3560.4.3.5 are provided. Further provided are methods and compositions that increase the yield of soybean event 3560.4.3.5.

BRIEF DESCRIPTION OF THE DRAWINGS

FIG. 4A-E provides a complete sequence of DNA insert and flanking genomic border regions in the 3560.4.3.5 soybean event (SEQ ID NO:6). The 5' and 3' flanking genomic border regions, by 1 to 3317 and by 8680 to 10849, respectively, are underlined.

FIG. 5 provides a breeding diagram for 3560.4.3.5 soybean.

FIG. 10A-I provides the left genomic border/internal transgene insert/right genomic border of the 3560.4.3.5 event (SEQ ID NO:6). The regions where various primers anneal are illustrated.

DETAILED DESCRIPTION OF THE INVENTION

Figure 1:
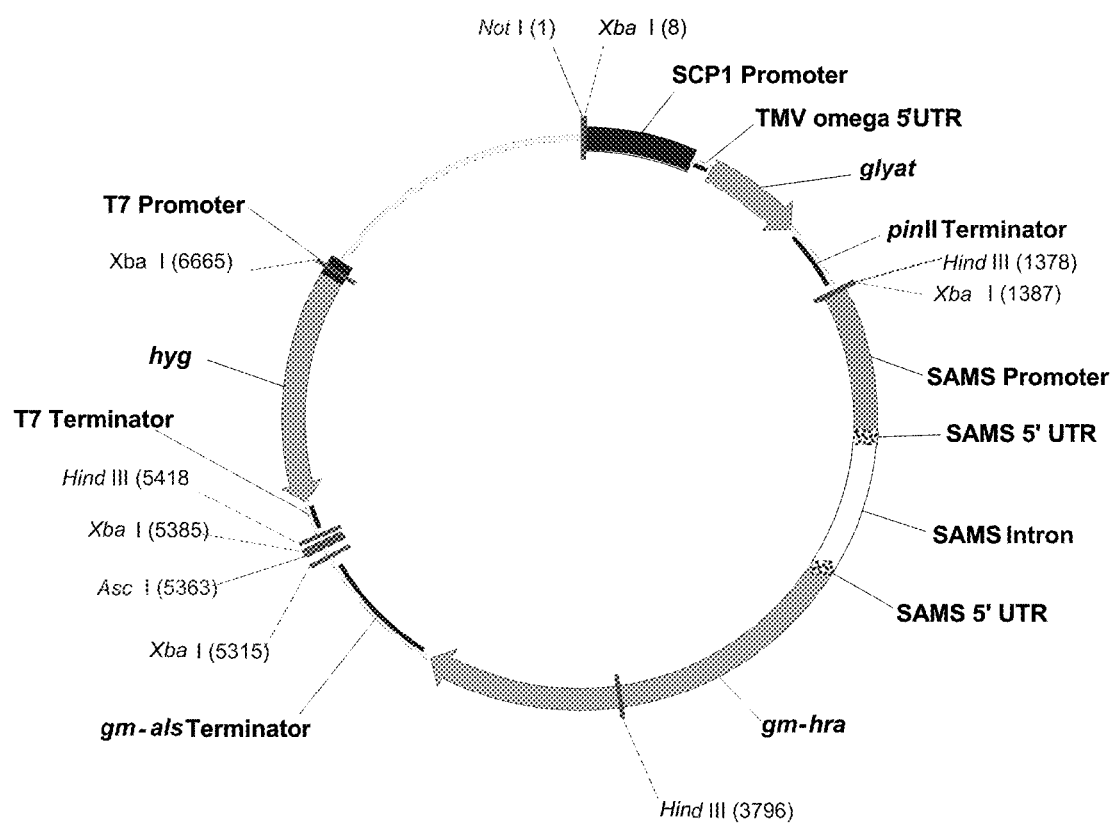
FIG. 1 provides a schematic map of PHP20163 indicating plasmid elements and restriction enzyme sites for Not I, Asc I, Xba I and Hind III. Not I and Asc I were used for isolation of fragment PHP20163A (FIG. 2).

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Compositions and methods related to transgenic glyphosate/ALS inhibitor-tolerant soybean plants are provided. Compositions include soybean plants having event 3560.4.3.5. A soybean plant having "event 3560.4.3.5" has been modified by the insertion of the glyphosate acetyltransferase (glyat) gene derived from *Bacillus licheniformis* and a modified version of the soybean acetolactate synthase gene (gm-hra). The glyat gene was functionally improved by a gene shuffling process to optimize the kinetics of glyphosate acetyltransferase (GLYAT) activity for acetylating the herbicide glyphosate. The insertion of the glyat gene in the plant confers tolerance to the herbicidal active ingredient glyphosate through the conversion of glyphosate to the non-toxic acetylated form. The insertion of the gm-hra gene produces a modified form of the acetolactate synthase (ALS) enzyme. ALS is essential for branched chain amino acid biosynthesis and is inhibited by certain herbicides. The modification in the gm-hra gene overcomes this inhibition and thus provides tolerance to a wide range of ALS-inhibiting herbicides. Thus, a soybean plant having an event 3560.4.3.5 is tolerant to glyphosate and at least one ALS-inhibiting herbicide. The soybean event 3560.4.3.5 is otherwise known as Event DP-356Ø43-5 or 356043 soybean.

The polynucleotides conferring the glyphosate and ALS inhibitor tolerance are linked on the same DNA construct and are inserted at a characterized position in the soybean genome and thereby produce the 3560.4.3.5 soybean event. The soybean plant harboring the 3560.4.3.5 event at the recited chromosomal location comprises genomic/transgene junctions having at least the polynucleotide sequence of SEQ ID NO:10 and/or 11. The characterization of the genomic insertion site of the 3560.4.3.5 event provides for an enhanced breeding efficiency and enables the use of molecular markers to track the transgene insert in the breeding populations and progeny thereof. Various methods and compositions for the identification, detection, and use of the soybean 3560,4,3,5 events are provided herein. As used herein, the term "event 3560.4.3.5 specific" refers to a polynucleotide sequence which is suitable for discriminatively identifying event 3560.4.3.5 in plants, plant material, or in products such as, but not limited to, food or feed products (fresh or processed) comprising, or derived from plant material.

Compositions further include seed deposited as Patent Deposit Nos. PTA-8287 and plants, plant cells, and seed derived therefrom. Applicant(s) have made a deposit of at least 2500 seeds of soybean event 3560.4.3.5 with the American Type Culture Collection (ATCC), Manassas, Va. 20110-2209 USA, on Mar. 27, 2007, and the deposits were assigned ATCC Deposit No. PTA-8287. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.The seeds deposited with the ATCC on Mar. 26, 2007 were taken from the deposit maintained by Pioneer Hi-Bred International, Inc., 7250 NW $62^{nd}$ Avenue, Johnston, Iowa 50131-1000. Access to this deposit will be available during the pendency of the application to the Commissioner of Patents and Trademarks and persons determined by the Commissioner to be entitled thereto upon request. Upon allowance of any claims in the application, the Applicant(s) will make available to the public, pursuant to 37 C.F.R. §1.808, sample(s) of the deposit of at least 2500 seeds of soybean event 3560.4.3.5 with the American Type Culture Collection (ATCC), 10801 University Boulevard, Manassas, Va. 20110-2209. This deposit of seed of soybean event 3560.4.3.5 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant(s) have satisfied all the requirements of 37 C.F.R. §§1.801-1.809, including providing an indication of the viability of the sample upon deposit. Applicant(s) have no authority to waive any restrictions imposed by law on the transfer of biological material or its transportation in commerce. Applicant(s) do not waive any infringement of their rights granted under this patent or rights applicable to event 3560.4.3.5 under the Plant Variety Protection Act (7 USC 2321 et seq.). Unauthorized seed multiplication prohibited. The seed may be regulated.

As used herein, the term "soybean" means *Glycine max* and includes all plant varieties that can be bred with soybean. As used herein, the term plant includes plant cells, plant organs, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise a 3650.4.3.5 event.

A transgenic "event" is produced by transformation of plant cells with a heterologous DNA construct(s), including a nucleic acid expression cassette that comprises a transgene of interest, the regeneration of a population of plants resulting from the insertion of the transgene into the genome of the plant, and selection of a particular plant characterized by insertion into a particular genome location. An event is characterized phenotypically by the expression of the transgene(s). At the genetic level, an event is part of the genetic makeup of a plant. The term "event" also refers to progeny produced by a sexual outcross between the transformant and another variety that include the heterologous DNA. Even after repeated back-crossing to a recurrent parent, the inserted DNA and flanking DNA from the transformed parent is present in the progeny of the cross at the same chromosomal location. The term "event" also refers to DNA from the original transformant comprising the inserted DNA and flanking sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

As used herein, "insert DNA" refers to the heterologous DNA within the expression cassettes used to transform the plant material while "flanking DNA" can comprise either genomic DNA naturally present in an organism such as a plant, or foreign (heterologous) DNA introduced via the transformation process which is extraneous to the original insert DNA molecule, e.g. fragments associated with the transformation event. A "flanking region" or "flanking sequence" as used herein refers to a sequence of at least 20, 50, 100, 200, 300, 400, 1000, 1500, 2000, 2500, or 5000 base pair or greater which is located either immediately upstream of and contiguous with or immediately downstream of and contiguous with the original foreign insert DNA molecule. Non-limiting examples of the flanking regions of the 3560.4.3.5 event are set forth in SEQ ID NO:4 and 5 and variants and fragments thereof.

Transformation procedures leading to random integration of the foreign DNA will result in transformants containing different flanking regions characteristic of and unique for each transformant. When recombinant DNA is introduced into a plant through traditional crossing, its flanking regions will generally not be changed. Transformants will also contain unique junctions between a piece of heterologous insert DNA and genomic DNA, or two pieces of genomic DNA, or two pieces of heterologous DNA. A "junction" is a point where two specific DNA fragments join. For example, a junction exists where insert DNA joins flanking DNA. A junction point also exists in a transformed organism where two DNA fragments join together in a manner that is modified from that found in the native organism. As used herein, "junction DNA" refers to DNA that comprises a junction point. Non-limiting examples of junction DNA from the 3560.4.3.5 event set are forth in SEQ ID NO:1, 2, 6, 10, 11, 12, 13, 14, 15, 27, 28, 41, 42 or variants and fragments thereof.

A 3560.4.3.5 plant can be bred by first sexually crossing a first parental soybean plant grown from the transgenic 3560.4.3.5 soybean plant (or progeny thereof derived from transformation with the expression cassettes of the embodiments that confer herbicide tolerance) and a second parental soybean plant that lacks the herbicide tolerance phenotype, thereby producing a plurality of first progeny plants; and then selecting a first progeny plant that displays the desired herbicide tolerance; and selfing the first progeny plant, thereby producing a plurality of second progeny plants; and then selecting from the second progeny plants which display the desired herbicide tolerance. These steps can further include the back-crossing of the first herbicide tolerant progeny plant or the second herbicide tolerant progeny plant to the second parental soybean plant or a third parental soybean plant, thereby producing a soybean plant that displays the desired herbicide tolerance. It is further recognized that assaying progeny for phenotype is not required. Various methods and compositions, as disclosed elsewhere herein, can be used to detect and/or identify the 3560.4.3.5 event.

It is also to be understood that two different transgenic plants can also be sexually crossed to produce offspring that contain two independently segregating added, exogenous genes. Selfing of appropriate progeny can produce plants that are homozygous for both added, exogenous genes. Backcrossing to a parental plant and out-crossing with a non-transgenic plant are also contemplated, as is vegetative propagation. Descriptions of other breeding methods that are commonly used for different traits and crops can be found in one of several references, e.g., Fehr, in *Breeding Methods for Cultivar Development*, Wilcos J. ed., American Society of Agronomy, Madison Wis. (1987).

The term "germplasm" refers to an individual, a group of individuals, or a clone representing a genotype, variety, species or culture, or the genetic material thereof.

A "line" or "strain" is a group of individuals of identical parentage that are generally inbred to some degree and that are generally isogenic or near isogenic.

Inbred soybean lines are typically developed for use in the production of soybean hybrids and for use as germplasm in breeding populations for the creation of new and distinct inbred soybean lines. Inbred soybean lines are often used as targets for the introgression of novel traits through traditional breeding and/or molecular introgression techniques. Inbred soybean lines need to be highly homogeneous, homozygous and reproducible to be useful as parents of commercial hybrids. Many analytical methods are available to determine the homozygosity and phenotypic stability of inbred lines.

The phrase "hybrid plants" refers to plants which result from a cross between genetically different individuals.

The term "crossed" or "cross" in the context of this invention means the fusion of gametes, e.g., via pollination to produce progeny (i.e., cells, seeds, or plants) in the case of plants. The term encompasses both sexual crosses (the pollination of one plant by another) and, in the case of plants, selfing (self-pollination, i.e., when the pollen and ovule are from the same plant).

The term "intro gression" refers to the transmission of a desired allele of a genetic locus from one genetic background to another. In one method, the desired alleles can be introgressed through a sexual cross between two parents, wherein at least one of one of the parents has the desired allele in its genome.

In some embodiments, the polynucleotide conferring the soybean 3560.4.3.5 event of the invention are engineered into a molecular stack. In other embodiments, the molecular stack further comprises at least one additional polynucleotide that confers tolerance to a $3^{rd}$ herbicide. In one embodiment, the sequence confers tolerance to glufosinate, and in a specific embodiment, the sequence comprises pat.

In other embodiments, the soybean 3560.4.3.5 event of the invention comprise one or more trait of interest, and in more specific embodiments, the plant is stacked with any combination of polynucleotide sequences of interest in order to create plants with a desired combination of traits. A trait, as used herein, refers to the phenotype derived from a particular sequence or groups of sequences. For example, herbicide-tolerance polynucleotides may be stacked with any other polynucleotides encoding polypeptides having pesticidal and/or insecticidal activity, such as *Bacillus thuringiensis* toxic proteins (described in U.S. Pat. Nos. 5,366,892; 5,747, 450; 5,737,514; 5,723,756; 5,593,881; Geiser et al. (1986) *Gene* 48: 109; Lee et al. (2003) *Appl. Environ. Microbiol.* 69: 4648-4657 (Vip3A); Galitzky et al. (2001) *Acta Crystallogr. D. Biol. Crystallogr.* 57: 1101-1109 (Cry3Bb1); and Herman et al. (2004) *J. Agric. Food Chem.* 52: 2726-2734 (Cry1F)), lectins (Van Damme et al. (1994) *Plant Mol. Biol.* 24: 825, pentin (described in U.S. Pat. No. 5,981,722), and the like. The combinations generated can also include multiple copies of any one of the polynucleotides of interest.

In some embodiments, soybean 3560.4.3.5 event may further comprise other herbicide-tolerance traits to create a transgenic plant of the invention with further improved properties. In specific embodiments, the additional herbicide-tolerance traits are stacked with the 3560.4.3.5 event. Other herbicide-tolerance polynucleotides that could be used in such embodiments include those conferring tolerance to glyphosate or to ALS inhibitors by other modes of action, such as, for example, a gene that encodes a glyphosate oxidoreductase enzyme as described more fully in U.S. Pat. Nos. 5,776,760 and 5,463,175. Other traits that could be combined with the soybean 3560.4.3.5 events include those derived from polynucleotides that confer on the plant the capacity to produce a higher level of 5-enolpyruvylshikimate-3-phosphate synthase (EPSPS), for example, as more fully described in U.S. Pat. Nos. 6,248,876 B1; 5,627,061; 5,804,425; 5,633, 435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491,288; and international publications WO 97/04103; WO 00/66746; WO 01/66704; and WO 00/66747. Other traits that could be combined with the soybean 3560.4.3.5 event include those conferring tolerance to sulfonylurea and/or imidazolinone, for example, as described more fully in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270.

Additional EPSPS sequences that are tolerant to glyphosate are described in U.S. Pat. Nos. 6,248,876; 5,627,061; 5,804,425; 5,633,435; 5,145,783; 4,971,908; 5,312,910; 5,188,642; 4,940,835; 5,866,775; 6,225,114; 6,130,366; 5,310,667; 4,535,060; 4,769,061; 5,633,448; 5,510,471; Re. 36,449; RE 37,287 E; and 5,491,288; and international publications WO 97/04103; WO 00/66746; WO 01/66704; and WO 00/66747; 6,040,497; 5,094,945; 5,554,798; 6,040,497; Zhou et al. (1995) *Plant Cell Rep.:* 159-163; WO 0234946; WO 9204449; U.S. Pat. Nos. 6,225,112; 4,535,060, and 6,040,497, which are incorporated herein by reference in their entireties for all purposes. Additional EPSP synthase sequences include, gdc-1 (U.S. App. Publication 20040205847); EPSP synthases with class III domains (U.S. App. Publication 20060253921); gdc-1 (U.S. App. Publication 20060021093); gdc-2 (U.S. App. Publication 20060021094); gro-1 (U.S. App. Publication 20060150269); grg23 or grg 51 (U.S. App. Publication 20070136840); GRG32 (U.S. App. Publication 20070300325); GRG33, GRG35, GRG36, GRG37, GRG38, GRG39 and GRG50 (U.S. App. Publication 20070300326); or EPSP synthase sequences disclosed in, U.S. App. Publication 20040177399; 20050204436; 20060150270; 20070004907; 20070044175; 2007010707; 20070169218; 20070289035; and, 20070295251; each of which is herein incorporated by reference in their entirety.

In one non-limiting embodiment, the glyphosate-tolerant EPSPS sequence employed is the EPSPS polypeptide from *Agrobacterium* sp. Strain CP4 as described in Pagette et al (1995) *Development, Identification, and Characterization of a Glyphosate-Tolerance Soybean Line. Crop Sci.* 35:1451-

1461, herein incorporated by reference in its entirety. See, also GenBank Accession number Q9R4E4, herein incorporated by reference and set forth in SEQ ID NO: 56. In still further embodiments, the EPSPS sequence from the glyphosate tolerant soybean line 40-3-2 is combined with a GLYAT sequence in planta. Other EPSPS events of interest include MON-89788-1 (MON89788). See, www.agbios.com/main.php.

In some embodiments, the soybean 3560.4.3.5 event may be combined or stacked with, for example, hydroxyphenylpyruvatedioxygenases which are enzymes that catalyze the reaction in which para-hydroxyphenylpyruvate (HPP) is transformed into homogentisate. Molecules which inhibit this enzyme and which bind to the enzyme in order to inhibit transformation of the HPP into homogentisate are useful as herbicides. Traits conferring tolerance to such herbicides in plants are described in U.S. Pat. Nos. 6,245,968 B1; 6,268, 549; and 6,069,115; and international publication WO 99/23886. Other examples of suitable herbicide-tolerance traits that could be stacked with the soybean 3560.4.3.5 event include aryloxyalkanoate dioxygenase polynucleotides (which reportedly confer tolerance to 2,4-D and other phenoxy auxin herbicides as well as to aryloxyphenoxypropionate herbicides as described, for example, in WO2005/107437) and dicamba-tolerance polynucleotides as described, for example, in Herman et al. (2005) *J. Biol. Chem.* 280: 24759-24767.

Other examples of herbicide-tolerance traits that could be combined or stacked with the soybean 3560.4.3.5 event include those conferred by polynucleotides encoding an exogenous phosphinothricin acetyltransferase, as described in U.S. Pat. Nos. 5,969,213; 5,489,520; 5,550,318; 5,874,265; 5,919,675; 5,561,236; 5,648,477; 5,646,024; 6,177,616; and 5,879,903. Plants containing an exogenous phosphinothricin acetyltransferase can exhibit improved tolerance to glufosinate herbicides, which inhibit the enzyme glutamine synthase. Other examples of herbicide-tolerance traits that could be combined with the soybean 3560.4.3.5 event include those conferred by polynucleotides conferring altered protoporphyrinogen oxidase (protox) activity, as described in U.S. Pat. Nos. 6,288,306 B1; 6,282,837 B1; and 5,767,373; and international publication WO 01/12825. Plants containing such polynucleotides can exhibit improved tolerance to any of a variety of herbicides which target the protox enzyme (also referred to as "protox inhibitors").

Other examples of herbicide-tolerance traits that could be combined or stacked with the soybean 3560.4.3.5 event include those conferring tolerance to at least one herbicide in a plant such as, for example, a soybean plant or horseweed. Herbicide-tolerant weeds are known in the art, as are plants that vary in their tolerance to particular herbicides. See, e.g., Green and Williams (2004) "Correlation of Corn (*Zea mays*) Inbred Response to Nicosulfuron and Mesotrione," poster presented at the WSSA Annual Meeting in Kansas City, Mo., Feb. 9-12, 2004; Green (1998) *Weed Technology* 12: 474-477; Green and Ulrich (1993) *Weed Science* 41: 508-516. The trait(s) responsible for these tolerances can be combined by breeding or via other methods with the soybean 3560.4.3.5 event to provide a plant of the invention as well as methods of use thereof.

The soybean 3560.4.3.5 event can also be combined or stacked with at least one other trait to produce plants of the present invention that further comprise a variety of desired trait combinations including, but not limited to, traits desirable for animal feed such as high oil content (e.g., U.S. Pat. No. 6,232,529); balanced amino acid content (e.g., hordothionins (U.S. Pat. Nos. 5,990,389; 5,885,801; 5,885,802; and 5,703,409; U.S. Pat. No. 5,850,016); barley high lysine (Williamson et al. (1987) *Eur. J. Biochem.* 165: 99-106; and WO 98/20122) and high methionine proteins (Pedersen et al. (1986) *J. Biol. Chem.* 261: 6279; Kirihara et al. (1988) *Gene* 71: 359; and Musumura et al. (1989) *Plant Mol. Biol.* 12:123)); increased digestibility (e.g., modified storage proteins (U.S. application Ser. No. 10/053,410, filed Nov. 7, 2001); and thioredoxins (U.S. application Ser. No. 10/005, 429, filed Dec. 3, 2001)); the disclosures of which are herein incorporated by reference. Desired trait combinations also include LLNC (low linolenic acid content; see, e.g., Dyer et al. (2002) *Appl. Microbiol. Biotechnol.* 59: 224-230) and OLCH (high oleic acid content; see, e.g., Fernandez-Moya et al. (2005) *J. Agric. Food Chem.* 53: 5326-5330).

The soybean 3560.4.3.5 event can also be combined or stacked with other desirable traits such as, for example, fumonisim detoxification genes (U.S. Pat. No. 5,792,931), avirulence and disease resistance genes (Jones et al. (1994) *Science* 266: 789; Martin et al. (1993) *Science* 262: 1432; Mindrinos et al. (1994) *Cell* 78: 1089), and traits desirable for processing or process products such as modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)); the disclosures of which are herein incorporated by reference. One could also combine herbicide-tolerant polynucleotides with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

In another embodiment, the soybean 3560.4.3.5 event can also be combined or stacked with the Rcg1 sequence or biologically active variant or fragment thereof. The Rcg1 sequence is an anthracnose stalk rot resistance gene in corn. See, for example, U.S. patent application Ser. Nos. 11/397, 153, 11/397,275, and 11/397,247, each of which is herein incorporated by reference.

These stacked combinations can be created by any method including, but not limited to, breeding plants by any conventional or TopCross methodology, or genetic transformation. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

As used herein, the use of the term "polynucleotide" is not intended to limit a polynucleotide to comprise DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides also encompass all forms of sequences including, but not limited to, single-stranded forms, double-stranded forms, hairpins, stem-and-loop structures, and the like.

A 3560.4.3.5 plant comprises an expression cassette having a glyphosate acetyltransferase polynucleotide and a genetically modified acetolactate synthase polynucleotide (gm-hra). The cassette can include 5' and 3' regulatory sequences operably linked to the glyat and the gm-hra polynucleotides. "Operably linked" is intended to mean a functional linkage between two or more elements. For example, an operable linkage between a polynucleotide of interest and a regulatory sequence (i.e., a promoter) is functional link that allows for the expression of the polynucleotide of interest. Operably linked elements may be contiguous or non-contiguous. When used to refer to the joining of two protein coding regions, by operably linked it is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the polynucleotide to be under the transcriptional regulation of the regulatory regions. The expression cassette may additionally contain selectable marker genes.

The expression cassette will include in the 5'-3' direction of transcription, a transcriptional and translational initiation region (i.e., a promoter), a coding region, and a transcriptional and translational termination region functional in plants. "Promoter" refers to a nucleotide sequence capable of controlling the expression of a coding sequence or functional RNA. In general, a coding sequence is located 3' to a promoter sequence. The promoter sequence can comprise proximal and more distal upstream elements, the latter elements are often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters that cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15: 1-82. It is further recognized that since in most cases the exact boundaries of regulatory sequences have not been completely defined, nucleic acid fragments of different lengths may have identical promoter activity.

The expression cassettes may also contain 5' leader sequences. Such leader sequences can act to enhance translation. The regulatory regions (i.e., promoters, transcriptional regulatory regions, RNA processing or stability regions, introns, polyadenylation signals, and translational termination regions) and/or the coding region may be native/analogous or heterologous to the host cell or to each other.

The "translation leader sequence" refers to a nucleotide sequence located between the promoter sequence of a gene and the coding sequence. The translation leader sequence is present in the fully processed mRNA upstream of the translation start sequence. The translation leader sequence may affect numerous parameters including, processing of the primary transcript to mRNA, mRNA stability and/or translation efficiency. Examples of translation leader sequences have been described (Turner and Foster (1995) *Mol. Biotechnol.* 3: 225-236). The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1: 671-680.

As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved. The expression cassette can also comprise a selectable marker gene for the selection of transformed cells. Selectable marker genes are utilized for the selection of transformed cells or tissues.

Isolated polynucleotides are provided that can be used in various methods for the detection and/or identification of the soybean 3560.4.3.5 event. An "isolated" or "purified" polynucleotide, or biologically active portion thereof, is substantially or essentially free from components that normally accompany or interact with the polynucleotide as found in its naturally occurring environment. Thus, an isolated or purified polynucleotide is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived.

In specific embodiments, the polynucleotides comprise the junction DNA sequence set forth in SEQ ID NO:10 or 11. In other embodiments, the polynucleotides comprise the junction DNA sequences set forth in SEQ ID NO:1, 2, 6, 12, 13, 14, 15, 27, 28, 41 or 42 or variants and fragments thereof. Fragments and variants of junction DNA sequences are suitable for discriminatively identifying event 3560.4.3.5. As discussed elsewhere herein, such sequences find use as primers and/or probes.

In other embodiments, the polynucleotides are provided that can detect a 3560.4.3.5 event or a 3560.4.3.5 specific region. Such sequences include any polynucleotide set forth in SEQ ID NOS:1-56 or variants and fragments thereof. In specific embodiments, the polynucleotide used to detect a 3560.4.3.5 event comprise the sequence set forth in SEQ ID NO: 43 or a fragment of SEQ ID NO:43 having at least 20, 30, 40, 50, 60, 70, 80, 90, 100, 110, 120, 130, 140, 150, 160, 170, or 180 nucleotides. Fragments and variants of polynucleotides that detect a 3560.4.3.5 event or a 3560.4.3.5 specific region are suitable for discriminatively identifying event 3560.4.3.5. As discussed elsewhere herein, such sequences find use as primers and/or probes. Further provided are isolated DNA nucleotide primer sequences comprising or consisting of a sequence set forth in SEQ ID NO:7, 8, 9, 16, 17, 18, 19, 20, 21, 22, 23, 24, 25, 26, 37, 38, 39, 40, 43, 44, 45, 46, 51, 52, 53, 54, or 55 or a complement thereof or variants and fragments of SEQ ID NO:1, 2, 3, 4, 5, 6, 10, 11, 12, 13, 14, 15, 27, 28, 41, 42, or 43.

"Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide.

As used herein, a "probe" is an isolated polynucleotide to which is attached a conventional detectable label or reporter molecule, e.g., a radioactive isotope, ligand, chemiluminescent agent, enzyme, etc. Such a probe is complementary to a strand of a target polynucleotide, in the instant case, to a strand of isolated DNA from soybean event 3560.4.3.5 whether from a soybean plant or from a sample that includes DNA from the event. Probes include not only deoxyribonucleic or ribonucleic acids but also polyamides and other probe materials that can specifically detect the presence of the target DNA sequence.

As used herein, "primers" are isolated polynucleotides that are annealed to a complementary target DNA strand by nucleic acid hybridization to form a hybrid between the primer and the target DNA strand, then extended along the target DNA strand by a polymerase, e.g., a DNA polymerase. Primer pairs refer to their use for amplification of a target polynucleotide, e.g., by the polymerase chain reaction (PCR) or other conventional nucleic-acid amplification methods. "PCR" or "polymerase chain reaction" is a technique used for the amplification of specific DNA segments (see, U.S. Pat. Nos. 4,683,195 and 4,800,159; herein incorporated by reference). Any combination of primers disclosed herein can be used such that the pair allows for the detection a 3560.4.3.5 event or specific region (i.e., SEQ ID NOS: 7-9, 16-26, 37, 38, 39, 40, 44-46, or 51-55). Non-limiting examples of primer pairs include SEQ ID NOS:16 and 17; SEQ ID NOS:23 and 20; SEQ ID NOS:23 and 19; SEQ ID NOS:18 AND 22; SEQ ID NOS:21 and 22; SEQ ID NO: 7 and 9; SEQ ID NO:8 and 9; SEQ ID NO:7 and 8; SEQ ID NO:37 and 39; and SEQ ID NO:38 and 39; and SEQ ID NO: 44 and 45 and SEQ ID NOS: 37 and 38.

Probes and primers are of sufficient nucleotide length to bind to the target DNA sequence and specifically detect and/or identify a polynucleotide having a 3560.4.3.5 event. It is recognized that the hybridization conditions or reaction conditions can be determined by the operator to achieve this result. This length may be of any length that is of sufficient length to be useful in a detection method of choice. Generally, 8, 11, 14, 16, 18, 20, 22, 24, 26, 28, 30, 40, 50, 75, 100, 200, 300, 400, 500, 600, 700 nucleotides or more, or between about 11-20, 20-30, 30-40, 40-50, 50-100, 100-200, 200-300, 300-400, 400-500, 500-600, 600-700, 700-800, or more nucleotides in length are used. Such probes and primers can hybridize specifically to a target sequence under high stringency hybridization conditions. Probes and primers according to embodiments may have complete DNA sequence identity of contiguous nucleotides with the target sequence, although probes differing from the target DNA sequence and that retain the ability to specifically detect and/or identify a target DNA sequence may be designed by conventional methods. Accordingly, probes and primers can share about 80%, 85%, 90%, 91%, 92%, 93%, 94%, 95%, 96%, 97%, 98%, 99% or greater sequence identity or complementarity to the target polynucleotide (i.e., SEQ ID NO:1-46 and 47-55), or can differ from the target sequence (i.e., SEQ ID NO: 1-46 and 47-55) by 1, 2, 3, 4, 5, 6 or more nucleotides. Probes can be used as primers, but are generally designed to bind to the target DNA or RNA and are not used in an amplification process.

Specific primers can be used to amplify an integration fragment to produce an amplicon that can be used as a "specific probe" or can itself be detected for identifying event 3560.4.3.5 in biological samples. Alternatively, a probe can be used during the PCR reaction to allow for the detection of the amplification event (i.e., a Taqman probe or a MGB probe) (so called real time PCR). When the probe is hybridized with the polynucleotides of a biological sample under conditions which allow for the binding of the probe to the sample, this binding can be detected and thus allow for an indication of the presence of event 3560.4.3.5 in the biological sample. Such identification of a bound probe has been described in the art. In an embodiment, the specific probe is a sequence which, under optimized conditions, hybridizes specifically to a region within the 5' or 3' flanking region of the event and also comprises a part of the foreign DNA contiguous therewith. The specific probe may comprise a sequence of at least 80%, between 80 and 85%, between 85 and 90%, between 90 and 95%, and between 95 and 100% identical (or complementary) to a specific region of the 3560.4.3.5 event.

As used herein, "amplified DNA" or "amplicon" refers to the product of polynucleotide amplification of a target polynucleotide that is part of a nucleic acid template. For example, to determine whether a soybean plant resulting from a sexual cross contains the 3560.4.3.5 event, DNA extracted from the soybean plant tissue sample may be subjected to a polynucleotide amplification method using a DNA primer pair that includes a first primer derived from flanking sequence adjacent to the insertion site of inserted heterologous DNA, and a second primer derived from the inserted heterologous DNA to produce an amplicon that is diagnostic for the presence of the 3560.4.3.5 event DNA. By "diagnostic" for a 3650.4.3.5 event the use of any method or assay which discriminates between the presence or the absence of a 3560.4.3.5 event in a biological sample is intended. Alternatively, the second primer may be derived from the flanking sequence. In still other embodiments, primer pairs can be derived from flanking sequence on both sides of the inserted DNA so as to produce an amplicon that includes the entire insert polynucleotide of the expression construct as well as the sequence flanking the transgenic insert. See, FIG. 1. The amplicon is of a length and has a sequence that is also diagnostic for the event (i.e., has a junction DNA from a 3560.4.3.5 event). The amplicon may range in length from the combined length of the primer pairs plus one nucleotide base pair to any length of amplicon producible by a DNA amplification protocol. A member of a primer pair derived from the flanking sequence may be located a distance from the inserted DNA sequence, this distance can range from one nucleotide base pair up to the limits of the amplification reaction, or about twenty thousand nucleotide base pairs. The use of the term "amplicon" specifically excludes primer dimers that may be formed in the DNA thermal amplification reaction.

Methods for preparing and using probes and primers are described, for example, in *Molecular Cloning: A Laboratory Manual*, 2.sup.nd ed, vol. 1-3, ed. Sambrook et al., Cold Spring Harbor Laboratory Press, Cold Spring Harbor, N.Y. 1989 (hereinafter, "Sambrook et al., 1989"); *Current Protocols in Molecular Biology*, ed. Ausubel et al., Greene Publishing and Wiley-Interscience, New York, 1992 (with periodic updates) (hereinafter, "Ausubel et al., 1992"); and Innis et al., PCR Protocols: A Guide to Methods and Applications, Academic Press: San Diego, 1990. PCR primer pairs can be derived from a known sequence, for example, by using computer programs intended for that purpose such as the PCR primer analysis tool in Vector NTI version 6 (Informax Inc., Bethesda Md.); PrimerSelect (DNASTAR Inc., Madison, Wis.); and Primer (Version 0.5.COPYRGT., 1991, Whitehead Institute for Biomedical Research, Cambridge, Mass.). Additionally, the sequence can be visually scanned and primers manually identified using guidelines known to one of skill in the art.

It is to be understood that as used herein the term "transgenic" includes any cell, cell line, callus, tissue, plant part, or plant, the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143: 277) and particle-accelerated or "gene gun" transformation technology (Klein et al. (1987) *Nature* (London) 327: 70-73; U.S. Pat. No. 4,945,050, incorporated herein by reference). Additional transformation methods are disclosed below.

Thus, isolated polynucleotides can be incorporated into recombinant constructs, typically DNA constructs, which are capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al. (1985; Supp. 1987) *Cloning Vectors: A Laboratory Manual*, Weissbach and Weissbach (1989) *Methods for Plant Molecular Biology* (Academic Press, New York); and Flevin et al. (1990) *Plant Molecular Biology Manual* (Kluwer Academic Publishers). Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Various methods and compositions for identifying event 3560.4.3.5 are provided. Such methods find use in identifying and/or detecting a 3560.4.3.5 event in any biological material. Such methods include, for example, methods to confirm seed purity and methods for screening seeds in a seed lot for a 3560.4.3.5 event. In one embodiment, a method for identifying event 3560.4.3.5 in a biological sample is provided and comprises contacting the sample with a first and a second primer; and, amplifying a polynucleotide comprising a 3560.4.3.5 specific region.

A biological sample can comprise any sample in which one desires to determine if DNA having event 3560.4.3.5 is present. For example, a biological sample can comprise any plant material or material comprising or derived from a plant material such as, but not limited to, food or feed products. As used herein, "plant material" refers to material which is obtained or derived from a plant or plant part. In specific embodiments, the biological sample comprises a soybean tissue.

Primers and probes based on the flanking DNA and insert sequences disclosed herein can be used to confirm (and, if necessary, to correct) the disclosed sequences by conventional methods, e.g., by re-cloning and sequencing such sequences. The polynucleotide probes and primers specifically detect a target DNA sequence. Any conventional nucleic acid hybridization or amplification method can be used to identify the presence of DNA from a transgenic event in a sample. By "specifically detect" it is intended that the polynucleotide can be used either as a primer to amplify a 3560.4.3.5 specific region or the polynucleotide can be used as a probe that hybridizes under stringent conditions to a polynucleotide having a 3560.4.3.5 event or a 3560.4.3.5 specific region. The level or degree of hybridization which allows for the specific detection of a 3560.4.3.5 event or a specific region of a 3560.4.3.5 event is sufficient to distinguish the polynucleotide with the 3560.4.3.5 specific region from a polynucleotide lacking this region and thereby allow for discriminately identifying a 3560.4.3.5 event. By "shares sufficient sequence identity or complementarity to allow for the amplification of a 3560.4.3.5 specific event" is intended the sequence shares at least 80%, 85%, 90%, 91%, 92%, 93%, 94%, 95%, 96%, 97%, 98%, 99% or 100% identity or complementarity to a fragment or across the full length of the polynucleotide having the 3560.4.3.5 specific region.

Regarding the amplification of a target polynucleotide (e.g., by PCR) using a particular amplification primer pair, "stringent conditions" are conditions that permit the primer pair to hybridize to the target polynucleotide to which a primer having the corresponding wild-type sequence (or its complement) would bind and preferably to produce an identifiable amplification product (the amplicon) having a 3560.4.3.5 specific region in a DNA thermal amplification reaction. In a PCR approach, oligonucleotide primers can be designed for use in PCR reactions to amplify a 3560.4.3.5 specific region. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Methods of amplification are further described in U.S. Pat. No. 4,683,195, 4,683,202 and Chen et al. (1994) *PNAS* 91:5695-5699, These methods as well as other methods known in the art of DNA amplification may be used in the practice of the other embodiments. It is understood that a number of parameters in a specific PCR protocol may need to be adjusted to specific laboratory conditions and may be slightly modified and yet allow for the collection of similar results. These adjustments will be apparent to a person skilled in the art.

The amplified polynucleotide (amplicon) can be of any length that allows for the detection of the 3560.4.3.5 event or a 3560.4.3.5 specific region. For example, the amplicon can be about 10, 50, 100, 200, 300, 500, 700, 100, 2000, 3000, 4000, 5000 nucleotides in length or longer.

In specific embodiments, the specific region of the 3560.4.3.5 event is detected.

Any primer that allows a 3560.4,3.5 specific region to be amplified and/or detected can be employed in the methods. For example, in specific embodiments, the first primer comprises a fragment of a polynucleotide of SEQ ID NO: 4 or 5, wherein the first or the second primer shares sufficient sequence identity or complementarity to the polynucleotide to amplify the 3560.4.3.5 specific region. The primer pair can comprise a fragment of SEQ ID NO:4 and a fragment of SEQ ID NO:5 or 3, or alternatively, the primer pair can comprise a fragment of SEQ ID NO:5 and a fragment of SEQ ID NO: 3 or 4. In still further embodiments, the first and the second primer can comprise any one or any combination of the sequences set forth in SEQ ID NO:7, 8, 9, 16-26, 37, 38, 39, 40, 44-46, or 51-55. The primers can be of any length sufficient to amplify a 3560.4.3.5 region including, for example, at least 6, 7, 8, 9, 10, 15, 20, 15, or 30 or about 7-10, 10-15, 15-20, 20-25, 25-30, 30-35, 35-40, 40-45 nucleotides or longer.

As discussed elsewhere herein, any method to PCR amplify the 3560.4.3.5 event or specific region can be employed, including for example, real time PCR. See, for example, Livak et al. (1995) *PCR Methods and Applications* 4:357-362; U.S. Pat. No. 5,538,848; U.S. Pat. No. 5,723,591; Applied Biosystems User Bulletin No. 2, "Relative Quantitation of Gene Expression," P/N 4303859; and, Applied Biosystems User Bulletin No. 5, "Multiplex PCR with Taqman VIC probes," P/N 4306236; each of which is herein incorporated by reference.

Thus, in specific embodiments, a method of detecting the presence of soybean event 3560.4.3.5 or progeny thereof in a biological sample is provided. The method comprises (a) extracting a DNA sample from the biological sample; (b) providing a pair of DNA primer molecules (i.e, any combination of SEQ ID NOS: 7-9, 16-26, 37, 38, 39, 40, 44-46, or 51-55, wherein said combination amplifies a 3560.4.3.5 event), including, but not limited to, i) the sequences of SEQ ID NO:16 and SEQ ID NO:17, ii) the sequences of SEQ ID NO:23 and SEQ ID NO:20; iii) the sequences of SEQ ID NO:23 and SEQ ID NO:19; iv) the sequences of SEQ ID NO:18 and SEQ ID NO:22; v) SEQ ID NO:21 and SEQ ID NO:22; vi) SEQ ID NO: 7 and 9; vii) SEQ ID NO: 8 and 9; iix) SEQ ID NO: 7 and 8; ix) SEQ ID NO: 37 and 39; x) SEQ ID NO: 38 and 39; xi) SEQ ID NO: 44 and 45; xii) SEQ ID NO: 25 and 26; xiii) SEQ ID NO:25 and SEQ ID NO:24; (c) providing DNA amplification reaction conditions; (d) performing the DNA amplification reaction, thereby producing a DNA amplicon molecule; and (e) detecting the DNA amplicon molecule, wherein the detection of said DNA amplicon molecule in the DNA amplification reaction indicates the presence of soybean event 3560.4.3.5. In order for a nucleic acid molecule to serve as a primer or probe it needs only be sufficiently complementary in sequence to be able to form a stable double-stranded structure under the particular solvent and salt concentrations employed.

In hybridization techniques, all or part of a polynucleotide that selectively hybridizes to a target polynucleotide having a 3560.4.3.5 specific event is employed. By "stringent conditions" or "stringent hybridization conditions" when referring to a polynucleotide probe conditions under which a probe will hybridize to its target sequence to a detectably greater degree than to other sequences (e.g., at least 2-fold over background) are intended. Regarding the amplification of a target polynucleotide (e.g., by PCR) using a particular amplification primer pair, "stringent conditions" are conditions that permit the primer pair to hybridize to the target polynucleotide to which a primer having the corresponding wild-type. Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of identity are detected (heterologous probing). Generally, a probe is less than about 1000 nucleotides in length or less than 500 nucleotides in length.

As used herein, a substantially identical or complementary sequence is a polynucleotide that will specifically hybridize to the complement of the nucleic acid molecule to which it is being compared under high stringency conditions. Appropriate stringency conditions which promote DNA hybridization, for example, 6× sodium chloride/sodium citrate (SSC) at about 45° C., followed by a wash of 2×SSC at 50° C., are known to those skilled in the art or can be found in *Current Protocols in Molecular Biology*, John Wiley & Sons, N.Y. (1989), 6.3.1-6.3.6. Typically, stringent conditions for hybridization and detection will be those in which the salt concentration is less than about 1.5 M Na ion, typically about 0.01 to 1,0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

In hybridization reactions, specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138: 267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.) and Haymes et al. (1985) In: *Nucleic Acid Hybridization, a Practical Approach*, IRL Press, Washington, D.C.

A polynucleotide is said to be the "complement" of another polynucleotide if they exhibit complementarity. As used herein, molecules are said to exhibit "complete complementarity" when every nucleotide of one of the polynucleotide molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions.

Further provided are methods of detecting the presence of DNA corresponding to the 3560.4.3.5 event in a sample. In one embodiment, the method comprises (a) contacting the biological sample with a polynucleotide probe that hybridizes under stringent hybridization conditions with DNA from soybean event 3560.4.3.5 and specifically detects the 3560.4.3.5 event; (b) subjecting the sample and probe to stringent hybridization conditions; and (c) detecting hybridization of the probe to the DNA, wherein detection of hybridization indicates the presence of the 3560.4.3.5 event. In one embodiment, the DNA is digested with appropriate enzymes are preformed prior to the hybridization event.

Various method can be used to detect the 3560.4.3.5 specific region or amplicon thereof, including, but not limited to, Genetic Bit Analysis (Nikiforov et al. (1994) *Nucleic Acid Res.* 22: 4167-4175). In one method, a DNA oligonucleotide is designed which overlaps both the adjacent flanking DNA sequence and the inserted DNA sequence. In other embodiments, DNA oligos are designed to allow for a 3560.4.3.5 specific amplicon. The oligonucleotide is immobilized in wells of a microwell plate. Following PCR of the region of interest a single-stranded PCR product can be hybridized to the immobilized oligonucleotide and serve as a template for a single base extension reaction using a DNA polymerase and labeled ddNTPs specific for the expected next base. Readout may be fluorescent or ELISA-based. A signal indicates presence of the insert/flanking sequence due to successful amplification, hybridization, and single base extension.

Another detection method is the Pyrosequencing technique as described by Winge ((2000) *Innov. Pharma. Tech.* 00: 18-24). In this method, an oligonucleotide is designed that overlaps the adjacent DNA and insert DNA junction or a pair of oligos are employed that can amplify a 3560.4.3.5 specific region. The oligonucleotide is hybridized to a single-stranded PCR product from the region of interest (one primer in the inserted sequence and one in the flanking sequence) and incubated in the presence of a DNA polymerase, ATP, sulfurylase, luciferase, apyrase, adenosine 5' phosphosulfate and luciferin. dNTPs are added individually and the incorporation results in a light signal which is measured. A light signal indicates the presence of the transgene insert/flanking sequence due to successful amplification, hybridization, and single or multi-base extension.

Fluorescence Polarization as described by Chen et al. ((1999) *Genome Res.* 9: 492-498, 1999) is also a method that can be used to detect an amplicon of the invention. Using this method, an oligonucleotide is designed which overlaps the flanking and inserted DNA junction or a pair of oligos are employed that can amplify a 3560.4.3.5 specific region. The oligonucleotide is hybridized to a single-stranded PCR product from the region of interest (one primer in the inserted DNA and one in the flanking DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

Taqman® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed which overlaps the flanking and insert DNA junction or a pair of oligos are employed that can amplify a 3560.4.3.5 specific region. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular Beacons have been described for use in sequence detection as described in Tyangi et al. ((1996) *Nature Biotech.* 14: 303-308). Briefly, a FRET oligonucleotide probe is designed that overlaps the flanking and insert DNA junction or a pair of oligos are employed that can amplify a 3560.4.3.5 specific region. The unique structure of the FRET probe results in it containing secondary structure that keeps the fluorescent and quenching moieties in close proximity. The FRET probe and PCR primers (one primer in the insert DNA sequence and one in the flanking sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking/transgene insert sequence due to successful amplification and hybridization.

A hybridization reaction using a probe specific to a sequence found within the amplicon is yet another method used to detect the amplicon produced by a PCR reaction.

As used herein, "kit" refers to a set of reagents for the purpose of performing the method embodiments, more particularly, the identification and/or the detection of the 3560.4.3.5 event in biological samples. The kit can be used, and its components can be specifically adjusted, for purposes of quality control (e.g. purity of seed lots), detection of event 3560.4.3.5 in plant material, or material comprising or derived from plant material, such as but not limited to food or feed products.

In specific embodiments, a kit for identifying event 3560.4.3.5 in a biological sample is provided. The kit comprises a first and a second primer, wherein the first and second primer amplify a polynucleotide comprising a 3560.4.3.5 specific region. In further embodiments, the kit also comprises a polynucleotide for the detection of the 3560.4.3.5 specific region. The kit can comprise, for example, a first primer comprising a fragment of a polynucleotide of SEQ ID NO:4 or 5, wherein the first or the second primer shares sufficient sequence homology or complementarity to the polynucleotide to amplify said 3560.4.3.5 specific region. For example, in specific embodiments, the first primer comprises a fragment of a polynucleotide of SEQ ID NO:4 or 5, wherein the first or the second primer shares sufficient sequence homology or complementarity to the polynucleotide to amplify said 3560.4.3.5 specific region. The primer pair can comprises a fragment of SEQ ID NO:4 and a fragment of SEQ ID NO:5 or 3, or alternatively, the primer pair can comprises a fragment of SEQ ID NO:5 and a fragment of SEQ ID NO:3 or 4. In still further embodiments, the first and the second primer can comprise any one or any combination of the sequences set forth in SEQ ID NO:7, 8, 9, 16, 17, 18, 19, 20, 21, 22, 23, 24, 25, 26, 37, 38, 39, 40, 43, 44, 45, 46, or 51-55. The primers can be of any length sufficient to amplify the 3560.4.3.5 region including, for example, at least 6, 7, 8, 9, 10, 15, 20, 15, or 30 or about 7-10, 10-15, 15-20, 20-25, 25-30, 30-35, 35-40, 40-45 nucleotides or longer.

Further provided are DNA detection kits comprising at least one polynucleotide that can specifically detect a 3560.4.3.5 specific region, wherein said polynucleotide comprises at least one DNA molecule of a sufficient length of contiguous nucleotides homologous or complementary to SEQ ID NO: 3, 4 or 5. In specific embodiments, the DNA detection kit comprises a polynucleotide having SEQ ID NO:10 or 11 or comprises a sequence which hybridizes with sequences selected from the group consisting of a) the sequences of SEQ ID NO: 4 and SEQ ID NO:3; and, b) the sequences of SEQ ID NO: 5 and SEQ ID NO: 3, and a sequence of SEQ ID NO:4 and 43.

Any of the polynucleotides and fragments and variants thereof employed in the methods and compositions can share sequence identity to a region of the transgene insert of the 3560.4.3.5 event, a junction sequence of the 3560.4.3.5 event or a flanking sequence of the 3560.4.3.5 event. Methods to determine the relationship of various sequences are known. As used herein, "reference sequence" is a defined sequence used as a basis for sequence comparison. A reference sequence may be a subset or the entirety of a specified sequence; for example, as a segment of a cDNA or gene sequence, or the complete cDNA or gene sequence. As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein. BLAST protein searches can be performed with the BLASTX program, score=50, wordlength=3, to obtain amino acid sequences homologous to a protein or polypeptide. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" any sequence comparison program that, for any two sequences in question, generates an alignment having identical nucleotide or amino acid residue matches and an identical percent sequence identity when compared to the corresponding alignment generated by GAP Version 10 is intended.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the Quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Methods are provided for controlling weeds in an area of cultivation, preventing the development or the appearance of herbicide resistant weeds in an area of cultivation, producing a crop, and increasing crop safety. The term "controlling," and derivations thereof, for example, as in "controlling weeds" refers to one or more of inhibiting the growth, germination, reproduction, and/or proliferation of; and/or killing, removing, destroying, or otherwise diminishing the occurrence and/or activity of a weed.

As used herein, an "area of cultivation" comprises any region in which one desires to grow a plant. Such areas of cultivations include, but are not limited to, a field in which a plant is cultivated (such as a crop field, a sod field, a tree field, a managed forest, a field for culturing fruits and vegetables, etc), a greenhouse, a growth chamber, etc.

The methods comprise planting the area of cultivation with the soybean 3560.4.3.5 seeds or plants, and in specific embodiments, applying to the crop, seed, weed or area of cultivation thereof an effective amount of a herbicide of interest. It is recognized that the herbicide can be applied before or after the crop is planted in the area of cultivation. Such herbicide applications can include an application of glyphosate, an ALS inhibitor chemistry, or any combination thereof. In specific embodiments, a mixture of an ALS inhibitor chemistry in combination with glyphosate is applied to the soybean 3560.4.3.5, wherein the effective concentration of at least the ALS inhibitor chemistry would significantly damage an appropriate control plant. In one non-limiting embodiment, the herbicide comprises at least one of a sulfonylaminocarbonyltriazolinone; a triazolopyrimidine; a pyrimidinyl(thio) benzoate; an imidazolinone; a triazine; and/or a phosphinic acid.

In another non-limiting embodiment, the combination of herbicides comprises glyphosate, imazapyr, chlorimuron-ethyl, quizalofop, and fomesafen, wherein an effective amount is tolerated by the crop and controls weeds. As disclosed elsewhere herein, any effective amount of these herbicides can be applied. In specific embodiments, this combination of herbicides comprises an effective amount of glyphosate comprising about 1110 to about 1130 g ai/hectare; an effective amount of imazapyr comprising about 7.5 to about 27.5 g ai/hectare; an effective amount of chlorimuron-ethyl comprising about 7.5 to about 27.5 g ai/hectare; an effective amount of quizalofop comprising about 50 to about 70 g ai/hectare; and, an effective amount of fomesafen comprising about 240 to about 260 g ai/hectare.

In other embodiments, a combination of at least two herbicides is applied, wherein the combination does not include glyphosate. In other embodiments, at least one ALS inhibitor and glyphosate is applied to the plant. More details regarding the various herbicide combinations that can be employed in the methods are discussed elsewhere herein.

In one embodiment, the method of controlling weeds comprises planting the area with the 3560.4.3.5 soybean seeds or plants and applying to the crop, crop part, seed of said crop or the area under cultivation, an effective amount of a herbicide, wherein said effective amount comprises i) an amount that is not tolerated by a first control crop when applied to the first control crop, crop part, seed or the area of cultivation, wherein said first control crop expresses a first polynucleotide encoding GLYAT polypeptide that confers tolerance to glyphosate and does not express a second polynucleotide that encodes the gm-hra polypeptide;

ii) an amount that is not tolerated by a second control crop when applied to the second crop, crop part, seed or the area of cultivation, wherein said second control crop expresses the gm-hra polynucleotide and does not express the glyat polynucleotide; and, iii) an amount that is tolerated when applied to the 3560.4.3.5 soybean crop, crop part, seed, or the area of cultivation thereof. The herbicide can comprise a combination of herbicides that either includes or does not include glyphosate. In specific embodiments, the combination of herbicides comprises ALS inhibitor chemistries as discussed in further detail below.

In another embodiment, the method of controlling weeds comprises planting the area with a 3560.4.3.5 soybean crop seed or plant and applying to the crop, crop part, seed of said crop or the area under cultivation, an effective amount of a herbicide, wherein said effective amount comprises a level that is above the recommended label use rate for the crop, wherein said effective amount is tolerated when applied to the 3560.4.3.5 soybean crop, crop part, seed, or the area of cultivation thereof. The herbicide applied can comprise a combination of herbicides that either includes or does not include glyphosate. In specific embodiments, the combination of herbicides comprises at least one ALS inhibitor chemistry as discussed in further detail below. Further herbicides and combinations thereof that can be employed in the various methods are discussed in further detail below.

A "control" or "control plant" or "control plant cell" provides a reference point for measuring changes in phenotype of the subject plant or plant cell, and may be any suitable plant or plant cell. A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell which is genetically identical to the subject plant or plant cell but which is not exposed to the same treatment (e.g., herbicide treatment) as the subject plant or plant cell; (e) the subject plant or plant cell itself, under conditions in which the gene of interest is not expressed; or (f) the subject plant or plant cell itself, under conditions in which it has not been exposed to a particular treatment such as, for example, a herbicide or combination of herbicides and/or other chemicals. In some instances, an appropriate control plant or control plant cell may have a different genotype from the subject plant or plant cell but may share the herbicide-sensitive characteristics of the starting material for the genetic alteration(s) which resulted in the subject plant or cell (see, e.g., Green (1998) *Weed Technology* 12: 474-477; Green and Ulrich (1993) *Weed Science* 41: 508-516. In some instances, an appropriate control soybean plant is a "Jack" soybean plant (Illinois Foundation Seed, Champaign, Ill.). In other embodiments, the null segregant can be used as a control, as they are near isogenic to 3560.4.3.5 with the exception of the transgenic insert DNA.

Any herbicide can be applied to the 3560.4.3.5 soybean crop, crop part, or the area of cultivation containing the crop plant. Classification of herbicides (i.e., the grouping of herbicides into classes and subclasses) is well-known in the art and includes classifications by HRAC (Herbicide Resistance Action Committee) and WSSA (the Weed Science Society of America) (see also, Retzinger and Mallory-Smith (1997) *Weed Technology* 11: 384-393). An abbreviated version of the HRAC classification (with notes regarding the corresponding WSSA group) is set forth below in Table 1.

Herbicides can be classified by their mode of action and/or site of action and can also be classified by the time at which they are applied (e.g., preemergent or postemergent), by the method of application (e.g., foliar application or soil application), or by how they are taken up by or affect the plant. For example, thifensulfuron-methyl and tribenuron-methyl are applied to the foliage of a crop and are generally metabolized there, while rimsulfuron and chlorimuron-ethyl are generally taken up through both the roots and foliage of a plant. "Mode of action" generally refers to the metabolic or physiological process within the plant that the herbicide inhibits or otherwise impairs, whereas "site of action" generally refers to the physical location or biochemical site within the plant where the herbicide acts or directly interacts. Herbicides can be classified in various ways, including by mode of action and/or site of action (see, e.g., Table 1).

Often, an herbicide-tolerance gene that confers tolerance to a particular herbicide or other chemical on a plant expressing it will also confer tolerance to other herbicides or chemicals in the same class or subclass, for example, a class or subclass set forth in Table 1. Thus, in some embodiments, a transgenic plant is tolerant to more than one herbicide or chemical in the same class or subclass, such as, for example, an inhibitor of PPO, a sulfonylurea, or a synthetic auxin.

Typically, the plants can tolerate treatment with different types of herbicides (i.e., herbicides having different modes of action and/or different sites of action) as well as with higher amounts of herbicides than previously known plants, thereby permitting improved weed management strategies that are recommended in order to reduce the incidence and prevalence of herbicide-tolerant weeds. Specific herbicide combinations can be employed to effectively control weeds.

Transgenic soybean plants are provided which can be selected for use in crop production based on the prevalence of herbicide-tolerant weed species in the area where the transgenic crop is to be grown. Weed management techniques, such as for example, crop rotation using a crop that is tolerant to a herbicide to which the local weed species are not tolerant can be used. See, for example, the Herbicide Resistance Action Committee (HRAC), the Weed Science Society of America, and various state agencies and the herbicide tolerance scores for various broadleaf weeds from the 2004 Illinois Agricultural Pest Management Handbook). See also, Owen and Hartzler (2004), 2005 *Herbicide Manual for Agricultural Professionals*, Pub. WC 92 Revised (Iowa State University Extension, Iowa State University of Science and Technology, Ames, Iowa); *Weed Control for Corn, Soybeans, and Sorghum*, Chapter 2 of "2004 Illinois Agricultural Pest Management Handbook" (University of Illinois Extension, University of Illinois at Urbana-Champaign, Ill.); *Weed Control Guide for Field Crops*, MSU Extension Bulletin E434 (Michigan State University, East Lansing, Mich.)).

TABLE 1

Abbreviated version of HRAC Herbicide Classification

I. ALS Inhibitors (WSSA Group 2)
   A. Sulfonylureas
      1. Azimsulfuron
      2. Chlorimuron-ethyl
      3. Metsulfuron-methyl
      4. Nicosulfuron
      5. Rimsulfuron
      6. Sulfometuron-methyl
      7. Thifensulfuron-methyl
      8. Tribenuron-methyl
      9. Amidosulfuron
     10. Bensulfuron-methyl
     11. Chlorsulfuron
     12. Cinosulfuron
     13. Cyclosulfamuron
     14. Ethametsulfuron-methyl
     15. Ethoxysulfuron
     16. Flazasulfuron
     17. Flupyrsulfuron-methyl
     18. Foramsulfuron
     19. Imazosulfuron
     20. Iodosulfuron-methyl
     21. Mesosulfuron-methyl
     22. Oxasulfuron
     23. Primisulfuron-methyl
     24. Prosulfuron
     25. Pyrazosulfuron-ethyl
     26. Sulfosulfuron
     27. Triasulfuron
     28. Trifloxysulfuron
     29. Triflusulfuron-methyl
     30. Tritosulfuron
     31. Halosulfuron-methyl
     32. Flucetosulfuron
   B. Sulfonylaminocarbonyltriazolinones
      1. Flucarbazone
      2. Procarbazone
   C. Triazolopyrimidines
      1. Cloransulam-methyl
      2. Flumetsulam
      3. Diclosulam
      4. Florasulam
      5. Metosulam
      6. Penoxsulam
      7. Pyroxsulam
   D. Pyrimidinyloxy(thio)benzoates
      1. Bispyribac
      2. Pyriftalid
      3. Pyribenzoxim
      4. Pyrithiobac
      5. Pyriminobac-methyl TABLE 1-continued Abbreviated version of HRAC Herbicide Classification E. Imidazolinones
      1. Imazapyr
      2. Imazethapyr
      3. Imazaquin
      4. Imazapic
      5. Imazamethabenz-methyl
      6. Imazamox
II. Other Herbicides - Active Ingredients/Additional Modes of Action
   A. Inhibitors of Acetyl CoA carboxylase (ACCase) (WSSA Group 1)
      1. Aryloxyphenoxypropionates ('FOPs')
        a. Quizalofop-P-ethyl
        b. Diclofop-methyl
        c. Clodinafop-propargyl
        d. Fenoxaprop-P-ethyl
        e. Fluazifop-P-butyl
        f. Propaquizafop
        g. Haloxyfop-P-methyl
        h. Cyhalofop-butyl
        i. Quizalofop-P-ethyl
      2. Cyclohexanediones ('DIMs')
        a. Alloxydim
        b. Butroxydim
        c. Clethodim
        d. Cycloxydim
        e. Sethoxydim
        f. Tepraloxydim
        g. Tralkoxydim
   B. Inhibitors of Photosystem II - HRAC Group C1/WSSA Group 5
      1. Triazines
        a. Ametryne
        b. Atrazine
        c. Cyanazine
        d. Desmetryne
        e. Dimethametryne
        f. Prometon
        g. Prometryne
        h. Propazine
        i. Simazine
        j. Simetryne
        k. Terbumeton
        l. Terbuthylazine
        m. Terbutryne
        n. Trietazine
      2. Triazinones
        a. Hexazinone
        b. Metribuzin
        c. Metamitron
      3. Triazolinone
        a. Amicarbazone
      4. Uracils
        a. Bromacil
        b. Lenacil
        c. Terbacil
      5. Pyridazinones
        a. Pyrazon
      6. Phenyl carbamates
        a. Desmedipham
        b. Phenmedipham
   C. Inhibitors of Photosystem II - HRAC Group C2/WSSA Group 7
      1. Ureas
        a. Fluometuron
        b. Linuron
        c. Chlorobromuron
        d. Chlorotoluron
        e. Chloroxuron
        f. Dimefuron
        g. Diuron
        h. Ethidimuron
        i. Fenuron
        j. Isoproturon
        k. Isouron
        l. Methabenzthiazuron TABLE 1-continued Abbreviated version of HRAC Herbicide Classification m. Metobromuron
   n. Metoxuron
   o. Monolinuron
   p. Neburon
   q. Siduron
   r. Tebuthiuron
  2. Amides
   a. Propanil
   b. Pentanochlor
D. Inhibitors of Photosystem II - HRAC Group C3/WSSA Group 6
  1. Nitriles
   a. Bromofenoxim
   b. Bromoxynil
   c. Ioxynil
  2. Benzothiadiazinone (Bentazon)
   a. Bentazon
  3. Phenylpyridazines
   a. Pyridate
   b. Pyridafol
E. Photosystem-I-electron diversion (Bipyridyliums) (WSSA Group 22)
  1. Diquat
  2. Paraquat
F. Inhibitors of PPO (protoporphyrinogen oxidase) (WSSA Group 14)
  1. Diphenylethers
   a. Acifluorfen-Na
   b. Bifenox
   c. Chlomethoxyfen
   d. Fluoroglycofen-ethyl
   e. Fomesafen
   f. Halosafen
   g. Lactofen
   h. Oxyfluorfen
  2. Phenylpyrazoles
   a. Fluazolate
   b. Pyraflufen-ethyl
  3. N-phenylphthalimides
   a. Cinidon-ethyl
   b. Flumioxazin
   c. Flumiclorac-pentyl
  4. Thiadiazoles
   a. Fluthiacet-methyl
   b. Thidiazimin
  5. Oxadiazoles
   a. Oxadiazon
   b. Oxadiargyl
  6. Triazolinones
   a. Carfentrazone-ethyl
   b. Sulfentrazone
  7. Oxazolidinediones
   a. Pentoxazone
  8. Pyrimidindiones
   a. Benzfendizone
   b. Butafenicil
  9. Others
   a. Pyrazogyl
   b. Profluazol
G. Bleaching: Inhibition of carotenoid biosynthesis at the phytoene desaturase step (PDS) (WSSA Group 12)
  1. Pyridazinones
   a. Norflurazon
  2. Pyridinecarboxamides
   a. Diflufenican
   b. Picolinafen
  3. Others
   a. Beflubutamid
   b. Fluridone
   c. Flurochloridone
   d. Flurtamone
H. Bleaching: Inhibition of 4-hydroxyphenyl-pyruvate-dioxygenase (4-HPPD) (WSSA Group 28)
  1. Triketones
   a. Mesotrione
   b. Sulcotrione
  2. Isoxazoles
   a. Isoxachlortole
   b. Isoxaflutole
  3. Pyrazoles
   a. Benzofenap
   b. Pyrazoxyfen
   c. Pyrazolynate
  4. Others
   a. Benzobicyclon
I. Bleaching: Inhibition of carotenoid biosynthesis (unknown target) (WSSA Group 11 and 13)
  1. Triazoles (WSSA Group 11)
   a. Amitrole
  2. Isoxazolidinones (WSSA Group 13)
   a. Clomazone
  3. Ureas
   a. Fluometuron
  3. Diphenylether
   a. Aclonifen
J. Inhibition of EPSP Synthase
  1. Glycines (WSSA Group 9)
   a. Glyphosate
   b. Sulfosate
K. Inhibition of glutamine synthetase
  1. Phosphinic Acids
   a. Glufosinate-ammonium
   b. Bialaphos
L. Inhibition of DHP (dihydropteroate) synthase (WSSA Group 18)
  1 Carbamates
   a. Asulam
M. Microtubule Assembly Inhibition (WSSA Group 3)
  1. Dinitroanilines
   a. Benfluralin
   b. Sutralin
   c. Dinitramine
   d. Ethalfluralin
   e. Oryzalin
   f. Pendimethalin
   g. Trifluralin
  2. Phosphoroamidates
   a. Amiprophos-methyl
   b. Butamiphos
  3. Pyridines
   a. Dithiopyr
   b. Thiazopyr
  4. Benzamides
   a. Pronamide
   b. Tebutam
  5. Benzenedicarboxylic acids
   a. Chlorthal-dimethyl
N. Inhibition of mitosis/microtubule organization WSSA Group 23)
  1. Carbamates
   a. Chlorpropham
   b. Propham
   c. Carbetamide
O. Inhibition of cell division (Inhibition of very long chain fatty acids as proposed mechanism; WSSA Group 15)
  1. Chloroacetamides
   a. Acetochlor
   b. Alachlor
   c. Butachlor
   d. Dimethachlor
   e. Dimethanamid
   f. Metazachlor
   g. Metolachlor
   h. Pethoxamid
   i. Pretilachlor
   j. Propachlor
   k. Propisochlor
   l. Thenylchlor
  2. Acetamides
   a. Diphenamid
   b. Napropamide
   c. Naproanilide
  3. Oxyacetamides
   a. Flufenacet
   b. Mefenacet

TABLE 1-continued

Abbreviated version of HRAC Herbicide Classification

- 4. Tetrazolinones
  - a. Fentrazamide
- 5. Others
  - a. Anilofos
  - b. Cafenstrole
  - c. Indanofan
  - d. Piperophos
- P. Inhibition of cell wall (cellulose) synthesis
  - 1. Nitriles (WSSA Group 20)
    - a. Dichlobenil
    - b. Chlorthiamid
  - 2. Benzamides (isoxaben (WSSA Group 21))
    - a. Isoxaben
  - 3. Triazolocarboxamides (flupoxam)
    - a. Flupoxam
- Q. Uncoupling (membrane disruption): (WSSA Group 24)
  - 1. Dinitrophenols
    - a. DNOC
    - b. Dinoseb
    - c. Dinoterb
- R. Inhibition of Lipid Synthesis by other than ACC inhibition
  - 1. Thiocarbamates (WSSA Group 8)
    - a. Butylate
    - b. Cycloate
    - c. Dimepiperate
    - d. EPTC
    - e. Esprocarb
    - f. Molinate
    - g. Orbencarb
    - h. Pebulate
    - i. Prosulfocarb
    - j. Benthiocarb
    - k. Tiocarbazil
    - l. Triallate
    - m. Vernolate
  - 2. Phosphorodithioates
    - a. Bensulide
  - 3. Benzofurans
    - a. Benfuresate
    - b. Ethofumesate
  - 4. Halogenated alkanoic acids (WSSA Group 26)
    - a. TCA
    - b. Dalapon
    - c. Flupropanate
- S. Synthetic auxins (IAA-like) (WSSA Group 4)
  - 1. Phenoxycarboxylic acids
    - a. Clomeprop
    - b. 2,4-D
    - c. Mecoprop
  - 2. Benzoic acids
    - a. Dicamba
    - b. Chloramben
    - c. TBA
  - 3. Pyridine carboxylic acids
    - a. Clopyralid
    - b. Fluroxypyr
    - c. Picloram
    - d. Tricyclopyr
  - 4. Quinoline carboxylic acids
    - a. Quinclorac
    - b. Quinmerac
  - 5. Others (benazolin-ethyl)
    - a. Benazolin-ethyl
- T. Inhibition of Auxin Transport
  - 1. Phthalamates; semicarbazones (WSSA Group 19)
    - a. Naptalam
    - b. Diflufenzopyr-Na

TABLE 1-continued

Abbreviated version of HRAC Herbicide Classification

- U. Other Mechanism of Action
  - 1. Arylaminopropionic acids
    - a. Flamprop-M-methyl/-isopropyl
  - 2. Pyrazolium
    - a. Difenzoquat
  - 3. Organoarsenicals
    - a. DSMA
    - b. MSMA
  - 4. Others
    - a. Bromobutide
    - b. Cinmethylin
    - c. Cumyluron
    - d. Dazomet
    - e. Daimuron-methyl
    - f. Dimuron
    - g. Etobenzanid
    - h. Fosamine
    - i. Metam
    - j. Oxaziclomefone
    - k. Oleic acid
    - l. Pelargonic acid
    - m. Pyributicarb In one embodiment, one ALS inhibitor or at least two ALS inhibitors are applied to the 3560.4.3.5 soybean crop or area of cultivation. In non-limiting embodiments, the combination of ALS inhibitor herbicides can include or does not include glyphosate. The ALS inhibitor can be applied at any effective rate that selectively controls weeds and does not significantly damage the crop. In specific embodiments, at least one ALS inhibitor is applied at a level that would significantly damage an appropriate control plant. In other embodiments, at least one ALS inhibitor is applied above the recommended label use rate for the crop. In still other embodiments, a mixture of ALS inhibitors is applied at a lower rate than the recommended use rate and weeds continue to be selectively controlled. Herbicides that inhibit acetolactate synthase (also known as acetohydroxy acid synthase) and are therefore useful in the methods include sulfonylureas as listed in Table 1, including agriculturally suitable salts (e.g., sodium salts) thereof; sulfonylaminocarbonyltriazolinones as listed in Table 1, including agriculturally suitable salts (e.g., sodium salts) thereof; triazolopyrimidines as listed in Table 1, including agriculturally suitable salts (e.g., sodium salts) thereof; pyrimidinyloxy(thio)benzoates as listed in Table 1, including agriculturally suitable salts (e.g., sodium salts) thereof; and imidazolinones as listed in Table 1, including agriculturally suitable salts (e.g., sodium salts) thereof. In some embodiments, methods comprise the use of a sulfonylurea which is not chlorimuron-ethyl, chlorsulfuron, rimsulfuron, thifensulfuron-methyl, or tribenuron-methyl.

In still further methods, glyphosate, alone or in combination with another herbicide of interest, can be applied to the 3560.4.3.5 soybean plants or their area of cultivation. Non-limiting examples of glyphosate formations are set forth in Table 2. In specific embodiments, the glyphosate is in the form of a salt, such as, ammonium, isopropylammonium, potassium, sodium (including sesquisodium) or trimesium (alternatively named sulfosate). In still further embodiments, a mixture of a synergistically effective amount of a combination of glyphosate and an ALS inhibitor (such as a sulfonylurea) is applied to the 3560.4.3.5 soybean plants or their area of cultivation.

TABLE 2

Glyphosate formulations comparisons.

| Herbicide by Registered Trademark | Manufacturer | Salt | Active Ingredient per gallon | Acid equivalent per gallon | Apply: fl oz/ acre | Acid equivalent per acre |
|---|---|---|---|---|---|---|
| Roundup Original | Monsanto | Isopropylamine | 4 | 3 | 32 | 0.750 |
| Roundup Original II | Monsanto | Isopropylamine | 4 | 3 | 32 | 0.750 |
| Roundup Original MAX | Monsanto | Potassium | 5.5 | 4.5 | 22 | 0.773 |
| Roundup UltraMax | Monsanto | Isopropylamine | 5 | 3.68 | 26 | 0.748 |
| Roundup UltraMax II | Monsanto | Potassium | 5.5 | 4.5 | 22 | 0.773 |
| Roundup Weathermax | Monsanto | Potassium | 5.5 | 4.5 | 22 | 0.773 |
| Touchdown | Syngenta | Diammomium | 3.7 | 3 | 32 | 0.750 |
| Touchdown HiTech | Syngenta | Potassium | 6.16 | 5 | 20 | 0.781 |
| Touchdown Total | Syngenta | Potassium | 5.14 | 4.17 | 24 | 0.782 |
| Durango | Dow AgroSciences | Isopropylamine | 5.4 | 4 | 24 | 0.750 |
| Glyphomax | Dow AgroSciences | Isopropylamine | 4 | 3 | 32 | 0.750 |
| Glyphomax Plus | Dow AgroSciences | Isopropylamine | 4 | 3 | 32 | 0.750 |
| Glyphomax XRT | Dow AgroSciences | Isopropylamine | 4 | 3 | 32 | 0.750 |
| Gly Star Plus | Albaugh/Agri Star | Isopropylamine | 4 | 3 | 32 | 0.750 |
| Gly Star 5 | Albaugh/Agri Star | Isopropylamine | 5.4 | 4 | 24 | 0.750 |
| Gly Star Original | Albaugh/Agri Star | Isopropylamine | 4 | 3 | 32 | 0.750 |
| Gly-Flo | Micro Flo | Isopropylamine | 4 | 3 | 32 | 0.750 |
| Credit | Nufarm | Isopropylamine | 4 | 3 | 32 | 0.750 |
| Credit Extra | Nufarm | Isopropylamine | 4 | 3 | 32 | 0.750 |
| Credit Duo | Nufarm | Isopro. + monoamm. | 4 | 3 | 32 | 0.750 |
| Credit Duo Extra | Nufarm | Isopro. + monoamm. | 4 | 3 | 32 | 0.750 |
| Extra Credit 5 | Nufarm | Isopropylamine | 5 | 3.68 | 26 | 0.748 |
| Cornerstone | Agriliance | Isopropylamine | 4 | 3 | 32 | 0.750 |
| Cornerstone Plus | Agriliance | Isopropylamine | 4 | 3 | 32 | 0.750 |
| Glyfos | Cheminova | Isopropylamine | 4 | 3 | 32 | 0.750 |
| Glyfos X-TRA | Cheminova | Isopropylamine | 4 | 3 | 32 | 0.750 |
| Rattler | Helena | Isopropylamine | 4 | 3 | 32 | 0.750 |
| Rattler Plus | Helena | Isopropylamine | 4 | 3 | 32 | 0.750 |
| Mirage | UAP | Isopropylamine | 4 | 3 | 32 | 0.750 |
| Mirage Plus | UAP | Isopropylamine | 4 | 3 | 32 | 0.750 |
| Glyphosate 41% | Helm Agro USA | Isopropylamine | 4 | 3 | 32 | 0.750 |
| Buccaneer | Tenkoz | Isopropylamine | 4 | 3 | 32 | 0.750 |
| Buccaneer Plus | Tenkoz | Isopropylamine | 4 | 3 | 32 | 0.750 |
| Honcho | Monsanto | Isopropylamine | 4 | 3 | 32 | 0.750 |
| Honcho Plus | Monsanto | Isopropylamine | 4 | 3 | 32 | 0.750 |
| Gly-4 | Univ. Crop Prot. Alli. | Isopropylamine | 4 | 3 | 32 | 0.750 |
| Gly-4 Plus | Univ. Crop Prot. Alli. | Isopropylamine | 4 | 3 | 32 | 0.750 |
| ClearOut 41 | Chemical Products Tech. | Isopropylamine | 4 | 3 | 32 | 0.750 |
| ClearOut 41 Plus | Chemical Products Tech. | Isopropylamine | 4 | 3 | 32 | 0.750 |
| Spitfire | Control Soultions | Isopropylamine | 4 | 3 | 32 | 0.750 |
| Spitfire Plus | Control Soultions | Isopropylamine | 4 | 3 | 32 | 0.750 |
| Glyphosate 4 | FarmerSaver.com | Isopropylamine | 4 | 3 | 32 | 0.750 |
| FS Glyphosate Plus | Growmark | Isopropylamine | 4 | 3 | 32 | 0.750 |
| Glyphosate Original | Griffin, LLC. | Isopropylamine | 4 | 3 | 32 | 0.750 |

Thus, in some embodiments, a transgenic plant is used in a method of growing a 3560.4.3.5 soybean crop by the application of herbicides to which the plant is tolerant. In this manner, treatment with a combination of one of more herbicides which include, but are not limited to: acetochlor, acifluorfen and its sodium salt, aclonifen, acrolein (2-propenal), alachlor, alloxydim, ametryn, amicarbazone, amidosulfuron, aminopyralid, amitrole, ammonium sulfamate, anilofos, asulam, atrazine, azimsulfuron, beflubutamid, benazolin, benazolin-ethyl, bencarbazone, benfluralin, benfuresate, bensulfuron-methyl, bensulide, bentazone, benzobicyclon, benzofenap, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clethodim, clodinafop-propargyl, clomazone, clomeprop, clopyralid, clopyralid-olamine, cloransulam-methyl, CUH-35 (2-methoxyethyl 2-[[[4-chloro-2-fluoro-5-[(1-methyl-2-propynyl)oxy]phenyl](3-fluorobenzoyl)amino]carbonyl]-1-cyclohexene-1-carboxylate), cumyluron, cyanazine, cycloate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron-methyl, ethofumesate, ethoxyfen, ethoxysulfuron, etobenzanid, fenoxaprop-ethyl, fenoxaprop-P-ethyl, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupyrsulfuron-methyl and its sodium salt, flurenol, flurenol-butyl, fluridone, flurochloridone, fluroxypyr, flurtamone, fluthiacet-methyl, fomesafen, foramsulfuron, fosamine-ammonium, glufosinate, glufosinate-ammonium, glyphosate and its salts such as ammonium, isopropylammonium, potassium, sodium (including sesquisodium) and trimesium (alternatively named sulfosate), halosulfuron-methyl, haloxyfop-etotyl, haloxyfop-methyl, hexazinone, HOK-201 (N-(2,4-difluorophenyl)-1,5-dihydro-N-(1-methylethyl)-5-oxo-1-[(tetrahydro-2H-pyran-2-yl)methyl]-4H-1,2,4-triazole-4-carboxamide), imazamox, imazamethabenz-methyl, imazapic, imazapyr, imazaquin, imazaquin-ammonium, imazethapyr, imazethapyr-ammonium, imazosulfuron, indanofan, iodosulfuron-methyl, ioxynil, ioxynil octanoate, ioxynil-sodium, isoproturon, isouron, isoxaben, isoxaflutole, isoxachlortole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, methabenzthiazuron, methylarsonic acid and its calcium, monoammonium, monosodium and disodium salts, methyldymron, metobenzuron, metobromuron, metolachlor, S-metholachlor, metosulam, metoxuron, metribuzin, metsulfuron-methyl, molinate, monolinuron, naproanilide, napropamide, naptalam, nebu-ron, nicosulfuron, norflurazon, orbencarb, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxyamid, phenmedipham, picloram, picloram-potassium, picolinafen, pinoxaden, piperofos, pretilachlor, primisulfuron-methyl, prodiamine, profoxydim, prometon, prometryn, propachlor, propanil, propaquizafop, propazine, propham, propisochlor, propoxycarbazone, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxsulam, quinclorac, quinmerac, quinoclamine, quizalofop-ethyl, quizalofop-P-ethyl, quizalofop-P-tefuryl, rimsulfuron, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiocarbazil, topramezone, tralkoxydim, tri-allate, triasulfuron, triaziflam, tribenuron-methyl, triclopyr, triclopyr-butotyl, triclopyr-triethylammonium, tridiphane, trietazine, trifloxysulfuron, trifluralin, triflusulfuron-methyl, tritosulfuron and vernolate is disclosed.

Other suitable herbicides and agricultural chemicals are known in the art, such as, for example, those described in WO 2005/041654. Other herbicides also include bioherbicides such as *Alternaria destruens* Simmons, *Colletotrichum gloeosporiodes* (Penz.) Penz. & Sacc., *Drechsiera monoceras* (MTB-951), *Myrothecium verrucaria* (Albertini & Schweinitz) Ditmar: Fries, *Phytophthora palmivora* (Butl.) Butl. and *Puccinia thlaspeos* Schub. Combinations of various herbicides can result in a greater-than-additive (i.e., synergistic) effect on weeds and/or a less-than-additive effect (i.e. safening) on crops or other desirable plants. In certain instances, combinations of glyphosate with other herbicides having a similar spectrum of control but a different mode of action will be particularly advantageous for preventing the development of resistant weeds. Herbicidally effective amounts of any particular herbicide can be easily determined by one skilled in the art through simple experimentation.

Herbicides may be classified into groups and/or subgroups as described herein above with reference to their mode of action, or they may be classified into groups and/or subgroups in accordance with their chemical structure.

Sulfonamide herbicides have as an essential molecular structure feature a sulfonamide moiety (—S(O)$_2$NH—). As referred to herein, sulfonamide herbicides particularly comprise sulfonylurea herbicides, sulfonylaminocarbonyltriazolinone herbicides and triazolopyrimidine herbicides. In sulfonylurea herbicides the sulfonamide moiety is a component in a sulfonylurea bridge (—S(O)$_2$NHC(O)NH(R)—). In sulfonylurea herbicides the sulfonyl end of the sulfonylurea bridge is connected either directly or by way of an oxygen atom or an optionally substituted amino or methylene group to a typically substituted cyclic or acyclic group. At the opposite end of the sulfonylurea bridge, the amino group, which may have a substituent such as methyl (R being CH$_3$) instead of hydrogen, is connected to a heterocyclic group, typically a symmetric pyrimidine or triazine ring, having one or two substituents such as methyl, ethyl, trifluoromethyl, methoxy, ethoxy, methylamino, dimethylamino, ethylamino and the halogens. In sulfonylaminocarbonyltriazolinone herbicides, the sulfonamide moiety is a component of a sulfonylaminocarbonyl bridge (—S(O)$_2$NHC(O)—). In sulfonylaminocarbonyltriazolinone herbicides the sulfonyl end of the sulfonylaminocarbonyl bridge is typically connected to substituted phenyl ring. At the opposite end of the sulfonylaminocarbonyl bridge, the carbonyl is connected to the 1-position of a triazolinone ring, which is typically substituted with groups such as alkyl and alkoxy. In triazolopyrimidine herbicides the sulfonyl end of the sulfonamide moiety is connected to the 2-position of a substituted [1,2,4]triazolopyrimidine ring system and the amino end of the sulfonamide moiety is connected to a substituted aryl, typically phenyl, group or alternatively the amino end of the sulfonamide moiety is connected to the 2-position of a substituted [1,2,4] triazolopyrimidine ring system and the sulfonyl end of the sulfonamide moiety is connected to a substituted aryl, typically pyridinyl, group.

Representative of the sulfonylurea herbicides useful in the embodiments are those of the formula:

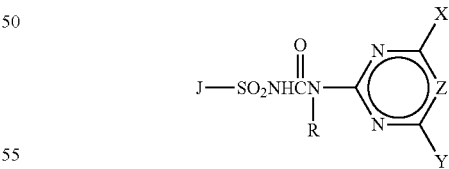

wherein:
J is selected from the group consisting of

J-1

-continued

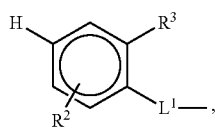

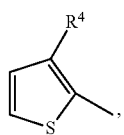

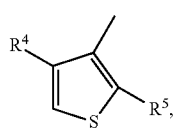

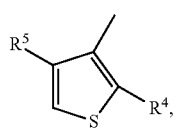

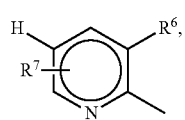

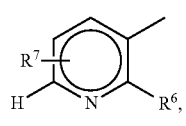

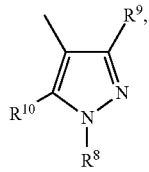

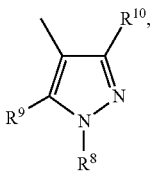

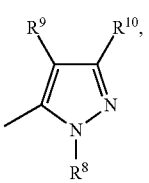

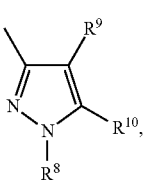

-continued

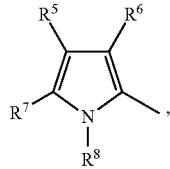

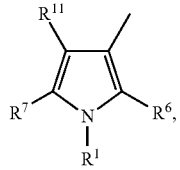

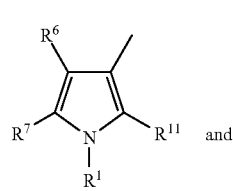

and

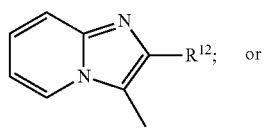

or

J is $R^{13}SO_2N(CH_3)$—;

R is H or $CH_3$;

$R^1$ is F, Cl, Br, $NO_2$, $C_1$-$C_4$ alkyl, $C_1$-$C_4$ haloalkyl, $C_3$-$C_4$ cycloalkyl, $C_2$-$C_4$ haloalkenyl, $C_1$-$C_4$ alkoxy, $C_1$-$C_4$ haloalkoxy, $C_2$-$C_4$ alkoxyalkoxy, $CO_2R^{14}$, $C(O)NR^{15}R^{16}$, $SO_2NR^{17}R^{18}$, $S(O)_nR^{19}$, $C(O)R^{20}$, $CH_2CN$ or L;

$R^2$ is H, F, Cl, Br, I, CN, $CH_3$, $OCH_3$, $SCH_3$, $CF_3$ or $OCF_2H$;

$R^3$ is Cl, $NO_2$, $CO_2CH_3$, $CO_2CH_2CH_3$, $C(O)CH_3$, $C(O)CH_2CH_3$, $C(O)$-cyclopropyl, $SO_2N(CH_3)_2$, $SO_2CH_3$, $SO_2CH_2CH_3$, $OCH_3$ or $OCH_2CH_3$;

$R^4$ is $C_1$-$C_3$ alkyl, $C_1$-$C_2$ haloalkyl, $C_1$-$C_2$ alkoxy, $C_2$-$C_4$ haloalkenyl, F, Cl, Br, $NO_2$, $CO_2R^{14}$, $C(O)NR^{15}R^{16}$, $SO_2NR^{17}R^{18}$, $S(O)_nR^{19}$, $C(O)R^{20}$ or L;

$R^5$ is H, F, Cl, Br or $CH_3$;

$R^6$ is $C_1$-$C_3$ alkyl optionally substituted with 0-3 F, 0-1 Cl and 0-1 $C_3$-$C_4$ alkoxyacetyloxy, or $R^6$ is $C_1$-$C_2$ alkoxy, $C_2$-$C_4$ haloalkenyl, F, Cl, Br, $CO_2R^{14}$, $C(O)NR^{15}R^{16}$, $SO_2NR^{17}R^{18}$, $S(O)_nR^{19}$, $C(O)R^{20}$ or L;

$R^7$ is H, F, Cl, $CH_3$ or $CF_3$;

$R^8$ is H, $C_1$-$C_3$ alkyl or pyridinyl;

$R^9$ is $C_1$-$C_3$ alkyl, $C_1$-$C_2$ alkoxy, F, Cl, Br, $NO_2$, $CO_2R^{14}$, $SO_2NR^{17}R^{18}$, $S(O)_nR^{19}$, $OCF_2H$, $C(O)R^{20}$, $C_2$-$C_4$ haloalkenyl or L;

$R^{10}$ is H, Cl, F, Br, $C_1$-$C_3$ alkyl or $C_1$-$C_2$ alkoxy;

$R^{11}$ is H, $C_1$-$C_3$ alkyl, $C_1$-$C_2$ alkoxy, $C_2$-$C_4$ haloalkenyl, F, Cl, Br, $CO_2R^{14}$, $C(O)NR^{15}R^{16}$, $SO_2NR^{17}R^{18}$, $S(O)_nR^{19}$, $C(O)R^{20}$ or L;

$R^{12}$ is halogen, $C_1$-$C_4$ alkyl or $C_1$-$C_3$ alkylsulfonyl;

$R^{13}$ is $C_1$-$C_4$ alkyl;

$R^{14}$ is allyl, propargyl or oxetan-3-yl; or $R^{14}$ is $C_1$-$C_3$ alkyl optionally substituted by at least one member independently selected from halogen, $C_1$-$C_2$ alkoxy and CN;

$R^{15}$ is H, $C_1$-$C_3$ alkyl or $C_1$-$C_2$ alkoxy;

$R^{16}$ is $C_1$-$C_2$ alkyl;

$R^{17}$ is H, $C_1$-$C_3$ alkyl, $C_1$-$C_2$ alkoxy, allyl or cyclopropyl;

$R^{18}$ is H or $C_1$-$C_3$ alkyl;
$R^{19}$ is $C_1$-$C_3$ alkyl, $C_1$-$C_3$ haloalkyl, allyl or propargyl;
$R^{20}$ is $C_1$-$C_4$ alkyl, $C_1$-$C_4$ haloalkyl or $C_3$-$C_5$ cycloalkyl optionally substituted by halogen;
n is 0, 1 or 2;
L is

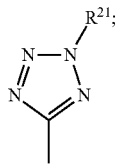

$L^1$ is $CH_2$, NH or O;
$R^{21}$ is H or $C_1$-$C_3$ alkyl;
X is H, $C_1$-$C_4$ alkyl, $C_1$-$C_4$ alkoxy, $C_1$-$C_4$ haloalkoxy, $C_1$-$C_4$ haloalkyl, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino or di($C_1$-$C_3$ alkyl)amino;
Y is H, $C_1$-$C_4$ alkyl, $C_1$-$C_4$ alkoxy, $C_1$-$C_4$ haloalkoxy, $C_1$-$C_4$ alkylthio, $C_1$-$C_4$ haloalkylthio, $C_2$-$C_5$ alkoxyalkyl, $C_2$-$C_5$ alkoxyalkoxy, amino, $C_1$-$C_3$ alkylamino, di($C_1$-$C_3$ alkyl)amino, $C_3$-$C_4$ alkenyloxy, $C_3$-$C_4$ alkynyloxy, $C_2$-$C_5$ alkylthioalkyl, $C_2$-$C_5$ alkylsulfinylalkyl, $C_2$-$C_5$ alkylsulfonylalkyl, $C_1$-$C_4$ haloalkyl, $C_2$-$C_4$ alkynyl, $C_3$-$C_5$ cycloalkyl, azido or cyano; and
Z is CH or N;
provided that (i) when one or both of X and Y is $C_1$ haloalkoxy, then Z is CH; and (ii) when X is halogen, then Z is CH and Y is $OCH_3$, $OCH_2CH_3$, $N(OCH_3)CH_3$, $NHCH_3$, $N(CH_3)_2$ or $OCF_2H$. Of note is the present single liquid herbicide composition comprising one or more sulfonylureas of Formula I wherein when $R^6$ is alkyl, said alkyl is unsubstituted.

Representative of the triazolopyrimidine herbicides contemplated for use in the embodiments are those of the formula:

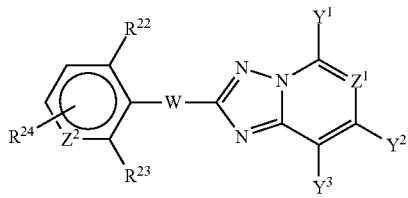

wherein:
$R^{22}$ and $R^{23}$ each independently halogen, nitro, $C_1$-$C_4$ alkyl, $C_1$-$C_4$ haloalkyl, $C_1$-$C_4$ alkoxy, $C_1$-$C_4$ haloalkoxy or $C_2$-$C_3$ alkoxycarbonyl;
$R^{24}$ is H, halogen, $C_1$-$C_2$ alkyl or $C_1$-$C_2$ alkoxy;
W is —NHS(O)$_2$— or —S(O)$_2$NH—;
$Y^1$ is H, $C_1$-$C_2$ alkyl or $C_1$-$C_2$ alkoxy;
$Y^2$ is H, F, Cl, Br, $C_1$-$C_2$ alkyl or $C_1$-$C_2$ alkoxy;
$Y^3$ is H, F or methoxy;
$Z^1$ is CH or N; and
$Z^2$ is CH or N;
provided that at least one of $Y^1$ and $Y^2$ is other than H.

In the above Markush description of representative triazolopyrimidine herbicides, when W is —NHS(O)$_2$— the sulfonyl end of the sulfonamide moiety is connected to the [1,2,4]triazolopyrimidine ring system, and when W is —S(O)$_2$NH— the amino end of the sulfonamide moiety is connected to the [1,2,4]triazolopyrimidine ring system.

In the above recitations, the term "alkyl", used either alone or in compound words such as "alkylthio" or "haloalkyl" includes straight-chain or branched alkyl, such as, methyl, ethyl, n-propyl, i-propyl, or the different butyl isomers. "Cycloalkyl" includes, for example, cyclopropyl, cyclobutyl and cyclopentyl. "Alkenyl" includes straight-chain or branched alkenes such as ethenyl, 1-propenyl, 2-propenyl, and the different butenyl isomers. "Alkenyl" also includes polyenes such as 1,2-propadienyl and 2,4-butadienyl. "Alkynyl" includes straight-chain or branched alkynes such as ethynyl, 1-propynyl, 2-propynyl and the different butynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxy" denotes alkoxy substitution on alkoxy. "Alkenyloxy" includes straight-chain or branched alkenyloxy moieties, Examples of "alkenyloxy" include $H_2C=CHCH_2O$, $(CH_3)CH=CHCH_2O$ and $CH_2=CHCH_2CH_2O$. "Alkynyloxy" includes straight-chain or branched alkynyloxy moieties. Examples of "alkynyloxy" include $HC\equiv CCH_2O$ and $CH_3C\equiv CCH_2O$. "Alkylthio" includes branched or straight-chain alkylthio moieties such as methylthio, ethylthio, and the different propylthio isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$; "alkylsulfinylalkyl" and "alkylsulfonyl-alkyl" include the corresponding sulfoxides and sulfones, respectively. Other substituents such as "alkylamino", "dialkylamino" are defined analogously.

The total number of carbon atoms in a substituent group is indicated by the "$C_i$-$C_j$" prefix where i and j are numbers from 1 to 5. For example, $C_1$-$C_4$ alkyl designates methyl through butyl, including the various isomers. As further examples, $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkoxy", "haloalkylthio", and the like, are defined analogously to the term "haloalkyl". Examples of "haloalkoxy" include $CF_3O$, $CCl_3CH_2O$, $HCF_2CH_2CH_2O$ and $CF_3CH_2O$. Examples of "haloalkylthio" include $CCl_3S$, $CF_3S$, $CCl_3CH_2S$ and $ClCH_2CH_2CH_2S$.

The following sulfonylurea herbicides illustrate the sulfonylureas useful for this invention: amidosulfuron (N-[[[[(4,6-dimethoxy-2-pyrimdinyl)amino]carbonyl]amino]-sulfonyl]-N-methylmethanesulfonamide), azimsulfuron (N-[[(4,6-dimethoxy-2-pyrimidinyl)amino]carbonyl]-1-methyl-4-(2-methyl-2H-tetrazol-5-yl)-1H-pyrazole-5-sulfonamide), bensulfuron-methyl (methyl 2-[[[[[(4,6-dimethoxy-2-pyrimidinyl)amino]carbonyl]amino]sulfonyl]methyl]benzoate), chlorimuron-ethyl (ethyl 2-[[[[(4-chloro-6-methoxy-2-pyrimidinyl)amino]carbonyl]amino]sulfonyl]-benzoate), chlorsulfuron (2-chloro-N-[[(4-methoxy-6-methyl-1,3,5-triazin-2-yl)amino]-carbonyl]benzenesulfonamide), cinosulfuron (N-[[(4,6-dimethoxy-1,3,5-triazin-2-yl)amino]carbonyl]-2-(2-methoxyethoxy)benzenesulfonamide), cyclosulfamuron (N-[[[2-(cyclopropylcarbonyl)phenyl]amino]sulfonyl]-N$^1$-(4,6-dimethoxypyrimidin-2-yl)urea), ethametsulfuron-methyl (methyl 2-[[[[[4-ethoxy-6-(methylamino)-1,3,5-triazin-2-yl]amino]carbonyl]amino]sulfonyl]benzoate), ethoxysulfuron (2-ethoxyphenyl[[(4,6-dimethoxy-2-pyrimidinyl)amino]carbonyl]sulfamate), flazasulfuron (N-[[(4,6-dimethoxy-2-pyrimidinyl)amino]carbonyl]-3-(trifluoromethyl)-2-pyridinesulfonamide), flucetosulfuron (1-[3-[[[[(4,6-dimethoxy-2-pyrimidinyl)amino]carbonyl]amino] sulfonyl]-2-pyridinyl]-2-fluoropropyl methoxyacetate), flupyrsulfuron-methyl (methyl 2-[[[[(4,6-dimethoxy-2-pyrimidinyl)amino]carbonyl]amino]sulfonyl]-6-(trifluoromethyl)-3-pyridinecarboxylate), foramsulfuron (2-[[[[(4,6-dimethoxy-2-pyrimidinyl)amino]carbonyl]amino]sulfonyl]-4-(formylamino)-N,N-dimethylbenzamide), halosulfuron-methyl (methyl 3-chloro-5-[[[[(4,6-dimethoxy-2-pyrimidinyl)amino]-carbonyl]amino]sulfonyl]-1-methyl-1H-pyrazole-4-carboxylate), imazosulfuron (2-chloro-N-[[(4,6-dimethoxy-2-pyrimidinyl)amino]carbonyl]imidazo [1,2-a]pyridine-3-sulfonamide), iodosulfuron-methyl (methyl 4-iodo-2-[[[[(4-methoxy-6-methyl-1,3,5-triazin-2-yl)amino]carbonyl]amino]sulfonyl]benzoate), mesosulfuron-methyl (methyl 2-[[[[(4,6-dimethoxy-2-pyrimidinyl)amino]carbonyl]amino]sulfonyl]-4-[[(methylsulfonyl)-amino]methyl]benzoate), metsulfuron-methyl (methyl 2-[[[[(4-methoxy-6-methyl-1,3,5-triazin-2-yl)amino]carbonyl]amino]sulfonyl]benzoate), nicosulfuron (2-[[[[(4,6-dimethoxy-2-pyrimidinyl)amino]carbonyl]amino]sulfonyl]-N,N-dimethyl-3-pyridinecarboxamide), oxasulfuron (3-oxetanyl 2-[[[[(4,6-dimethyl-2-pyrimidinyl)-amino]carbonyl]amino]sulfonyl]benzoate), primisulfuron-methyl (methyl 2-[[[[[4,6-bis(trifluoromethoxy)-2-pyrimidinyl]amino] carbonyl]amino]sulfonyl]benzoate), prosulfuron (N-[[(4-methoxy-6-methyl-1,3,5-triazin-2-yl)amino]carbonyl]-2-(3,3,3-trifluoropropyl)benzenesulfonamide), pyrazosulfuron-ethyl (ethyl 5-[[[[(4,6-dimethoxy-2-pyrimidinyl)amino] carbonyl]amino]sulfonyl]-1-methyl-1H-pyrazole-4-carboxylate), rimsulfuron (N-[[(4,6-dimethoxy-2-pyrimidinyl)amino]carbonyl]-3-(ethylsulfonyl)-2-pyridinesulfonamide), sulfometuron-methyl (methyl 2-[[[[(4,6-dimethyl-2-pyrimidinyl)amino]carbonyl]amino] sulfonyl]-benzoate), sulfosulfuron (N-[[(4,6-dimethoxy-2-pyrimidinyl)amino]carbonyl]-2-(ethylsulfonyl)imidazo[1,2-a]pyridine-3-sulfonamide), thifensulfuron-methyl (methyl 3-[[[[(4-methoxy-6-methyl-1,3,5-triazin-2-yl)amino]carbonyl]amino]sulfonyl]-2-thiophenecarboxylate), triasulfuron (2-(2-chloroethoxy)-N-[[(4-methoxy-6-methyl-1,3,5-triazin-2-yl)amino]carbonyl]benzenesulfonamide), tribenuron-methyl (methyl 2-[[[[N-(4-methoxy-6-methyl-1,3,5-triazin-2-yl)-N-methylamino]carbonyl]-amino]sulfonyl] benzoate), trifloxysulfuron (N-[[(4,6-dimethoxy-2-pyrimidinyl)amino]-carbonyl]-3-(2,2,2-trifluomethoxy)-2-pyridinesulfonamide), triflusulfuron-methyl (methyl 2-[[[[[4-dimethylamino)-6-(2,2,2-trifluoroethoxy)-1,3,5-triazin-2-yl]amino]-carbonyl]amino]sulfonyl]-3-methylbenzoate) and tritosulfuron (N-[[[4-methoxy-6-(trifluoromethyl)-1,3,5-triazin-2-yl]amino]carbonyl]-2-(trifluoromethyl)benzene-sulfonamide).

The following triazolopyrimidine herbicides illustrate the triazolopyrimidines useful for this invention: cloransulam-methyl (methyl 3-chloro-2-[[(5-ethoxy-7-fluoro-[1,2,4]triazolo[1,5-c]pyrimidin-2-yl)sulfonyl]amino]benzoate, diclosulam (N-(2,6-dichlorophenyl)-5-ethoxy-7-fluoro[1,2,4] triazolo[1,5-c]pyrimidine-2-sulfonamide, florasulam (N-(2, 6-difluorophenyl)-8-fluoro-5-methoxy[1,2,4]triazolo[1,5-c] pyrimidine-2-sulfonamide), flumetsulam (N-(2,6-difluorophenyl)-5-methyl[1,2,4]triazolo[1,5-a]pyrimidine-2-sulfonamide), metosulam (N-(2,6-dichloro-3-methylphenyl)-5,7-dimethoxy[1,2,4]triazolo[1,5-a] pyrimidine-2-sulfonamide), penoxsulam (2-(2,2-difluoroethoxy)-N-(5,8-dimethoxy[1,2,4]triazolo[1,5-c] pyrimidin-2-yl)-6-(trifluoromethyl)benzenesulfonamide) and pyroxsulam (N-(5,7-dimethoxy[1,2,4]triazolo[1,5-a]pyrimidin-2-yl)-2-methoxy-4-(trifluoromethyl)-3-pyridinesulfonamide).

The following sulfonylaminocarbonyltriazolinone herbicides illustrate the sulfonylaminocarbonyltriazolinones useful for this invention: flucarbazone (4,5-dihydro-3-methoxy-4-methyl-5-oxo-N-[[2-(trifluoromethoxy)phenyl]sulfonyl]-1H-1,2,4-triazole-1-carboxamide) and procarbazone (methyl 2-[[[(4,5-dihydro-4-methyl-5-oxo-3-propoxy-1H-1,2,4-triazol-1-yl)carbonyl]amino]sulfonyl]benzoate).

Additional herbicides include phenmedipham, triazolinones, and the herbicides disclosed in WO2006/012981, herein incorporated by reference in its entirety.

The methods further comprise applying to the crop and the weeds in a field a sufficient amount of at least one herbicide to which the crop seeds or plants is tolerant, such as, for example, glyphosate, a hydroxyphenylpyruvatedioxygenase inhibitor (e.g., mesotrione or sulcotrione), a phytoene desaturase inhibitor (e.g., diflufenican), a pigment synthesis inhibitor, sulfonamide, imidazolinone, bialaphos, phosphinothricin, azafenidin, butafenacil, sulfosate, glufosinate, triazolopyrimidine, pyrimidinyloxy(thio)benzoate, or sulonylaminocarbonyltriazolinone, an acetyl Co-A carboxylase inhibitor such as quizalofop-P-ethyl, a synthetic auxin such as quinclorac, or a protox inhibitor to control the weeds without significantly damaging the crop plants.

Generally, the effective amount of herbicide applied to the field is sufficient to selectively control the weeds without significantly affecting the crop. "Weed" as used herein refers to a plant which is not desirable in a particular area. Conversely, a "crop plant" as used herein refers to a plant which is desired in a particular area, such as, for example, a soybean plant. Thus, in some embodiments, a weed is a non-crop plant or a non-crop species, while in some embodiments, a weed is a crop species which is sought to be eliminated from a particular area, such as, for example, an inferior and/or non-transgenic soybean plant in a field planted with soybean event 3560.4.3.5, or a soybean plant in a field planted with 3560.4.3.5. Weeds can be either classified into two major groups: monocots and dicots.

Many plant species can be controlled (i.e., killed or damaged) by the herbicides described herein. Accordingly, the methods are useful in controlling these plant species where they are undesirable (i.e., where they are weeds). These plant species include crop plants as well as species commonly considered weeds, including but not limited to species such as: blackgrass (*Alopecurus myosuroides*), giant foxtail (*Setaria faberi*), large crabgrass (*Digitaria sanguinalis*), Surinam grass (*Brachiaria decumbens*), wild oat (*Avena fatua*), common cocklebur (*Xanthium pensylvanicum*), common lambsquarters (*Chenopodium album*), morning glory (*Ipomoea coccinea*), pigweed (*Amaranthus* spp.), velvetleaf (*Abutilion theophrasti*), common barnyardgrass (*Echinochloa crus-galli*), bermudagrass (*Cynodon dactylon*), downy brome (*Bromus tectorum*), goosegrass (*Eleusine indica*), green foxtail (*Setaria viridis*), Italian ryegrass (*Lolium multiflorum*), Johnsongrass (*Sorghum halepense*), lesser canarygrass (*Phalaris minor*), windgrass (*Apera spicaventi*), wooly cupgrass (*Erichloa villosa*), yellow nutsedge (*Cyperus esculentus*), common chickweed (*Stellaria media*), common ragweed (*Ambrosia artemisiifolia*), *Kochia scoparia*, horseweed (*Conyza canadensis*), rigid ryegrass (*Lolium rigidum*), goosegrass (*Eleucine indica*), hairy fleabane (*Conyza bonariensis*), buckhorn plantain (*Plantago lanceolata*), tropical spiderwort (*Commelina benghalensis*), field bindweed (*Convolvulus arvensis*), purple nutsedge (*Cyperus rotundus*), redvine (*Brunnichia ovata*), hemp sesbania (*Sesbania exaltata*), sicklepod (*Senna obtusifolia*), Texas blueweed (*Helianthus ciliaris*), and Devil's claws (*Proboscidea louisianica*). In other embodiments, the weed comprises a herbicide-resistant ryegrass, for example, a glyphosate resistant ryegrass, a paraquat resistant ryegrass, a ACCase-inhibitor resistant ryegrass, and a non-selective herbicide resistant ryegrass. In some embodiments, the undesired plants are proximate the crop plants.

As used herein, by "selectively controlled" it is intended that the majority of weeds in an area of cultivation are significantly damaged or killed, while if crop plants are also present in the field, the majority of the crop plants are not significantly damaged. Thus, a method is considered to selectively control weeds when at least 55%, 60%, 65%, 70%, 75%, 80%, 85%, 90%, 95%, or more of the weeds are significantly damaged or killed, while if crop plants are also present in the field, less than 45%, 40%, 35%, 30%, 25%, 20%, 15%, 10%, 5%, or 1% of the crop plants are significantly damaged or killed.

In some embodiments, a soybean 3560.4.3.5 plant is not significantly damaged by treatment with a particular herbicide applied to that plant at a dose equivalent to a rate of at least 0.5, 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 110, 120, 150, 170, 200, 300, 400, 500, 600, 700, 800, 800, 1000, 2000, 3000, 4000, 5000 or more grams or ounces (1 ounce=29.57 ml) of active ingredient or commercial product or herbicide formulation per acre or per hectare, whereas an appropriate control plant is significantly damaged by the same treatment.

In specific embodiments, an effective amount of an ALS inhibitor herbicide comprises at least about 0.1, 1, 5, 10, 25, 50, 75, 100, 150, 200, 250, 300, 350, 400, 450, 500, 600, 700, 750, 800, 850, 900, 950, 1000, 2000, 3000, 4000, 5000, or more grams or ounces (1 ounce=29.57 ml) of active ingredient per hectare. In other embodiments, an effective amount of an ALS inhibitor comprises at least about 0.1-50, about 25-75, about 50-100, about 100-110, about 110-120, about 120-130, about 130-140, about 140-150, about 150-200, about 200-500, about 500-600, about 600-800, about 800-1000, or greater grams or ounces (1 ounce=29.57 ml) of active ingredient per hectare. Any ALS inhibitor, for example, those listed in Table 1 can be applied at these levels.

In other embodiments, an effective amount of a sulfonylurea comprises at least 0.1, 1, 5, 10, 25, 50, 75, 100, 150, 200, 250, 300, 350, 400, 450, 500, 600, 700, 800, 900, 1000, 5000 or more grams or ounces (1 ounce=29.57 ml) of active ingredient per hectare. In other embodiments, an effective amount of a sulfonylurea comprises at least about 0.1-50, about 25-75, about 50-100, about 100-110, about 110-120, about 120-130, about 130-140, about 140-150, about 150-160, about 160-170, about 170-180, about 190-200, about 200-250, about 250-300, about 300-350, about 350-400, about 400-450, about 450-500, about 500-550, about 550-600, about 600-650, about 650-700, about 700-800, about 800-900, about 900-1000, about 1000-2000, or more grams or ounces (1 ounce=29.57 ml) of active ingredient per hectare. Representative sulfonylureas that can be applied at this level are set forth in Table 1.

In other embodiments, an effective amount of a sulfonylaminocarbonyltriazolinones, triazolopyrimidines, pyrimidinyloxy(thio)benzoates, and imidazolinones can comprise at least about 0.1, 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1500, 1550, 1600, 1650, 1700, 1800, 1850, 1900, 1950, 2000, 2500, 3500, 4000, 4500, 5000 or greater grams or ounces (1 ounce=29.57 ml) active ingredient per hectare. In other embodiments, an effective amount of a sulfonyluminocarbonyltriazolines, triazolopyrimidines, pyrimidinyloxy(thio) benzoates, or imidazolinones comprises at least about 0.1-50, about 25-75, about 50-100, about 100-110, about 110-120, about 120-130, about 130-140, about 140-150, about 150-160, about 160-170, about 170-180, about 190-200, about 200-250, about 250-300, about 300-350, about 350-400, about 400-450, about 450-500, about 500-550, about 550-600, about 600-650, about 650-700, about 700-800, about 800-900, about 900-1000, about 1000-2000, or more grams or ounces (1 ounce=29.57 ml) active ingredient per hectare.

Additional ranges of the effective amounts of herbicides can be found, for example, in various publications from University Extension services. See, for example, Bernards et al. (2006) *Guide for Weed Management in Nebraska* (www.ianrpubs.url.edu/sendlt/ec130); Regher et al. (2005) *Chemical Weed Control for Fields Crops, Pastures, Rangeland, and Noncropland*, Kansas State University Agricultural Extension Station and Corporate Extension Service; Zollinger et al. (2006) *North Dakota Weed Control Guide*, North Dakota Extension Service, and the Iowa State University Extension at www.weeds.iastate.edu, each of which is herein incorporated by reference.

In some embodiments, glyphosate is applied to an area of cultivation and/or to at least one plant in an area of cultivation at rates between 8 and 32 ounces of acid equivalent per acre, or at rates between 10, 12, 14, 16, 18, 20, 22, 24, 26, 28, and 30 ounces of acid equivalent per acre at the lower end of the range of application and between 12, 14, 16, 18, 20, 22, 24, 26, 28, 30, and 32 ounces of acid equivalent per acre at the higher end of the range of application (1 ounce=29.57 ml). In other embodiments, glyphosate is applied at least at 1, 5, 10, 20, 30, 40, 50, 60, 70, 80, 90 or greater ounce of active ingredient per hectare (1 ounce=29.57 ml). In some embodiments, a sulfonylurea herbicide is applied to a field and/or to at least one plant in a field at rates between 0.04 and 1.0 ounces of active ingredient per acre, or at rates between 0.1, 0.2, 0.4, 0.6, and 0.8 ounces of active ingredient per acre at the lower end of the range of application and between 0.2, 0.4, 0.6, 0.8, and 1.0 ounces of active ingredient per acre at the higher end of the range of application. (1 ounce=29.57 ml)

Glyphosate herbicides as a class contain the same active ingredient, but the active ingredient is present as one of a number of different salts and/or formulations. However, herbicides known to inhibit ALS vary in their active ingredient as well as their chemical formulations. One of skill in the art is familiar with the determination of the amount of active ingredient and/or acid equivalent present in a particular volume and/or weight of herbicide preparation.

In some embodiments, an ALS inhibitor herbicide is employed. Rates at which the ALS inhibitor herbicide is applied to the crop, crop part, seed or area of cultivation can be any of the rates disclosed herein. In specific embodiments, the rate for the ALS inhibitor herbicide is about 0.1 to about 5000 g ai/hectare, about 0.5 to about 300 g ai/hectare, or about 1 to about 150 g ai/hectare.

Generally, a particular herbicide is applied to a particular field (and any plants growing in it) no more than 1, 2, 3, 4, 5, 6, 7, or 8 times a year, or no more than 1, 2, 3, 4, or 5 times per growing season.

By "treated with a combination of" or "applying a combination of herbicides to a crop, area of cultivation or field" it is intended that a particular field, crop or weed is treated with each of the herbicides and/or chemicals indicated to be part of the combination so that a desired effect is achieved, i.e., so that weeds are selectively controlled while the crop is not significantly damaged. In some embodiments, weeds which are susceptible to each of the herbicides exhibit damage from treatment with each of the herbicides which is additive or synergistic. The application of each herbicide and/or chemical may be simultaneous or the applications may be at different times, so long as the desired effect is achieved. Furthermore, the application can occur prior to the planting of the crop.

The proportions of herbicides used with other herbicidal active ingredients in herbicidal compositions are generally in the ratio of 5000:1 to 1:5000, 1000:1 to 1:1000, 100:1 to 1:100, 10:1 to 1:10 or 5:1 to 1:5 by weight. The optimum ratios can be easily determined by those skilled in the art based on the weed control spectrum desired. Moreover, any combinations of ranges of the various herbicides disclosed in Table 1 can also be applied in the methods.

Thus, in some embodiments, improved methods for selectively controlling weeds in a field are provided wherein the total herbicide application may be less than 90%, 85%, 80%, 75%, 70%, 65%, 60%, 55%, 50%, 45%, 40%, 35%, 30%, 25%, 20%, 15%, 10%, 5%, or 1% of that used in other methods. Similarly, in some embodiments, the amount of a particular herbicide used for selectively controlling weeds in a field may be less than 90%, 85%, 80%, 75%, 70%, 65%, 60%, 55%, 50%, 45%, 40%, 35%, 30%, 25%, 20%, 15%, 10%, 5%, or 1% of the amount of that particular herbicide that would be used in other methods, i.e., methods not utilizing a plant of the invention.

In some embodiments, a 3560.4.3.5 soybean plant benefits from a synergistic effect wherein the herbicide tolerance conferred by the GLYAT polypeptide and the GM-HRA polypeptide is greater than expected from simply combining the herbicide tolerance conferred by each gene separately to a transgenic plant containing them individually. See, e.g., McCutchen et al. (1997) *J. Econ. Entomol.* 90: 1170-1180; Priesler et al. (1999) *J. Econ. Entomol.* 92: 598-603. As used herein, the terms "synergy," "synergistic," "synergistically" and derivations thereof, such as in a "synergistic effect" or a "synergistic herbicide combination" or a "synergistic herbicide composition" refer to circumstances under which the biological activity of a combination of herbicides, such as at least a first herbicide and a second herbicide, is greater than the sum of the biological activities of the individual herbicides. Synergy, expressed in terms of a "Synergy Index (SI)," generally can be determined by the method described by Kull et al. *Applied Microbiology* 9, 538 (1961). See also Colby "Calculating Synergistic and Antagonistic Responses of Herbicide Combinations," *Weeds* 15, 20-22 (1967).

In other instances, the herbicide tolerance conferred on a 3560.4.3.5 plant is additive; that is, the herbicide tolerance profile conferred by the herbicide tolerance genes is what would be expected from simply combining the herbicide tolerance conferred by each gene separately to a transgenic plant containing them individually. Additive and/or synergistic activity for two or more herbicides against key weed species will increase the overall effectiveness and/or reduce the actual amount of active ingredient(s) needed to control said weeds. Where such synergy is observed, the plant may display tolerance to a higher dose or rate of herbicide and/or the plant may display tolerance to additional herbicides or other chemicals beyond those to which it would be expected to display tolerance. For example, a 3560.4.3.5 soybean plant may show tolerance to organophosphate compounds such as insecticides and/or inhibitors of 4-hydroxyphenylpyruvate dioxygenase.

Thus, for example, the 3560.4.3.5 soybean plants can exhibit greater than expected tolerance to various herbicides, including but not limited to glyphosate, ALS inhibitor chemistries, and sulfonylurea herbicides. The 3560.4.3.5 soybean plants may show tolerance to a particular herbicide or herbicide combination that is at least 1%, 2%, 3%, 4%, 5%, 6%, 7%, 8%, 9%, 10%, 12%, 15%, 17%, 20%, 22%, 25%, 27%, 30%, 35%, 40%, 45%, 50%, 55%, 60%, 65%, 70%, 80%, 90%, 100%, 125%, 150%, 175%, 200%, 300%, 400%, or 500% or more higher than the tolerance of an appropriate control plant that contains only a single herbicide tolerance gene which confers tolerance to the same herbicide or herbicide combination. Thus, 3560.4.3.5 soybean plants may show decreased damage from the same dose of herbicide in comparison to an appropriate control plant, or they may show the same degree of damage in response to a much higher dose of herbicide than the control plant. Accordingly, in specific embodiments, a particular herbicide used for selectively containing weeds in a field is more than 1%, 5%, 10%, 15%, 20%, 25%, 30%, 35%, 40%, 45%, 50%, 60%, 70%, 80%, 90%, 100% or greater than the amount of that particular herbicide that would be used in other methods, i.e., methods not utilizing a plant of the invention.

In the same manner, in some embodiments, a 3560.4.3.5 soybean plant shows improved tolerance to a particular formulation of a herbicide active ingredient in comparison to an appropriate control plant. Herbicides are sold commercially as formulations which typically include other ingredients in addition to the herbicide active ingredient; these ingredients are often intended to enhance the efficacy of the active ingredient. Such other ingredients can include, for example, safeners and adjuvants (see, e.g., Green and Foy (2003) "Adjuvants: Tools for Enhancing Herbicide Performance," in *Weed Biology and Management*, ed. Inderjit (Kluwer Academic Publishers, The Netherlands)). Thus, a 3560.4.3.5 soybean plant can show tolerance to a particular formulation of a herbicide (e.g., a particular commercially available herbicide product) that is at least 1%, 2%, 3%, 4%, 5%, 6%, 7%, 8%, 9%, 10%, 12%, 15%, 17%, 20%, 22%, 25%, 27%, 30%, 35%, 40%, 45%, 50%, 55%, 60%, 65%, 70%, 80%, 90%, 100%, 125%, 150%, 175%, 200%, 300%, 400%, 500%, 600%, 700%, 800%, 900%, 1000%, 1100%, 1200%, 1300%, 1400%, 1500%, 1600%, 1700%, 1800%, 1900%, or 2000% or more higher than the tolerance of an appropriate control plant that contains only a single herbicide tolerance gene which confers tolerance to the same herbicide formulation.

In some embodiments, a 3560.4.3.5 soybean plant shows improved tolerance to a herbicide or herbicide class to which at least one other herbicide tolerance gene confers tolerance as well as improved tolerance to at least one other herbicide or chemical which has a different mechanism or basis of action than either glyphosate or the herbicide corresponding to said at least one other herbicide tolerance gene. This surprising benefit finds use in methods of growing crops that comprise treatment with various combinations of chemicals, including, for example, other chemicals used for growing crops. Thus, for example, a 3560.4,3.5 soybean plant may also show improved tolerance to chlorpyrifos, a systemic organophosphate insecticide. Thus, further provided is a 3560.4.3.5 soybean plant that confers tolerance to glyphosate (i.e., a glyat gene) and a sulfonylurea herbicide tolerance gene which shows improved tolerance to chemicals which affect the cytochrome P450 gene, and methods of use thereof. In some embodiments, the 3560.4.3.5 soybean plants also show improved tolerance to dicamba. In these embodiments, the improved tolerance to dicamba may be evident in the presence of glyphosate and a sulfonylurea herbicide.

In other methods, a herbicide combination is applied over a 3560.4.3.5 soybean plant, where the herbicide combination produces either an additive or a synergistic effect for controlling weeds. Such combinations of herbicides can allow the application rate to be reduced, a broader spectrum of undesired vegetation to be controlled, improved control of the undesired vegetation with fewer applications, more rapid onset of the herbicidal activity, or more prolonged herbicidal activity.

An "additive herbicidal composition" has a herbicidal activity that is about equal to the observed activities of the individual components. A "synergistic herbicidal combination" has a herbicidal activity higher than what can be expected based on the observed activities of the individual components when used alone, Accordingly, the presently disclosed subject matter provides a synergistic herbicide combination, wherein the degree of weed control of the mixture exceeds the sum of control of the individual herbicides. In some embodiments, the degree of weed control of the mixture exceeds the sum of control of the individual herbicides by any statistically significant amount including, for example, about 1% to 5%, about 5% to about 10%, about 10% to about 20%, about 20% to about 30%, about 30% to 40%, about 40% to about 50%, about 50% to about 60%, about 60% to about 70%, about 70% to about 80%, about 80% to about 90%, about 90% to about 100%, about 100% to 120% or greater. Further, a "synergistically effective amount" of a herbicide refers to the amount of one herbicide necessary to elicit a synergistic effect in another herbicide present in the herbicide composition. Thus, the term "synergist," and derivations thereof, refer to a substance that enhances the activity of an active ingredient (ai), i.e., a substance in a formulation from which a biological effect is obtained, for example, a herbicide.

Accordingly, in some embodiments, the presently disclosed subject matter provides a method for controlling weeds in an area of cultivation. In some embodiments, the method comprises: (a) planting the area with a 3560.4,3.5 crop seeds or crop plants; and (b) applying to the weed, the crop plants, a crop part, the area of cultivation, or a combination thereof, an effective amount of a herbicide composition comprising at least one of a synergistically effective amount of glyphosate and a synergistically effective amount of an ALS inhibitor (for example, but not limited to, a sulfonylurea herbicide), or agriculturally suitable salts thereof, wherein at least one of: (i) the synergistically effective amount of the glyphosate is lower than an amount of glyphosate required to control the weeds in the absence of the sulfonylurea herbicide; (ii) the synergistically effective amount of the ALS inhibitor herbicide is lower than an amount of the ALS inhibitor required to control the weeds in the absence of glyphosate; and (iii) combinations thereof; and wherein the effective amount of the herbicide composition is tolerated by the crop seeds or crop plants and controls the weeds in the area of cultivation.

In some embodiments, the herbicide composition used in the presently disclosed method for controlling weeds comprises a synergistically effective amount of glyphosate and a sulfonylurea herbicide. In further embodiments, the presently disclosed synergistic herbicide composition comprises glyphosate and a sulfonylurea herbicide selected from the group consisting of metsulfuron-methyl, chlorsulfuron, and triasulfuron.

In particular embodiments, the synergistic herbicide combination further comprises an adjuvant such as, for example, an ammonium sulfate-based adjuvant, e.g., ADD-UP® (Wenkem S. A., Halfway House, Midrand, South Africa). In additional embodiments, the presently disclosed synergistic herbicide compositions comprise an additional herbicide, for example, an effective amount of a pyrimidinyloxy(thio)benzoate herbicide. In some embodiments, the pyrimidinyloxy (thio)benzoate herbicide comprises bispyribac, e.g., (VELOCITY®, Valent U.S.A. Corp., Walnut Creek, Calif., United States of America), or an agriculturally suitable salt thereof.

In some embodiments of the presently disclosed method for controlling undesired plants, the glyphosate is applied pre-emergence, post-emergence or pre- and post-emergence to the undesired plants or plant crops; and/or the ALS inhibitor herbicide (i.e., the sulfonylurea herbicide) is applied pre-emergence, post-emergence or pre- and post-emergence to the undesired plants or plant crops. In other embodiments, the glyphosate and/or the ALS inhibitor herbicide (i.e., the sulfonylurea herbicide) are applied together or are applied separately. In yet other embodiments, the synergistic herbicide composition is applied, e.g. step (b) above, at least once prior to planting the crop(s) of interest, e.g., step (a) above.

Weeds that can be difficult to control with glyphosate alone in fields where a crop is grown (such as, for example, a soybean crop) include but are not limited to the following: horseweed (e.g., *Conyza canadensis*); rigid ryegrass (e.g., *Lolium rigidum*); goosegrass (e.g., *Eleusine indica*); Italian ryegrass (e.g., *Lolium multiflorum*); hairy fleabane (e.g., *Conyza bonariensis*); buckhorn plantain (e.g., *Plantago lanceolata*); common ragweed (e.g., *Ambrosia artemisifolia*); morning glory (e.g., *Ipomoea* spp.); waterhemp (e.g., *Amaranthus* spp.); field bindweed (e.g., *Convolvulus arvensis*); yellow nutsedge (e.g., *Cyperus esculentus*); common lambsquarters (e.g., *Chenopodium album*); wild buckwheat (e.g., *Polygonium convolvulus*); velvetleaf (e.g., *Abutilon theophrasti*); kochia (e.g., *Kochia scoparia*); and Asiatic dayflower (e.g., *Commelina* spp.). In areas where such weeds are found, the 3560.4.3.5 soybeans are particularly useful in allowing the treatment of a field (and therefore any crop growing in the field) with combinations of herbicides that would cause unacceptable damage to crop plants that did not contain both of these polynucleotides. Plants that are tolerant to glyphosate and other herbicides such as, for example, sulfonylurea, imidazolinone, triazolopyrimidine, pyrimidinyl(thio)benzoate, and/or sulfonylaminocarbonyltriazolinone herbicides in addition to being tolerant to at least one other herbicide with a different mode of action or site of action are particularly useful in situations where weeds are tolerant to at least two of the same herbicides to which the plants are tolerant. In this manner, plants of the invention make possible improved control of weeds that are tolerant to more than one herbicide.

For example, some commonly used treatments for weed control in fields where current commercial crops (including, for example, soybeans) are grown include glyphosate and, optionally, 2,4-D; this combination, however, has some disadvantages. Particularly, there are weed species that it does not control well and it also does not work well for weed control in cold weather. Another commonly used treatment for weed control in soybean fields is the sulfonylurea herbicide chlorimuron-ethyl, which has significant residual activity in the soil and thus maintains selective pressure on all later-emerging weed species, creating a favorable environment for the growth and spread of sulfonylurea-resistant weeds. However, the 3560.4.3.5 soybean can be treated with herbicides (e.g., chlorimuron-ethyl) and combinations of herbicides that would cause unacceptable damage to standard plant varieties. Thus, for example, fields containing the 3560.4.3.5 soybean can be treated with sulfonylurea, imidazolinone, triazolopyrimidines, pyrimidiny(thio)benzoates, and/or sulfonylaminocarbonyltriazonlinone such as the sulfonylurea chlorimuron-ethyl, either alone or in combination with other herbicides. For example, fields containing soybean plants of the invention can be treated with a combination of glyphosate and tribenuron-methyl (available commercially as Express®). This combination has several advantages for weed control under some circumstances, including the use of herbicides with different modes of action and the use of herbicides having a relatively short period of residual activity in the soil. A herbicide having a relatively short period of residual activity is desirable, for example, in situations where it is important to reduce selective pressure that would favor the growth of herbicide-tolerant weeds. Of course, in any particular situation where weed control is required, other considerations may be more important, such as, for example, the need to prevent the development of and/or appearance of weeds in a field prior to planting a crop by using a herbicide with a relatively long period of residual activity. The 3560.4.3.5 soybean plants can also be treated with herbicide combinations that include at least one of nicosulfuron, metsulfuron-methyl, tribenuron-methyl, thifensulfuron-methyl, and/or rimsulfuron. Treatments that include both tribenuron-methyl and thifensulfuron-methyl may be particularly useful.

Other commonly used treatments for weed control in fields where current commercial varieties of crops (including, for example, soybeans) are grown include the sulfonylurea herbicide thifensulfuron-methyl (available commercially as Harmony GT®). However, one disadvantage of thifensulfuron-methyl is that the higher application rates required for consistent weed control often cause injury to a crop growing in the same field. The 3560.4.3.5 soybean plants can be treated with a combination of glyphosate and thifensulfuron-methyl, which has the advantage of using herbicides with different modes of action. Thus, weeds that are resistant to either herbicide alone are controlled by the combination of the two herbicides, and the 3560.4.3.5 soybean plants are not significantly damaged by the treatment.

Other herbicides which are used for weed control in fields where current commercial varieties of crops (including, for example, soybeans) are grown are the triazolopyrimidine herbicide cloransulam-methyl (available commercially as FirstRate®) and the imidazolinone herbicide imazaquin (available commercially as Sceptor®). When these herbicides are used individually they may provide only marginal control of weeds. However, fields containing the 3560.4.3.5 soybean can be treated, for example, with a combination of glyphosate (e.g., Roundup® (glyphosate isopropylamine salt)), imazapyr (currently available commercially as Arsenal®), chlorimuron-ethyl (currently available commercially as Classic®), quizalofop-P-ethyl (currently available commercially as Assure II®), and fomesafen (currently available commercially as Flexstar®). This combination has the advantage of using herbicides with different modes of action. Thus, weeds that are tolerant to just one or several of these herbicides are controlled by the combination of the five herbicides, and the 3560.4.3.5 soybeans are not significantly damaged by treatment with this herbicide combination. This combination provides an extremely broad spectrum of protection against the type of herbicide-tolerant weeds that might be expected to arise and spread under current weed control practices.

Fields containing the 3560.4.3.5 soybean plants may also be treated, for example, with a combination of herbicides including glyphosate, rimsulfuron, and dicamba or mesotrione. This combination may be particularly useful in controlling weeds which have developed some tolerance to herbicides which inhibit ALS. Another combination of herbicides which may be particularly useful for weed control includes glyphosate and at least one of the following: metsulfuron-methyl (commercially available as Ally®), imazapyr (commercially available as Arsenal®), imazethapyr, imazaquin, and sulfentrazone. It is understood that any of the combinations discussed above or elsewhere herein may also be used to treat areas in combination with any other herbicide or agricultural chemical.

Some commonly-used treatments for weed control in fields where current commercial crops (including, for example, maize) are grown include glyphosate (currently available commercially as Roundup®), rimsulfuron (currently available commercially as Resolve® or Matrix®), dicamba (commercially available as Clarity®), atrazine, and mesotrione (commercially available as Callisto®). These herbicides are sometimes used individually due to poor crop tolerance to multiple herbicides. Unfortunately, when used individually, each of these herbicides has significant disadvantages. Particularly, the incidence of weeds that are tolerant to individual herbicides continues to increase, rendering glyphosate less effective than desired in some situations. Rimsulfuron provides better weed control at high doses which can cause injury to a crop, and alternatives such as dicamba are often more expensive than other commonly-used herbicides. However, 3560.4.3.5 soybean can be treated with herbicides and combinations of herbicides that would cause unacceptable damage to standard plant varieties, including combinations of herbicides that comprise rimsulfuron and/or dicamba. Other suitable combinations of herbicides for use with 3560.4.3.5 soybean plants include glyphosate, sulfonylurea, imidazolinone, triazolopyrimidine, pryimidinyloxy(thio)benzoates, and/or sulfonylaminocarbonyltriazonlinone herbicides, including, for example, and at least one of the following: metsulfuron-methyl, tribenuron-methyl, chlorimuron-ethyl, imazethapyr, imazapyr, and imazaquin.

For example, 3560.4.3.5 soybean plants can be treated with a combination of glyphosate and rimsulfuron, or a combination or rimsulfuron and at least one other herbicide. 3560.4.3.5 soybean plants can also be treated with a combination of glyphosate, rimsulfuron, and dicamba, or a combination of glyphosate, rimsulfuron, and at least one other herbicide. In some embodiments, at least one other herbicide has a different mode of action than both glyphosate and rimsulfuron. The combination of glyphosate, rimsulfuron, and dicamba has the advantage that these herbicides have different modes of action and short residual activity, which decreases the risk of incidence and spread of herbicide-tolerant weeds.

Some commonly-used treatments for weed control in fields where current commercial crops are grown include glyphosate (currently available commercially as Roundup®), chlorimuron-ethyl, tribenuron-methyl, rimsulfuron (currently available commercially as Resolve® or Matrix®), imazethapyr, imazapyr, and imazaquin. Unfortunately, when used individually, each of these herbicides has significant disadvantages. Particularly, the incidence of weeds that are tolerant to individual herbicides continues to increase, rendering each individual herbicide less effective than desired in some situations. However, 3560.4.3.5 soybean can be treated with a combination of herbicides that would cause unacceptable damage to standard plant varieties, including combinations of herbicides that include at least one of those mentioned above.

In the methods, a herbicide may be formulated and applied to an area of interest such as, for example, a field or area of cultivation, in any suitable manner. A herbicide may be applied to a field in any form, such as, for example, in a liquid spray or as solid powder or granules. In specific embodiments, the herbicide or combination of herbicides that are employed in the methods comprises a tankmix or a premix. A herbicide may also be formulated, for example, as a "homogenous granule blend" produced using blends technology (see, e.g., U.S. Pat. No. 6,022,552, entitled "Uniform Mixtures of Pesticide Granules"). The blends technology of U.S. Pat. No. 6,022,552 produces a nonsegregating blend (i.e., a "homogenous granule blend") of formulated crop protection chemicals in a dry granule form that enables delivery of customized mixtures designed to solve specific problems. A homogenous granule blend can be shipped, handled, subsampled, and applied in the same manner as traditional premix products where multiple active ingredients are formulated into the same granule.

Briefly, a "homogenous granule blend" is prepared by mixing together at least two extruded formulated granule products. In some embodiments, each granule product comprises a registered formulation containing a single active ingredient which is, for example, a herbicide, a fungicide, and/or an insecticide. The uniformity (homogeneity) of a "homogenous granule blend" can be optimized by controlling the relative sizes and size distributions of the granules used in the blend. The diameter of extruded granules is controlled by the size of the holes in the extruder die, and a centrifugal sifting process may be used to obtain a population of extruded granules with a desired length distribution (see, e.g., U.S. Pat. No. 6,270,025).

A homogenous granule blend is considered to be "homogenous" when it can be subsampled into appropriately sized aliquots and the composition of each aliquot will meet the required assay specifications. To demonstrate homogeneity, a large sample of the homogenous granule blend is prepared and is then subsampled into aliquots of greater than the minimum statistical sample size.

In non-limiting embodiments, the 3560.4.5.3 soybean plant can be treated with herbicides (e.g., chlorimuron-ethyl and combinations of other herbicides that without the 3560.4.3.5 event would have caused unacceptable crop response to plant varieties without the glyphosate/ALS inhibitor genetics). Thus, for example, fields planted with and containing 3560.4.3.5 soybeans can be treated with sulfonylurea, imidazolinone, triazolopyrimidine, pyrimidinyl(thio)benzoate, and/or sulfonylaminocarbonyltriazonlinone herbicides, either alone or in combination with other herbicides. Since ALS inhibitor chemistries have different herbicidal attributes, blends of ALS inhibitor plus other chemistries will provide superior weed management strategies including varying and increased weed spectrum, the ability to provide specified residual activity (SU/ALS inhibitor chemistry with residual activity leads to improved foliar activity which leads to a wider window between glyphosate applications, as well as, an added period of control if weather conditions prohibit timely application).

Blends also afford the ability to add other agrochemicals at normal, labeled use rates such as additional herbicides (a $3^{rd}/4^{th}$ mechanism of action), fungicides, insecticides, plant growth regulators and the like thereby saving costs associated with additional applications.

Any herbicide formulation applied over the 3560.4.3.5 soybean plant can be prepared as a "tank-mix" composition. In such embodiments, each ingredient or a combination of ingredients can be stored separately from one another. The ingredients can then be mixed with one another prior to application. Typically, such mixing occurs shortly before application. In a tank-mix process, each ingredient, before mixing, typically is present in water or a suitable organic solvent. For additional guidance regarding the art of formulation, see T. S. Woods, "The Formulator's Toolbox—Product Forms for Modern Agriculture" *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; and Hance et al., *Weed Control Handbook*, 8th Ed., Blackwell Scientific Publications, Oxford, 1989, each of which is incorporated herein by reference in their entirety.

The methods further allow for the development of herbicide combinations to be used with the 3560.4.3.5 soybean plants. In such methods, the environmental conditions in an area of cultivation are evaluated. Environmental conditions that can be evaluated include, but are not limited to, ground and surface water pollution concerns, intended use of the crop, crop tolerance, soil residuals, weeds present in area of cultivation, soil texture, pH of soil, amount of organic matter in soil, application equipment, and tillage practices. Upon the evaluation of the environmental conditions, an effective amount of a combination of herbicides can be applied to the crop, crop part, seed of the crop or area of cultivation.

In some embodiments, the herbicide applied to the 3560.4.3.5 soybean plants serves to prevent the initiation of growth of susceptible weeds and/or serve to cause damage to weeds that are growing in the area of interest. In some embodiments, the herbicide or herbicide mixture exert these effects on weeds affecting crops that are subsequently planted in the area of interest (i.e., field or area of cultivation). In the methods, the application of the herbicide combination need not occur at the same time. So long as the field in which the crop is planted contains detectable amounts of the first herbicide and the second herbicide is applied at some time during the period in which the crop is in the area of cultivation, the crop is considered to have been treated with a mixture of herbicides according to the invention. Thus, methods encompass applications of herbicide which are "preemergent," "at plant," "postemergent," "preplant incorporation" and/or seed treatment prior to planting.

In one embodiment, methods are provided for coating seeds. The methods comprise coating a seed with an effective amount of a herbicide or a combination of herbicides (as disclosed elsewhere herein). The seeds can then be planted in an area of cultivation. Further provided are seeds having a coating comprising an effective amount of a herbicide or a combination of herbicides (as disclosed elsewhere herein).

"Preemergent" refers to a herbicide which is applied to an area of interest (e.g., a field or area of cultivation) before a plant emerges visibly from the soil. "Postemergent" refers to a herbicide which is applied to an area after a plant emerges visibly from the soil. In some instances, the terms "preemergent" and "postemergent" are used with reference to a weed in an area of interest, and in some instances these terms are used with reference to a crop plant in an area of interest. When used with reference to a weed, these terms may apply to only a particular type of weed or species of weed that is present or believed to be present in the area of interest. While any herbicide may be applied in a preemergent and/or postemergent treatment, some herbicides are known to be more effective in controlling a weed or weeds when applied either preemergence or postemergence. For example, rimsulfuron has both preemergence and postemergence activity, while other herbicides have predominately preemergence (metolachlor) or postemergence (glyphosate) activity. These properties of particular herbicides are known in the art and are readily determined by one of skill in the art. Further, one of skill in the art would readily be able to select appropriate herbicides and application times for use with the transgenic plants of the invention and/or on areas in which transgenic plants of the invention are to be planted. "Preplant incorporation" involves the incorporation of compounds into the soil prior to planting.

Thus, improved methods of growing a crop and/or controlling weeds are provided such as, for example, "pre-planting burn down," wherein an area is treated with herbicides prior to planting the crop of interest in order to better control weeds. Further provided are methods of growing a crop and/or controlling weeds which are "no-till" or "low-till" (also referred to as "reduced tillage"). In such methods, the soil is not cultivated or is cultivated less frequently during the growing cycle in comparison to traditional methods; these methods can save costs that would otherwise be incurred due to additional cultivation, including labor and fuel costs.

The methods encompass the use of simultaneous and/or sequential applications of multiple classes of herbicides. In some embodiments, the methods involve treating a plant of the invention and/or an area of interest (e.g., a field or area of cultivation) and/or weed with just one herbicide or other chemical such as, for example, a sulfonylurea herbicide.

The time at which a herbicide is applied to an area of interest (and any plants therein) may be important in optimizing weed control. The time at which a herbicide is applied may be determined with reference to the size of plants and/or the stage of growth and/or development of plants in the area of interest, e.g., crop plants or weeds growing in the area. The stages of growth and/or development of plants are known in the art. For example, soybean plants normally progress through vegetative growth stages known as $V_E$ (emergence), $V_C$ (unifoliolate), $V_1$ (first trifoliolate), and $V_2$ to $V_N$. Soybeans then switch to the reproductive growth phase in response to photoperiod cues; reproductive stages include $R_1$ (beginning bloom), $R_2$ (full bloom), $R_3$ (beginning pod), $R_4$ (full pod), $R_5$ (beginning seed), $R_6$ (full seed), $R_7$ (beginning maturity), and $R_8$ (full maturity). Thus, for example, the time at which a herbicide or other chemical is applied to an area of interest in which plants are growing may be the time at which some or all of the plants in a particular area have reached at least a particular size and/or stage of growth and/or development, or the time at which some or all of the plants in a particular area have not yet reached a particular size and/or stage of growth and/or development.

In some embodiments, the 3560.4.3.5 soybean plants show improved tolerance to postemergence herbicide treatments. For example, the 3560.4.3.5 plants may be tolerant to higher doses of herbicide, tolerant to a broader range of herbicides (i.e., tolerance to more ALS inhibitor chemistries), and/or may be tolerant to doses of herbicide applied at earlier or later times of development in comparison to an appropriate control plant. For example, in some embodiments, the 3560.4.3.5 soybean plants show an increased resistance to morphological defects that are known to result from treatment at particular stages of development.

Different chemicals such as herbicides have different "residual" effects, i.e., different amounts of time for which treatment with the chemical or herbicide continues to have an effect on plants growing in the treated area. Such effects may be desirable or undesirable, depending on the desired future purpose of the treated area (e.g., field or area of cultivation). Thus, a crop rotation scheme may be chosen based on residual effects from treatments that will be used for each crop and their effect on the crop that will subsequently be grown in the same area. One of skill in the art is familiar with techniques that can be used to evaluate the residual effect of a herbicide; for example, generally, glyphosate has very little or no soil residual activity, while herbicides that act to inhibit ALS vary in their residual activity levels. Residual activities for various herbicides are known in the art, and are also known to vary with various environmental factors such as, for example, soil moisture levels, temperature, pH, and soil composition (texture and organic matter). The 3560.4.3.5 soybean plants find particular use in methods of growing a crop where improved tolerance to residual activity of a herbicide is beneficial.

For example, in one embodiment, the 3560.4.3.5 soybean plants have an improved tolerance to glyphosate as well as to ALS inhibitor chemistries (such as sulfonylurea herbicides) when applied individually, and further provide improved tolerance to combinations of herbicides such as glyphosate and/or ALS inhibitor chemistries. Moreover, the transgenic plants disclosed herein provide improved tolerance to treatment with additional chemicals commonly used on crops in conjunction with herbicide treatments, such as safeners, adjuvants such as ammonium sulfonate and crop oil concentrate, and the like.

The term "safener" refers to a substance that when added to a herbicide formulation eliminates or reduces the phytotoxic effects of the herbicide to certain crops. One of ordinary skill in the art would appreciate that the choice of safener depends, in part, on the crop plant of interest and the particular herbicide or combination of herbicides included in the synergistic herbicide composition. Exemplary safeners suitable for use with the presently disclosed herbicide compositions include, but are not limited to, those disclosed in U.S. Pat. Nos. 4,808,208; 5,502,025; 6,124,240 and U.S. Patent Application Publication Nos. 2006/0148647; 2006/0030485; 2005/0233904; 2005/0049145; 2004/0224849; 2004/0224848; 2004/0224844; 2004/0157737; 2004/0018940; 2003/0171220; 2003/0130120; 2003/0078167, the disclosures of which are incorporated herein by reference in their entirety. The methods can involve the use of herbicides in combination with herbicide safeners such as benoxacor, BCS (1-bromo-4-[(chloromethyl)sulfonyl]benzene), cloquintocet-mexyl, cyometrinil, dichlormid, 2-(dichloromethyl)-2-methyl-1,3-dioxolane (MG 191), fenchlorazole-ethyl, fenclorim, flurazole, fluxofenim, furilazole, isoxadifen-ethyl, mefenpyr-diethyl, methoxyphenone ((4-methoxy-3-methylphenyl)(3-methylphenyl)-methanone), naphthalic anhydride (1,8-naphthalic anhydride) and oxabetrinil to increase crop safety. Antidotally effective amounts of the herbicide safeners can be applied at the same time as the compounds, or applied as seed treatments. Therefore an aspect of the present invention relates to the use of a mixture comprising glyphosate, at least one other herbicide, and an antidotally effective amount of a herbicide safener.

Seed treatment is particularly useful for selective weed control, because it physically restricts antidoting to the crop plants. Therefore a particularly useful embodiment is a method for selectively controlling the growth of weeds in a field comprising treating the seed from which the crop is grown with an antidotally effective amount of safener and treating the field with an effective amount of herbicide to control weeds. Antidotally effective amounts of safeners can be easily determined by one skilled in the art through simple experimentation. An antidotally effective amount of a safener is present where a desired plant is treated with the safener so that the effect of a herbicide on the plant is decreased in comparison to the effect of the herbicide on a plant that was not treated with the safener; generally, an antidotally effective amount of safener prevents damage or severe damage to the plant treated with the safener. One of skill in the art is capable of determining whether the use of a safener is appropriate and determining the dose at which a safener should be administered to a crop.

In specific embodiments, the herbicide or herbicide combination applied to the 3560.4.3.5 plant acts as a safener. In this embodiment, a first herbicide or a herbicide mixture is applied at an antidotally effect amount to the plant. Accordingly, a method for controlling weeds in an area of cultivation is provided. The method comprises planting the area with crop seeds or plants which comprise a first polynucleotide encoding a polypeptide that can confer tolerance to glyphosate operably linked to a promoter active in a plant; and, a second polynucleotide encoding an ALS inhibitor-tolerant polypeptide operably linked to a promoter active in a plant. A combination of herbicides comprising at least an effective amount of a first and a second herbicide is applied to the crop, crop part, weed or area of cultivation thereof. The effective amount of the herbicide combination controls weeds; and, the effective amount of the first herbicide is not tolerated by the crop when applied alone when compared to a control crop that has not been exposed to the first herbicide; and, the effective amount of the second herbicide is sufficient to produce a safening effect, wherein the safening effect provides an increase in crop tolerance upon the application of the first and the second herbicide when compared to the crop tolerance when the first herbicide is applied alone.

In specific embodiments, the combination of safening herbicides comprises a first ALS inhibitor and a second ALS inhibitor. In other embodiments, the safening effect is achieved by applying an effective amount of a combination of glyphosate and at least one ALS inhibitor chemistry. In still other embodiments, a safening affect is achieved when the 3560.4.3.5 soybean crops, crop part, crop seed, weed, or area of cultivation is treated with at least one herbicide from the sulfonylurea family of chemistries in combination with at least one herbicide from the ALS family of chemistries (such as, for example, an imidazolinone).

Such mixtures provide increased crop tolerance (i.e., a decrease in herbicidal injury). This method allows for increased application rates of the chemistries post or pretreatment. Such methods find use for increased control of unwanted or undesired vegetation. In still other embodiments, a safening affect is achieved when the 3560.4.3.5 soybean crops, crop part, crop seed, weed, or area of cultivation is treated with at least one herbicide from the sulfonylurea family of chemistry in combination with at least one herbicide from the imidazolinone family. This method provides increased crop tolerance (i.e., a decrease in herbicidal injury). In specific embodiments, the sulfonylurea comprises rimsulfuron and the imidazolinone comprises imazethapyr. In other embodiments, glyphosate is also applied to the crop, crop part, or area of cultivation.

As used herein, an "adjuvant" is any material added to a spray solution or formulation to modify the action of an agricultural chemical or the physical properties of the spray solution. See, for example, Green and Foy (2003) "Adjuvants: Tools for Enhancing Herbicide Performance," in *Weed Biology and Management*, ed. Inderjit (Kluwer Academic Publishers, The Netherlands). Adjuvants can be categorized or subclassified as activators, acidifiers, buffers, additives, adherents, antiflocculants, antifoamers, defoamers, antifreezes, attractants, basic blends, chelating agents, cleaners, colorants or dyes, compatibility agents, cosolvents, couplers, crop oil concentrates, deposition agents, detergents, dispersants, drift control agents, emulsifiers, evaporation reducers, extenders, fertilizers, foam markers, formulants, inerts, humectants, methylated seed oils, high load COCs, polymers, modified vegetable oils, penetrators, repellants, petroleum oil concentrates, preservatives, rainfast agents, retention aids, solubilizers, surfactants, spreaders, stickers, spreader stickers, synergists, thickeners, translocation aids, uv protectants, vegetable oils, water conditioners, and wetting agents.

In addition, methods can comprise the use of a herbicide or a mixture of herbicides, as well as, one or more other insecticides, fungicides, nematocides, bactericides, acaricides, growth regulators, chemosterilants, semiochemicals, repellents, attractants, pheromones, feeding stimulants or other biologically active compounds or entomopathogenic bacteria, virus, or fungi to form a multi-component mixture giving an even broader spectrum of agricultural protection. Examples of such agricultural protectants which can be used in methods include: insecticides such as abamectin, acephate, acetamiprid, amidoflumet (S-1955), avermectin, azadirachtin, azinphos-methyl, bifenthrin, bifenazate, buprofezin, carbofuran, cartap, chlorfenapyr, chlorfluazuron, chlorpyrifos, chlorpyrifos-methyl, chromafenozide, clothianidin, cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, metaflumizone, metaldehyde, methamidophos, methidathion, methomyl, methoprene, methoxychlor, metofluthrin, monocrotophos, methoxyfenozide, nitenpyram, nithiazine, novaluron, noviflumuron (XDE-007), oxamyl, parathion, parathion-methyl, permethrin, phorate, phosalone, phosmet, phosphamidon, pirimicarb, profenofos, profluthrin, pymetrozine, pyrafluprole, pyrethrin, pyridalyl, pyriprole, pyriproxyfen, rotenone, ryanodine, spinosad, spirodiclofen, spiromesifen (BSN 2060), spirotetramat, sulprofos, tebufenozide, teflubenzuron, tefluthrin, terbufos, tetrachlorvinphos, thiacloprid, thiamethoxam, thiodicarb, thiosultap-sodium, tralomethrin, triazamate, trichlorfon and triflumuron; fungicides such as acibenzolar, aldimorph, amisulbrom, azaconazole, azoxystrobin, benalaxyl, benomyl, benthiavalicarb, benthiavalicarbisopropyl, binomial, biphenyl, bitertanol, blasticidin-S, Bordeaux mixture (Tribasic copper sulfate), boscalid/nicobifen, bromuconazole, bupirimate, buthiobate, carboxin, carpropamid, captafol, captan, carbendazim, chloroneb, chlorothalonil, chlozolinate, clotrimazole, copper oxychloride, copper salts such as copper sulfate and copper hydroxide, cyazofamid, cyflunamid, cymoxanil, cyproconazole, cyprodinil, dichlofluanid, diclocymet, diclomezine, dicloran, diethofencarb, difenoconazole, dimethomorph, dimoxystrobin, diniconazole, diniconazole-M, dinocap, discostrobin, dithianon, dodemorph, dodine, econazole, etaconazole, edifenphos, epoxiconazole, ethaboxam, ethirimol, ethridiazole, famoxadone, fenamidone, fenarimol, fenbuconazole, fencaramid, fenfuram, fenhexamide, fenoxanil, fenpiclonil, fenpropidin, fenpropimorph, fentin acetate, fentin hydroxide, ferbam, ferfurazoate, ferimzone, fluazinam, fludioxonil, flumetover, fluopicolide, fluoxastrobin, fluquinconazole, fluquinconazole, flusilazole, flusulfamide, flutolanil, flutriafol, folpet, fosetyl-aluminum, fuberidazole, furalaxyl, furametapyr, hexaconazole, hymexazole, guazatine, imazalil, imibenconazole, iminoctadine, iodicarb, ipconazole, iprobenfos, iprodione, iprovalicarb, isoconazole, isoprothiolane, kasugamycin, kresoxim-methyl, mancozeb, mandipropamid, maneb, mapanipyrin, mefenoxam, mepronil, metalaxyl, metconazole, methasulfocarb, metiram, metominostrobin/fenominostrobin, mepanipyrim, metrafenone, miconazole, myclobutanil, neo-asozin (ferric methanearsonate), nuarimol, octhilinone, ofurace, orysastrobin, oxadixyl, oxolinic acid, oxpoconazole, oxycarboxin, paclobutrazol, penconazole, pencycuron, penthiopyrad, perfurazoate, phosphonic acid, phthalide, picobenzamid, picoxystrobin, polyoxin, probenazole, prochloraz, procymidone, propamocarb, propamocarb-hydrochloride, propiconazole, propineb, proquinazid, prothioconazole, pyraclostrobin, pryazophos, pyrifenox, pyrimethanil, pyrifenox, pyrolnitrine, pyroquilon, quinconazole, quinoxyfen, quintozene, silthiofam, simeconazole, spiroxamine, streptomycin, sulfur, tebuconazole, techrazene, tecloftalam, tecnazene, tetraconazole, thiabendazole, thifluzamide, thiophanate, thiophanate-methyl, thiram, tiadinil, tolclofos-methyl, tolyfluanid, triadimefon, triadimenol, triarimol, triazoxide, tridemorph, trimoprhamide tricyclazole, trifloxystrobin, triforine, triticonazole, uniconazole, validamycin, vinclozolin, zineb, ziram, and zoxamide; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents including entomopathogenic bacteria, such as *Bacillus thuringiensis* subsp. *Aizawai*, *Bacillus thuringiensis* subsp. *Kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and ganulosis virus (GV) such as CpGV. The weight ratios of these various mixing partners to other compositions (e.g., herbicides) used in the methods typically are between 100:1 and 1:100, or between 30:1 and 1:30, between 10:1 and 1:10, or between 4:1 and 1:4.

Further provide are compositions comprising a biologically effective amount of a herbicide of interest or a mixture of herbicides, and an effective amount of at least one additional biologically active compound or agent and can further comprise at least one of a surfactant, a solid diluent or a liquid diluent. Examples of such biologically active compounds or agents are: insecticides such as abamectin, acephate, acetamiprid, amidoflumet (S-1955), avermectin, azadirachtin, azinphos-methyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenvalerate, fipronil, flonicamid, flucythrinate, tau-fluvalinate, flufenerim (UR-50701), flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, noviflumuron (XDE-007), oxamyl, parathion, parathion-methyl, permethrin, phorate, phosalone, phosmet, phosphamidon, pirimicarb, profenofos, pymetrozine, pyridalyl, pyriproxyfen, rotenone, spinosad, spiromesifin (BSN 2060), sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron; fungicides such as acibenzolar, azoxystrobin, benomyl, blasticidin-S, Bordeaux mixture (tribasic copper sulfate), bromuconazole, carpropamid, captafol, captan, carbendazim, chloroneb, chlorothalonil, copper oxychloride, copper salts, cyflufenamid, cymoxanil, cyproconazole, cyprodinil, (S)-3,5-dichloro-N-(3-chloro-1-ethyl-1-methyl-2-oxopropyl)-4-methylbenzamide (RH 7281), diclocymet (S-2900), diclomezine, dicloran, difenoconazole, (S)-3,5-dihydro-5-methyl-2-(methylthio)-5-phenyl-3-(phenyl-amino)-4H-imidazol-4-one (RP 407213), dimethomorph, dimoxystrobin, diniconazole, diniconazole-M, dodine, edifenphos, epoxiconazole, famoxadone, fenamidone, fenarimol, fenbuconazole, fencaramid (SZX0722), fenpiclonil, fenpropidin, fenpropimorph, fentin acetate, fentin hydroxide, fluazinam, fludioxonil, flumetover (RPA 403397), flumorf/flumorlin (SYP-L190), fluoxastrobin (HEC 5725), fluquinconazole, flusilazole, flutolanil, flutriafol, folpet, fosetyl-aluminum, furalaxyl, furametapyr (S-82658), hexaconazole, ipconazole, iprobenfos, iprodione, isoprothiolane, kasugamycin, kresoxim-methyl, mancozeb, maneb, mefenoxam, mepronil, metalaxyl, metconazole, metominostrobin/fenominostrobin (SSF-126), metrafenone (AC375839), myclobutanil, neo-asozin (ferric methane-arsonate), nicobifen (BAS 510), orysastrobin, oxadixyl, penconazole, pencycuron, probenazole, prochloraz, propamocarb, propiconazole, proquinazid (DPX-KQ926), prothioconazole (JAU 6476), pyrifenox, pyraclostrobin, pyrimethanil, pyroquilon, quinoxyfen, spiroxamine, sulfur, tebuconazole, tetraconazole, thiabendazole, thifluzamide, thiophanate-methyl, thiram, tiadinil, triadimefon, triadimenol, tricyclazole, trifloxystrobin, triticonazole, validamycin and vinclozolin; nematocides such as aldicarb, oxamyl and fenamiphos; bactericides such as streptomycin; acaricides such as amitraz, chinomethionat, chlorobenzilate, cyhexatin, dicofol, dienochior, etoxazole, fenazaquin, fenbutatin oxide, fenpropathrin, fenpyroximate, hexythiazox, propargite, pyridaben and tebufenpyrad; and biological agents including entomopathogenic bacteria, such as *Bacillus thuringiensis* subsp. *Aizawai*, *Bacillus thuringiensis* subsp. *Kurstaki*, and the encapsulated delta-endotoxins of *Bacillus thuringiensis* (e.g., Celicap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV. Methods may also comprise the use of plants genetically transformed to express proteins toxic to invertebrate pests (such as *Bacillus thuringiensis* delta-endotoxins). In such embodiments, the effect of exogenously applied invertebrate pest control compounds may be synergistic with the expressed toxin proteins.

General references for these agricultural protectants include *The Pesticide Manual*, 13th Edition, C. D. S. Tomlin, Ed., British Crop Protection Council, Farnham, Surrey, U.K., 2003 and *The BioPesticide Manual*, 2nd Edition, L. G. Copping, Ed., British Crop Protection Council, Farnham, Surrey, U.K., 2001.

In certain instances, combinations with other invertebrate pest control compounds or agents having a similar spectrum of control but a different mode of action will be particularly advantageous for resistance management. Thus, compositions can further comprise a biologically effective amount of at least one additional invertebrate pest control compound or agent having a similar spectrum of control but a different mode of action. Contacting a plant genetically modified to express a plant protection compound (e.g., protein) or the locus of the plant with a biologically effective amount of a compound can also provide a broader spectrum of plant protection and be advantageous for resistance management.

Thus, methods can employ a herbicide or herbicide combination and may further comprise the use of insecticides and/or fungicides, and/or other agricultural chemicals such as fertilizers. The use of such combined treatments can broaden the spectrum of activity against additional weed species and suppress the proliferation of any resistant biotypes.

Methods can further comprise the use of plant growth regulators such as aviglycine, N-(phenylmethyl)-1H-purin-6-amine, ethephon, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as *Bacillus cereus* strain BP01.

In further embodiments, methods and compositions for increasing yield in a plant are provided. Specifically, soybean plants having the 3560.4.3.5 event and further comprising a second sequence which encodes a polypeptide that imparts tolerance to glyphosate via a distinct mode of action from the glyphosate N-acetyltransferase are provided. Such plants produce an increase in yield in the presence of an effective amount of glyphosate when compared to an appropriate control plant. Accordingly, further provided are various methods of increasing yield employing such plants.

As used herein, the term "yield" refers to the measurable produce of economic value from a crop. This term may be defined in terms of quantity and/or quality. As used herein, the term "improved yield" means any improvement in the yield of any measured plant product when compared to an appropriate control. The improvement in yield can comprise an increase between about 0.1% to about 90%, about 0.5% to about 10%, about 10% to about 20%, about 20% to about 30%, about 30% to about 40%, about 40% to about 50%, about 50% to about 60%, about 60% to about 70%, about 70% to about 80%, about 80% to about 90% or greater increase in measured plant product. In other embodiments, the increase in yield can comprise at least a 0.1%. 0.5%, 1%, 3%, 5%. 10%, 15%, 20%, 30%, 40%, 50%, 60%, 70%, 80%, 90% or greater increase in the measured plant product. Alternatively, the improved plant yield can comprise between a 0.1 fold to 64 fold, about a 0.1 fold to about a 10 fold, about a 10 fold to about a 20 fold, about a 20 fold to about a 30 fold, about a 30 fold to about a 40 fold, about a 40 fold to about a 50 fold, about a 50 fold to about a 60 fold, about a 60 fold to about a 64 fold increase in measured plant products.

An improved yield relative to a proper control plant can be measured as (i) increased biomass (weight) of one or more parts of a plant, including aboveground parts or increased biomass of any other harvestable part; (ii) increased seed yield, which includes an increase in seed biomass (seed weight) and which may be an increase in the seed weight per plant or on an individual seed basis or an increase in seed weight per hectare or acre; (iii) increased number of flowers (florets) per panicle, which is expressed as a ratio of the number of filled seeds over the number of primary panicles; (iv) increased number of (filled) seeds; (v) increased fill rate of seeds (which is the number of filled seeds divided by the total number of seeds and multiplied by 100); (vi) increased seed size, which may also influence the composition of seeds; (vii) increased seed volume, which may also influence the composition of seeds (for example due to an increase in amount or a change in the composition of oil, protein or carbohydrate); (viii) increased seed area; (ix) increased seed length; (x) increased seed width; (x) increased seed perimeter; (xi) increased harvest index, which is expressed as a ratio of the yield of harvestable parts, such as seeds, over the total biomass; and (xii) increased thousand kernel weight (TKW), which is extrapolated from the number of filled seeds counted and their total weight. An increased TKW may result from an increased seed size and/or seed weight and may also result from an increase in embryo size and/or endosperm size. For example, an increase in the bu/acre yield of corn derived from a crop having sequence that confer a multi-mode of action glyphosate tolerance as compared with the bu/acre yield from corn having only one of the glyphosate tolerant sequences cultivated under the same conditions would be considered an improved yield.

A "glyphosate-tolerance polypeptide" is a polypeptide that confers glyphosate tolerance on a plant (i.e., that makes a plant glyphosate-tolerant), and a "glyphosate-tolerance polynucleotide" is a polynucleotide that encodes a glyphosate-tolerance polypeptide. "Mode of action" refers to the specific metabolic or physiological process within the plant by which the glyphosate-tolerant polypeptide acts to protect the plant from glyphosate. Thus, polypeptides having "distinct" modes of action for providing glyphosate tolerance comprise any two or more polypeptides that protect a plant from glyphosate by a number of mechanisms including detoxifying the chemical via different metabolic or physiological processes. For example, glyphosate N-acetyl transferase polypeptides acetylate glyphosate and thereby detoxify the herbicide, while glyphosate-tolerant EPSPS polypeptides prevent or decrease the ability of glyphosate to inhibit the shikimic acid pathway. In light of the distinct mechanism of action of these two enzymes, these polypeptides represent two non-limiting examples of polypeptides that confer tolerance to glyphosate via distinct modes of action.

Methods of increasing yield comprise planting the area of cultivation with the multi-mode of action glyphosate-tolerant 3560.4.3.5 soybean seeds or plants, and applying to any of the soybean plant, soybean part, weed or area of cultivation thereof an effective amount of glyphosate. It is recognized that the herbicide can be applied before or after the crop is planted in the area of cultivation. A "control" or "control plant" or "control plant cell" provides a reference point for measuring changes in phenotype (i.e., improved yield) of the subject plant or plant cell, and may be any suitable plant or plant cell. An improved yield can be evaluated by statistical analysis of suitable parameters. The plant being evaluated is referred to as the "test plant." Typically, when measuring an improved yield, an appropriate control plant is one that expresses one of the glyphosate-tolerance sequences that is present in the test plant but lacks or does not express additional (second, third, etc.) glyphosate-tolerance sequences in the test plant. For example, in evaluating multi-mode of action glyphosate-tolerant 3560.4.3.5 soybean plant for an increased yield, an appropriate control plant would be a plant that expresses GLYAT and not EPSPS or one that expresses EPSPS and not GLYAT, or one that expresses GLYAT and not glyphosate oxido-reductase or one that expresses glyphosate oxido-reductase and not GLYAT. One skilled in the art will be able to design, perform, and evaluate a suitable controlled experiment to assess the glyphosate tolerance of a plant of interest and the improved yield, including the selection of appropriate test plants, control plants, and treatments.

The improved yield of the multi-mode of action glyphosate-tolerant 3560.4.3.5 soybean plant can be assessed at various times after a plant has been treated with the glyphosate. Improved yield is ultimately determined as productivity relative for the product (fresh cut weight, silage yield, mature grain harvest). Improved yield determination can occur at any stage of maturity of the test plant by assessing yield component measures. Any time of assessment is suitable as long as it permits detection of an improved yield of test plants as compared to the control plants. Flower number could be measured at R2. Plant biomass could be measured at anytime during the growing season but measurements would be applicable to only that exact point in crop stage. Seed yield, seed size, and seed number is reliably measured at crop growth stage R7 and R8. In the case of crops such as vegetables, plant fresh weight is determined at or before peak produce harvest.

As used herein, an "effective amount of glyphosate" in reference to improving yield is one that is sufficient to improve the yield in the plants having the glyphosate-tolerant sequences which act via two distinct modes of action and further comprises an amount that is tolerated by the plant, and in specific embodiments, the effective amount is further capable of controlling weeds in the area of cultivation. It is further recognized that when the multi-mode of action glyphosate tolerant plants further comprises additional traits that impart tolerance to other herbicides, the methods of the invention can comprise applying to such plants glyphosate plus an additional appropriate herbicide. In such cases, an "effective amount of a herbicide" is one that is tolerated by the plant and controls weeds in the area of cultivation.

"Herbicide-tolerant" or "tolerant" or "crop tolerance" in the context of herbicide or other chemical treatment as used herein means that a plant or other organism treated with a particular herbicide or class or subclass of herbicide or other chemical or class or subclass of other chemical will show no significant damage or less damage following that treatment in comparison to an appropriate control plant.

Thus, a plant is tolerant to a herbicide if it shows damage in comparison to an appropriate control plant that is less than the damage exhibited by the control plant by at least 5%, 10%, 15%, 20%, 25%, 30%, 35%, 40%, 45%, 50%, 55%, 60%, 65%, 70%, 75%, 80%, 90%, 100%, 150%, 200%, 250%, 300%, 400%, 500%, 600%, 700%, 800%, 900%, or 1000% or more. In this manner, a plant that is tolerant to a herbicide or other chemical shows "improved tolerance" in comparison to an appropriate control plant. Damage resulting from herbicide or other chemical treatment is assessed by evaluating any parameter of plant growth or well-being deemed suitable by one of skill in the art. Damage can be assessed by visual inspection and/or by statistical analysis of suitable parameters of individual plants or of a group of plants. Thus, damage may be assessed by evaluating, for example, parameters such as plant height, plant weight, leaf color, leaf length, flowering, fertility, silking, yield, seed production, and the like. Damage may also be assessed by evaluating the time elapsed to a particular stage of development (e.g., silking, flowering, or pollen shed) or the time elapsed until a plant has recovered from treatment with a particular chemical and/or herbicide.

In making such assessments, particular values may be assigned to particular degrees of damage so that statistical analysis or quantitative comparisons may be made. The use of ranges of values to describe particular degrees of damage is known in the art, and any suitable range or scale may be used. For example, herbicide injury scores (also called tolerance scores) can be assigned using the scale set forth are known in the art.

By "no significant damage" is intended that the concentration of herbicide either has no effect on the plant or when it has some effect on a plant from which the plant later recovers, or when it has an effect which is detrimental but which is offset, for example, by the impact of the particular herbicide on weeds. Thus, for example, a crop plant is not "significantly damaged by" a herbicide or other treatment if it exhibits less than 50%, 40%, 35%, 30%, 25%, 20%, 15%, 10%, 9%, 8%, 7%, 6%, 5%, 4%, 3%, 2%, or 1% decrease in at least one suitable parameter that is indicative of plant health and/or productivity in comparison to an appropriate control plant (e.g., an untreated crop plant). Suitable parameters that are indicative of plant health and/or productivity include, for example, plant height, plant weight, leaf length, time elapsed to a particular stage of development, flowering, yield, seed production, and the like. The evaluation of a parameter can be by visual inspection and/or by statistical analysis of any suitable parameter. Comparison may be made by visual inspection and/or by statistical analysis. Accordingly, a crop plant is not "significantly damaged by" a herbicide or other treatment if it exhibits a decrease in at least one parameter but that decrease is temporary in nature and the plant recovers fully within 1 week, 2 weeks, 3 weeks, 4 weeks, 5 weeks, or 6 weeks.

Conversely, a plant is significantly damaged by a herbicide or other treatment if it exhibits more than a 50%, 55%, 60%, 65%, 70%, 75%, 80%, 85%, 90%, 95%, 100%, 105%, 110%, 115%, 120%, 125%, 130%, 135%, 140%, 145%, 150%, or higher decrease in at least one suitable parameter that is indicative of plant health and/or productivity in comparison to an appropriate control plant (e.g., an untreated weed of the same species). Thus, a plant is significantly damaged if it exhibits a decrease in at least one parameter and the plant does not recover fully within 1 week, 2 weeks, 3 weeks, 4 weeks, 5 weeks, or 6 weeks.

Glyphosate can be applied to the multi-mode of action glyphosate-tolerant 3560.4.3.5 soybean plants or their area of cultivation. Non-limiting examples of glyphosate formations are set forth above in Table 2. In specific embodiments, the glyphosate is in the form of a salt, such as, ammonium, isopropylammonium, potassium, sodium (including sesquisodium) or trimesium (alternatively named sulfosate).

In some embodiments, a method of improving yield in a multi-mode of action glyphosate-tolerant 3560.4.3.5 soybean plant comprises a treatment with the glyphosate applied to that plant at a dose equivalent to a rate of at least 210, 420, 840, 1260, 1680, 2100, 2520, 2940, 3360, 3780, 4200, 4620, 5040, 5460, 5880, 6300, 6720, or more grams of acid equivalent of glyphosate in a commercial herbicide formulation herbicide per hectare.

In other embodiments, glyphosate is applied to an area of cultivation and/or to at least one multi-mode of action glyphosate tolerant 3560.4.3.5 soybean plant in an area of cultivation at rates between 210 and 3360, between 210 and 500, between 500 and 1000, between 1000 and 1500, between 1500 and 2000, between 2000 and 2500, between 2500 and 3000, and between 3000 and 3360 grams acid equivalent per hectare at the lower end of the range of application and between 3780 and 6720, 3780 and 4000, between 4000 and 4500, between 4500 and 5000, between 5000 and 5500, between 5500 and 6000, between 6500 and 6720 grams of acid equivalent per hectare at the higher end of the range of application. In one embodiment, the range of glyphosate application for soybean is a single dose of up to 1680 grams acid equivalent per hectare, and a full in-crop season dose up to 2520 grams acid equivalent per hectare.

Methods to improve yield allow for the application of glyphosate pre-plant, at plant or any time after planting multi-mode of action glyphosate tolerant 3560.4.3.5 soybean seeds are planted in an area of cultivation. Such timing of applications are discussed in further detail elsewhere herein. The time at which glyphosate is applied may be determined with reference to the size of plants and/or the stage of growth and/or development of plants in the area of interest, e.g., crop plants or weeds growing in the area. The stages of growth and/or development of soybean plants are known in the art and are discussed in further detail elsewhere herein. Thus, for example, the time at which glyphosate is applied to an area of interest which plants are growing to increase the yield of the plant may be the time at which some or all of the plants in a particular area have reached at least a particular size and/or stage of growth and/or development, or the time at which some or all of the plants in a particular area have not yet reached a particular size and/or stage of growth and/or development.

As discussed above, the multi-mode of action glyphosate-tolerant 3560.4.3.5 soybean plant can further comprise sequences that impart tolerance to additional herbicides. Thus, depending on the additional sequences present in the plant, the methods of the invention can further comprise applying additional herbicides of interest to the plant and thereby improve yield and control weeds in an area of cultivation. Thus, as discussed above, the methods of the invention encompass the use of simultaneous and/or sequential applications of multiple classes of herbicides.

When glyphosate is used with additional herbicides of interest, the application of the herbicide combination need not occur at the same time. So long as the field in which the crop is planted contains detectable amounts of the first herbicide and the second herbicide is applied at some time during the period in which the crop is in the area of cultivation, the crop is considered to have been treated with a mixture of herbicides according to the invention.

The classifications of herbicides (i.e., the grouping of herbicides into classes and subclasses) is well-known in the art and includes classifications by HRAC (Herbicide Resistance Action Committee) and WSSA (the Weed Science Society of America) (see also, Retzinger and Mallory-Smith (1997) *Weed Technology* 11: 384-393). An abbreviated version of the HRAC classification (with notes regarding the corresponding WSSA group) is set forth below in Table 2. A more comprehensive list of specific herbicides can be found for example, in U.S. Application Publication 2007/0130641, herein incorporated by reference. In some embodiments, when additional herbicides are applied to increase yield, the rate of application will be sufficient to control weeds and such rates of application are disclosed elsewhere herein.

In non-limiting embodiments, the multi-mode of action glyphosate-tolerant 3560.4.3.5 soybean plant comprises a sequence encoding a glyphosate N-acetyl transferase polypeptide and an EPSPS polypeptide, where the plant or the area of cultivation is treated with an effective amount of glyphosate to thereby improve the yield of the plant. Such methods to improve yield can comprise applying to the plant or area of cultivation an effective amount of glyphosate to thereby improve the yield of said plant and further applying an effective concentration of an additional herbicide, such as an ALS chemistry, to effectively control the weeds in said area of cultivation. Since ALS inhibitor chemistries have different herbicidal attributes, blends of ALS inhibitors plus other chemistries can provide superior weed management strategies including varying and increased weed spectrum, the ability to provide specified residual activity (SU/ALS inhibitor chemistry with residual activity leads to improved herbicidal activity which leads to a wider window between glyphosate applications, as well as, an added period of control if weather conditions prohibit timely application).

Embodiments are further defined in the following Examples. It should be understood that these Examples are given by way of illustration only. From the above discussion and these Examples, one skilled in the art can ascertain the essential characteristics, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

EXPERIMENTAL

Example 1

Insert and Flanking Border Sequence Characterization of Soybean Event 3560.4.3.5

Soybean event 3560.4.3.5, hereafter referred to as 3560.4.3.5 soybean, was obtained by microprojectile bombardment with the Not I-Asc I fragment from plasmid PHP20163. This fragment, PHP20163A, contains the glyphosate acetlytransferase (glyat 4601) gene under the control of the SCP1 promoter that is a synthetic constitutive promoter comprising a portion of the CaMV 35S promoter (Odell et al. (1985) Nature 313:810-812) and the Rsyn7-Syn II Core synthetic consensus promoter (U.S. Pat. Nos. 6,072,050 and 6,555,673). See also, for example, US20030226166, Table 13, and SEQ ID NO:3. Downstream of this element is the Tobacco Mosaic Virus (TMV) omega 5'UTR translational enhancer element (Gallie et al. (1992) *Nucleic Acid Research* 20:4631-4638) and the proteinase inhibitor II (pinII) terminator from *Solanum tuberosum* (Keil et al. (1986) *Nucleic Acid Research* 14:5641-5650 and An et al. (1989) *Plant Cell* 1:115-122). PHP20163A also contains the gm-hra gene that is a modified version of the acetolactate synthase gene from soybean with 15 additional nucleotides on the 5' end (2697-2711) derived from the als 5' UTR and two nucleotides changes within the coding sequence under the control of the S-adenosyl-L-methionine synthetase (SAMS) promoter (US Application Publication 2003/0226166) with its 5'UTR and intron (SAMS Pro) and the acetolactate synthase (gm-als) terminator, both from soybean.

To characterize the integrity of the inserted DNA from PHP20163A and the genomic insertion site, the sequence of the insert and flanking genomic DNA border regions of 3560.4.3.5 soybean was determined. In total, 10849 base pairs (bp) of 3560.4.3.5 soybean was sequenced, comprising 5362 bp of DNA insert from PHP20163A, 3317 bp of 5' flanking genomic border sequence, and 2170 bp of 3' flanking genomic border sequence. When compared to the expected sequence from the DNA fragment used for transformation, the insert was confirmed to be intact and identical to PHP20163A and precisely integrated into the soy genome.

PCR amplification from the 3560.4.3.5 soybean insert and border sequences confirmed that the border regions were of soybean origin and that the junction regions could be used for identification of 3560.4.3.5 soybean.

BLASTn analysis of the border regions resulted in significant identities to public and proprietary soybean genomic sequences. Overall, characterization of the insert and genomic border sequence of 3560.4.3.5 soybean along with Southern blot data (data not show) indicated that a single insertion of the DNA fragment, PHP20613A, was present in the soybean genome.

The following abbreviations are used in describing the present invention.
ALS acetolactate synthase protein
bp base pair
glyat glyphosate acetyltransferase gene
GLYAT glyphosate acetyltransferase protein
GLYAT4601 glyphosate acetyltransferase protein derived from glyat4601 gene
gm-als wild type acetolactate synthase gene from soybean
gm-hra modified version of acetolactate synthase gene from soybean
kb kilobase
PCR polymerase chain reaction
UTR untranslated region
als acetolactate synthase gene
AMS ammonium sulfate
DAT days after treatment
glyat4601 glyphosate acetyl transferase gene from the 7$^{th}$ round of DNA shuffling a glyat gene family isolated from *Bacillus licheniformis* (Castle et al. (2004) *Science* 304: 1151-1154; Siehl et al. (2005) *Pest Manag. Sci.* 61:235-240).
GLYAT4601 glyphosate acetyl transferase protein from the 7$^{th}$ round of DNA shuffling a glyat gene family isolated from *Bacillus licheniformis* (Castle et al. (2004) *Science* 304:1151-1154; Siehl et al. (2005) *Pest Manag. Sci.* 61:235-240).
hra highly resistant allele of the acetolactate synthase gene
glyat+gm-hra transgenic event expressing both the glyat4601 and gm-hra genes
NILs near isogenic lines
NIS non-ionic surfactant
SAMS S-adenosyl-L-methionine synthase promoter (US Patent Application No 2003/0226166)
SCP1 Synthetic constitutive promoter I (U.S. Pat. Nos. 6,072,050 and 6,555,673 B1.

Soybean (*Glycine max*) has been modified by the insertion of the glyphosate acetyltransferase (glyat4601) gene derived from *Bacillus licheniformis* and a modified version of the soybean acetolactate synthase gene (gm-hra). The glyat4601 gene was functionally improved by a gene shuffling process to optimize the kinetics of glyphosate acetyltransferase (GLYAT) activity for acetylating the herbicide glyphosate. The insertion of the glya4601t gene in the plant confers tolerance to the herbicidal active ingredient glyphosate through the conversion of glyphosate to the non-toxic acetylated form. The insertion of the gm-hra gene produces a modified form of the acetolactate synthase enzyme. ALS is essential for branched chain amino acid biosynthesis and the modification in the gm-hra gene overcomes this inhibition and thus provides tolerance to a wide range of ALS-inhibiting herbicides.

The publicly available cultivar Jack was used as the recipient line for generation of 3560.4.3.5 soybean. The 3560.4.3.5 soybean was obtained by microprojectile bombardment with the Not I-Asc I fragment from plasmid PHP20163 (FIG. 1). This fragment, PHP20163A (FIG. 2), contains the glyat4601 gene under the control of the SCP1 promoter and Tobacco Mosaic Virus (TMV) omega 5' UTR translational enhancer element and the proteinase inhibitor II (pinII) terminator from *Solanum tuberosum*. PHP20163A also contains the gm-hra gene under the control of the S-adenosyl-L-methionine synthetase (SAMS) promoter and the acetolactate synthase (gm-als) terminator, both from soybean.

The transgenic 3560.4.3.5 soybean was generated using the Biolistics PDS-1000/He particle gun, manufactured by Bio-Rad (Hercules, Calif.), essentially as described by Klein et al. (1987). The targets for transformation were clumps of secondary somatic embryos derived from explants from small, immature soybean seeds of the cultivar Jack. The secondary somatic embryos were excised from immature explants, transferred to a liquid soybean culture maintenance medium, and subcultured at regular intervals until prepared for bombardment.

Soybean somatic embryogenic cultures were used in transformation experiments 2-4 months after initiation. On the day of transformation, microscopic gold particles were coated with the purified fragment PHP20163A DNA and accelerated into the embryogenic soybean cultures. Only PHP20163A DNA was used, and no additional DNA (e.g., carrier DNA) was used in the transformation process.

Following the transformation, the soybean tissue was transferred to flasks of fresh liquid culture maintenance medium for recovery. After seven days, the liquid culture medium was changed to culture maintenance medium supplemented with chlorsulfuron as the selection agent. Chlorsulfuron belongs to a family of ALS-inhibiting herbicides, and therefore only soybean cells that had stably inherited the gm-hra transgene continued to grow.

After several weeks in the culture maintenance medium supplemented with chlorsulfuron, small islands of healthy, chlorsulfuron-tolerant green tissue became visible and started to grow out of pieces of dying somatic embryogenic tissue. Green embryogenic clumps were excised from associated pieces of dying or dead tissue and received regular changes of fresh liquid selection medium until the start of the regeneration process. Embryogenic tissue samples were analyzed to confirm the presence of the glyat4601 and gm-hra transgenes by Southern blot hybridization. T0 plants were regenerated and transferred to the greenhouse for seed production. FIG. 5 describes a breeding diagram.

In the microprojectile bombardment transformation the 3560.4.3.5 soybean, DNA is inserted into the plant genome. The integration of the DNA fragment can occur at virtually any site in the plant genome. Once inserted, the genes that contain plant expression elements are recognized by the plant and may be expressed. Various molecular techniques are then used to specifically characterize the integration site in the 3560.4.3.5 soybean.

Southern blot analyses indicated that a single, intact PHP20163A fragment inserted into the soybean genome to produce the 3560.4.3.5 soybean (data not shown). Cloning and sequencing of the flanking genomic border regions of 3560.4.3.5 soybean and the inserted DNA was undertaken to characterize the insertion site in the soybean genome and obtain sequence that could be used to uniquely identify 3560.4.3.5 soybean.

Leaf tissue from the T5 generation of 3560.4.3,5 soybean was used as for additional sequence characterization. The T5 generation represents transformation of a Jack soybean variety, followed by two self-crossings. A single plant from this second self-crossing was selected fro three subsequent rounds of self-crossing and seed bulking. Southern blot analysis was used for event confirmation on plant leaf tissue of 3560.4.3.5 soybean (data not shown).

Leaf tissue from soybean plants that were not genetically modified was used as a control for sequence characterization. The unmodified soybean plants have a genetic background representative of 3560.4.3.5 soybean background; however, they do not contain the plant transcription units for the glyat4601 and gm-hra genes.

The 100 bp and 1 kb step DNA Ladders (Promega, Madison, Wis.) were used to estimate DNA fragment sizes on agarose gels.

Soybean seed for 3560.4.3.5 soybean and unmodified control seed were planted to produce sufficient numbers of plants for DNA analysis. For characterization of 3560.4.3.5 soybean line, eight T5 seeds were planted. Eight seeds were planted for control soybean line as well. One seed was planted per pot, and the pot was uniquely identified. Planting and growing conditions were conducive to healthy plant growth including regulated light and water.

Leaf samples were collected for each of the control and 3560.4.3.5 soybean plants. For each sample, sufficient leaf material from above the growing point was collected and placed in a pre-labeled sample bag. The samples were placed on dry ice and were transferred to an ultra low freezer following collection. All samples were maintained frozen until processing.

Frozen leaf samples (1-2 gram quantities) were ground, and the genomic DNA was isolated using a modified Urea Extraction Buffer procedure (Chen et al. (1994) Urea-based plant DNA miniprep in Reeling M. and Walbot V., eds, *The Maize Handbook*, Springer-Verlag, New York, p 526-527). Genomic DNA was extracted from leaf tissue harvested from individual plants as described above. Specifically, the tissue was pulverized in tubes containing grinding beads using a Geno/Grinder™ (SPEX CertiPrep, Inc., Metuchen, N.J.) instrument and the genomic DNA isolated using a standard procedure. Approximately 1 gram ground tissue was extracted with 5 mL Urea Extraction Buffer (7 M Urea, 0.34 M NaCl, 0.05 M Tris-HCl, pH 8.0, 0.02 M EDTA, 1% N-Lauroylsarcosine) for 12-30 minutes at 37° C., followed by two extractions with phenol/chloroform/isoamyl alcohol (25:24:1) and one extraction with water saturated chloroform. The DNA was precipitated from the aqueous phase by the addition of ⅒ volume of 3 M NaOAc (pH 5.2) and 1 volume of isopropyl alcohol, followed by centrifugation to pellet the DNA. After washing the pellet twice with 70% ethanol, the DNA was dissolved in 0.5 mL TE buffer (10 mM Tris, 1 mM EDTA, pH 7.5) and treated with 10 µg Ribonuclease A for 15 minutes at 37° C. The sample was extracted once with phenol:chloroform:isoamyl alcohol (25:24:1) and once with water saturated chloroform, followed by precipitation with isopropyl alcohol and washing with 70% ethanol. After drying, the DNA was re-dissolved with 0.5 mL TE buffer and stored at 4° C. Following extraction, the DNA was visualized on an agarose gel to determine the DNA quality, and was quantified using Pico Green® reagent (Molecular Probes, Inc., Eugene, Oreg.) and spectrofluorometric analysis.

Phenotypic analysis of 3560.4.3.5 soybean plants and control plants was carried out by western blot analysis using antibodies to the GLYAT4601 protein to confirm the absence or presence of the GLYAT4601 protein in material used for Southern blot analysis and sequence characterization. Total protein was extracted by grinding several leaf punches to homogeneity in 150 µl of protein extraction buffer (50 mM Tris-HCl (pH 7.5), 0.1% SDS, and 10 mM β-mercaptoethanol). An aliquot of each crude extract was mixed with LDS Sample Buffer and reducing agent (Invitrogen) and heated to approximately 95° C. for 5 minutes. Proteins were separated by size under denaturing conditions through a NuPAGE™ Bis/Tris Gel system as described (Invitrogen). Selected molecular weight standards were used to determine sufficient migration in the gel and for molecular weight determination on the western blot (Invitrogen). The Bis/Tris gel was transferred to a nitrocellulose membrane using the method as described for the Novex™ XCell II™ Blot Module Western Transfer (Invitrogen). Alternatively, gels were stained with SimplyBlue™ SafeStain (Invitrogen) to visualize the proteins to verify equivalent sample loading.

The GLYAT4601 protein band was detected using the WesternBreeze® Chemiluminescent Western Blot Immunodetection Kit as described (Invitrogen). Primary monoclonal antibodies specific for the GLYAT4601 protein were used with the WesternBreeze® Kit, Bands were then visualized using a chemiluminescent substrate. Blots were exposed to X-ray film for one or more time points to detect protein bands. Purified GLYAT4601 protein was used as a positive control on the western blots. Plants were scored as positive for GLYAT4601 when a band of the appropriate size was present and scored as negative when the band was absent on the western blots.

A preliminary Southern blot analysis of DNA isolated from all 3560.4.3.5 soybean plants was used to verify the presence of both the glyat4601 and gm-hra genes. Methods for this preliminary characterization are described below. Final Southern blot analysis was carried out on a subset of 3560.4.3.5 soybean plants (data not shown).

Genomic DNA samples extracted from selected 3560.4.3.5 soybean and control soybean plants were digested with restriction enzymes following a standard procedure. Approximately 2 µg of genomic DNA was digested in a volume of 100 µL using 50 units of enzyme according to manufacturer's recommendations. The digestions were carried out at 37° C. for three hours, followed by ethanol precipitation with ⅒ volume of 3 M NaOAc (pH 5.2) and 2 volumes of 100% ethanol. After incubation at 4° C. and centrifugation, the DNA was allowed to dry and re-dissolved in TE buffer. The reference plasmid, PHP20163, was spiked into a control plant DNA sample in an amount equivalent to approximately one or three gene copies per soybean genome and digested with the same enzyme to serve as a positive control for probe hybridization and to verify sizes of internal fragments on the Southern blot.

Following restriction enzyme digestion, the DNA fragments produced were electrophoretically separated by size through an agarose gel and a molecular weight standard ΦX174 RF DNA/Hae III Fragments (Invitrogen) was used to determine sufficient migration and separation of the fragments on the gel. DIG labeled DNA Molecular Weight Marker VII (Roche), visible after DIG detection as described below, was used to determine hybridizing fragment size on the Southern blots.

Agarose gels containing the separated DNA fragments were depurinated, denatured, and neutralized in situ, and transferred to a nylon membrane in 20×SSC buffer (3M NaCl, 0.3 M Sodium Citrate) using the method as described for the TURBOBLOTTER™ Rapid Downward Transfer System (Schleicher & Schuell, Keene, N.H.). Following transfer to the membrane, the DNA was bound to the membrane by UV crosslinking (Stratalinker, Stratagene, La Jolla, Calif.). Probes for the SCP1 promoter, glyat4601, pinII terminator, SAMS, gm-hra, and als terminator were used to detect genes and elements within the insertion (Table 3). Backbone and hygromycin resistance gene cassette regions (backbone 20163 and hyg20163 probes) of the PHP20163 plasmid were used to verify absence of plasmid backbone DNA in 3560.4.3.5 soybean (Table 3). DNA fragments of the probe elements were generated by PCR from plasmid PHP20163 (FIG. 1) or a plasmid with equivalent elements using specific primers. PCR fragments were electrophoretically separated on an agarose gel, excised and purified using a gel purification kit (Qiagen, Valencia, Calif.). DNA probes were generated from these fragments by PCR that incorporated a DIG labeled nucleotide, [DIG-11]-dUTP, into the fragment. PCR labeling of isolated fragments was carried out according to the procedures supplied in the PCR DIG Probe Synthesis Kit (Roche).

TABLE 3

Description of DNA Probes Used for Southern Blot Hybridization

Figure 6:
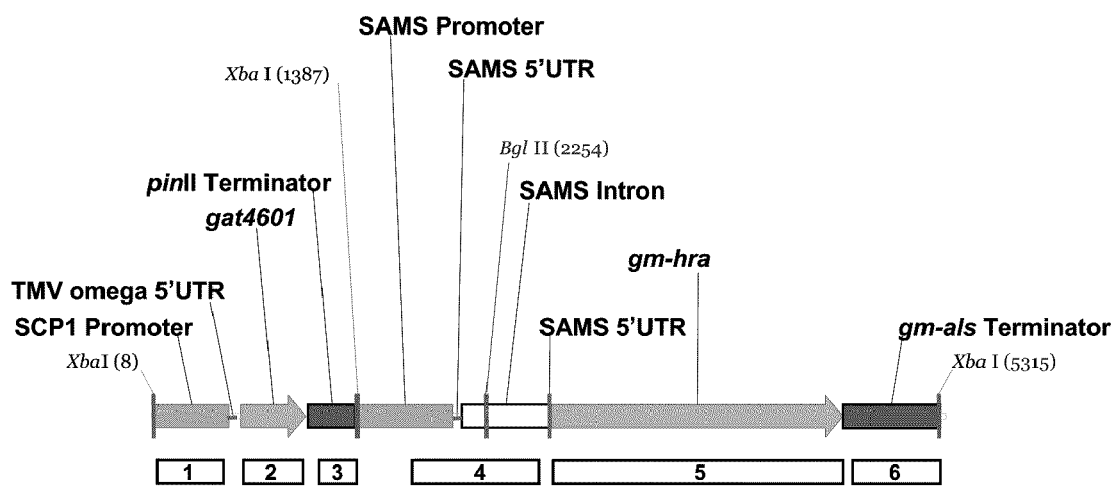
FIG. 6 provides a schematic map of fragment PHP20163A indicating location of the genetic elements contained in the two gene expression cassettes and base pair positions for Bgl II and Xba I restriction enzyme sites. The Not I and Asc I restriction enzyme sites are lost upon excision of this fragment from PHP20163. The total fragment size is 5362 base pairs. Approximate locations of the probes used are shown as numbered boxes below the fragment and are identified below. Additional details on these probes are provided in Table 3.
Figure 7:
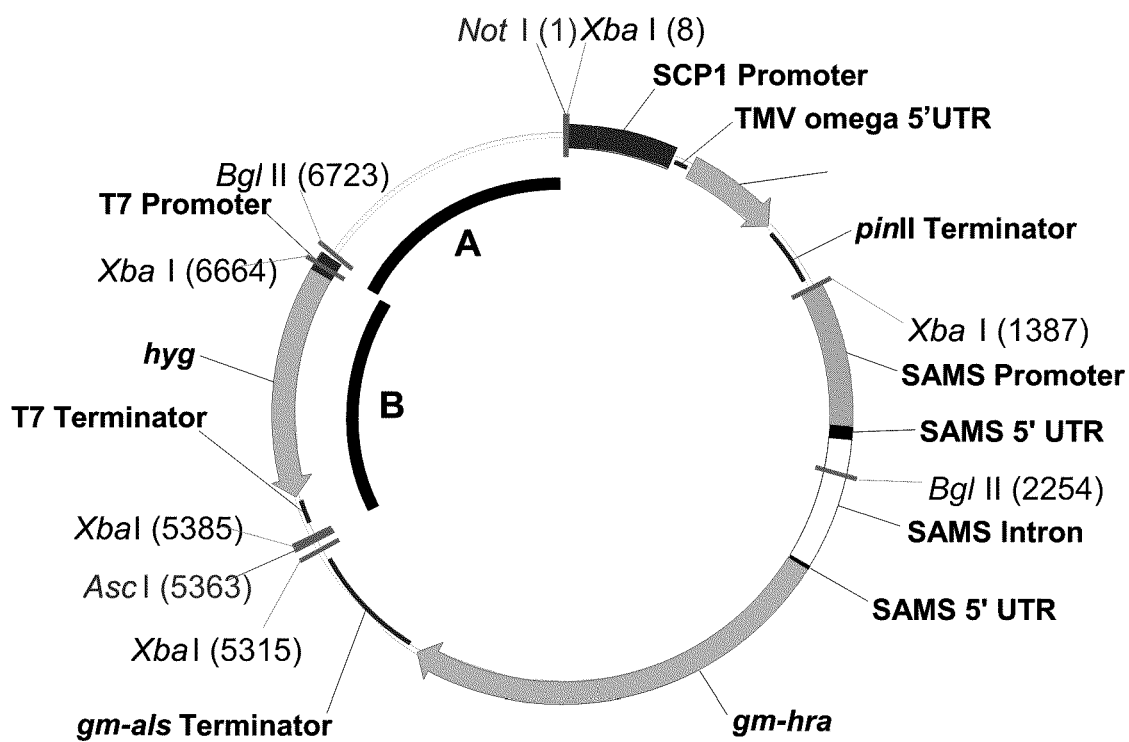
FIG. 7 provides a schematic plasmid map of PHP20163 indicating the location of genetic elements and base pair positions for restriction enzyme sites for Not I, Bgl II, Xba I, and Asc I. The Not I-Asc I fragment of this plasmid was isolated (PHP20163A; map, FIG. 2) and used for transformation to produce 3560.4.3.5 soybean. The Xba I site located at by 1387 contains a Dam methylase recognition site and is resistant to digestion by Xba I if the plasmid is prepared from a Dam$^+$ strain. The total plasmid size is 7954 base pairs. Backbone probes are indicated schematically as lines within the plasmid diagram and are identified below. Each probe is comprised of two non-overlapping segments that were combined for hybridization.

| Probe Name | Genetic Element | Figure Probe | Position on PHP20163A (bp to bp) | Position on PHP20163 (bp to bp) | Length (bp) |
|---|---|---|---|---|---|
| SCP1 promoter | SCP1 promoter | FIG. 6 probe 1 | 12 to 479 (SEQ ID NO: 29) | 12 to 479 | 486 |
| glyat4601 | glyat4601 gene | FIG. 6 probe 2 | 597 to 1012 (SEQ ID NO: 30) | 597 to 1012 | 416 |
| pinII terminator | pinII terminator | FIG. 6 probe 3 | 1107 to 1340 (SEQ ID NO: 31) | 1107 to 1340 | 234 |
| SAMS[1] | SAMS promoter and intron elements | FIG. 6 probe 4 | 1702 to 2146 (SEQ ID NO: 32) 2147 to 2638 (SEQ ID NO: 33) | 1702 to 2146 2147 to 2638 | 445 492 |
| gm-hra[1] | gm-hra gene | FIG. 6 probe 5 | 2700 to 3629 (SEQ ID NO: 34) 3635 to 4664 (SEQ ID NO: 35) | 2700 to 3629 3635 to 4664 | 930 1030 |
| gm-als terminator | gm-als terminator | FIG. 6 probe 6 | 4670 to 5318 (SEQ ID NO: 36) | 4670 to 5318 | 649 |
| backbone 20163[1] | plasmid backbone of PHP20163 | FIG. 7 probe A | N/A[2] | 7427-7954 6665-7416 | 528 752 |
| hyg 20163[1] | hygromycin resistance gene of PHP20163 | FIG. 7 probe B | N/A | 6097-6619 5389-6091 | 523 703 |

[1]Two non-overlapping segments were generated for this probe and were combined for hybridization.
[2]Not Applicable; these are not present on the PHP20163A fragment.

Genomic DNA isolated from 3560.4.3.5 soybean plants was digested with Hind III and Xba I, and electrophoretically separated, transferred to nylon membranes, and hybridized to the glyat4601 and gm-hra gene probes. Labeled probes were hybridized to the target DNA on nylon membranes for detection of the specific fragments using the procedures essentially as described for DIG Easy Hyb solution (Roche). After stringent washes, the hybridized DIG-labeled probes and DIG-labeled DNA standards were visualized using CDP-Star Chemiluminescent Nucleic Acid Detection System with DIG Wash and Block Buffer Set (Roche). Blots were exposed to X-ray film for one or more time points to detect hybridizing fragments and to visualize molecular weight standards. Images were then digitally captured by detection with the Luminescent Image Analyzer LAS-3000 (Fujifilm Medical Systems, Stamford, Conn.). The sizes of detected bands were documented for each digest and each probe, Following hybridization and detection, membranes were stripped of DIG-labeled probe to prepare the blot for subsequent re-hybridization to additional probes. Membranes were rinsed briefly in distilled, de-ionized water and then stripped in a solution of 0.2 M NaOH and 1.0% SDS at 40° C. with constant shaking. The membranes were then rinsed in 2×SSC and either used directly for subsequent hybridizations or stored at 4° C. or −20° C. for later use. The alkali-based stripping procedure effectively removes probes labeled with the alkali-labile DIG. This preliminary Southern blot analysis showed the presence of the insertion in 3560.4.3.5 soybean plants and confirmed that 3560.4.3.5 soybean plants used for this study contained the same insertion (Table 4).

TABLE 4

Summary of Preliminary Southern Screen Data for 3560.4.3.5 Soybean Line.

| Plant ID | Sample ID | Southern Blot glyat4601 Probe[2] | Southern Blot gm-hra Probe[2] |
|---|---|---|---|
| T-F-05-140S-17 | T-17 | + | + |
| T-F-05-140S-18 | T-18 | + | + |
| T-F-05-140S-19 | T-19 | + | + |
| T-F-05-140S-20 | T-20 | + | + |
| T-F-05-140S-21 | T-21 | + | + |
| T-F-05-140S-22 | T-22 | + | + |
| T-F-05-140S-23 | T-23 | + | + |
| T-F-05-140S-24 | T-24 | + | + |

+ indicates hybridization signal on Southern blot.

Four plants were chosen for insert and border sequence analysis: 3560.4.3.5 soybean plants T17 and T18, and control plants C1 and C2. PCR primers were synthesized by Sigma-Genosys, Inc. (The Woodlands, Tex.) and MWG (Ebersberg, Germany), and used at concentrations of 0.3-0.4 uM. For amplification of the PHP20163A insert region, both the Advantage-GC-2 PCR system (Clontech) and the Expand Long Template PCR System (Roche) were used to amplify genomic DNA (100-500 ng); and for the 5' and 3' flanking genomic border PCR, the Advantage-GC-2 PCR system was used to amplify from genomic DNA (100 ng). The PCR products were visualized under UV light following electrophoresis through a 1% agarose gel with 1× TAE and ethidium bromide; excised, and purified from the gel using Qiaquick gel purification kit (Qiagen, Valencia, Calif.).

The PCR products were cloned using the TOPO TA-cloning Kit (pCR2.1-TOPO vector, Invitrogen, Carlsbad, Calif.). Plasmids were isolated using QIAprep Spin Miniprep Kit (Qiagen), screened by restriction enzyme digestions, and sequenced.

For complete sequence coverage of the cloned PCR products representing the insert of the 3560,4.3.5 soybean, the clones were sequenced by a transposon-based sub-cloning method to facilitate bi-directional sequencing of a cloned insert from the site of the transposition event (MJ Research TGS system; Happa et al. (1999) *Nucleic Acid Research*

27:2777-2784. Since unintended mutations can occur during the generation of the PCR products, we cloned and sequenced products from two separate PCR reactions with T17 and T18 DNA. In all cases, any PCR-induced sequence error was present in only one of the four clones, allowing reliable consensus calls to be made on every base of the sequence.

Figure 3:
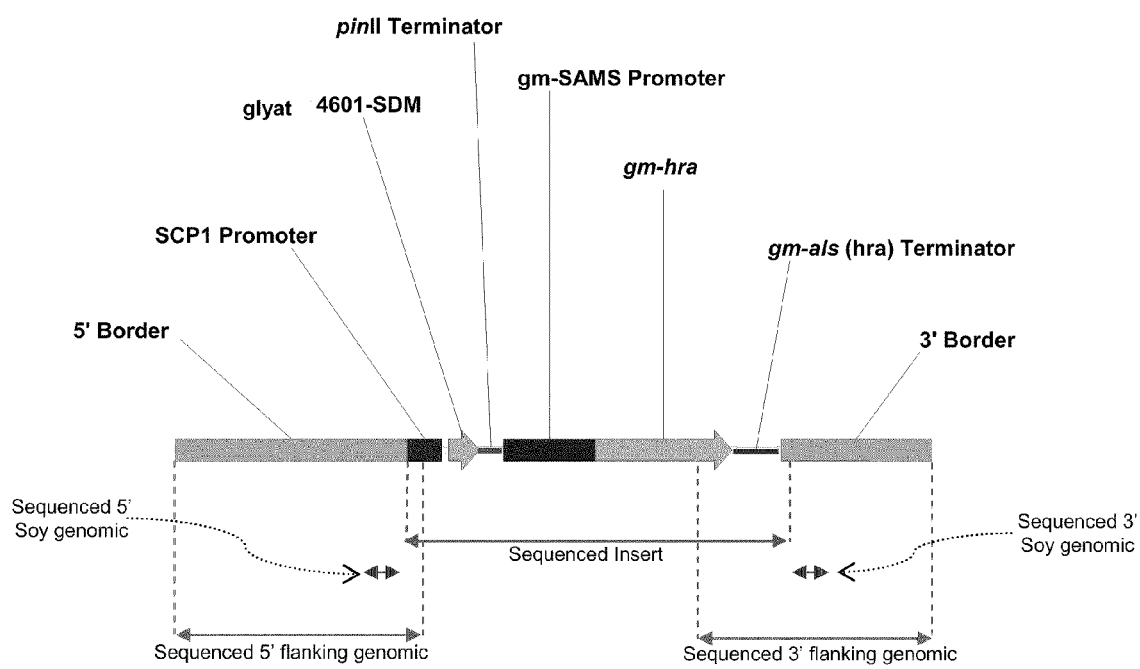
FIG. 3 provides a schematic map of the insertion region in soybean event 3560.4.3.5 and shows the three regions that were sequenced from PCR products generated using genomic DNA as template: inserted DNA from the bombarded PHP20163A DNA fragment, 5' flanking soybean genomic DNA and 3' flanking soybean genomic DNA.

Initial sequence characterization of the 5' flanking border was carried out using the BD GenomeWalker Universal Kit (Clontech, Mountain View, Calif.). The GenomeWalker protocol involves digesting the genomic DNA with various restriction enzymes and ligating these digests with an adaptor, thereby creating "libraries" to be used as template for two rounds of PCR. The PCR primers for the 2 rounds of PCR consisted of an insert-specific (SCP1 promoter) primer, and an adaptor-specific primer. Based on sequence information generated from the Genome Walker experiments, primers were designed to perform PCR on genomic DNA from 3560.4.3.5 and control soybean plants, using primers that spanned the 5' junction. (FIG. 3 and data not shown). To extend the 5' border sequence further, we used the DNA Walking SpeedUp Kit (Seegene, Inc. Rockville, Md.) was used, which is another PCR-based genomic DNA walking approach based on the DNA Walking Annealing Control Primer PCR Technology (Ochman et al. (1988) *Genetics* 120:621; Silver et al. (1989) *Journal of Virology* 63:1924; Triglia et al. (1988) *NAR* 16:8186). The last round of border extension was performed by anchoring within the 5'-most end of the border and again using the Genome Walker kit. The final 5' flanking border sequence was verified by cloning and sequencing of 5' flanking genomic border PCR products. In order to demonstrate that the identified 5' flanking genomic border sequence is of soybean origin, PCR was performed within this 5' flanking genomic region on genomic DNA from 3560.4.3.5 soybean and control soybean plants (FIG. 3 and data not shown).

Initial sequence characterization of the 3' flanking border was carried out using inverse PCR (Silver et al. (1989) *Journal of Virology* 63:1924; Ochman et al. (1988) *Genetics* 120: 621; Triglia et al. (1988) *NAR* 16:8186), with insert-specific primers anchored in the glyat4601 and gm-hra genes. Sequence obtained from products generated using inverse PCR was then used to design primers for PCR on genomic DNA from 3560.4.3.5 and control soybean plants, using primers that spanned the 3' junction. (FIG. 3 and data not shown). The 3' flanking genomic border sequence was verified by cloning and sequencing the 3' flanking genomic border PCR products. The genomic flanking border was extended further using the sequence information from proprietary soybean sequence that matched this flanking border to design PCR primers. Cloning and sequencing the resulting PCR products confirmed this additional flanking border sequence. In order to demonstrate that the identified 3' flanking genomic border sequences were of soybean origin, PCR was performed within this 3' genomic region on DNA from 3560.4.3.5 soybean and control soybean plants (FIG. 3 and data not shown).

For verification of the DNA sequence that inserted into the soybean genome, PCR was performed to amplify, clone, and sequence the inserted DNA from 3560.4.3.5 soybean. PCR primers just outside the insert (primer pair 1297/1298) were used to amplify the entire insert from DNA of 3560.4.3.5 soybean plants. This amplification produced products of the expected size (5.4 kb) from two separate reactions from each of two test samples; these were cloned and sequenced. In addition, the DNA fragment PHP20163A used for creating 3560.4.3.5 soybean line was sequenced, and compared with the insert sequence generated from 3560.4.3.5 soybean genomic DNA.

Both the 5' and 3' flanking border sequences of the 3560.4.3.5 soybean were subjected to BLASTn analysis in order to identify the nature and potential function of the flanking sequences in the soybean genome. The searches were performed against the NCBI Genbank Nucleotide ("nt") dataset (www.ncbi.nlm.nih.gov/), Release 154, last updated Jul. 31, 2006, U.S. Pat. No. 4,302,011 total sequences), as well as to Genome Survey Sequence dataset (GSS, Release Jul. 28, 2006). Finally, sequences were compared to a dataset consisting of all proprietary soybean genomic and EST sequences generated by Pioneer. Default parameters were used in all cases. Both 5' and 3' border/insert junctions were also screened for the presence of novel open reading frames (ORFs)≧100 amino acids (300 bp) in length using Vector NTI 9.1 (Invitrogen, Carlsbad, Calif.).

Figure 2:
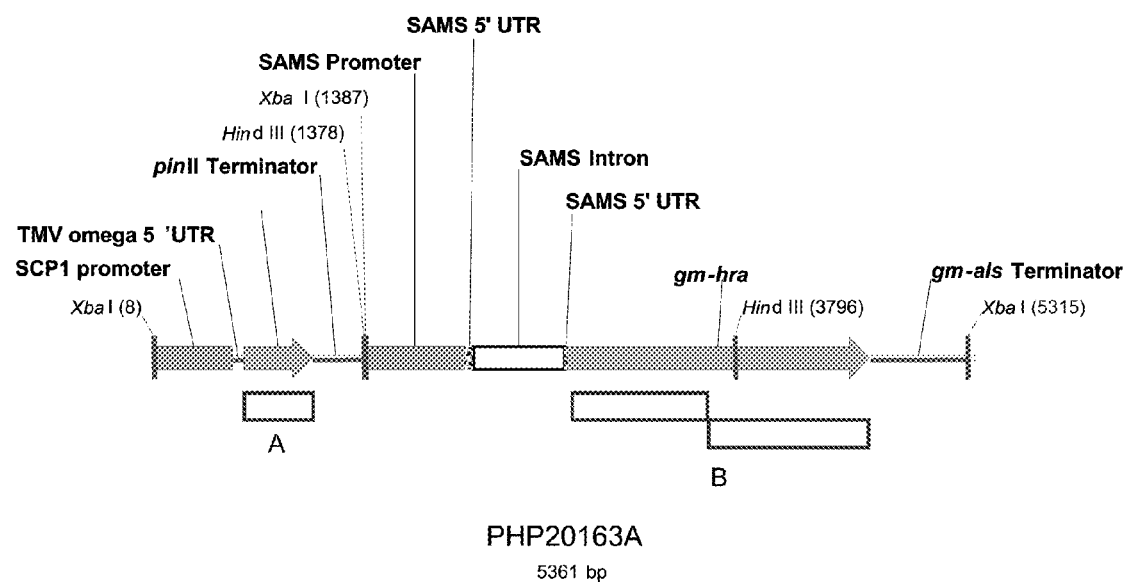
FIG. 2 provides a schematic map of fragment PHP20163A indicating restriction enzyme sites for Xba I, Hind III and various genetic elements. This fragment was used for microprojectile bombardment to produce the 3560.4.3.5 soybean event. Probes used for Southern hybridization are indicated as boxes beneath the fragment map and are identified as follows: A: glyat4601 (glyphosate acetyltransferase) probe B: gm-hra probe (two non-overlapping segments were generated covering the entire region and used together for hybridization.

DNA isolated from eight 3560.4.3.5 soybean plants was digested with Xba I and Hind III, and hybridized to gm-hra and glyat4601 gene probes to verify the presence of the insertion and to verify the molecular equivalence of the insertion among all 8 plants analyzed. The preliminary Southern blot screen indicated that 3560.4.3.5 soybean plants exhibited identical hybridization patterns (Table 4 and data not shown). In the Xba I digests, the glyat4601 probe hybridized to a 1.4 kb band and the gm-hra probe hybridized to a 3.9 kb band as expected (FIG. 2), demonstrating the intact insertion of PHP20163A. In the Hind III digests, the glyat4601 probe hybridized to a 5' flanking 6.1 kb band, the gm-hra probe hybridized to 3' flanking 7.4 kb band, and an internal 2.4 kb band, demonstrating that the insertion exists as a single copy in the genome (FIG. 2). The gm-hra probe also hybridizes to other bands corresponding to endogenous sequences. Four plants were chosen for insert and border sequence analysis: 3560.4.3.5 soybean plants T17 and T18, and control Jack plants C1 and C2.

In the initial characterization of the 3560.4.3.5 soybean line, the flanking genomic border regions were cloned and sequenced using the GenomeWalker and inverse PCR methods. This preliminary sequence information was used to design primers for PCR to generate products in the three regions of interest from 3560.4.3.5 soybean genomic DNA: 5' flanking border, entire insert, and 3' flanking border (Table 11, Table 4; Table 10; and, FIG. 3). Using information from the flanking border sequence, PCR was performed on 3560.4.3.5 soybean genomic DNA and unmodified control genomic DNA.

For the 5' flanking sequence, PCR was performed with a forward primer in the 5' border (primer 1679) and a reverse primer in the SCP1 Promoter (primer 1658), resulting in the expected products in 3560.4.3.5 soybean plants (396 bp), and not in the control DNAs (FIG. 3 and data not shown). Following two more rounds of walking (with the DNA Walking SpeedUp and GenomeWalker Kits), additional 5' flanking border sequence was obtained. To verify the 5' flanking border sequence, PCR products were generated from 3560.4.3.5 DNA, cloned and sequenced. The complete sequence information is presented in FIG. 4A-E.

For the 3' flanking sequence, PCR was performed with a forward primer in the gm-hra (primer 1439) and a reverse primer in the 3' border sequence (primer 1666), resulting in the expected products in 3560,4.3.5 soybean plants (1029 bp) and not the control DNAs (FIG. 3 and data not shown). The 3' flanking border PCR products were generated from 3560.4.3.5 soybean DNA, cloned and sequenced. This sequence showed the same identity to a proprietary soybean DNA sequence, which was used to design primers to further extend the flanking border. Again, the resulting 3' flanking border PCR products generated from 3560.4.3.5 soybean DNA were cloned and sequenced. The complete sequence information is presented in FIG. 4A-E.

For amplification of the insert, PCR primers situated in each flanking region were used to amplify the entire insert from DNA of event 3560.4.3.5 plants (primer pair: 1297/1298). As expected, the predicted PCR products of 5.5 kb were generated only from 3560.4.3.5 soybean DNA, and not from the control DNA. The insert PCR products were cloned and sequenced. The sequence information is presented in FIG. 4A-E.

In addition, the DNA fragment PHP20163A used for creating 3560.4.3.5 soybean line was sequenced, and compared with the insert sequence generated from 3560.4.3.5 soybean genomic DNA. The sequence of the insert in 3560.4.3.5 soybean is identical to the sequence of the PHP20163A DNA fragment.

In total, 10849 bp of sequence from genomic DNA of 3560.4.3.5 soybean was confirmed: 3317 bp of the 5' flanking genomic border, 2170 bp of the 3' flanking genomic border, and the 5362 bp comprising the inserted DNA (FIG. 3 and FIG. 4A-E).

To demonstrate that the identified 5' and 3' flanking border sequences are of soybean origin, PCR was performed within the 5' and 3' flanking genomic regions (primer pairs 1679/1514 and 1660/1666, respectively) from 3560.4.3.5 soybean DNA samples and unmodified control samples. The expected size PCR products (246 bp for 5' genomic region and 297 bp for 3' genomic region) were generated using genomic DNA from both 3560.4.3.5 soybean and control soybean plants, indicating that the sequences were of soybean genomic origin and not specific to 3560.4.3.5 soybean (FIG. 3 and data not data shown). These PCR products from both the 3560.4.3.5 and control soybean DNAs were cloned and sequenced and shown to have identical sequence.

When the 3317 bp sequence from the 5' flanking region of 3560.4.3.5 soybean was compared to the Genbank Nucleotide ("nt") dataset (www.ncbi.nlm.nih.gov/), no significant alignments were returned. Analysis using the GSS subset returned a two areas of the flanking region (nt 2723-2863; 2881-3203) with significant similarity (98% and 92%, respectively) to genomic sequences from the legume *Medicago truncatula* (barrel medic). The BLASTn search against Pioneer proprietary soybean genomic and EST sequences returned a 98% identity alignment encompassing nt 2860-3317 to a single soybean genomic sequence. An additional region (nt 531-2144) returned lower, yet significant identities (84%-92%) to several different soybean genomic clones. The 3' flanking sequence produced two highly significant alignments (97-99% identity) to two different public soybean genomic sequences (accessions CL868338.1 and CL867466.1) and a single proprietary genomic sequence in the region from nt 9772-10849. An additional region (nt 9250-9554) displayed significant identity (92-94%) to wheat genomic and mitochondrial sequences. The 5' and 3' junction regions between the soybean genomic border sequence and the insertion in 3560.4.3.5 soybean were analyzed for the presence of novel open reading frames. No open reading frames greater than or equal to 100 amino acids were identified in the 5' or 3' border junction regions, indicating that no novel open reading frames were generated as a result of the insertion.

Southern blot analysis also confirmed that the DNA insertion remained stable during traditional soybean breeding procedures. The analysis was conducted on two self-crossed generations, T4 and T5, and verified that the insertion remained intact and stably integrated as demonstrated by identical hybridization patterns in the two generations. The F3 generation was also analyzed by Southern blot analysis and confirmed the same stable, event-specific hybridization pattern as exhibited by the T4 and T5 generations. These results confirmed the stability of the insertion in 3560.4.3.5 soybean across multiple breeding generations.

As discussed below, the Bgl II restriction enzyme has a single site (bp position 2254) located within the PHP20163A fragment (FIG. 6) and will generate a unique event-specific hybridization pattern for 3560.4.3.5 soybean when hybridized to the glyat4601 and gm-hra probes. This analysis confirms event stability across generations as changes to the insertion structure in 3560.4.3.5 soybean would be detected. As discussed below, a band of approximately 2500 bp would be expected with the glyat4601 probe to confirm stability across generations (Table 5). Likewise, for the gm-hra probe, a band of approximately 3500 bp would be expected to confirm stability across generations (Table 6).

TABLE 5

Predicted and Observed Hybridizing Bands on Southern Blots with glyat4601 Cassette Probes

| Probe | Restriction Enzyme | Predicted Fragment Size from PHP20163A[1] (bp) | Predicted Fragment Size from PHP20163[2] (bp) | Observed Fragment Size in GLYAT 3560.4.3.5 soybean[3] (bp) |
|---|---|---|---|---|
| SCP1 promoter | Bgl II | >2300[4] | 3485 | ~2500 |
| glyat4601 | Bgl II | >2300[4] | 3485 | ~2500 |
| pinII terminator | Bgl II | >2300[4] | 3485 | ~2500 |
| SCP1 promoter | Xba I | 1379 | 1379[5] | 1379[6] |
| glyat4601 | Xba I | 1379 | 1379[5] | 1379[6] |
| pinII terminator | Xba I | 1379 | 1379[5] | 1379[6] |

[1]Predicted fragment sizes for 3560.4.3.5 soybean are based on the map of PHP20163A as shown in FIG. 6.

[2]Predicted fragment sizes for hybridization to samples containing the plasmid positive control are based on the PHP20163 plasmid map as shown in FIG. 7.

[3]Observed fragment sizes are considered approximate from these analyses and are based on the indicated sizes of the DIG-labeled DNA Molecular Weight Marker VII fragments on the Southern blots. Due to incorporation of DIG molecules for visualization, the marker fragments typically run approximately 5-10% larger than their actual indicated molecular weight.

[4]Minimum fragment size predicted based on an intact insertion of PHP20163A (data not shown).

[5]Predicted hybridizing Xba I fragment size from plasmid PHP20163 grown in a Dam⁻ strain. For plasmid grown in a Dam⁺ strain, the hybridizing Xba I fragment size is predicted to be 5307 bp.

[6]Observed fragment is equal to the predicted size based on blot (data not shown) showing comparison to plasmid PHP20163 grown in a Dam⁻ strain.

TABLE 6

Predicted and Observed Hybridizing Bands on Southern Blots with gm-hra Cassette Probes

| Probe | Restriction Enzyme | Predicted Fragment Size from PHP20163A[1] (bp) | Predicted Fragment Size from PHP20163[2] (bp) | Observed Fragment Size in GLYAT 3560.4.3.5 Soybean[3] (bp) |
|---|---|---|---|---|
| SAMS | Bgl II | >3100[4] >2300[4] | 4468 4385 | ~3500 ~2500 ~6900* ~4700* |
| gm-hra | Bgl II | >3100[4] | 4468 | ~3500 ~8600* ~8600* |
| gm-als terminator | Bgl II | >3100[4] | 4468 | ~3500 ~8600* |
| SAMS | Xba I | 3928 | 3928[5] | 3928[6] ~8600* |
| gm-hra | Xba I | 3928 | 3928[5] | 3928[6] ~8600* ~8600* ~7400* ~6800* ~5800* ~4500* |
| gm-als terminator | Xba I | 3928 | 3928[5] | 3928[6] ~5800* |

An asterisk (*) and gray shading indicates the designated band is due to probe hybridization to endogenous soybean genome sequences, as can be determined by the presence of the same band in all lanes, both 3560.4.3.5 soybean and control.
[1]Predicted fragment sizes for 3560.4.3.5 soybean are based on the map of PHP20163A as shown in FIG. 6.
[2]Predicted fragment sizes for hybridization in samples containing the plasmid positive control are based on the PHP20163 plasmid map as shown in FIG. 7.
[3]Observed fragment sizes are considered approximate from these analyses and are based on the indicated sizes of the DIG-labeled DNA Molecular Weight Marker VII fragments on the Southern blots. Due to incorporation of DIG molecules for visualization, the marker fragments typically run approximately 5-10% larger than their actual indicated molecular weight.
[4]Minimum fragment size predicted based on an intact insertion of PHP20163A (data not shown).
[5]Predicted hybridizing Xba I fragment size from plasmid PHP20163 grown in a Dam⁻ strain. For plasmid grown in a Dam⁺ strain, the hybridizing Xba I fragment size is predicted to be 5307 bp.
[6]Observed fragment is equal to the predicted size based on blot (data not shown) showing comparison to plasmid PHP20163 grown in a Dam⁻ strain.

Genomic DNA of T4 and T5 generations of 3560.4.3.5 soybean was digested with Bgl II and hybridized to the glyat4601 and gm-hra probes to confirm stability across generations (data not shown). A band of approximately 2500 bp specific to 3560.4.3.5 soybean hybridized to the glyat4601 probe in both the T4 and T5 generations (Table 5 and data not shown). With the gm-hra probe, a single band of approximately 3500 bp specific to 3560.4.3.5 soybean was present in both generations (Table 6 and data not shown). In addition to the 3500 bp band, the gm-hra probe also hybridized to additional bands that were determined to be endogenous to the soybean genome since these bands were present in both 3560.4.3.5 soybean and control soybean plants (data not shown). Hybridization results from both the glyat4601 and gm-hra probes confirmed that the insertion of the PHP20163A DNA fragment in 3560.4.3.5 soybean remained stable across the self-crossed T4 and T5 generations.

Southern blot analysis of the F3 generation of 3560.4.3.5 soybean was also conducted. A total of 77 individual plants were analyzed (data not shown). Genomic DNA of the F3 generation was digested with Bgl II and hybridized to the glyat4601 and gm-hra probes. A band of approximately 2500 bp was observed with the glyat4601 probe (data not shown) and a single band of approximately 3500 bp specific to 3560.4.3.5 soybean was observed with the gm-hra probe (data not shown). As with the previous analysis conducted, the gm-hra probe hybridized to additional bands in 3560.4.3.5 soybean and control samples which were due to endogenous sequences within the soybean genome (data not shown). Hybridizations results from both the glyat4601 and gm-hra probes were consistent with the results from the T4 and T5 generations described above and confirmed the stability of inheritance of the insertion during traditional soybean breeding.

Both the T4 and T5 generations were analyzed to confirm the absence of plasmid sequence from plasmid PHP20163 outside of the transformation fragment PHP20163A, i.e. the plasmid backbone sequence removed prior to transformation. The results verified the absence of backbone sequences in 3560.4.3.5 soybean.

The backbone 20163 and hyg 20163 probes (Table 3 and FIG. 7) were designed to hybridize to areas of plasmid PHP20163 outside of the transformation fragment (data not shown) and were hybridized to Xba I-digested genomic DNA to confirm absence of these sections of the plasmid in 3560.4.3.5 soybean. Neither of the two backbone probes hybridized to 3560.4.3.5 soybean samples (data not shown), confirming the absence of these sequences.

Genomic DNA from leaf material of the Jack soybean variety was used as a negative control for all Southern blot analyses. Genomic DNA from an elite soybean variety (Elite 1) was included as an additional negative control for analysis of the F3 generation. Plasmid PHP20163 was used as a positive control for probe hybridization and to verify fragment sizes internal to the transformation fragment PHP20163A. All probes used for the analysis are indicated on the schematic maps of PHP20163A and PHP20163 (FIGS. 6 and 7, respectively) and outlined in Table 3, The integration pattern of the insertion in 3560.4.3.5 soybean was investigated with Bgl II digestion to determine copy number and with Xba I digestion to determine insertion integrity. Southern blots were hybridized to several probes to confirm copy number and integrity of each genetic element. SCP1 promoter, glyat4601, and pinII terminator probes were used to characterize the glyat4601 cassette (Table 3 data not shown). SAMS, gm-hra, and als terminator probes were used to characterize the gm-hra cassette (Table 3 and data not shown).

The Bgl II digest provides information about number of copies integrated into the genome of 3560.4.3.5 soybean as there is a single restriction enzyme site in the PHP20163A fragment at base pair (bp) position 2254 (data not shown) and additional sites outside the fragment in the soybean genome. Hybridization with the probes from each cassette, except for the SAMS probe, would indicate the number of copies of each element found in 3560.4.3.5 soybean based on the number of hybridizing bands (e.g. one hybridizing band indicates one copy of the element). For the SAMS probe, since the Bgl II site is located within the probe region, two hybridizing bands would be expected for every one copy of the element. Predicted and observed fragment sizes for 3560.4.3.5 soybean with Bgl II are given in Table 5 for the glyat4601 cassette and in Table 6 for the gm-hra cassette.

Figure 8:
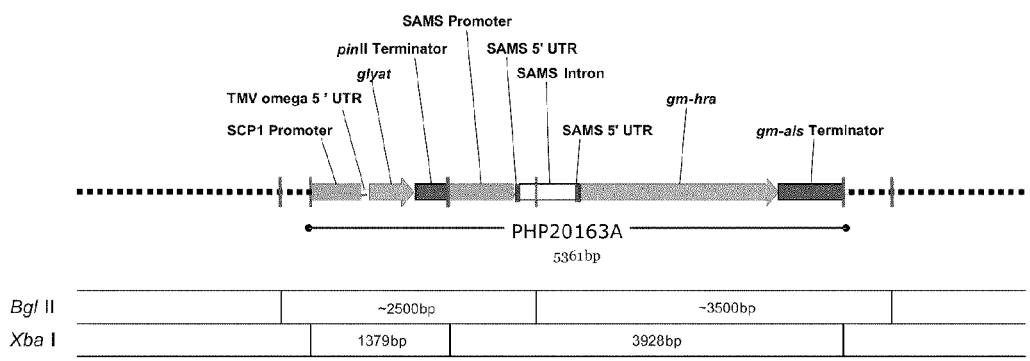
FIG. 8 provides a schematic map of the transgene insertion in 3560.4.3.5 soybean based on Southern blot analysis. The flanking soybean genome is represented by the horizontal dotted line. A single, intact copy of the PHP20163A fragment integrated into the soybean genome. Bgl II and Xba I restriction enzyme sites are indicated with the sizes of observed fragments on Southern blots shown below the map in base pairs (bp).
Figure 9:
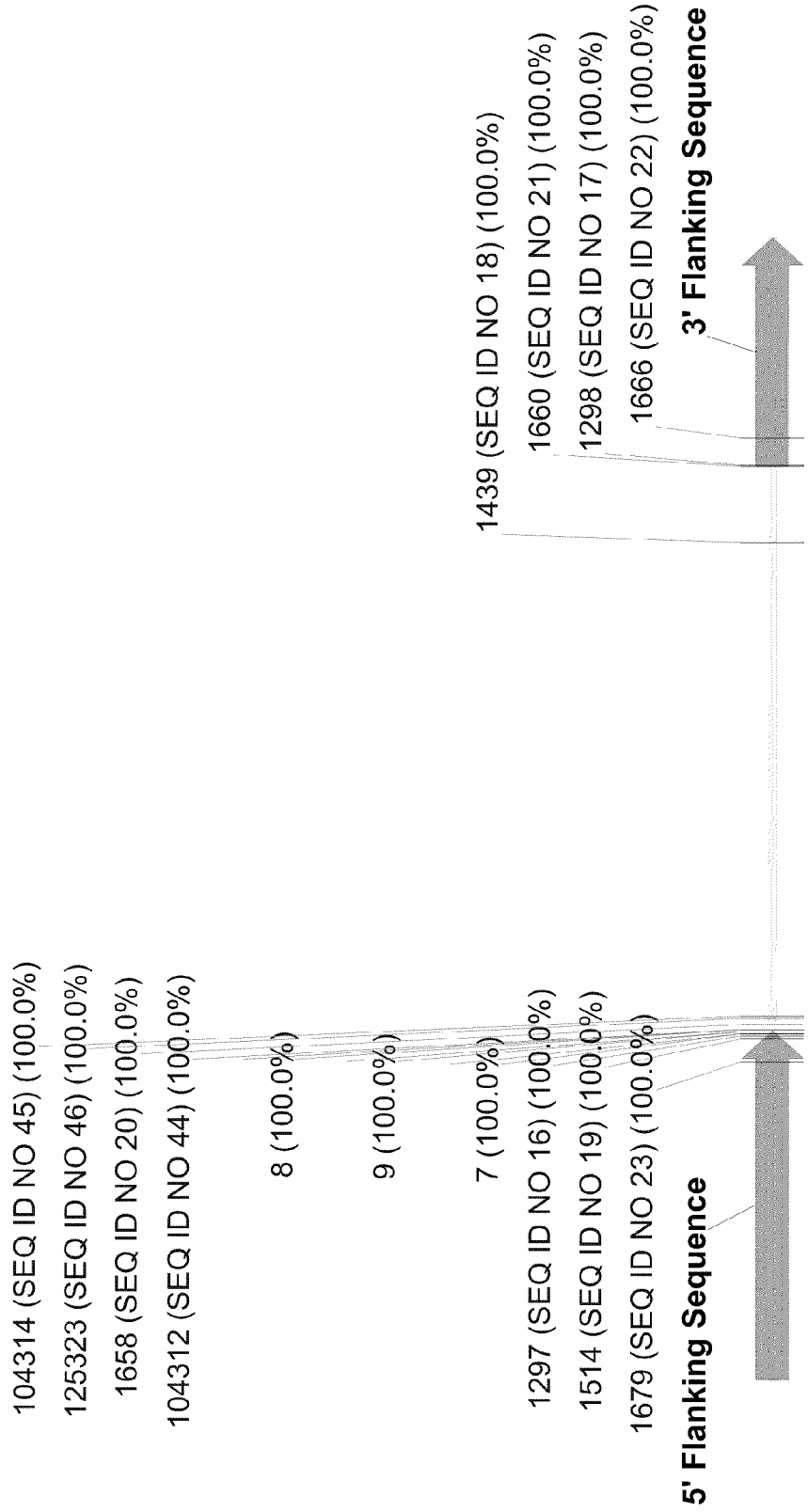
FIG. 9 provides a map of the 3560.4.3.5 event and depicts where various primers anneal.

Based on the Southern blot analyses as discussed below, it was determined that a single, intact PHP20163A fragment has been inserted into the genome of 3560.4.3.5 soybean as diagramed in the insertion map (FIG. 8).

A single copy of all the elements of the glyat4601 cassette was inserted into 3560.4.3.5 soybean. SCP1 promoter, glyat4601, and pinII terminator probes were hybridized to Bgl II-digested genomic DNA from individual 3560.4.3.5 soybean plants of the T4 generation (Table 5 and data not shown). Each of the probes hybridized to the same single fragment of approximately 2500 base pairs (bp) (Table 5 and data not shown), indicating the expected arrangement of genetic elements on the fragment inserted in 3560.4.3.5 soybean.

Likewise, a single copy of all the elements of the gm-hra cassette was inserted into 3560.4.3.5 soybean. The elements comprising this cassette—the SAMS promoter region, gm-hra gene, and als terminator—were used as probes to determine number of copies inserted. The probes of this cassette are homologous to elements endogenous to the soybean genome and therefore each probe hybridized to bands in control soybean samples. The hybridizing bands in 3560.4.3.5 soybean from the endogenous soybean genome are indicated by asterisks in the shaded boxes of Table 6 and were determined by their presence in control soybean samples and are thus not associated with the insertion.

The SAMS probe hybridized to one band of approximately 2500 bp and a second band of approximately 3500 bp in 3560.4.3.5 soybean (Table 6 and data not shown, SAMS probe). Two bands would be expected to indicate one insertion of this element with this probe as the Bgl II site is located within the SAMS region of PHP20163A (FIG. 6) and the results indicated one copy of the element. The 2500 bp fragment was determined to be the same fragment containing the glyat4601 cassette as described above.

The gm-hra and als terminator probes hybridized to the same 3500 bp fragment as the SAMS probe (Table 6 and data not shown, gm-hra and gm-als terminator probes). The hybridization of all three probes to the same 3500 bp fragment and of the SAMS probe to the 2500 bp fragment confirmed the expected arrangement of the genetic elements in the DNA insertion in 3560.4.3.5 soybean.

Xba I digestion was used to verify that the glyat4601 and gm-hra cassettes were complete and intact in 3560.4.3.5 soybean as there are three sites in the PHP20163A fragment (base pair positions 8, 1387, and 5315) which precisely flank each gene expression cassette (FIG. 6). Hybridization with the probes of the glyat4601 and gm-hra cassettes confirmed that all the elements were found on the appropriate internal fragments containing the cassette. Expected and observed fragment sizes with Xba I are given in Table 6 for the glyat4601 cassette and Table 6 for the gm-hra cassette.

The SCP1 promoter, glyat4601, and pinII terminator probes each hybridized to the expected internal band of 1378 bp (Table 5 and data not shown) and the size was confirmed by additional hybridizations as described in the section below and data not shown. Because these probes hybridized to the same internal fragment of the predicted size, the glyat4601 cassette in 3560.4.3.5 soybean was determined to be intact and all elements of the cassette were confirmed on this fragment.

The SAMS, gm-hra, and als terminator probes each hybridized to the expected internal band of 3927 bp band (Table 6 and data not shown) and the size was confirmed by additional hybridization described in the section below. Because these probes hybridized to the same fragment, the gm-hra cassette in 3560.4.3.5 soybean was determined to be intact and all elements were present.

Plasmid PHP20163 was prepared from a strain of E. coli that expresses a DNA methylase (a Dam+ strain). This plasmid did not produce the expected bands when digested with Xba I and probed with the glyat4601 and gm-hra cassette probes. A band of approximately 5300 bp was observed in lanes containing plasmid PHP20163 for all probes (data not shown) instead of the predicted 1379 bp and 3928 bp size bands (Tables 5 and 6). Based on the plasmid sequence, it was determined that the Xba I site at by position 1387 of PHP20163 (FIG. 7) overlaps a Dam methylation recognition sequence. The final adenine in this site is methylated, thus blocking digestion by Xba I.

The inability for Xba I enzyme to cut at this site affected the size prediction from fragment PHP20163A in 3560.4.3.5 soybean (Tables 5 and 6, FIG. 6). In order to confirm the size in 3560.4.3.5 soybean and the plasmid result, plasmid PHP20163 was prepared from a strain of E. coli lacking Dam methylase (Dam− strain) and was compared to the plasmid PHP20163 (data not shown). Southern hybridization results (data not shown) show the plasmid comparison alongside samples of the T4 and T5 generations of 3560.4.3.5 soybean digested with Xba I. The blot probed with glyat4601 and gm-hra probes demonstrated that plasmid PHP20163 prepared from the Dam− strain digested as expected by Xba I and produced the predicted size bands of 1379 bp and 3927 bp (data not shown), while the original plasmid from the Dam+ strain again produced a band of approximately 5300 bp for both probes (data not shown). These results confirmed that the central Xba I site at position 1387 was blocked from digestion due to Dam methylation. Furthermore, the hybridizing bands in 3560.4.3.5 soybean were of the equivalent size as those in the unmethylated plasmid PHP20163 from the Dam− strain confirming that 3560.4.3.5 soybean contained a complete and intact insertion (data not shown).

A Chi squared analysis of trait inheritance data from five different generations (T1, F2, F3, BC1F2, C2F2) was performed to determine the Mendelian heritability and stability of the glyat4601 and gm-hra genes in the progeny of 3560.4.3.5 soybean. The breeding history of the five generations evaluated for Mendelian inheritance is described in FIG. 5. For each of the generations tested, the plants were expected to segregate 1:2:1 (homozygous positive plants:hemizygous plants:homozygous negative [null] plants). Various approaches, as outlined below, were used to confirm this segregation ratio in the progeny of 3560.4.3.5 soybean.

In some studies, homozygous positive plants were not differentiated from hemizygous plants, resulting in a 3:1 positive:negative segregation pattern (Table 7). For the three generations listed in Table 7, three different methods, respectively, were used to score the plants as positive or negative:

qualitative PCR analysis to identify the plants containing the glyat4601 gene (T1 generation); or western analysis to score plants for GLYAT4601 protein expression followed by confirmation of those same plants by Southern analysis with both glyat4601 and gm-hra probes (F3 generation), or an ALS seed soak assay (BC1F2 generation). In this assay, seeds are soaked in an ALS-inhibiting herbicide containing the active ingredient chlorsulfuron. Only seed expressing the gm-hra gene will emerge after planting.

In certain studies, plants that did not contain either the glyat4601 or gm-hra genes were removed from the study prior to the conduct of segregation analysis. Remaining plants were then scored as homozygous positive or hemizygous, resulting in a 1:2 homozygous positive:hemizygous segregation pattern (Table 8).

For the F2 generation listed in Table 8, two methods were used to remove the negative plants and score the remaining plants as homozygous positive or hemizygous:

A glyphosate spray was applied after the plants had emerged, removing all of the homozygous negative (null) plants. This was followed by an ALS-inhibiting herbicide "ragdoll" assay for the gm-hra gene, where progeny seed from the F2 plants were screened to determine the F2 parent plant genotype. In the ragdoll assay, paper towels were wetted with an ALS-inhibiting herbicide containing the active ingredient chlorsulfuron. Ten progeny seeds from a single F2 parent plant were rolled into the wetted towel and allowed to germinate. An F2 parent plant was scored as homozygous positive for the gm-hra gene if all ten progeny seeds germinated and grew normally. An F2 parent plant was scored as homozygous negative for the gm-hra gene if all ten progeny seeds did not germinate and grow normally. A hemizygous F2 parent genotype was characterized by having a mixture of resistant and susceptible plants within the ten seed sample.

An ALS seed soak assay of the seeds prior to planting removed all of the homozygous negative (null) plants, followed by a quantitative real time PCR (qPCR) assay to distinguish plants that were homozygous positive or hemizygous for the glyat4601 gene.

In some studies, all plants were identified as homozygous positive, hemizygous, or homozygous negative to confirm a 1:11 expected segregation ratio (Table 9). Segregation analysis was conducted for the C2F2 generation using quantitative real time PCR (qPCR) assays for both the glyat4601 and gm-hra genes. Because the glyat4601 and gm-hra genes were physically linked in the DNA fragment used for transformation and are expected to have identical segregation ratios in the progeny of 3560.4.3.5 soybean, the glyat4601 results are applicable to the inheritance of gm-hra and vice versa. In generations where both traits were analyzed in the same plants (F3 and C2F2), identical segregation data would experimentally confirm co-segregation of the glyat4601 and gm-hra genes Results from the Mendelian analysis are summarized in Tables 7, 8 and 9. All P-values were greater than 0.05, indicating no statistically significant differences between the observed and expected frequencies of the glyat4601 and/or gm-hra genes in five generations of 3560.4.3.5 soybean. The results of this analysis are consistent with the finding of a single locus of insertion of the glyat4601 and gm-hra genes that segregates in 3560.4.3.5 soybean progeny according to Mendel's laws of genetics. The stability of the insert has been demonstrated in five generations of self- and cross-pollinations.

TABLE 7

Comparison of Observed and Expected 3:1 Segregation Ratios for 3560.4.3.5 Soybean

| | | Observed | | Expected | | Chi-squared |
|---|---|---|---|---|---|---|
| Generation | Method | Positives +/+ or +/− | Negatives −/− | Positives +/+ or +/− | Negatives −/− | test P-value |
| T1 | Glyat4601 PCR | 59 | 23 | 61.5 | 20.5 | 0.610 |
| F3 Elite 1 background | GLYAT 4601 westerns followed by Southern analyses with glyat4601 and gm-hra probes | 75 | 15 | 67.5 | 22.5 | 0.088 |
| BC1F2 Elite 7 background | ALS seed soak | 700 | 222 | 691.5 | 230.5 | 0.543 |
| Elite 8 background | | 761 | 273 | 775.5 | 258.5 | 0.315 |
| Elite 9 background | | 160 | 54 | 160.5 | 53.5 | 1.000 |
| Elite 10 background | | 205 | 79 | 213 | 71 | 0.304 |

TABLE 8

Comparison of Observed and Expected 1:2 Segregation Ratios for 3560.4.3.5 Soybean

| | | Observed | | Expected | | Chi-squared |
|---|---|---|---|---|---|---|
| Generation | Method | Homozygous +/+ | Hemizygous +/− | Homozygous +/+ | Hemizygous +/− | test P-value |
| F2 | | | | | | |
| Elite 1 background | Glyphosate spray to remove nulls and followed by ALS inhibitor ragdoll test | 16 | 24 | 13.3 | 26.7 | 0.467 |
| Elite 2 background | | 32 | 53 | 28.3 | 56.7 | 0.466 |
| F2 | | | | | | |
| Elite 3 background | ALS seed soak to remove nulls followed by qPCR for | 110 | 182 | 97.3 | 194.7 | 0.131 |
| Elite 4 background | | 124 | 284 | 136 | 272 | 0.227 |

TABLE 8-continued

Comparison of Observed and Expected 1:2
Segregation Ratios for 3560.4.3.5 Soybean

| Generation | Method | Observed Homozygous +/+ | Observed Hemizygous +/− | Expected Homozygous +/+ | Expected Hemizygous +/− | Chi-squared test P-value |
|---|---|---|---|---|---|---|
| Elite 5 background | glyat4601 | 27 | 61 | 29.3 | 58.7 | 0.678 |
| Elite 6 background | | 22 | 29 | 17 | 34 | 0.181 |

TABLE 9

Comparison of Observed and Expected 1:2:1
Segregation Ratios for 3560.4.3.5 Soybean

| Generation | Method | Observed +/+ | Observed +/− C2F2 | Observed −/− | Expected +/+ | Expected +/− | Expected −/− | Chi-squared test P-value |
|---|---|---|---|---|---|---|---|---|
| Elite 44 background | Glyat4601 and gm-hra qPCR | 41 | 76 | 43 | 40 | 80 | 40 | 0.799 |
| Elite 45 background | | 160 | 294 | 142 | 149 | 298 | 149 | 0.550 |

TABLE 10

Description and Sizes of PCR Products

| Forward Primer | Reverse Primer | Description of amplified region | Size (bp) of PCR product |
|---|---|---|---|
| 1297 | 1298 | Inserted DNA | 5457 |
| 1679 | 1658 | 5' flanking genomic border to SCP1 Promoter | 396 |
| 1679 | 1514 | 5' flanking genomic border | 246 |
| 1439 | 1666 | gm-hra to 3' flanking genomic border | 1029 |
| 1660 | 1666 | 3' flanking genomic border | 297 |

TABLE 11

List of Primer Sequences Used in PCR Reactions

| Primer Name | Abbreviated Primer Name | Sequence (5'-3') | Target Sequence Location (bp to bp)[1] | SEQ ID NO |
|---|---|---|---|---|
| 05-0-1227 | 1227 | TGGTCTTCTGAGACTGTATCTTTGATATTC | 3402-3373 | 24 |
| 05-0-1297 | 1297 | TGCCCGAGGTCGTTAGGTCGAATAGGCTAG | 3268-3297 | 25 |
| 05-0-1298 | 1298 | TCCTATTCAAGATGGGCAGTGTCTTCCTAATGATG | 8724-8690 | 17 |
| 06-0-1439 | 1439 | GATAACTGAGGGTGATGGTAGAACGAGGTACTGATTG | 7951-7987 | 18 |
| 06-0-1440 | 1440 | TGTGATAACTGAGGGTGATGGTAGAACGAGGTACTG | 7948-7983 | 26 |
| 06-0-1473 | 1473 | TTATTTCCGATCGGATCCTGCCAGTGGAG | 10849-10821 | 50 |
| 06-0-1504 | 1504 | CCACCATGTTGACGGATCTCTAG | 3347-3325 | 51 |

TABLE 11-continued

List of Primer Sequences Used in PCR Reactions

| Primer Name | Abbreviated Primer Name | Sequence (5'-3') | Target Sequence Location (bp to bp)[1] | SEQ ID NO |
|---|---|---|---|---|
| 06-0-1505 | 1505 | GCAATGGAATCCGAGGAGGTTTC | 3463-3441 | 52 |
| 06-0-1506 | 1506 | GCAATGATGGCATTTGTAGGTG | 3532-3511 | 53 |
| 06-0-1514 | 1514 | TCGATCGGTCAAGAATCCGGTTCTC | 3263-3239 | 19 |
| 06-0-1549 | 1549 | AAACTGAAGCGATGGCAGAACCGCACAG | 1962-1935 | 54 |
| 06-0-1550 | 1550 | TCGAAGTGGCAATAGAGCCACACAATATCGATAAG | 2012-1978 | 55 |
| 06-0-1610 | 1610 | AGCAATTGTTTTGTGCATTTCCAAATTTCAATCTG | 1-35 | 40 |
| 06-0-1658 | 1658 | CAATAGCCCTTTGGTCTTCTGAGACTGTATCTTTG | 3413-3379 | 20 |
| 06-0-1660 | 1660 | GTAATATCATCATTAGGAAGACACTGCCCATCTTG | 8683-8717 | 21 |
| 06-0-1666 | 1666 | CCATATTTGAAAGCCTAAGCAGATGGCATAATTC | 8979-8946 | 22 |
| 06-0-1679 | 1679 | TTCAGCAACAAACTCTCATCGTGAGCAG | 3018-3045 | 23 |

[1]Location in sequence of 356043 soybean. (See FIG. 4)
Bases 1-3317 = 5' genomic border, bases 3318-8679 = insert, bases 8680-10849 = 3' genomic border.

TABLE 12

Additional Primers for Detecting 3560.4.3.5 soybean

| Primer | Characteristics | SEQ ID NO |
|---|---|---|
| GGTCGAATAGGCTAGGTTTACGAA | (start 751, length 24 nt, tm 59, % GC 59) | 7 |
| AAGAGACTAAGGCCGCTC | (taqman mgb probe, start 776, lenth 18, tm 68, % gc 56) | 9 |
| CCACCATGTTGACGGATCTCT | (start 815, length 21, tm 58) | 8 |
| GTCGAATAGGCTAGGTTTACGAAAA | primer DP-356-f1 | 37 |
| TTTGATATTCTTGGAGTAGACGAGAGTGT | Primer Dp-356-r1 | 38 |
| 6FAM-CTCTAGAGATCCGTCAACATGGTGGAGCAC-TAMRA | Dp356-p (Taqman probe) | 39 |

Example 2

Additional Methods to Identify a 3560.4.3.5 Event

Oligonucleotide PCR reagents:

(SEQ ID NO: 7)
Forward Primer: 5' GGTCGAATAGGCTAGGTTTACGAA (SEQ ID NO: 8)
Reverse Primer: 5' CCACCATGTTGACGGATCTCT (SEQ ID NO: 9)
Taqman MGB probe: 5' Fam-AAGAGACTAAGGCCGCTC-MGB 3'

Each primer is used at a concentration of 900 nM in the PCR. The MGB probe was used at a concentration of 80 nM in the PCR. The PCR mixture used was "Extract-N-Amp PCR Ready Mix" (Cat. No. E3004) from Sigma-Aldrich. Rox reference dye was also included in the PCR mixture by adding 0.01 volumes of Sigma-Aldrich "Reference Dye for Quantitative PCR" (Cat. No. R4526). PCR was performed for 40 cycles with one cycle consisting of the following two steps: Step 1: 15 seconds at 95° C. and Step 2: 60 seconds at 60° C. Amplicon product had a size of 85 bp.

Additional primers that can be used to identify a 3560.4.3.5 soybean event are set forth in Table 13.

TABLE 13

| Primer | Sequence | Product Size (bp) | SEQ ID NO |
|---|---|---|---|
| 104312 | AGATCCGTCAACATGGTGGAGCAC | | 44 |
| 104314 | TGACAGATAGCTGGGCAATGGAATCC | 150 | 45 |
| Probe 125323 | 6FAM-TATCGGGAAACCTC-MGB | | 46 |
| 109893 (endogenous control) | CTTTGCTGTTTGATTGCTGGGTTGTC | | 47 |
| 109894 (endogenous control) | TGTGTGGACCCATTGGCCTTTAGATTAT | 144 | 48 |
| Probe 125322 (endogenous control) | VIC-ACTCTGCAGTTGCCTT-MGB | | 49 |

These primers were used in a presence/absence assay to detect a 3560.4.3.5 soybean event. Primers 104312+104314/SCP1TP10 detect the transgenic insertion; control primers, such as, 109893+109894/probe P94032A2 were used to detect house-keeping gene (aspartate aminotransferase gene) and were used as internal control. A 3560.4.3.5 soybean event will show heterozygous signals (FAM and VIC) and the non-transgenic genotypes will show homozygous P94032A2 (VIC) positive. PCR conditions employed in this method of dectecting the 3560.4.3.5 soybean are shown below.

TABLE 14

| PCR Conditions | | |
|---|---|---|
| Initial denat | 120 sec | 95 C. |
| Anneal | 90 sec | 66 C. |
| Extend | 90 sec | 72 C. |
| Denat | 30 sec | 95 C. |
| | 14 cycles | |
| Final extend | 120 | 72 C. |
| Initial denat | 120 sec | 95 C. |
| Anneal | 60 sec | 60 C. |
| Extend | 10 sec | 82 C. |
| Denat | 30 sec | 95 C. |
| Final extend | 0 | 82 C. |
| | 32 cycles | |

Those skilled in the art would also include a control PCR using an endogenous gene to verify that the isolated genomic DNA was suitable for PCR amplification. Soybean endogenous genes that have been used successfully with soybean samples are the following: Lectin gene (Schmidt, M and Parrott, W, 2001) and conglycinina α'-subunit gene (Shirai (1998) Biosci Biotechnol Biochem 62:1461-1464). Another location to find endogenous gene targets for PCR is the web site (www.//biotech,jrc.it) which is sponsored by the Joint Research Centre (JRC) of the European Commission. See, also, Schmidt et al. (2001) *Plant Cell Rep* 20:422-428.

Example 3

Soybean event 3560.4,3.5 was selected as a lead event and BC1F3 lines were created by backcrossing 3560.4.3.5 soybean into four different conventional lines. Across these four backcross populations, lines with the 3560.4.3.5 event (sprayed with glyphosate) were not significantly different for yield compared to negative null segregant lines (sprayed with conventional herbicides). Soybean event 3560.4,3.5 confers a high level of tolerance to glyphosate and ALS inhibitor herbicides with no yield impact.

The first objective of this study was to evaluate 3560.4.3.5 soybean to determine the level of tolerance to different application rates of glyphosate and ALS inhibitor herbicides. The second objective was to develop homozygous positive and homozygous negative null segregants (NILs) of 3560.4.3.5 soybean event to determine if yield was impacted due to presence of the 3560.4.3.5 event. The third objective was to integrate event 3560.4,3.5 into different genetic backgrounds to determine if there was any impact on herbicide tolerance or yield performance.

Materials and Methods

For early generation transgenic event testing, T0 plants were sprayed at the V2 to V6 growth stage (Fehr et al. (1977) Coop. Ext. Ser. Special Report 80. Iowa State Univ., Ames Iowa) with 1.68 kg ae ha$^{-1}$ or 3.36 kg ae ha$^{-1}$ glyphosate plus adjuvants (0.25% v/v nonionic surfactant (NIS)+2.24 kg ai ha$^{-1}$ ammonium sulfate (AMS)) in the Newark, Del. greenhouses. Plants were rated using a 1 to 9 scale ten days after treatment (DAT), where 1=dead plant to 9=no observed spray response.

Selected events were advanced at the T1 generation for herbicide tolerance confirmation in greenhouses. Plants were sprayed at the V3 growth stage with either 1.68 kg ae ha$^{-1}$ glyphosate, 60 g ai ha$^{-1}$ thifensulfuron methyl(methyl 3-[[[[(4-methoxy-6-methyl-1,3,5-triazin-2-yl)amino]carbonyl]amino]sulfonyl]-2-thiophenecarboxylate), or a sequential application of 70 g ai ha$^{-1}$ thifensulfuron methyl at V3 followed by 2.24 kg ai ha-1 glyphosate at V6. All spray treatments included 0.25% v/v NIS+2.24 kg ai ha$^{-1}$ AMS. At ten days after spray application, plants were rated using a 1 to 9 scale. Since the T1 events were segregating, only the non-susceptible plants were scored, and an average rating of tolerant plants within each event was calculated.

Plants from individual T1 events were grown separately in 2.4 m rows (76.2 cm row spacing). Presence or absence of glyat+hra in each individual T1 plant was determined by using polymerase chain reaction (PCR) amplification of the glyat4601 insert. PCR results for each event were analyzed using chi square analyses to identify events with Mendelian segregation. For each of the events evaluated, T1 plants that were positive for the glyat+hra were harvested separately and advanced as plant-to-row T2 short rows (2.4 m rows with 76.2 cm row spacing). Twelve remnant seed from each T2field entry were grown and V3 plants were sprayed with 3.36 kg ae ha$^{-1}$ glyphosate plus 0.25% v/v NIS+2.24 kg ai ha$^{-1}$ AMS to determine zygosity of the corresponding short row. Lines were considered homozygous positive if all 12 plants were tolerant, homozygous negative if all 12 plants were susceptible, and heterozygous if the 12 plants were a mixture of tolerant and susceptible phenotypes.

Chi square was used to analyze T2 results to identify events with Mendelian segregation across generations. Twenty four different lines at the T3 generation with the glyat+hra were selected for advancement to herbicide tolerance trials. Homozygous positive and homozygygous negative NILs from ten events were advanced to isoline yield trials. 3560.4.3.5 soybean event was one of the events selected for advancement.

The 3560.4.3.5 soybean event was evaluatead for glyphosate tolerance. 3560.4.3.5 soybean was grown in a randomized complete block (RCB) design in a split plot arrangement with three replications of paired 3.7 m rows (76.2 cm row spacing). Treatments consisted of an unsprayed control, and three spray rates applied at the V5 growth stage using either 3.36 kg ae ha$^{-1}$, 6.72 kg ae ha$^{-1}$, or 13.44 kg ae ha$^{-1}$ glyphosate. Plots were evaluated for crop response at 7 and 14 days after treatment (DAT), and rated using a 1-9 score. Crop response data were analyzed using the general linear model (GLM) and mixed model analysis of variance (ANOVA) procedures of SAS. (The SAS System is a registered trademark of SAS Institute, Inc., Cary, N.C., USA)

Selected T4 lines were tested for glyphosate tolerance. This experiment was a RCB design in a split plot arrangement with two replications of individual 1.2 m rows (76.2 cm row spacing). At the V3 growth stage, 6.72 kg ae ha$^{-1}$ glyphosate was applied to one block, while another was unsprayed for use as a control. The third block received a sequential application of 6.72 kg ae ha$^{-1}$ glyphosate at V3 followed by 6.72 kg ae ha$^{-1}$ glyphosate at R1. Plots were evaluated for crop response at 7 DAT and 14 DAT, and assigned a visual response score from 0% to 100% response, where 0%=no response observed to 100%=plot completely dead. Crop response data were analyzed using the GLM and mixed model ANOVA procedures of SAS.

ALS inhibitor herbicide tolerance of the gm-hra gene was compared to sulfonylurea tolerant soybeans (STS®) by growing T4 plants of event 3560.4.3.5 and a STS® cultivar. The experiment was designed as a RCB design in a split plot arrangement with two replications of paired 3.7 m rows (76.2 cm row spacing). Spray treatments were applied at the V3 growth stage and consisted of one of the following: an unsprayed control, 8.8 g ai ha$^{-1}$ rimsulfuron (N-[[(4,6-dimethoxy-2-pyrimidinyl)amino]carbonyl]-3-(ethylsulfonyl)-2-pyridinesulfonamide), 8.8 g ai ha$^{-1}$ tribenuron methyl (methyl 2-[[[[(4-methoxy-6-methyl-1,3,5-triazin-2-yl)methylamino]carbonyl]amino]sulfonyl]benzoate), or 30.0 g ai ha$^{-1}$ chlorimuron ethyl (ethyl 2-[[[[(4-chloro-6-methoxypyrimidin-2-yl)amino]carbonyl]amino]sulfonyl]benzoate)+ 9.67 g ai ha$^{-1}$ thifensulfuron methyl. All spray treatments listed had 0.25% v/v NIS+2.24 kg ai ha$^{-1}$ AMS added. Plots were evaluated for crop response at 7 DAT and 14 DAT, and assigned a visual response score from 0% to 100% response. Crop response data were analyzed using the mixed model ANOVA procedure of SAS.

ALS inhibitor herbicide tolerance trials were completed at two separate locations. Plants from the T5 generation of event 3560.4.3.5 and a STS® cultivar were grown in a RCB design in a split plot arrangement with three replications of paired 2.4 m rows (76.2 cm row spacing). Treatments were applied at the V3 growth stage and consisted of an unsprayed control, 4.2 g ai ha$^{-1}$ metsulfuron methyl (methyl 2-[[[[(4-methoxy-6-methyl-1,3,5-triazin-2-yl)amino]carbonyl]amino]sulfonyl]benzoate), 70.0 g ai ha$^{-1}$ thifensulfuron methyl, and 17.5 g ai ha$^{-1}$ tribenuron methyl. All spray treatments listed had 0.25% v/v NIS+2.24 kg ai ha$^{-1}$ AMS added. Visual response ratings (0% to 100%) were assigned to each plot at 7 DAT, 14 DAT, and 28 DAT. Crop response data were analyzed using the mixed model ANOVA procedure of SAS.

Multiple trials were conducted with the lead event 3560.4.3.5 soybean to observe the level of tolerance to different rates and application timings of glyphosate with and without other pesticide mixtures. The first experiments were grown in an RCB design of three replications of paired 3.7 m rows (76.2 cm row spacing), blocked by replication with randomized spray treatments within each replication. Treatments were applied at the V2 or R2 growth stage, and consisted of the following: unsprayed control, 3.36 kg ae ha$^{-1}$ glyphosate, 3.36 kg ae ha$^{-1}$ glyphosate+560.4 g ai ha$^{-1}$ chlorpyrifos (O,O-diethyl O-3,5,6-trichloro-2-pyridyl phosphorothioate), 3.36 kg ae ha$^{-1}$ glyphosate+1120.9 g ai ha$^{-1}$ bentazon (3-isopropyl-1H-2,1,3-benzothiadiazin-4(3H)-one 2,2-dioxide), 3.36 kg ae ha$^{-1}$ glyphosate+141.3 g ai ha$^{-1}$ imazethapyr (2-[4.5-dihydro-4-methyl-4-(1-methylethyl)-5-oxo-1H-imidazol-2-yl]-5-ethyl-3-pyridinecarboxylic acid), 3.36 kg ae ha$^{-1}$ glyphosate+263.4 g ai ha$^{-1}$ fomesafen (5-[2-chloro-4-(trifluoromethyl)phenoxy]-N-(methylsulfonyl)-2-nitrobenzamide), 3.36 kg ae ha$^{-1}$ glyphosate+17.5 g ai ha$^{-1}$ thifensulfuron methyl+17.5 g ai ha$^{-1}$ tribenuron methyl, 3.36 kg ae ha$^{-1}$ glyphosate+17.5 g ai ha$^{-1}$ thifensulfuron methyl+17.5 g ai ha$^{-1}$ tribenuronmethyl+560.4 g ai ha$^{-1}$ chlorpyrifos, 3.36 kg ae ha$^{-1}$ glyphosate+17.5 g ai ha$^{-1}$ thifensulfuron methyl+17.5 g ai ha$^{-1}$ tribenuron methyl+1120.9 g ai ha$^{-1}$ bentazon, 3.36 kg ae ha$^{-1}$ glyphosate+17.5 g ai ha$^{-1}$ thifensulfuron methyl+17.5 g ai ha$^{-1}$ tribenuron methyl+141.3 g ai ha$^{-1}$ imazethapyr, and 3.36 kg ae ha$^{-1}$ glyphosate+17.5 g ai ha$^{-1}$ thifensulfuron methyl+17.5 g ai ha$^{-1}$ tribenuron methyl+263.4 g ai ha$^{-1}$ fomesafen. All spray treatments listed had 0.25% v/v NIS+2.24 kg ai ha$^{-1}$ AMS added. Visual response ratings (0% to 100%) were assigned to each plot at 7 DAT, 14 DAT, and 28 DAT. Crop response data were analyzed using the GLM and mixed model ANOVA procedures of SAS.

The second set of tolerance experiments were designed to measure yield potential of 3560.4.3.5 soybean after application of common field use rates of glyphosate and/or ALS inhibitor herbicides. These experiments were six replications of paired 3.7 m rows (76.2 cm row spacing), grown in a RCB design, blocked by replication, with randomized spray treatments within each replication. One experiment was grown at field A and two experiments were grown at field B and C (which were separated by planting date and physical distance of field locations.) In addition, the two fields had different environmental influence; one field experienced drought stress through the spring and early summer, the other was well irrigated throughout the growing season. Treatments were randomized within each of the replications and sprayed at the VC, V2, R2, or R5 growth stages. Treatments consisted of 1.68 kg ai ha$^{-1}$ glyphosate, 5.8 g ai ha$^{-1}$ chlorimuron ethyl+ 4.4 g ai ha$^{-1}$ thifensulfuron methyl, and 1.68 kg ai ha$^{-1}$ glyphosate+5.8 g ai ha$^{-1}$ chlorimuron ethyl+4.4 g ai ha$^{-1}$ thifensulfuron methyl. All spray treatments listed had 0.25% v/v NIS+2.24 kg ai ha$^{-1}$ AMS) added. Visual response ratings (0% to 100%) were assigned to each plot at 7 DAT, 14 DAT, and 28 DAT. Plots were harvested and yield was calculated for each plot. Crop response data were analyzed using the GLM and mixed model ANOVA procedures of SAS.

Homozygous positive and homozygous negative null segregants (NILs) of 3560.4.3.5 soybean from T3 generation events were grown in preliminary yield trials to determine if yield was impacted due to the presence of 3560.4.3.5 event. Isoline yield trials were designed as a RCB (blocked by event), with a single replication of paired 3.7 m rows (76.2 cm row spacing). Trials were mechanically cultivated and/or had labeled use rates of conventional soybean herbicides applied, as needed, to ensure weed-free conditions. Maturity scores and yield data were collected for each entry and subject to ANOVA using the mixed model procedure of SAS.

T3 seed for each isoline entry was also advanced to the T4 generation. Remnant T3 seed from each line was confirmed to be either homozygous positive or homozygous negative by evaluating 12 seedlings that were germinated in chlorsulfuron herbicide solution. Conventional soybean lines are not tolerant to spray application of chlorsulfuron, which is currently utilized in small grain production to control broadleaf weeds. The chlorsulfuron herbicide stock solution was created by mixing 66.7 mg of chlorsulfuron with 1 liter of water. The mixture was buffered to a pH of 7.5 using 1 mM phosphate buffer. From this stock solution, 20 ml was mixed with 1 liter of water, which was then used to saturate germination paper. Seeds were added to the germination paper and observed 10 days after initial treatment for their response. Seedlings that possessed the 3560.4.3.5 event germinated and grew normally, while seedlings that lacked the event created hooked unifoliolate leaves that did not expand and develop any further (data not shown). Lines were scored as homozygous positive if all 12 seedlings grew normally through the solution (data not shown). Lines were scored as homozygous negative if all 12 plants had the inhibited hooked unifoliolate phenotype (data not shown).

Homozygous positive 3560.4.3.5 event and homozygous negative NILs were grown in isoline yield trial experiments. Trials were mechanically cultivated and/or had labeled use rates of conventional soybean herbicides applied, as needed, to ensure weed-free conditions. Maturity scores and yield data were collected for each entry and subject to ANOVA using the mixed model procedure of SAS.

Remnant T4 seed from each line was confirmed to be either homozygous positive or homozygous negative by evaluating 12 seedlings using the chlorsulfuron herbicide screen. T4 seed for each selected isoline entry was advanced to the T5 generation.

Event 3560.4.3.5 was selected for additional isoline yield trial evaluations. Homozygous positive and homozygous negative NILs from event 3560.4.3.5 were grown using the same experimental yield test design implemented above. Experiments were planted and trials were mechanically cultivated and/or had labeled use rates of conventional soybean herbicides applied, as needed, to ensure weed-free conditions. Maturity scores and yield data were collected for each entry and subject to ANOVA using the mixed model procedure of SAS.

Event 3560.4.3.5 was selected for introgression into four different Pioneer® conventional (non-transgenic) elite lines with different genetic parentage. The four elite lines had relative maturities (RM) of 22, 27, 30, and 38. After the initial cross, F1 seed was backcrossed to the respective recurrent parent and BC1F1 seed was advanced to the F2 generation. The four BC1F2 populations created were grown and harvested as individual plants. BC1F3 lines were created using single plant-to-row 2.4 m increase rows. Homozygous positive or homozygous negative sister lines were selected for yield testing based upon screening of 12 remnant seedlings for each line using the chlorsulfuron herbicide seedling test. Based upon the remnant screening across the four populations, 328 positive 3560.4.3.5 soybean lines, and 116 negative lines were selected for preliminary yield trials For the 3560.4.3.5× elite preliminary yield trials, BC1F3 lines were blocked by the recurrent parent and presence or absence of the 3560.4.3.5 event. Positive and negative blocks were planted adjacent to each other at different locations, based upon expected maturity of the lines within the population. The 3560.4.3.5 event positive blocks had a V3 application of 2.24 kg ai ha$^{-1}$ glyphosate plus 0.25% v/v NIS+2.24 kg ai ha$^{-1}$ AMS, while negative blocks had conventional herbicides applied (as needed) to maintain weed free plots. Maturity scores and yield data were collected for each entry at each location and subject to multiple regression and ANOVA using the GLM and mixed model procedures of SAS.

Results and Discussion

T0 3560.4.3.5 soybean were evaluated for glyphosate tolerance. The 3560.4.3.5 soybean were sprayed with 2.24 kg ai ha$^{-1}$ glyphosate and 4.48 kg ae ha$^{-1}$ glyphosate (Table 15). The 2.24 kg ai ha$^{-1}$ treatment would correspond to 2× the typical labeled field application rate of glyphosate, while the 4.48 kg ae ha$^{-1}$ treatment would correspond to 4× the typical labeled field application rate of glyphosate. The untransformed parental line (sprayed as a control) did not survive either glyphosate application rate and was consistently rated a 1.

The 3560.4.3.5 event was advanced to the T1 generation in a greenhouse to confirm herbicide tolerance. The 3560.4.3.5 event had tolerance after application of 1.68 kg ae ha$^{-1}$ glyphosate, after application of 60.0 g ai ha$^{-1}$ thifensulfuron methyl, and after a sequential application of 70 g ai ha$^{-1}$ thifensulfuronmethyl at V3, followed by 1.68 kg ae ha$^{-1}$ glyphosate at V5 as shown in Table 15. These data indicate event 3560.4.3.5 confers tolerance to both glyphosate and thifensulfuron methyl application at early generations after transformation.

The 3560.4.3.5 event was analyzed for Mendelian segregation across early generations (Table 16).

TABLE 15

Southern copy number estimates and average visual response ratings† ten days after herbicide application on T0 and T1 generation transgenic event 3560.4.3.5

| | Southern bands‡ | | Generation | | | |
|---|---|---|---|---|---|---|
| | | | T0 | | T1 | |
| Event | glyat4601 | hra | 1.68§ | 3.36§ | 1.68§ | 60.0¶ | 70.0 + 1.68# |
| 3560.4.3.5 | 1 | 1 | 7.0 | 6.5 | 7.0 | 7.0 | 8.0 | 8.0 |

†Average visual response rating of tolerant plants 10 days after herbicide application in the greenhouse (0 = dead plant to 9 = no response detected)
‡Estimated number of copies based upon Southern analysis using HindIII and the glyat4601 gene or gm-hra gene as a probe
§Glyphosate application (1.68 kg ae ha$^{-1}$, or 3.36 kg ae ha$^{-1}$) + 0.25% v/v NIS + 2.24 kg ai ha$^{-1}$ AMS applied at the V3 growth stage
¶Thifensulfuron methyl application (60.0 g ai ha$^{-1}$ or 70.0 g ai ha$^{-1}$) + 0.25% v/v NIS + 2.24 kg ai ha$^{-1}$ AMS applied at the V3 growth stage.
Sequential application; initially sprayed at the V3 growth stage with 70 g ai ha$^{-1}$ thifensulfuron methyl + 0.25% v/v NIS + 2.24 kg ai ha$^{-1}$ AMS, followed by spray of 1.68 kg ae ha$^{-1}$ glyphosate + 0.25% v/v NIS + 2.24 kg ae ha$^{-1}$ AMS at the V6 growth stage. The first score is 10 days after the V3 thifensulfuron methyl application, the second score is 10 days after the V6 glyphosate application

TABLE 16

Segregation ratios of T1 plants and T2 progeny rows of event 3560.4.3.5.

| | Generation | | | | | | | | |
|---|---|---|---|---|---|---|---|---|---|
| | T1 plants† | | | | | T2 lines‡ | | | |
| | Observed | | Expected | | | Observed | | Expected | |
| Event | Positive | Negative | Positive | Negative | chi² P§ | Positive | Negative | Positive | Negative | chi² P§ |
| 3560.4.3.5 | 59 | 23 | 61.5 | 21.1 | 0.605 | 34 | 9 | 32.3 | 10.3 | 0.609 |

†T1 plants were identified to be positive or negative for the glyat transgene insert using PCR amplification
‡T2 lines (derived from individual glyat positive T1 plants) were screened by spraying 3.36 kg ae ha$^{-1}$ glyphosate plus 0.25% v/v NIS + 2.24 kg ai ha$^{-1}$ AMS on 12 remnant V3 plants in a greenhouse.
§chi² probability that deviation from expected model is due to chance alone The T3 plants from the 3560.4.3.5 plants were sprayed in a glyphosate herbicide tolerance field trial. Table 17 shows the herbicide response at seven DAT after application of 3.36 kg ae ha$^{-1}$ glyphosate, after application of 6.72 kg ae ha$^{-1}$ glyphosate, and after application of 13.44 kg ae ha$^{-1}$ glyphosate.

The untransformed control line was susceptible to any glyphosate application and was consistently rated as a 1. 3560.4.3.5 soybean T4 plants were advanced for additional glyphosate tolerance testing. Table 17 shows the spray ratings at seven and fourteen DAT with 6.72 kg ae ha$^{-1}$ glyphosate.

TABLE 17

LSMeans for visual ratings[†] of selected T3 and T4 3560.4.3.5 plants, sprayed with experimental rates of glyphosate in field experiments.

| | 2004 (T3 plants)[‡] Glyphosate spray rate (kg ae ha$^{-1}$) | | | | 2005 (T4 plants)[§] Glyphosate spray rate (kg ae ha$^{-1}$) | | | | | |
|---|---|---|---|---|---|---|---|---|---|---|
| | Unsprayed | 3.36 | 6.72 | 13.44 | Unsprayed | | 6.72 | | 6.72 sequential[¶] | |
| Event | 7 DAT | 7 DAT | 7 DAT | 7 DAT | 7 DAT | 14 DAT | 7 DAT | 14 DAT | 7 DAT | 14 DAT |
| 3560.4.3.5 | 9.0 | 8.0 | 6.7 | 5.7 | 9.0 | 9.0 | 6.8 | 7.8 | 7.8 | 7.7 |

[†]Visual response ratings on a 1 to 9 scale, where 1 = completely dead plot to 9 = no response observed
[‡]test consisted of three randomized replications of paired 3.7 m rows (76.2 cm row spacing) sprayed at the V3 growth stage
[§]test consisted of two randomized replications of paired 1.2 m rows (76.2 cm row spacing) sprayed at the V3 growth stage
[¶]Sequential spray; 6.72 kg ae ha$^{-1}$ glyphosate sprayed at V3, followed by 6.72 kg ae ha$^{-1}$ glyphosate sprayed on the same plots at R1 (rating data listed below this treatment is after the R1 application)

In addition to the glyphosate herbicide tolerance trials, event 3560.4.3.5 was compared to a STS® cultivar in two experiments to determine if the hra gene had better tolerance to different ALS inhibitor herbicides(Table 18). Across these two experiments, the 3560.4.3.5 soybean had significantly lower crop response compared to STS® at 7 DAT and 14 DAT after application of 8.8 g ai ha$^{-1}$ rimsulfuron, 8.8 g ai ha$^{-1}$ tribenuron methyl, 4.2 g ai ha$^{-1}$ metsulfuron methyl, and 17.5 g ai ha$^{-1}$ tribenuron methyl (Table 18). These chemistries are currently not labeled for use on soybean, and will cause high levels of crop response on current STS® and conventional soybean cultivars. The tolerance data obtained indicate that 3560.4.3,5 soybean had significantly higher tolerance to multiple ALS inhibitor chemistries when compared directly to the STS® trait.

TABLE 18

Difference of LSMeans for crop response ratings[†] of 3560.4.3.5 soybean compared to STS ® across different ALS inhibitor herbicide treatments in experiments.

| Treatment[‡] | Rate (g ai ha$^{-1}$) | Location[§] | Reps | 7 DAT | | | | 14 DAT | |
|---|---|---|---|---|---|---|---|---|---|
| | | | | 3560.4.3.5 | STS ® | Difference | Pr > \|t\| | 3560.4.3.5 | STS ® |
| Rimsulfuron | 8.8 | A | 2 | 10.0 | 50.0 | −40.0 | <.0001 | 5.0 | 55.0 |
| Tribenuron methyl | 8.8 | A | 2 | 5.0 | 35.0 | −30.0 | <.0001 | 5.0 | 42.5 |
| Chlorimuron ethyl + thifensulfuron methyl | 30.0 + 9.67 | A | 2 | 0.0 | 5.0 | −5.0 | 0.200 | 0.0 | 5.0 |
| Unsprayed control | 0 | A | 2 | 0.0 | 0.0 | 0.0 | 1.000 | 0.0 | 0.0 |
| Metsulfuron methyl | 4.2 | B | 6 | 58.3 | 79.2 | −20.8 | <.0001 | 64.2 | 90.8 |
| Thifensulfuron methyl | 70 | B | 6 | 23.3 | 27.5 | −4.20 | 0.549 | 6.7 | 8.3 |
| Tribenuron methyl | 17.5 | B | 6 | 11.7 | 36.7 | −25.0 | <.0001 | 15.0 | 48.3 |
| Unsprayed control | 0 | B | 6 | 0.0 | 0.0 | 0.0 | 1.000 | 1.7 | 0.0 |

| Treatment[‡] | 14 DAT | | 28 DAT[¶] | | | |
|---|---|---|---|---|---|---|
| | Difference | Pr > \|t\| | 3560.4.3.5 | STS ® | Difference | Pr > \|t\| |
| Rimsulfuron | −50.0 | <.0001 | | | | |
| Tribenuron methyl | −37.5 | <.0001 | | | | |
| Chlorimuron ethyl + thifensulfuron methyl | −5.0 | 0.171 | | | | |
| Unsprayed control | −45.0 | <.0001 | | | | |

TABLE 18-continued

Difference of LSMeans for crop response ratings[†] of 3560.4.3.5 soybean compared to STS ® across different ALS inhibitor herbicide treatments in experiments.

| | | | | | | |
|---|---|---|---|---|---|---|
| Metsulfuron methyl | −26.7 | <.0001 | 29.2 | 95.0 | −65.8 | <.0001 |
| Thifensulfuron methyl | −1.7 | 0.797 | 8.3 | 6.7 | 1.7 | 0.803 |
| Tribenuron methyl | −33.3 | <.0001 | 5.0 | 21.7 | −16.7 | 0.015 |
| Unsprayed control | 1.7 | 0.747 | 1.7 | 0.0 | 1.7 | 0.804 |

[†]Visual response ratings from 0% to 100%, where 0% = no response observed to 100% = plot completely dead.
[‡]0.25% v/v NIS + 2.24 kg ai ha$^{-1}$ AMS was added to all spray treatments
[§]A location consisted of two replications of paired 3.7 m rows (76 cm row spacing); B location consisted of three replications of paired 3.7 m rows (76.2 cm row spacing), grown at two different locations.
[¶]Due to minimal response of 35604.3.5 at 14 DAT, the 28 DAT ratings were not recorded for the A experiment Event 3560.4.3.5 was evaluated for herbicide tolerance and yield performance in more extensive testing. For the first set of experiments, event 3560.4.3.5 was sprayed at a vegetative stage and a reproductive stage with different tank mixes of glyphosate and other pesticides. Across the treatments evaluated, there was minimal crop response at 7 DAT and 14 DAT (10% or less) for the glyphosate and all glyphosate plus pesticide mixtures applied at the V2 growth stage, except those containing bentazon or fomesafen (Table 19). The treatments with bentazon or fomesafen caused up to 20% initial phytotoxicity at 7 DAT, which diminished to less than 12% by 14 DAT. These results were expected, as the leaf bronzing observed was equivalent to phytotoxicity that is typically observed on commodity soybeans up to 14 days after application with either bentazon of fomesafen chemistry. It should also be noted that herbicide response ratings are very subjective, and in general, a 10% response cannot be easily distinguished unless there is an unsprayed control right next to the plot being evaluated. By 28 DAT, there was essentially no crop response to any of the treatments applied at the V2 growth stage (Table 19). For the mixtures applied at R2, all of the treatments had 10% or less response at 7 DAT, 14 DAT, and 28 DAT except for the treatment containing bentazon (Table 19). For this treatment an average crop response of 11.4% was recorded at 7 DAT, which diminished to less than 5% at 14 DAT and 0% at 28 DAT (Table 19). The crop response observed was the typical leaf bronzing that is commonly observed up to 14 DAT after application of bentazon on commodity soybeans. In general, 3560.4.3.5 soybean had excellent tolerance to different mixtures of glyphosate with and without other pesticides across two different growth stages evaluated in different environments.

TABLE 19

LSMeans for crop response ratings[†] of 3560.4.3.5 soybean treated at two different growth stages with different tank mixed pesticide formulations.

| Treatment[‡] | Glyphosate rate (kg ae ha−1) | Other pesticides rate (g ai ha$^{-1}$) | Application Stage | Reps | 7 DAT Average | 14 DAT Average | 28 DAT Average |
|---|---|---|---|---|---|---|---|
| Glyphosate | 3.36 | | V2 | 9 | 3.9 | 3.3 | 0.6 |
| Glyphosate + chlorpyrifos | 3.36 | 560.4 | V2 | 9 | 5.6 | 3.3 | 0.0 |
| Glyphosate + bentazon | 3.36 | 1120.9 | V2 | 9 | 16.6 | 6.3 | 0.6 |
| Glyphosate + imazethapyr | 3.36 | 141.3 | V2 | 9 | 5.0 | 2.2 | 0.6 |
| Glyphosate + fomesafen | 3.36 | 263.4 | V2 | 9 | 20.3 | 12.0 | 0.6 |
| Glyphosate + tribenuron-methyl + thifensulfuron-methyl | 3.36 | 17.5 + 17.5 | V2 | 9 | 5.0 | 8.3 | 0.0 |
| Glyphosate + tribenuron-methyl + thifensulfuron-methyl + chlorpyrifos | 3.36 | 17.5 + 17.5 + 560.4 | V2 | 9 | 7.6 | 10.8 | 0.0 |
| Glyphosate + tribenuron-methyl + thifensulfuron-methyl + bentazon | 3.36 | 17.5 + 17.5 + 1120.9 | V2 | 9 | 17.9 | 5.0 | 0.0 |
| Glyphosate + tribenuron-methyl + thifensulfuron-methyl + imazethapyr | 3.36 | 17.5 + 17.5 + 141.3 | V2 | 9 | 5.1 | 7.8 | 0.0 |
| Glyphosate + tribenuron-methyl + thifensulfuron-methyl + fomesafen | 3.36 | 17.5 + 17.5 + 263.4 | V2 | 9 | 19.8 | 11.4 | 1.1 |
| Glyphosate | 3.36 | | R2 | 9 | 1.7 | 0.6 | 0.0 |
| Glyphosate + chlorpyrifos | 3.36 | 560.4 | R2 | 9 | 1.7 | 0.6 | 0.0 |
| Glyphosate + bentazon | 3.36 | 1120.9 | R2 | 9 | 11.4 | 2.2 | 0.0 |
| Glyphosate + imazethapyr | 3.36 | 141.3 | R2 | 9 | 0.6 | 0.0 | 0.0 |
| Glyphosate + fomesafen | 3.36 | 263.4 | R2 | 9 | 9.6 | 1.7 | 0.0 |
| Glyphosate + tribenuron-methyl + thifensulfuron-methyl | 3.36 | 17.5 + 17.5 | R2 | 9 | 1.1 | 0.0 | 0.0 |
| Glyphosate + tribenuron-methyl + thifensulfuron-methyl + chlorpyrifos | 3.36 | 17.5 + 17.5 + 560.4 | R2 | 9 | 2.8 | 0.0 | 0.0 |
| Glyphosate + tribenuron-methyl + thifensulfuron-methyl + bentazon | 3.36 | 17.5 + 17.5 + 1120.9 | R2 | 9 | 7.0 | 1.7 | 0.0 |
| Glyphosate + tribenuron-methyl + thifensulfuron-methyl + imazethapyr | 3.36 | 17.5 + 17.5 + 141.3 | R2 | 9 | 1.7 | 0.0 | 0.0 |
| Glyphosate + tribenuron-methyl + thifensulfuron-methyl + fomesafen | 3.36 | 17.5 + 17.5 + 263.4 | R2 | 9 | 5.3 | 2.8 | 0.0 |
| Unsprayed control | 3.36 | | R2 | 9 | 0.0 | 0.0 | 0.0 |
| LSD (a = 0.05) | | | | | 3.3 | 3.3 | 2.0 |

[†]Visual response ratings from 0% to 100%, where 0% = no response observed to 100% = plot completely dead.
[‡]All treatments had 0.25% v/v NIS + 2.24 kg ai ha$^{-1}$ AMS added.

The second set of experiments conducted with event 3560.4.3.5 were designed to measure yield potential after application of different herbicides at field use rates that would be commonly utilized for soybean production. Across the glyphosate, ALS inhibitor, and glyphosate plus ALS inhibitor treatments there was minimal (10% or less) to essentially no response at 7, 14, and 28 DAT (Table 20). When yield data was collected, there were no significant yield differences detected for any of the herbicide treatments applied at different the growth stages (Table 20). In addition, the replications that received herbicide treatments were not statistically different from the unsprayed control replications for yield (Table 20). Based upon multiple year herbicide tolerance trials, it can be concluded that event 3560.4.3.5 had excellent tolerance to field use rates of glyphosate, ALS inhibitor, and glyphosate plus ALS inhibitor herbicides. In addition, yield potential was not affected when event 3560.4.3.5 was sprayed with glyphosate, ALS inhibitor, and glyphosate plus ALS inhibitor chemistries at different vegetative and reproductive growth stages.

TABLE 20

LSMeans for crop response ratings[†] and yield (kg ha$^{-1}$) for 3560.4.3.5 soybean treated at four different growth stages with different herbicide combinations.

| Treatment[‡] | Glyphosate rate (kg ae ha$^{-1}$) 7 DAT | ALS inhibitor rate (g ai ha$^{-1}$) 14 DAT | Application Stage 28 DAT | Reps Yield |
|---|---|---|---|---|
| Glyphosate | 1.68 | | VC | 18 |
| | 1.6 | 0.8 | 0.6 | 2745.7 |
| Glyphosate | 1.68 | | V2 | 18 |
| | 5.3 | 2.8 | 0.6 | 2851.7 |
| Glyphosate | 1.68 | | R2 | 18 |
| | 2.0 | 0.6 | 0.0 | 2702.9 |
| Glyphosate | 1.68 | | R5 | 18 |
| | 0.3 | 0.3 | 0.0 | 2718.8 |
| Chlorimuron ethyl + thifensulfuron methyl | 0.7 | 5.8 + 4.4 0.6 | VC 0.6 | 18 2756.4 |
| Chlorimuron ethyl + thifensulfuron methyl | 0.6 | 5.8 + 4.4 0.0 | V2 0.3 | 18 2864.0 |
| Chlorimuron ethyl + thifensulfuron methyl | 0.0 | 5.8 + 4.4 0.0 | R2 0.3 | 18 2899.2 |
| Chlorimuron ethyl + thifensulfuron methyl | 0.0 | 5.8 + 4.4 0.0 | R5 0.6 | 18 2861.1 |
| Glyphosate + chlorimuron ethyl + thifensulfuron methyl | 1.68 2.6 | 5.8 + 4.4 1.7 | VC 0.0 | 18 2647.3 |
| Glyphosate + chlorimuron ethyl + thifensulfuron methyl | 1.68 6.9 | 5.8 + 4.4 3.8 | V2 2.2 | 18 2829.7 |
| Glyphosate + chlorimuron ethyl + thifensulfuron methyl | 1.68 0.8 | 5.8 + 4.4 0.0 | R2 0.3 | 18 2841.6 |
| Glyphosate + chlorimuron ethyl + thifensulfuron methyl | 1.68 1.1 | 5.8 + 4.4 0.0 | R5 0.0 | 18 2768.3 |
| Hand weeded control | 0.0 | 0.0 | Control 0.0 | 18 2813.1 |
| Unsprayed control | 0.0 | 0.0 | Control 0.0 | 18 2742.4 |
| LSD (a = 0.05) | 1.3 | 1.1 | 0.8 | 155.6 |

[†]Visual response ratings from 0% to 100%, where 0% = no response observed to 100% = plot completely dead
[‡]Two different field locations were utilized; one field had severe drought stress during the spring and early summer, the other was well irrigated.
[‡]All treatments had 0.25% v/v NIS + 2.24 kg ai ha$^{-1}$ AMS added Isoline yield test data were collected in five additional environments for event 3560.4.3.5 soybean. When isoline yield data were subject to mixed model ANOVA, the year, and location (nested within year) were significantly different (Table 21). Positive 3560.4.3.5 soybean and negative NILs, and the interactions with the 3560.4.3.5 event were not significantly different for yield (Table 21). These data indicate that presence of event 3560.4.3.5 does not impact final yield potential when NILs were tested across multiple years and environments.

TABLE 21

Mixed model ANOVA for yield (kg ha$^{-1}$) of positive and negative NILs of event 3560.4.3.5, tested in fourteen environments.
Type 3 Tests of Fixed Effects

| Effect | Num DF | Den DF | F Value | Pr > F |
|---|---|---|---|---|
| Year | 2 | 80 | 26.92 | <.0001 |
| Location(Year) | 11 | 80 | 7.82 | <.0001 |
| glyat + hra | 1 | 80 | 0.04 | 0.850 |
| Year * glyat + hra | 2 | 80 | 0.63 | 0.533 |
| Location(Year) * glyat + hra | 11 | 80 | 1.75 | 0.077 |

Event 3560.4.3.5 was backcrossed into four different Pioneer® conventional elite lines to confirm Mendelian segregation, and to measure yield impact of the event in different genetic backgrounds. For each of the four different BC1F2 populations tested, the seedlings segregated in a 3:1 (tolerant: susceptible) ratio, when analyzed using chlorsulfuron screening (Table 22). When event 3560.4.3.5 was forward crossed into 31 different genetic backgrounds, all F2 populations examined segregated in a 3:1 (tolerant:susceptible) ratio when sprayed in the field with glyphosate (Table 22). These data suggest that in different genetic backgrounds, event 3560.4.3.5 will confer tolerance to glyphosate and ALS inhibitor herbicides, and will segregate as a single dominant gene.

TABLE 22

F2 segregation ratios of event 3560.4.3.5 backcrossed into four different elite genetic backgrounds, and forward crossed into 31 different elite genetic backgrounds.

| Population | Generation[†] | plants observed Resistant | plants observed Susceptible | plants expected Resistant | plants expected Susceptible | P[‡] |
|---|---|---|---|---|---|---|
| 3560.4.3.5x Elite7 | BC1F2 | 700 | 222 | 691.5 | 230.5 | 0.518 |
| 3560.4.3.5x Elite8 | BC1F2 | 761 | 273 | 775.5 | 258.5 | 0.298 |

TABLE 22-continued

F2 segregation ratios of event 3560.4.3.5 backcrossed into four different elite genetic backgrounds, and forward crossed into 31 different elite genetic backgrounds.

| Population | Generation[†] | plants observed Resistant | plants observed Susceptible | plants expected Resistant | plants expected Susceptible | P[‡] |
|---|---|---|---|---|---|---|
| 3560.4.3.5x Elite9 | BC1F2 | 160 | 54 | 160.5 | 53.5 | 0.937 |
| 3560.4.3.5x Elite10 | BC1F2 | 205 | 79 | 213.0 | 71.0 | 0.273 |
| 3560.4.3.5x PHI1 | F2 | 53 | 23 | 57.0 | 19.0 | 0.289 |
| 3560.4.3.5x PHI2 | F2 | 76 | 20 | 72.0 | 24.0 | 0.346 |
| 3560.4.3.5x PHI3 | F2 | 66 | 24 | 67.5 | 22.5 | 0.715 |
| 3560.4.3.5x PHI4 | F2 | 75 | 23 | 73.5 | 24.5 | 0.726 |
| 3560.4.3.5x PHI5 | F2 | 99 | 23 | 91.5 | 30.5 | 0.117 |
| 3560.4.3.5x PHI6 | F2 | 96 | 24 | 90.0 | 30.0 | 0.206 |
| 3560.4.3.5x PHI11 | F2 | 72 | 18 | 67.5 | 22.5 | 0.273 |
| 3560.4.3.5x PHI12 | F2 | 115 | 36 | 113.3 | 37.8 | 0.742 |
| 3560.4.3.5x PHI13 | F2 | 91 | 22 | 84.8 | 28.3 | 0.175 |
| 3560.4.3.5x PHI14 | F2 | 97 | 26 | 92.3 | 30.8 | 0.323 |
| 3560.4.3.5x PHI15 | F2 | 88 | 28 | 87.0 | 29.0 | 0.830 |
| 3560.4.3.5x PHI16 | F2 | 66 | 24 | 67.5 | 22.5 | 0.715 |
| 3560.4.3.5x PHI17 | F2 | 75 | 34 | 81.8 | 27.3 | 0.135 |
| 3560.4.3.5x PHI18 | F2 | 108 | 25 | 99.8 | 33.3 | 0.099 |
| 3560.4.3.5x PHI19 | F2 | 78 | 26 | 78.0 | 26.0 | 1.000 |
| 3560.4.3.5x PHI20 | F2 | 95 | 29 | 93.0 | 31.0 | 0.678 |
| 3560.4.3.5x PHI21 | F2 | 109 | 37 | 109.5 | 36.5 | 0.924 |
| 3560.4.3.5x PHI22 | F2 | 75 | 26 | 75.8 | 25.3 | 0.863 |
| 3560.4.3.5x PHI23 | F2 | 85 | 19 | 78.0 | 26.0 | 0.113 |
| 3560.4.3.5x PHI24 | F2 | 81 | 18 | 74.3 | 24.8 | 0.117 |
| 3560.4.3.5x PHI25 | F2 | 76 | 23 | 74.3 | 24.8 | 0.685 |
| 3560.4.3.5x PHI26 | F2 | 97 | 36 | 99.8 | 33.3 | 0.582 |
| 3560.4.3.5x PHI27 | F2 | 98 | 28 | 94.5 | 31.5 | 0.471 |
| 3560.4.3.5x PHI28 | F2 | 89 | 22 | 83.3 | 27.8 | 0.208 |
| 3560.4.3.5x PHI29 | F2 | 71 | 24 | 71.3 | 23.8 | 0.953 |
| 3560.4.3.5x PHI30 | F2 | 54 | 15 | 51.8 | 17.3 | 0.532 |
| 3560.4.3.5x PHI31 | F2 | 73 | 20 | 69.8 | 23.3 | 0.436 |
| 3560.4.3.5x PHI32 | F2 | 53 | 12 | 48.8 | 16.3 | 0.223 |
| 3560.4.3.5x PHI33 | F2 | 96 | 26 | 91.5 | 30.5 | 0.347 |
| 3560.4.3.5x PHI34 | F2 | 76 | 20 | 72.0 | 24.0 | 0.346 |
| 3560.4.3.5x PHI35 | F2 | 69 | 18 | 65.3 | 21.8 | 0.353 |

[†]BC1F2 populations were screened using chlorsulfuron solution on emerging seedlings. F2 populations were grown in the field and sprayed with 2.24 kg ai ha$^{-1}$ glyphosate + 0.25% v/v NIS + 2.24 kg ai ha$^{-1}$ AMS at the V4 growth stage. Resistant and susceptible plants were counted approximately 7 days after treatment for all populations examined.
[‡]chi$^2$ probability that deviation from expected model is due to chance alone To test the yield impact of event 3560.4.3.5 in different genetic backgrounds, BC1F3 lines were developed that were either homozygous positive or homozygous negative for the 3560.4.3.5 event (Table 23). Since these lines are not true NILs, there may be some confounding error associated with the preliminary yield tests evaluated. For example, later maturing soybean lines typically have higher yield compared to earlier maturing lines within the same population. Therefore, maturity for each BC1F3 line was calculated as the number of days from planting to the estimated R8 growth stage (date when 95% of the pods had reached their mature pod color). Maturity estimates for each line were developed based upon direct comparison at each location to several non-transgenic Pioneer® experimental lines of known maturity. For the preliminary yield trail data analysis, maturity was analyzed as a covariate by nesting within the 3560.4.3.5 event to allow for a yield comparison between 3560.4.3.5 event positive and 3560.4.3.5 event negative lines at the same estimated maturity. It should be noted that the BC1F3 glyat+hra positive versus glyat+hra negative comparisons reported may also be confounded by the different herbicide programs utilized. However, blocking conventional cultivar trials from glyphosate tolerant trials has been a common practice in soybean cultivar development programs. In addition, for the 3560.4.3.5x elite data analysis presented, it was assumed that segregation of background maturity alleles, disease resistance alleles, and all other background genetic effects would occur at the same frequency within a population of 3560.4.3.5 event positive lines and within a population of 3560.4.3.5 event negative lines derived from the same initial BC1F1 plant.

Yield LSMeans of 3560.4.3.5 event positive and 3560.4.3.5 event negative lines were examined for each of the four BC1F3 populations tested across different locations (Table 23). For the BC1F3 population of 3560.4.3.5×RM22 Elite, the 3560.4.3.5 event positive lines within maturity group 113 had significantly higher yield compared to the 3560.4.3.5 event negative lines within maturity group 113 (Table 23). This difference was most likely due to environmental effect, as for all the other maturity groupings, 3560.4.3.5 event positive and 3560.4.3.5 event negative lines were not statistically different for yield (Table 23). In addition, at a specific location, and when yield data from all locations tested were pooled, 3560.4.3.5 event positive lines were not significantly different for yield compared to 3560.4.3.5 event negative lines within the 3560.4.3.5×RM22 Elite population (Table 23).

For the population of 3560.4.3.5×RM27 Elite BC1F3 lines, the 3560.4.3.5 event positive lines tested had a significant yield advantage compared to the 3560.4.3.5 event negative lines (Table 23). This observation is most likely due to an environmental effect, as when all locations were pooled, there were no significant differences detected for yield between 3560.4.3.5 event positive and 3560.4.3.5 event negative lines (Table 23). In addition, there were no significant differences detected for yield when 3560.4.3.5 event positive lines were compared to 3560.4.3.5 event negative lines at each specific maturity grouping (Table 23).

At two locations, there were significant yield differences observed within the population of 3560.4.3.5×RM30 Elite BC1F3 lines. 3560.4.3.5 event positive lines had significantly higher yield compared to 3560.4.3.5 event negative lines, while at a different location, the opposite effect was noted (Table 23). When all locations are pooled, there was not a significant difference detected for yield between 3560.4.3.5 event positive and 3560.4.3.5 event negative lines (Table 23). These results suggest environmental influence was most likely causing the effect, as at each specific maturity grouping, there were no significant differences detected for yield when 3560.4.3.5 event positive lines were directly compared to 3560.4.3.5 event negative sister lines (Table 23).

Two significant yield differences were also observed within the population of 3560.4.3.5×RM38 Elite BC1F3 lines at specific locations. In one of the replications, 3560.4.3.5 event positive lines had significantly higher yield compared to glyat-hra negative lines, while in another location, 3560.4.3.5 event negative lines had a yield advantage (Table 23). There was not a significant difference detected for yield when all locations were pooled for this population, which suggested environmental influence within a single location is causing the difference. At each of the maturity groupings, there was only a significant yield effect detected at maturity group 125, and in that case the 3560.4.3.5 event positive lines had significantly higher yield compared to 3560.4.3.5 event negative lines (Table 23). No distinct yield trends were evident across the four populations tested, indicating presence of the 3560.4.3.5 event does not impact yield potential when integrated into different genetic backgrounds.

TABLE 23

LSMeans for yield (kg ha$^{-1}$) at a location and a specific maturity for homozygous 3560.4.3.5 event positive and 3560.4.3.5 event negative BC1F3 lines within four different populations of event 3560.4.3.5x elite backgrounds.

| Population | Location† | Maturity‡ | 3560.4.3.5 event Positive | 3560.4.3.5 event Negative | Difference§ | Pr > |t| |
|---|---|---|---|---|---|---|
| 3560.4.3.5x RM22 ELITE | A | All | 2471.74 | 2439.77 | 31.97 | 0.675 |
| 3560.4.3.5x RM22 ELITE | B | All | 3491.77 | 3393.32 | 98.45 | 0.193 |
| 3560.4.3.5x RM22 ELITE | C | All | 2683.63 | 2747.03 | −63.40 | 0.402 |
| 3560.4.3.5x RM22 ELITE | D | All | 3180.61 | 3144.42 | 36.19 | 0.632 |
| 3560.4.3.5x RM22 ELITE | E | All | 2996.18 | 2912.63 | 83.55 | 0.271 |
| 3560.4.3.5x RM22 ELITE | All | All | 2964.78 | 2927.43 | 37.35 | 0.341 |
| 3560.4.3.5x RM22 ELITE | All | 111 | 2801.79 | 2836.18 | −34.39 | 0.807 |
| 3560.4.3.5x RM22 ELITE | All | 112 | 2927.15 | 2704.48 | 222.68 | 0.072 |
| 3560.4.3.5x RM22 ELITE | All | 113 | 2881.95 | 2686.65 | 195.30* | 0.041 |
| 3560.4.3.5x RM22 ELITE | All | 114 | 2625.92 | 2811.09 | −185.17 | 0.285 |
| 3560.4.3.5x RM22 ELITE | All | 115 | 2899.19 | 2839.28 | 59.91 | 0.633 |
| 3560.4.3.5x RM22 ELITE | All | 116 | 2848.24 | 2859.77 | −11.53 | 0.920 |
| 3560.4.3.5x RM22 ELITE | All | 125 | 3183.30 | 2969.74 | 213.56 | 0.231 |
| 3560.4.3.5x RM22 ELITE | All | 126 | 2976.31 | 3045.30 | −69.00 | 0.770 |
| 3560.4.3.5x RM22 ELITE | All | 127 | 2853.20 | 3029.97 | −176.77 | 0.327 |
| 3560.4.3.5x RM22 ELITE | All | 128 | 3031.55 | 3030.07 | 1.48 | 0.986 |
| 3560.4.3.5x RM22 ELITE | All | 129 | 3088.60 | 2994.95 | 93.65 | 0.350 |
| 3560.4.3.5x RM22 ELITE | All | 130 | 3198.18 | 3166.12 | 32.06 | 0.803 |
| 3560.4.3.5x RM22 ELITE | All | 131 | 3117.01 | 2981.93 | 135.08 | 0.435 |
| 3560.4.3.5x RM22 ELITE | All | 132 | 3074.62 | 3028.53 | 46.09 | 0.705 |
| 3560.4.3.5x RM27 ELITE | B | All | 3331.34 | 3406.61 | −75.26 | 0.640 |
| 3560.4.3.5x RM27 ELITE | C | All | 3218.79 | 2886.77 | 332.02* | 0.014 |
| 3560.4.3.5x RM27 ELITE | D | All | 3475.08 | 3417.17 | 57.91 | 0.656 |
| 3560.4.3.5x RM27 ELITE | E | All | 3028.48 | 3149.72 | −121.24 | 0.530 |
| 3560.4.3.5x RM27 ELITE | F | All | 3099.48 | 3021.84 | 77.64 | 0.600 |
| 3560.4.3.5x RM27 ELITE | All | All | 3230.63 | 3176.42 | 54.21 | 0.487 |
| 3560.4.3.5x RM27 ELITE | All | 122 | 3311.82 | 3145.60 | 166.22 | 0.497 |
| 3560.4.3.5x RM27 ELITE | All | 123 | 3226.68 | 3164.15 | 62.53 | 0.668 |
| 3560.4.3.5x RM27 ELITE | All | 125 | 3148.80 | 3238.51 | −89.71 | 0.660 |
| 3560.4.3.5x RM27 ELITE | All | 126 | 3086.18 | 3213.06 | −126.88 | 0.449 |
| 3560.4.3.5x RM27 ELITE | All | 127 | 3271.69 | 3168.42 | 103.28 | 0.670 |
| 3560.4.3.5x RM27 ELITE | All | 128 | 3237.08 | 3106.81 | 130.27 | 0.436 |
| 3560.4.3.5x RM27 ELITE | All | 130 | 3127.15 | 2987.23 | 139.92 | 0.594 |
| 3560.4.3.5x RM27 ELITE | All | 133 | 3435.66 | 3387.58 | 48.08 | 0.843 |
| 3560.4.3.5x RM30 ELITE | C | All | 3298.88 | 2983.11 | 315.77* | <.0001 |
| 3560.4.3.5x RM30 ELITE | D | All | 3544.23 | 3693.09 | −148.86* | 0.029 |
| 3560.4.3.5x RM30 ELITE | G | All | 3472.84 | 3481.88 | −9.05 | 0.888 |
| 3560.4.3.55 x RM30 ELITE | E | All | 3177.69 | 3229.61 | −51.92 | 0.418 |
| 3560.4.3.5x RM30 ELITE | F | All | 3002.89 | 2975.75 | 27.13 | 0.673 |
| 3560.4.3.5x RM30 ELITE | All | All | 3299.30 | 3272.69 | 26.62 | 0.512 |
| 3560.4.3.5x RM30 ELITE | All | 123 | 3356.46 | 3010.13 | 346.33 | 0.063 |
| 3560.4.3.5x RM30 ELITE | All | 125 | 3276.10 | 3172.47 | 103.63 | 0.194 |
| 3560.4.3.5x RM30 ELITE | All | 126 | 3266.42 | 3168.61 | 97.81 | 0.228 |
| 3560.4.3.5x RM30 ELITE | All | 127 | 3297.75 | 3299.10 | −1.35 | 0.984 |
| 3560.4.3.5x RM30 ELITE | All | 128 | 3285.84 | 3282.21 | 3.63 | 0.934 |
| 3560.4.3.5x RM30 ELITE | All | 129 | 3278.27 | 3407.86 | −129.59 | 0.051 |
| 3560.4.3.5x RM30 ELITE | All | 130 | 3334.29 | 3568.44 | −234.15 | 0.118 |
| 3560.4.3.5x RM38 ELITE | C | All | 2734.84 | 2659.09 | 75.75 | 0.256 |
| 3560.4.3.5x RM38 ELITE | G | All | 3228.83 | 3305.91 | −77.08 | 0.248 |

TABLE 23-continued

LSMeans for yield (kg ha$^{-1}$) at a location and a specific maturity for homozygous 3560.4.3.5 event positive and 3560.4.3.5 event negative BC1F3 lines within four different populations of event 3560.4.3.5x elite backgrounds.

| Population | Location† | Maturity‡ | 3560.4.3.5 event Positive | 3560.4.3.5 event Negative | Difference§ | Pr > \|t\| |
|---|---|---|---|---|---|---|
| 3560.4.3.5x RM38 ELITE | E | All | 3049.84 | 3190.55 | −140.71* | 0.040 |
| 3560.4.3.5x RM38 ELITE | F1 | All | 2678.11 | 2611.45 | 66.65 | 0.344 |
| 3560.4.3.5x RM38 ELITE | F2 | All | 2687.71 | 2507.70 | 180.02* | 0.008 |
| 3560.4.3.5x RM38 ELITE | All | All | 2875.87 | 2854.94 | 20.93 | 0.608 |
| 3560.4.3.5x RM38 ELITE | All | 122 | 2700.19 | 2803.14 | −102.96 | 0.547 |
| 3560.4.3.5x RM38 ELITE | All | 124 | 2743.61 | 2824.11 | −80.50 | 0.564 |
| 3560.4.3.5x RM38 ELITE | All | 125 | 3206.30 | 2880.53 | 325.77* | 0.001 |
| 3560.4.3.5x RM38 ELITE | All | 126 | 2788.26 | 2864.36 | −76.10 | 0.550 |
| 3560.4.3.5x RM38 ELITE | All | 127 | 2849.14 | 2929.84 | −80.71 | 0.514 |
| 3560.4.3.5x RM38 ELITE | All | 128 | 2842.31 | 2989.39 | −147.07 | 0.306 |
| 3560.4.3.5x RM38 ELITE | All | 129 | 2928.44 | 2884.00 | 44.44 | 0.490 |
| 3560.4.3.5x RM38 ELITE | All | 130 | 2918.29 | 2864.10 | 54.19 | 0.325 |
| 3560.4.3.5x RM38 ELITE | All | 131 | 2906.27 | 2655.01 | 251.26 | 0.057 |

‡Maturity is calculated as the average number of days between planting and R8 growth stage for the plot.
§Estimated yield LSMean difference between 3560.4.3.5 event positive and 3560.4.3.5 event negative lines.
*Indicates estimated yield difference is significant at P = 0.05.

TABLE 24

Description of Genetic Elements in Fragment PHP20163A

| Location on fragment PHP20163A (base pair position) | Genetic Element | Size (base pairs) | Description |
|---|---|---|---|
| 1 to 16 | polylinker region | 16 | Region for cloning genetic elements |
| 17 to 502 | SCP1 promoter | 486 | Constitutive synthetic promoter comprising a portion of the CaMV 35S promoter (Odell et al. (1985) Nature 313: 801-812 and the Rsyn7-Syn II Core consensus promoter (U.S. Pat. No. 6,0720,050 and 6,555,673). |
| 503 to 504 | polylinker region | 2 | Region for cloning genetic elements |
| 505 to 571 | TMV omega 5'-UTR | 67 | An enhancer element derived from the Tobacco Mosaic Virus omega 5' untranslated leader (Gallie and Walbot (1992) NAR 20: 4631-4638. |
| 572 to 596 | polylinker region | 25 | Region for cloning genetic elements |
| 597 to 1037 | glyat4601 gene | 441 | Synthetic glyphosate N-acetyltransferase (glyat) gene (Castle et al. (2004) Science 304: 1151-1154). |
| 1038 to 1053 | polylinker region | 16 | Region for cloning genetic elements |
| 1054 to 1369 | pinII terminator | 316 | Terminator region from *Solanum tuberosum* proteinase inhibitor II (pinII) gene (Keil et al. (1986) NAR 14: 5641-5650; An et al. (1989) Plant Cell 1: 115-122. |
| 1370 to 1385 | polylinker region | 16 | Region for cloning genetic elements |
| 1386 to 2030 | SAMS promoter | 645 | Promoter of the S-adenosyl-L-methionine synthetase (SAMS) gene from soybean (Falco and Li (2003) US publication 2003/0226166). |
| 2031 to 2089 | SAMS 5'-UTR | 59 | 5' untranslated region of the SAMS gene from soybean (Falco and Li, 2003 US publication 2003/0226166). |
| 2090 to 2680 | SAMS intron | 591 | Intron within the 5'-untranslated region of the SAMS gene from soybean (Falco and Li, 2003 US publication 2003/0226166). |
| 2681 to 2696 | SAMS 5'-UTR | 16 | 5' untranslated region (UTR) of the SAMS gene from soybean (Falco and Li, 2003 US publication 2003/0226166). |

TABLE 24-continued

Description of Genetic Elements in Fragment PHP20163A

| Location on fragment PHP20163A (base pair position) | Genetic Element | Size (base pairs) | Description |
|---|---|---|---|
| 2697 to 4667 | gm-hra gene | 1971 | Modified version of the acetolactate synthase gene from soybean with 15 additional nucleotides on the 5' end (2697 to 2711) derived from the SAMS gene and two nucleotide changes within the coding sequence. |
| 4668 to 5319 | als terminator | 652 | Native terminator from the soybean acetolactate synthase gene. |
| 5319 to 5362 | polylinker region | 43 | Region for cloning genetic elements |

Example 4

Improved Yield of Soybean Event 3560.4.3-5 in Ten Populations Adapted for the Southern Growing Region of the United States Soybean with the GLYAT gene from event 3560.4.3.5 and an EPSPS gene corresponding to the EPSPS described in S. R. Pagette et al (1995) *Development, Identification, and Characterization of a Glyphosate-Tolerance Soybean Line. Crop Sci.* 35:1451-1461 (herein incorporated by reference) were generated. The EPSPS event of the glyphosate-tolerant soybean line 40-3-2 and the GLYAT event of the glyphosate-tolerant soybean line 3560.4.3.5 were brought together via conventional breeding to generate ten unique populations. The lines for each population were identified as containing the GLYAT event 3560.4.3.5, the EPSPS event 40-3-2, or containing both the GLYAT and EPSPS events, Lines were grown in the summer season as a plant row yield trials (PRYT) near West Memphis, Ark. PRYT rows were 1.2 meters in length, with 76 cm between row spacing. Plots were sprayed 24 days following planting with 840 g ae/ha glyphosate and sprayed 44 days after planting with 1680 g ae/ha glyphosate. Maturity and yield data were collected for each line and analyzed using the PROC Mixed function of SAS (SAS Institute, Cary N.Y.). Yields were adjusted for maturity for valid comparisons. When pooling the three classes (GLYAT, EPSPS, GLYAT+EPSPS) over the ten populations, the GLYAT+EPSPS lines were significantly higher yielding (48.1 bu/acre) compared to the EPSPS lines (40.6 bu/acre) and the GLYAT lines (44.7 bu/ac).

Figure 11:
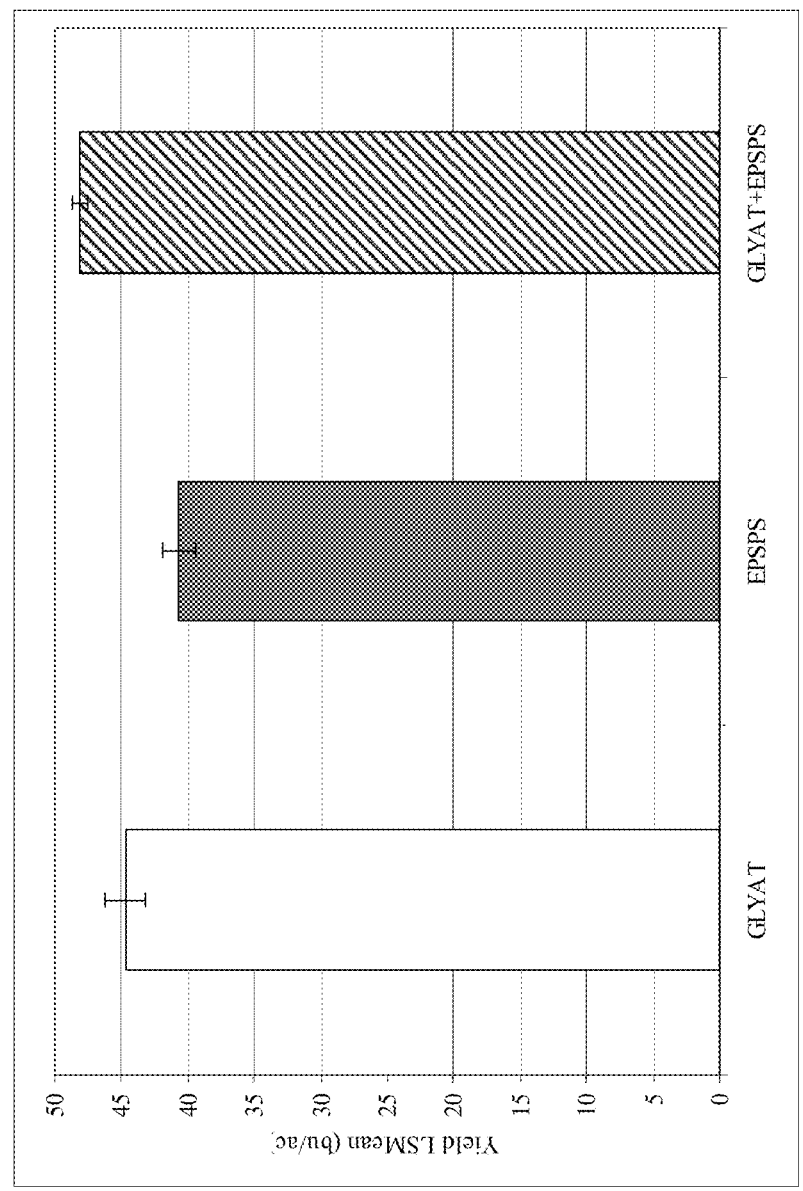
FIG. 11 provides LSMean comparisons for yield (bu/ac) of ten different populations of lines classified for glyphosate tolerance transgenes (GLYAT, EPSPS, GLYAT+EPSPS).

Table 25 shows the differences between LSMean estimates (bu/ac) for yield of ten different populations of related lines classified for glyphosate tolerance transgenes (GLYAT, EPSPS, GLYAT+EPSPS). FIG. 11 provides LSMean comparisons for yield (bu/ac) of ten different populations of lines classified for glyphosate tolerance transgenes (GLYAT, EPSPS, GLYAT+EPSPS). Lines were adapted to the Southern United States growing region.

TABLE 25

| Population | Herbicide1 | n1 | LSMean1 | Herbicide2 | n2 | LSMean2 | Difference | Probt |
|---|---|---|---|---|---|---|---|---|
| All | GLYAT | 80 | 44.7 | GLYAT + EPSPS | 575 | 48.1 | −3.5 | 0.032 |
| All | GLYAT | 80 | 44.7 | EPSPS | 129 | 40.6 | 4.0 | 0.040 |
| All | GLYAT + EPSPS | 575 | 48.1 | EPSPS | 129 | 40.6 | 7.5 | 0.000 |
| Population1 | GLYAT | 6 | 36.3 | GLYAT + EPSPS | 64 | 43.8 | −7.5 | NS |
| Population1 | GLYAT | 6 | 36.3 | EPSPS | 18 | 43.9 | −7.6 | NS |
| Population1 | GLYAT + EPSPS | 64 | 43.8 | EPSPS | 18 | 43.9 | −0.1 | NS |
| Population2 | GLYAT | 6 | 41.8 | GLYAT + EPSPS | 29 | 42.3 | −0.5 | NS |
| Population2 | GLYAT | 6 | 41.8 | EPSPS | 8 | 31.6 | 10.2 | NS |
| Population2 | GLYAT + EPSPS | 29 | 42.3 | EPSPS | 8 | 31.6 | 10.7 | 0.035 |
| Population3 | GLYAT | 9 | 47.6 | GLYAT + EPSPS | 88 | 51.7 | −4.1 | NS |
| Population3 | GLYAT | 9 | 47.6 | EPSPS | 21 | 47.1 | 0.4 | NS |
| Population3 | GLYAT + EPSPS | 88 | 51.7 | EPSPS | 21 | 47.1 | 4.6 | NS |
| Population4 | GLYAT | 6 | 33.8 | GLYAT + EPSPS | 43 | 39.1 | −5.2 | NS |
| Popalation4 | GLYAT | 6 | 33.8 | EPSPS | 5 | 25.2 | 8.6 | NS |
| Popalation4 | GLYAT + EPSPS | 43 | 39.1 | EPSPS | 5 | 25.2 | 13.9 | 0.021 |
| Population5 | GLYAT | 4 | 49.5 | GLYAT + EPSPS | 37 | 43.9 | 5.6 | NS |
| Population5 | GLYAT | 4 | 49.5 | EPSPS | 12 | 35.1 | 14.4 | 0.049 |
| Population5 | GLYAT + EPSPS | 37 | 43.9 | EPSPS | 12 | 35.1 | 8.8 | 0.036 |
| Population6 | GLYAT | 9 | 52.7 | GLYAT + EPSPS | 32 | 51.6 | 1.0 | NS |
| Population6 | GLYAT | 9 | 52.7 | EPSPS | 10 | 49.9 | 2.8 | NS |
| Population6 | GLYAT + EPSPS | 32 | 51.6 | EPSPS | 10 | 49.9 | 1.7 | NS |
| Population7 | GLYAT | 12 | 41.8 | GLYAT + EPSPS | 87 | 43.2 | −1.3 | NS |
| Population7 | GLYAT | 12 | 41.8 | EPSPS | 10 | 38.3 | 3.5 | NS |
| Population7 | GLYAT + EPSPS | 87 | 43.2 | EPSPS | 10 | 38.3 | 4.9 | NS |
| Population8 | GLYAT | 13 | 51.7 | GLYAT + EPSPS | 61 | 53.6 | −1.9 | NS |
| Population8 | GLYAT | 13 | 51.7 | EPSPS | 24 | 45.5 | 6.2 | NS |

TABLE 25-continued

| Population | Herbicide1 | n1 | LSMean1 | Herbicide2 | n2 | LSMean2 | Difference | Probt |
|---|---|---|---|---|---|---|---|---|
| Population8 | GLYAT + EPSPS | 61 | 53.6 | EPSPS | 24 | 45.5 | 8.0 | 0.008 |
| Population9 | GLYAT | 10 | 50.7 | GLY AT + EPSPS | 70 | 61.1 | −10.4 | 0.015 |
| Population9 | GLYAT | 10 | 50.7 | EPSPS | 10 | 43.7 | 7.0 | NS |
| Population9 | GLYAT + EPSPS | 70 | 61.1 | EPSPS | 10 | 43.7 | 17.4 | 0.000 |
| Population10 | GLYAT | 5 | 40.6 | GLYAT + EPSPS | 64 | 51.0 | −10.4 | NS |
| Population10 | GLYAT | 5 | 40.6 | EPSPS | 11 | 46.0 | −5.4 | NS |
| Population10 | GLYAT + EPSPS | 64 | 51.0 | EPSPS | 11 | 46.0 | 5.0 | NS |

Example 5

Figure 12:
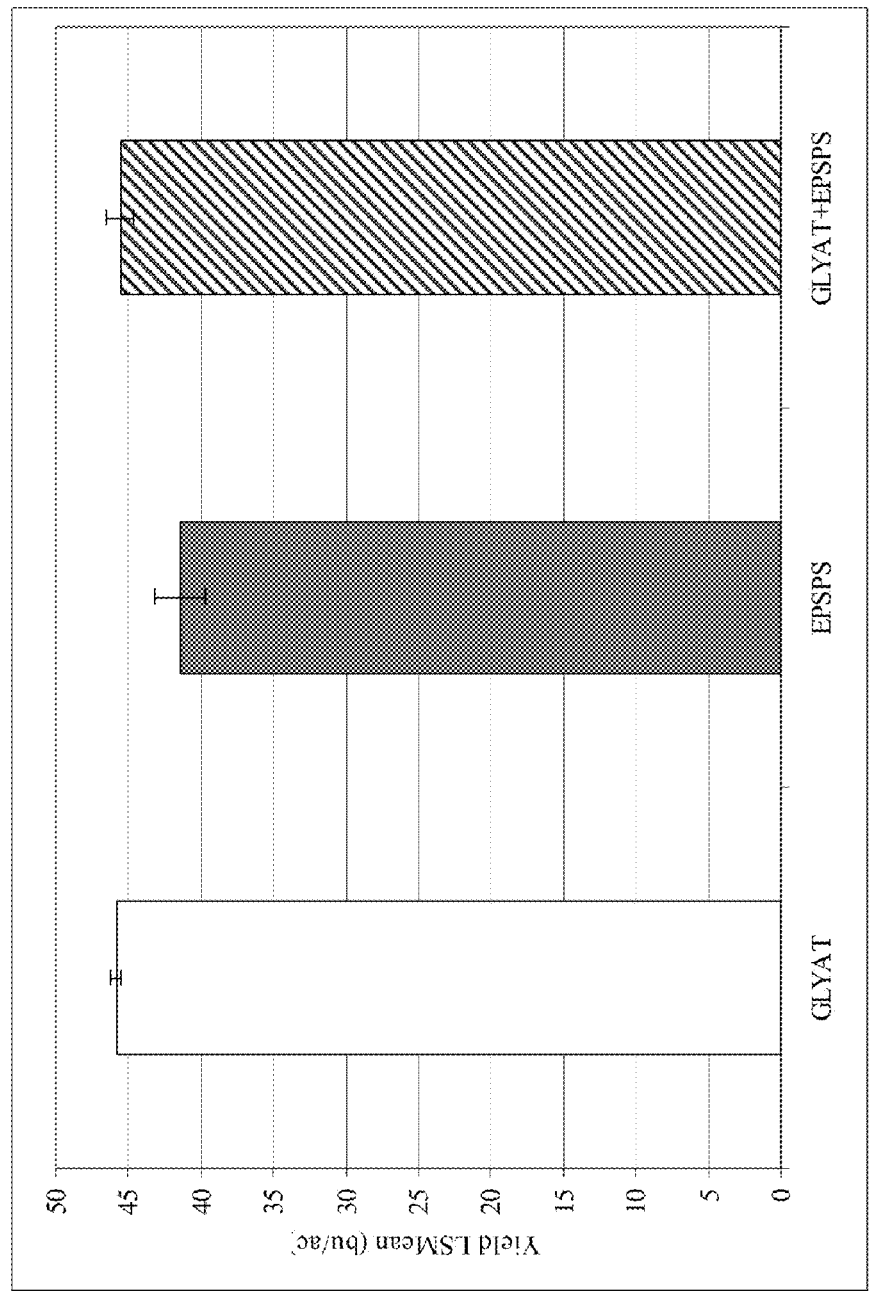
FIG. 12 provides LSMean comparisons for yield of two different populations of related lines classified for glyphosate tolerance transgenes (GLYAT, EPSPS, GLYAT+EPSPS).

Improved Yield of Soybean Event 3560.4.3.5 in Two Populations Adapted for the Mid-Maturity Growing Region of the United States Soybean with the 3560.4.3.5 event and an EPSPS gene corresponding to the EPSPS described in S. R. Pagette et al (1995) *Development, Identification, and Characterization of a Glyphosate-Tolerance Soybean Line. Crop Sci.* 35:1451-1461 (herein incorporated by reference) were generated. The EPSPS event of the glyphosate-tolerant soybean line 40-3-2 and the GLYAT event of the glyphosate-tolerant soybean line 3560.4.3.5 were brought together via conventional breeding to generate two unique populations. The lines for each population were identified as containing the GLYAT event 3560.4.3.5, the EPSPS event 40-3-2, or containing both the GLYAT and EPSPS events. Lines were grown in the summer season as a plant row yield trials (PRYT) near Napoleon, Ohio. PRYT rows were 1.2 meters in length, with 76 cm between row spacing. Plots were sprayed 31 days after planting with 3360 g ae/ha glyphosate. Maturity and yield data were collected for each line and analyzed using the PROC Mixed function of SAS (SAS Institute, Cary N.Y.). Yields were adjusted for maturity for valid comparisons. When pooling the three across the two populations, the GLYAT+EPSPS lines were significantly higher yielding (45.6 bu/acre) compared to the EPSPS lines (41.4 bu/acre) and not significantly different compared to the GLYAT lines (45.8 bu/acre). p Table 26 shows the differences between LSMean estimates for yield of two different populations of lines classified for glyphosate tolerance transgenes (GLYAT, EPSPS, GLYAT+EPSPS). FIG. 12 provides LSMean comparisons for yield of two different populations of related lines classified for glyphosate tolerance transgenes (GLYAT, EPSPS, GLYAT+EPSPS). Lines are adapted to the Midwestern United States growing region.

TABLE 27

Summary Table of SEQ ID NOS

| SEQ ID NO | Description |
|---|---|
| 1 | Left sequence junction SC36 |
| 2 | Right sequence junction D32ALS |
| 3 | complete inserted transgene |
| 4 | Left genomic border |
| 5 | Right genomic border |
| 6 | complete flanking and complete transgene insert |
| 7 | Forward primer |
| 8 | Reverse primer |
| 9 | Taqman MGB probe |
| 10 | Left flanking genomic/left border transgene (10 nt/10 nt) |
| 11 | Right flanking genomic/right border transgene (10 nt/10 nt) |
| 12 | Left flanking genomic/left border transgene (20 nt/20 nt) |
| 13 | Right flanking genomic/right border transgene (20 nt/20 nt) |
| 14 | Left flanking genomic/5' transgene |
| 15 | Right flanking genomic/3' transgene |
| 16 | Primer 1297 |
| 17 | Primer 1298 |
| 18 | Primer 1439 |
| 19 | Primer 1514 |
| 20 | Primer 1558 |
| 21 | Primer 1660 |
| 22 | Primer 1666 |
| 23 | Primer 1679 |
| 24 | Primer 1227 |
| 25 | Primer 1297 |
| 26 | Primer 1440 |
| 27 | left flanking genomic/left border transgene (30 nt/30 nt) |
| 28 | Right flanking genomic/right border transgene (30 nt/30 nt) |
| 29 | SCP1 promoter probe |
| 30 | glyat4601 probe |
| 31 | pinII terminator probe |
| 32 | SAMS probe (5' end) |
| 33 | SAMS probe (3' end) |
| 34 | gm-hra probe (5' end) |
| 35 | gm-hra probe (3' end) |
| 36 | als probe |

TABLE 26

| Population | Comparison Class 1 | N1 | Yield LSMean1 Bu/acre | Comparison Class 2 | N2 | Yield LSMean2 Bu/acre | Difference Bu/acre | Probt |
|---|---|---|---|---|---|---|---|---|
| All | GLYAT | 619 | 45.8 | GLYAT + EPSPS | 95 | 45.6 | 0.2 | NS |
| All | GLYAT | 619 | 45.8 | EPSPS | 21 | 41.4 | 4.4 | 0.016 |
| All | GLYAT + EPSPS | 95 | 45.6 | EPSPS | 21 | 41.4 | 4.1 | 0.043 |
| Population1 | GLYAT | 219 | 49.2 | GLYAT + EPSPS | 72 | 47.9 | 1.3 | NS |
| Population1 | GLYAT | 219 | 49.2 | EPSPS | 10 | 47.6 | 1.6 | NS |
| Population1 | GLYAT + EPSPS | 72 | 47.9 | EPSPS | 10 | 47.6 | 0.3 | NS |
| Population2 | GLYAT | 400 | 42.4 | GLYAT + EPSPS | 23 | 43.3 | −0.9 | NS |
| Population2 | GLYAT | 400 | 42.4 | EPSPS | 11 | 35.3 | 7.1 | 0.004 |
| Population2 | GLYAT + EPSPS | 23 | 43.3 | EPSPS | 11 | 35.3 | 8.0 | 0.008 |

TABLE 27-continued

Summary Table of SEQ ID NOS

| SEQ ID NO | Description |
|---|---|
| 37 | Primer DP-356-f1 |
| 38 | Primer DP-356-r1 |
| 39 | Primer DP-356-p |
| 40 | Primer 1610 |
| 41 | Left flanking genomic/transgene |
| 42 | Right flanking genomic/transgene |
| 43 | 181 nucleotides of the 5' end of transgene insert |
| 44 | Primer 104312 |
| 45 | Primer 104314 |
| 46 | Probe 125323 |
| 47 | Primer 109893 (endogenous control) |
| 48 | Primer 109894 (endogenous control) |
| 49 | Probe 125322 (endogenous control) |
| 50 | Primer 1473 |
| 51 | Primer 1504 |
| 52 | Primer 1505 |
| 53 | Primer 1506 |
| 54 | Primer 1549 |
| 55 | Primer 1550 |
| 56 | EPSP synthase from *Agrobacterium* sp. Cp4 |

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for improving yield in a soybean plant comprising treating said soybean plant with an effective amount of glyphosate,
    wherein said soybean plant comprises a 3560.4.3.5 soybean plant or a plant that is a progeny of a plant grown from seeds of ATCC Seed Deposit PTA-8287, wherein said progeny comprises the 3560.3.5 event;
    wherein said soybean plant further comprises a polynucleotide sequence encoding a polypeptide that imparts tolerance to glyphosate by a mode of action different than glyphosate N-acetyltransferase; and,
    wherein said soybean plant further comprise a polynucleotide sequence that imparts tolerance to an additional herbicide.

2. The method of claim 1, wherein said additional herbicide comprises a synthetic auxin.

3. The method of claim 1, wherein said additional herbicide comprises a phenoxy auxin herbicide.

4. The method of claim 1, wherein said additional herbicide comprise 2, 4-D.

5. The method of claim 1, wherein said polynucleotide sequence encodes a glyphosate-tolerant 5-enol-pyruvylshikimate-3-phosphate synthase (EPSPS) polypeptide.

6. The method of either claim 1, wherein the glyphosate is applied in a single treatment or in successive treatments.

7. The method of claim 1, wherein the glyphosate is a glyphosate derivative comprising a salt or a mixture of glyphosate salts selected from the group consisting of monoisopropylammonium glyphosate, ammonium glyphosate, and sodium glyphosate.

8. The method of claim 1, wherein the glyphosate or derivative thereof is used in a formulation comprising an adjuvant selected from the group consisting of: amines, ethoxylated alkyl amines, tallow amines, cocoamines, amine oxides, quaternary ammonium salts, ethoxylated quaternary ammonium salts, propoxylated quaternary ammonium salts, alkylpolyglycoside, alkylglycoside, glucose-esters, sucrose- esters, and ethoxylated polypropoxylated quaternary ammonium surfactants.

9. The method of claim 1 wherein said polynucleotide sequence encodes a glyphosate oxidoreductase enzyme.

10. The method of claim 1 wherein said polynucleotide sequence encodes a class II EPSPS enzyme.

* * * * *

UNITED STATES PATENT AND TRADEMARK OFFICE
CERTIFICATE OF CORRECTION

PATENT NO. : 8,324,457 B2  
APPLICATION NO. : 13/109797  
DATED : December 4, 2012  
INVENTOR(S) : Guida, Jr. et al.

Page 1 of 1

It is certified that error appears in the above-identified patent and that said Letters Patent is hereby corrected as shown below:

On the Title Page, Item (73)

Assignees should be shown as --Pioneer Hi-Bred International, Inc, Johnston, IA (US); E.I. du Pont de Nemours and Company, Wilmington, DE (US)--.

In the Specification

Column 3, line 34, delete both occurrences of "by" and insert --bp-- therefor.

Column 7, line 20, delete "Selling" and insert --Selfing--.

Column 7, line 44, delete "intro gression" and insert --introgression--.

Column 22, line 12, insert --full length-- before "cDNA".

Column 48, line 39, delete "buckhom" and insert --buckhorn--.

Column 64, line 45, delete "(pinll)" and insert --(pinII)--.

Column 66, line 30, delete "embryogenie" and insert --embryogenic--.

Column 67, line 18, delete "Reeling" and insert --Freeling--.

Column 67, line 37, delete "chloroforrn" and insert --chloroform--.

Column 68, line 2, delete "WestermBreeze®" and insert --WesternBreeze®--.

Column 78, line 3, delete "by" and insert --bp--.

Signed and Sealed this  
Thirtieth Day of April, 2013

Teresa Stanek Rea  
*Acting Director of the United States Patent and Trademark Office*

SEQUENCE LISTING

```
<160> NUMBER OF SEQ ID NOS: 56

<210> SEQ ID NO 1
<211> LENGTH: 787
<212> TYPE: DNA
<213> ORGANISM: Glycine max
<220> FEATURE:
<221> NAME/KEY: misc_feature
<222> LOCATION: (0)...(0)
<223> OTHER INFORMATION: 785 bp of 5' genomic sequence of Event
      3560.4.3.5 (SC36)

<400> SEQUENCE: 1
aaagttaaaa atatcactaa tacgtttcta aatgcatttt ttttagaaat tataagtttc     60
tagcactcca ttggagttgt atagaactac tactaatcta ctattaataa caatttatct    120
cctccaaata tttaagtaaa ctgcatattt agagaatgtt ggacagtaaa gctagccact    180
caatatttag gtgctccccg aaagaggaaa gcaaacaagc caccagcact tcaatcagta    240
aagctagcca ctcaactcgc tctcttcaaa ttccctttta cattttattt cagatcctcc    300
acctagccaa gtaggtctca aaaggtttac cccgcatatg cttagtcgcc gcaagctcca    360
tataggttac tttgcgggct actgaataga atcttcggtg aaaggcgtct accatatcgg    420
cgcaactatt gatcgagtgc gtgtatacca cgtgaatgcg acacccgaaa gactagcaga    480
aaagtgcttc agcaacaaac tctcatcgtg agcagtgtct ctgctggcaa tttcgaaatt    540
actaatatgc tgctctcgag atctccactt ccatcataca accgaaacca gctaaggaag    600
gagcgatcca taagaatcgc ctcgaatagc cataacctca tctcgccttc caccgcacca    660
gcaagaggaa accgaattag agctgaaaga atactagagc catcgtagga gaaccggatt    720
cttgaccgat cgactttgc ccgaggtcgt taggtcgaat aggctaggtt tacgaaaaag    780
agactaa                                                              787

<210> SEQ ID NO 2
<211> LENGTH: 845
<212> TYPE: DNA
<213> ORGANISM: Glycine max
```

```
<220> FEATURE:
<221> NAME/KEY: misc_feature
<222> LOCATION: (0)...(0)
<223> OTHER INFORMATION: 845 bp of 3' genomic sequence of Event
      3560.4.3.5 (glyatD32ALS)

<400> SEQUENCE: 2
cgcgtaatat catcattagg aagacactgc ccatcttgaa taggatttta gctactaaat     60
atgttgatgg tctttatgaa aaactattaa ctaggaatat tatgctaccc atatggaaag    120
aagacgctag gggaatagaa agaccatcaa ataaacgaag tcaacaccag gtcttccgaa    180
gcattaacaa ttacctattt aatatgtact cagtccgggt ggatatctca ctacattgac    240
gcagtttgtt caaagacgaa cgccctgaat tatgccatct gcttaggctt tcaaatatgg    300
tacgctctaa tgccaagcct tatgctggtc ttagggtatt atcatcaaat ctttaagcca    360
gaggtagtta aatacatcaa ggacaccata ggagtatggc acaacgatat tgtcaagatc    420
gcatcagatc taataggcaa taatgaattc ttcatgcagc ccgacgtggg aacgctcgaa    480
agcagtgggg cctctgggac agggaccaga cctgagtcgc taacatttgg gaataagaga    540
agtagatata cccaattttt taactagcca aggaaggaaa gcgggaaagg tccgatacaa    600
aggaaagggt tgcgaggctt aacgatttag aatatagctg ttgaggtggc acttgttccc    660
ccggggcggg ggtatatgcc cgtagcttta ttctgtcact tctttcagat caatgaagtt    720
gaaaagttat agagtaaggg acccttgttt acaaagctgt cactccaaga actcgaagtc    780
aagcatcttc gggaatatcc agattagtct tcaactagag aaaggatagg aatctccttt    840
gcaga                                                                845

<210> SEQ ID NO 3
<211> LENGTH: 5362
<212> TYPE: DNA
<213> ORGANISM: Artificial Sequence
<220> FEATURE:
<223> OTHER INFORMATION: transgene insert for event 3560.4.3.5

<400> SEQUENCE: 3
ggccgctcta gagatccgtc aacatggtgg agcacgacac tctcgtctac tccaagaata     60
tcaaagatac agtctcagaa gaccaaaggg ctattgagac ttttcaacaa agggtaatat    120
cgggaaacct cctcggattc cattgcccag ctatctgtca cttcatcaaa aggacagtag    180
aaaaggaagg tggcacctac aaatgccatc attgcgataa aggaaaggct atcgttcaag    240
atgcctctgc cgacagtggt cccaaagatg gacccccacc cacgaggagc atcgtggaaa    300
aagaagacgt tccaaccacg tcttcaaagc aagtggattg atgtgatgat cctatgcgta    360
tggtatgacg tgtgttcaag atgatgactt caaacctacc tatgacgtat ggtatgacgt    420
gtgtcgactg atgacttaga tccactcgag cggctataaa tacgtaccta cgcaccctgc    480
gctaccatcc ctagagctgc agcttatttt tacaacaatt accaacaaca acaaacaaca    540
aacaacatta caattactat ttacaattac agtcgacccg ggatccacac gacaccatga    600
tagaggtgaa accgattaac gcagaggata cctatgaact aaggcataga atactcagac    660
caaaccagcc gatagaagcg tgtatgtttg aaagcgattt acttcgtggt gcatttcact    720
taggcggctt ttacagggggc aaactgattt ccatagcttc attccaccag gccgagcact    780
cggaactcca aggccagaaa cagtaccagc tccgaggtat ggctaccttg gaaggttatc    840
gtgagcagaa agcgggatca actctagtta aacacgctga agaaatcctt cgtaagaggg    900
gggcggacat gctttggtgt aatgcgagga catccgcctc aggctactac aaaaagttag    960
```

```
gcttcagcga gcagggagag atatttgaca cgccgccagt aggacctcac atcctgatgt    1020
ataaaaggat cacataacta gctagtcagt taacctagac ttgtccatct tctggattgg    1080
ccaacttaat taatgtatga aataaaagga tgcacacata gtgacatgct aatcactata    1140
atgtgggcat caaagttgtg tgttatgtgt aattactagt tatctgaata aaagagaaag    1200
agatcatcca tatttcttat cctaaatgaa tgtcacgtgt ctttataatt ctttgatgaa    1260
ccagatgcat ttcattaacc aaatccatat acatataaat attaatcata tataattaat    1320
atcaattggg ttagcaaaac aaatctagtc taggtgtgtt ttgcgaattc gatatcaagc    1380
tttgctctag atcaaactca catccaaaca taacatggat atcttcctta ccaatcatac    1440
taattatttt gggttaaata ttaatcatta tttttaagat attaattaag aaattaaaag    1500
attttttaaa aaaatgtata aaattatatt attcatgatt tttcatacat ttgattttga    1560
taataaatat attttttttta atttcttaaa aaatgttgca agacacttat tagacatagt    1620
cttgttctgt ttacaaaagc attcatcatt taatacatta aaaaatattt aatactaaca    1680
gtagaatctt cttgtgagtg gtgtgggagt aggcaacctg gcattgaaac gagagaaaga    1740
gagtcagaac cagaagacaa ataaaagta tgcaacaaac aaatcaaaat caaagggcaa     1800
aggctggggt tggctcaatt ggttgctaca ttcaattttc aactcagtca acggttgaga    1860
ttcactctga cttccccaat ctaagccgcg gatgcaaacg gttgaatcta acccacaatc    1920
caatctcgtt acttaggggc ttttccgtca ttaactcacc cctgccaccc ggtttcccta    1980
taaattggaa ctcaatgctc ccctctaaac tcgtatcgct tcagagttga gaccaagaca    2040
cactcgttca tatatctctc tgctcttctc ttctcttcta cctctcaagg tacttttctt    2100
ctccctctac caaatcctag attccgtggt tcaatttcgg atcttgcact tctggttttgc   2160 tttgccttgc ttttttcctca actgggtcca tctaggatcc atgtgaaact ctactctttc   2220
tttaatatct gcggaatacg cgtttgactt tcagatctag tcgaaatcat ttcataattg    2280
cctttctttc ttttagctta tgagaaataa aatcactttt tttttattc aaaataaacc     2340 ttgggccttg tgctgactga gatggggttt ggtgattaca gaattttagc gaattttgta    2400
attgtacttg tttgtctgta gttttgtttt gttttcttgt ttctcataca ttccttaggc    2460 ttcaattttta ttcgagtata ggtcacaata ggaattcaaa ctttgagcag gggaattaat   2520
cccttccttc aaatccagtt tgtttgtata tatgtttaaa aaatgaaact tttgctttaa    2580
attctattat aactttttttt atggctgaaa ttttgcatg tgtctttgct ctctgttgta    2640 aattactgt ttaggtacta actctaggct tgttgtgcag ttttttgaagt ataaccatgc    2700 cacacaacac aatggcggcc accgcttcca gaaccacccg attctcttct tcctcttcac    2760
accccacctt ccccaaacgc attactagat ccaccctccc tctctctcat caaaccctca    2820
ccaaacccaa ccacgctctc aaaatcaaat gttccatctc caaaccccc acggcggcgc     2880 ccttcaccaa ggaagcgccg accacggagc ccttcgtgtc acggttcgcc tccggcgaac    2940
ctcgcaaggg cgcggacatc cttgtggagg cgctggagag gcagggcgtg acgacggtgt    3000
tcgcgtaccc cggcggtgcg tcgatggaga tccaccaggc gctcacgcgc tccgccgcca    3060
tccgcaacgt gctcccgcgc cacgagcagg gcggcgtctt cgccgccgaa ggctacgcgc    3120
gttcctccgg cctccccggc gtctgcattg ccacctccgg ccccggcgcc accaacctcg    3180
tgagcggcct cgccgacgct ttaatggaca gcgtcccagt cgtcgccatc accggccagg    3240
tcgcccgccg gatgatcggc accgacgcct tccaagaaac cccgatcgtg gaggtgagca    3300
gatccatcac gaagcacaac tacctcatcc tcgacgtcga cgacatcccc cgcgtcgtcg    3360
```

| | |
|---|---|
| ccgaggctttt cttcgtcgcc acctccggcc gccccggtcc ggtcctcatc gacattccca | 3420 |
| aagacgttca gcagcaactc gccgtgccta attgggacga gcccgttaac ctccccggtt | 3480 |
| acctcgccag gctgcccagg ccccccgccg aggcccaatt ggaacacatt gtcagactca | 3540 |
| tcatggaggc ccaaaagccc gttctctacg tcggcggtgg cagtttgaat tccagtgctg | 3600 |
| aattgaggcg ctttgttgaa ctcactggta ttcccgttgc tagcacttta atgggtcttg | 3660 |
| gaactttttcc tattggtgat gaatattccc ttcagatgct gggtatgcat ggtactgttt | 3720 |
| atgctaacta tgctgttgac aatagtgatt tgttgcttgc ctttggggta aggtttgatg | 3780 |
| accgtgttac tgggaagctt gaggcttttg ctagtagggc taagattgtt cacattgata | 3840 |
| ttgattctgc cgagattggg aagaacaagc aggcgcacgt gtcggtttgc gcggatttga | 3900 |
| agttggcctt gaagggaatt aatatgattt tggaggagaa aggagtggag ggtaagtttg | 3960 |
| atcttggagg ttggagagaa gagattaatg tgcagaaaca caagtttcca ttgggttaca | 4020 |
| agacattcca ggacgcgatt tctccgcagc atgctatcga ggttcttgat gagttgacta | 4080 |
| atggagatgc tattgttagt actggggttg ggcagcatca aatgtgggct gcgcagtttt | 4140 |
| acaagtacaa gagaccgagg cagtggttga cctcagggg tcttggagcc atgggttttg | 4200 |
| gattgcctgc ggctattggt gctgctgttg ctaaccctgg ggctgttgtg gttgacattg | 4260 |
| atggggatgt tagtttcatc atgaatgttc aggagttggc cactataaga gtggagaatc | 4320 |
| tcccagttaa gatattgttg ttgaacaatc agcatttggg tatggtggtt cagttggagg | 4380 |
| ataggttcta caagtccaat agagctcaca cctatcttgg agatccgtct agcgagagcg | 4440 |
| agatattccc aaacatgctc aagtttgctg atgcttgtgg gataccggca gcgcgagtga | 4500 |
| cgaagaagga agagcttaga gcggcaattc agagaatgtt ggacacccct ggcccctacc | 4560 |
| ttcttgatgt cattgtgccc catcaggagc atgtgttgcc gatgattccc agtaatggat | 4620 |
| ccttcaagga tgtgataact gagggtgatg gtagaacgag gtactgattg cctagaccaa | 4680 |
| atgttccttg atgcttgttt tgtacaatat atataagata atgctgtcct agttgcagga | 4740 |
| tttggcctgt ggtgagcatc atagtctgta gtagttttgg tagcaagaca tttattttc | 4800 |
| cttttattta acttactaca tgcagtagca tctatctatc tctgtagtct gatatctcct | 4860 |
| gttgtctgta ttgtgccgtt ggatttttg ctgtagtgag actgaaaatg atgtgctagt | 4920 |
| aataatattt ctgttagaaa tctaagtaga gaatctgttg aagaagtcaa aagctaatgg | 4980 |
| aatcaggtta catattcaat gttttttcttt ttttagcggt tggtagacgt gtagattcaa | 5040 |
| cttctcttgg agctcaccta ggcaatcagt aaaatgcata ttcctttttt aacttgccat | 5100 |
| ttatttactt ttagtggaaa ttgtgaccaa tttgttcatg tagaacggat ttggaccatt | 5160 |
| gcgtccacaa aacgtctctt ttgctcgatc ttcacaaagc gataccgaaa tccagagata | 5220 |
| gttttcaaaa gtcagaaatg gcaaagttat aaatagtaaa acagaataga tgctgtaatc | 5280 |
| gacttcaata caagtggca tcacgtttct agttctagac ccatcagctg ggccggccac | 5340 |
| tagtgagctc ggtacccggg gg | 5362 |

<210> SEQ ID NO 4
<211> LENGTH: 3317
<212> TYPE: DNA
<213> ORGANISM: Glycine max
<220> FEATURE:
<221> NAME/KEY: misc_feature
<222> LOCATION: (0)...(0)
<223> OTHER INFORMATION: 5' genomic sequence of event 3560.4.3.5

<400> SEQUENCE: 4

```
agcaattgtt ttgtgcattt ccaaatttca atctgattta ttaaataaaa aaatttttaat      60 tcgggttgat tgtaaatcag ctaaagacat tttacagaaa gacgtcaaaa atcttggctc     120
caaacaaatt tttgcaagat ggcaagcaat attaagtgtt tttgattttg acagaatata     180
tcaagggcac tttaaactct ctacctaact atccttacacg tgaattctta tagacaaatt     240
ctcatgccac ctaaggcatc aggcaccct  ctcagggta gacgaagcac gagtaaagga     300
ttcaagttgg ccctaccaga gccaactatc aaaagagtt  cttccgcatc ctctgggtca     360
tctacccaaa aacctaaaat aaaagggtca tcaacccaaa tagtcaccat caaacctgag     420
tcatccactc aggaatcccc aaaaccttca acctcaaaac aaacaaaggc cgactatacc     480
ttctcagtac aacactccag gccctacaag aaattggtct aaccaaactc ccaaaactcg     540
ccaaaaagac ttgggcagac attgcctcag aatctaatga tgaatttgaa actgatttac     600
aaatcatgat tcaaaactcc aaacaatcca aaacgattgt caatccaaaa ggaaaacaga     660
ccttatccca acaaaagaca ccattaccaa aacctactaa cagttatatt tacaaaaata     720
aatttccaac tgttttgtag atggagccaa aattttggga caaaaatccc ttcaaggcta     780
cagccaaggc atttccaccg ggcttccatt tcaaacctat ttccaccaat aaaacaagaa     840
tcttttacga attcatactg atagacacaa actcagtgtc tattaaacac ttcaaagacc     900
caaatgacat aaatttaaac actcattcaa ccatccagat tttaaagttc atacaacctc     960
gacaatgtgg aacaaatata atcaagcca  aacaattctt tgtaccctt  gatcctatag    1020 gttacactat tgggattatg tagatgcatg gaccaatgta ttctggcatc aaaataacaa    1080
attcaaacat tcttggctta tttatttcaa aactaacacc gtctataatt ttccaaattg    1140
gttcctccaa cggtgggact tttttggacc aaactttgat atctacccgg agcaagtcca    1200
acaagggttt gatcagttca aaaaaatgtt caattctcag gaatcacgaa tccctgtaga    1260
cctaaaatac ttttccaatt ttgcattgtc gtggatattt tcatggcaat acagatatgg    1320
gaaaactgaa aacaacaagc agtttccatc actgcaacat catgcattta tcaagtggtg    1380
gaattagttt gatacatcaa aagcagcacc agatcaagtg agaatctggt ttcaagccca    1440
tccagaattt ttgaaagttg ctaatcctga gacttcttta ttcctcaatc agaagtctca    1500
attagctgct ttcctttcta gttccaagtc aaaagaaatt ctggcacaaa atctaaaaga    1560
agtcctacag cttctccaac aagaagaaga taaaggctct tcctcaaaga aggaagataa    1620
caattcttca aaagaagatg acgaccctt  ctaccaaaat gaaaatgatt gttttggtat    1680
ttctctaaat gatgattaat taaaaaatta catgtactat gtaaatagtt tcggtcacga    1740
aactggcact gtagctacag taaatttat  ggctatttaa ggagttctcg gcccatttgt    1800
gaggtacctt ttcaggtagt cagatctcta ttttagaga  gagaaactct aggaaacaat    1860
ctttgtaagt ttttctttcg atttcaataa attcaaagtt ttctcttcat atctcttctc    1920
cctcttgacc ggtcctgtgc ggttctgcca tcgcttcagt ttcttctctt ctctcccctt    1980
atcgatattg tgtggctcta ttgccacttc gatttctttt atgttgcttt catttaatt    2040 tgttttacca ttttctttg  atattataat ttctatttaa ctcttggtca tactgcatat    2100
attcataata tattcttaca tcctatctat ccgtttgatc tcttttcact gttatatata    2160
tatatatata tatatatatc gtttaacttc atgttagtaa taagattaga gtaaaaaata    2220
tatatataac gaagttattt taacaaaagg tatttttgta aaaaaaaatt atatgctaaa    2280
aaagttttac tatatctaag catgattttt tttaattccc aaaacacgtg taaatatttt    2340
taggaatatt ttgtaaaaaa tcaaacattt ttttaattat tcgtataaaa catcaatctt    2400
```

| | |
|---|---|
| taagaatcat aatttttaga aatcatgatt tctggatata aaaatacttt ttcttgcagc | 2460 |
| caaacgtctt ctaaagccac atgttaatgg gtgtacaaat tataaagttt ttataaacat | 2520 |
| atcactttt aaagttaaaa atatcactaa tacgtttcta aatgcatttt ttttagaaat | 2580 |
| tataagtttc tagcactcca ttggagttgt atagaactac tactaatcta ctattaataa | 2640 |
| caatttatct cctccaaata tttaagtaaa ctgcatattt agagaatgtt ggacagtaaa | 2700 |
| gctagccact caatatttag gtgctccccg aaagaggaaa gcaaacaagc caccagcact | 2760 |
| tcaatcagta aagctagcca ctcaactcgc tctcttcaaa ttcccttta cattttattt | 2820 |
| cagatcctcc acctagccaa gtaggtctca aaaggtttac cccgcatatg cttagtcgcc | 2880 |
| gcaagctcca tataggttac tttgcgggct actgaataga atcttcggtg aaaggcgtct | 2940 |
| accatatcgg cgcaactatt gatcgagtgc gtgtatacca cgtgaatgcg acacccgaaa | 3000 |
| gactagcaga aaagtgcttc agcaacaaac tctcatcgtg agcagtgtct ctgctggcaa | 3060 |
| tttcgaaatt actaatatgc tgctctcgag atctccactt ccatcataca accgaaacca | 3120 |
| gctaaggaag gagcgatcca taagaatcgc ctcgaatagc cataacctca tctcgccttc | 3180 |
| caccgcacca gcaagaggaa accgaattag agctgaaaga atactagagc catcgtagga | 3240 |
| gaaccggatt cttgaccgat cgacttttgc ccgaggtcgt taggtcgaat aggctaggtt | 3300 |
| tacgaaaaag agactaa | 3317 |

<210> SEQ ID NO 5
<211> LENGTH: 2170
<212> TYPE: DNA
<213> ORGANISM: Glycine max
<220> FEATURE:
<221> NAME/KEY: misc_feature
<222> LOCATION: (0)...(0)
<223> OTHER INFORMATION: 3' genomic sequence for event 3560.4.3.5

<400> SEQUENCE: 5

| | |
|---|---|
| cgcgtaatat catcattagg aagacactgc ccatcttgaa taggatttta gctactaaat | 60 |
| atgttgatgg tctttatgaa aaactattaa ctaggaatat tatgctaccc atatggaaag | 120 |
| aagacgctag gggaatagaa agaccatcaa ataaacgaag tcaacaccag gtcttccgaa | 180 |
| gcattaacaa ttacctattt aatatgtact cagtccgggt ggatatctca ctacattgac | 240 |
| gcagtttgtt caaagacgaa cgccctgaat tatgccatct gcttaggctt tcaaatatgg | 300 |
| tacgctctaa tgccaagcct tatgctggtc ttagggtatt atcatcaaat ctttaagcca | 360 |
| gaggtagtta aatacatcaa ggacaccata ggagtatggc acaacgatat tgtcaagatc | 420 |
| gcatcagatc taataggcaa taatgaattc ttcatgcagc ccgacgtggg aacgctcgaa | 480 |
| agcagtgggg cctctgggac agggaccaga cctgagtcgc taacatttgg gaataagaga | 540 |
| agtagatata cccaattttt taactagcca aggaaggaaa gcgggaaagg tccgatacaa | 600 |
| aggaaagggt tgcgaggctt aacgatttag aatatagctg ttgaggtggc acttgttccc | 660 |
| ccggggcggg ggtatatgcc cgtagcttta ttctgtcact tctttcagat caatgaagtt | 720 |
| gaaaagttat agagtaaggg accccttgttt acaaagctgt cactccaaga actcgaagtc | 780 |
| aagcatcttc gggaatatcc agattagtct tcaactagag aaaggatagg aatctccttt | 840 |
| gcagagtttt cttctcctgc tgatgtagcg gtaaagtcaa aagttggatg ccctttttc | 900 |
| tttatttaat taattccgtt gatagagctt ttgagcggat gcaagcacta gattcttcaa | 960 |
| cgagtaccaa taataaatga attcaccaga ctaagagaaa aaaacagaac aaaaagatta | 1020 |
| agcccagccg ccttcgggaa gacctatctt cgtcgggagg aagagccctc tttacaccat | 1080 |

```
tgtgattaga aaaaaccgaa aagtggaccg gcctagtaac caatagagcg gggcttgatc    1140
cccactttaa atctattgga tagagccctc agcccagggc aagcgattga attctatttg    1200
attatgggtt aggtggaacc tgaaactagc acttacaaat gagttagcaa aaggaaaaag    1260
acaattctca aatgcgtaca agactttctt ccttctttgt ttaagaggcc agtctgcgat    1320
ggatgctcgt gcatgaaaaa gggctttgat ctattcacca cttatataat agagccaatc    1380
tctgcaggac aagatatcta ttttgtcatt gggaagtaag gcttaagtcg acgaaaaagt    1440
taggaaaggg gatcatatgg ctagggttgc cctcggggct caagggttta gcgatgaaga    1500
gtgccaagca aaaggtcaat accggtacgc cgatcaaaga agtccagtgg caaggccctt    1560
tcagccaagc tagcgtgctg aacagaaagt cgtagagtga tgacagcttc ttcttcttga    1620
gtcattcgtg tgcaacatc aggatctcgt cgaaagacct cctctgccta tctctcccgc     1680
aagagaggac tcgttatggc gcacctcttt ttagcagtct cgtcaataag ataagattgc    1740
ccctcccttc ttattgattt gataaagggc tttgtccact ccctctcttc ttagccgagc    1800
ggagtgacgg tttagtttag gctttagatg ccactgcgaa agactctaga gatccactct    1860
cacagcgtat acgcgacatc cctatgtata cacaatcctt tcaagcagct aggacagcta    1920
gcaagcaagt tatctgttcg cggacaagct ctctggatga caaaaaacat gctctttcat    1980
gcggaaaaaa cacggtcttt cgtggaagtt ggtcgatttg aagtcgcttt atgagtgaaa    2040
atgggtcgat gacgaaaaag acggggaaaa tgatcaactg tcacattttg atgccagttt    2100
agggctaaaa tgaactttca tccaaaaaga ccgagaaaac gctccactgg caggatccga    2160
tcggaaataa                                                            2170

<210> SEQ ID NO 6
<211> LENGTH: 10849
<212> TYPE: DNA
<213> ORGANISM: Artificial Sequence
<220> FEATURE:
<223> OTHER INFORMATION: transgene insert for event 3560.4.3.5 plus 5'
      and 3' genomic flanking sequence

<400> SEQUENCE: 6
agcaattgtt ttgtgcattt ccaaatttca atctgattta ttaaataaaa aaattttaat      60
tcgggttgat tgtaaatcag ctaaagacat tttacagaaa gacgtcaaaa atcttggctc    120
caaacaaatt tttgcaagat ggcaagcaat attaagtgtt tttgattttg acagaatata    180
tcaagggcac tttaaactct ctacctaact atcttacacg tgaattctta tagacaaatt    240
ctcatgccac ctaaggcatc aggcacccct ctcagggta gacgaagcac gagtaaagga     300
ttcaagttgg ccctaccaga gccaactatc aaaagagtt cttccgcatc ctctgggtca     360
tctacccaaa aacctaaaat aaaagggtca tcaacccaaa tagtcaccat caaacctgag    420
tcatccactc aggaatcccc aaaaccttca acctcaaaac aaacaaaggc cgactatacc    480
ttctcagtac aacactccag gccctacaag aaattggtct aaccaaactc ccaaaactcg    540
ccaaaaagac ttgggcagac attgcctcag aatctaatga tgaatttgaa actgatttac    600
aaatcatgat tcaaaactcc aaacaatcca aacgattgt caatccaaaa ggaaacaga      660 ccttatccca acaaaagaca ccattaccaa aacctactaa cagttatatt tacaaaaata    720
aatttccaac tgttttgtag atggagccaa attttgggca caaaatccc ttcaaggcta     780 cagccaaggc atttccaccg ggcttccatt tcaaacctat ttccaccaat aaaacaagaa    840
tcttttacga attcatactg atagacacaa actcagtgtc tattaaacac ttcaagacc     900 caaatgacat aaatttaaac actcattcaa ccatccagat tttaaagttc atacaacctc    960
```

```
gacaatgtgg aacaaatata aatcaagcca aacaattctt tgtaccctt gatcctatag   1020 gttacactat tgggattatg tagatgcatg gaccaatgta ttctggcatc aaaataacaa   1080
attcaaacat tcttggctta tttatttcaa aactaacacc gtctataatt ttccaaattg   1140
gttcctccaa cggtgggact tttttggacc aaactttgat atctacccgg agcaagtcca   1200
acaagggttt gatcagttca aaaaaatgtt caattctcag gaatcacgaa tccctgtaga   1260
cctaaaatac ttttccaatt ttgcattgtc gtggatattt tcatggcaat acagatatgg   1320
gaaaactgaa acaacaagc agtttccatc actgcaacat catgcattta tcaagtggtg     1380
gaattagttt gatacatcaa aagcagcacc agatcaagtg agaatctggt ttcaagccca   1440
tccagaattt ttgaaagttg ctaatcctga gacttcttta ttcctcaatc agaagtctca   1500
attagctgct ttcctttcta gttccaagtc aaaagaaatt ctggcacaaa atctaaaaga   1560
agtcctacag cttctccaac aagaagaaga taaaggctct tcctcaaaga aggaagataa   1620
caattcttca aaagaagatg acgaccttt ctaccaaaat gaaaatgatt gttttggtat     1680
ttctctaaat gatgattaat taaaaaatta catgtactat gtaaatagtt tcggtcacga   1740
aactggcact gtagctacag taaatttat ggctatttaa ggagttctcg gcccatttgt     1800
gaggtacctt tcaggtagt cagatctcta ttttagaga gagaaactct aggaaacaat     1860
ctttgtaagt tttctttcg atttcaataa attcaaagtt ttctcttcat atctcttctc     1920
cctcttgacc ggtcctgtgc ggttctgcca tcgcttcagt ttcttctctt ctctcccctt   1980
atcgatattg tgtggctcta ttgccacttc gattttttt atgttgcttt cattttaatt     2040
tgttttacca ttttctttg atattataat ttctatttaa ctcttggtca tactgcatat     2100
attcataata tattcttaca tcctatctat ccgtttgatc tcttttcact gttatatata   2160
tatatatata tatatatatc gtttaacttc atgttagtaa taagattaga gtaaaaaata   2220
tatatataac gaagttattt taacaaaagg tattttgta aaaaaaaatt atatgctaaa     2280
aaagttttac tatatctaag catgattttt tttaattccc aaaacacgtg taaatatttt   2340
taggaatatt ttgtaaaaaa tcaaacattt ttttaattat tcgtataaaa catcaatctt   2400
taagaatcat aattttaga aatcatgatt tctggatata aaaatacttt ttcttgcagc     2460
caaacgtctt ctaaagccac atgttaatgg gtgtacaaat tataaagttt ttataaacat   2520 atcactttt aaagttaaaa atatcactaa tacgtttcta aatgcatttt ttttagaaat     2580
tataagtttc tagcactcca ttggagttgt atagaactac tactaatcta ctattaataa   2640
caatttatct cctccaaata tttaagtaaa ctgcatattt agagaatgtt ggacagtaaa   2700
gctagccact caatatttag gtgctccccg aaagaggaaa gcaaacaagc caccagcact   2760
tcaatcagta aagctagcca ctcaactcgc tctcttcaaa ttccctttta cattttattt   2820
cagatcctcc acctagccaa gtaggtctca aaaggtttac cccgcatatg cttagtcgcc   2880
gcaagctcca tataggttac tttgcgggct actgaataga atcttcggtg aaaggcgtct   2940
accatatcgg cgcaactatt gatcgagtgc gtgtatacca cgtgaatgcg acacccgaaa   3000
gactagcaga aaagtgcttc agcaacaaac tctcatcgtg agcagtgtct ctgctggcaa   3060
tttcgaaatt actaatatgc tgctctcgag atctccactt ccatcataca accgaaacca   3120
gctaaggaag gagcgatcca taagaatcgc ctcgaatagc cataacctca tctcgccttc   3180
caccgcacca gcaagaggaa accgaattag agctgaaaga atactagagc catcgtagga   3240
gaaccggatt cttgaccgat cgactttgc ccgaggtcgt taggtcgaat aggctaggtt     3300
tacgaaaaag agactaaggc cgctctagag atccgtcaac atggtggagc acgacactct   3360
```

```
cgtctactcc aagaatatca aagatacagt ctcagaagac caaagggcta ttgagacttt    3420
tcaacaaagg gtaatatcgg gaaacctcct cggattccat tgcccagcta tctgtcactt    3480
catcaaaagg acagtagaaa aggaaggtgg cacctacaaa tgccatcatt gcgataaagg    3540
aaaggctatc gttcaagatg cctctgccga cagtggtccc aaagatggac ccccacccac    3600
gaggagcatc gtggaaaaag aagacgttcc aaccacgtct tcaaagcaag tggattgatg    3660
tgatgatcct atgcgtatgg tatgacgtgt gttcaagatg atgacttcaa acctacctat    3720
gacgtatggt atgacgtgtg tcgactgatg acttagatcc actcgagcgg ctataaatac    3780
gtacctacgc accctgcgct accatcccta gagctgcagc ttattttac aacaattacc    3840 aacaacaaca aacaacaaac aacattacaa ttactattta caattacagt cgacccggga    3900
tccacacgac accatgatag aggtgaaacc gattaacgca gaggatacct atgaactaag    3960
gcatagaata ctcagaccaa accagccgat agaagcgtgt atgtttgaaa gcgatttact    4020
tcgtggtgca tttcacttag gcggctttta caggggcaaa ctgatttcca tagcttcatt    4080
ccaccaggcc gagcactcgg aactccaagg ccagaaacag taccagctcc gaggtatggc    4140
taccttggaa ggttatcgtg agcagaaagc gggatcaact ctagttaaac acgctgaaga    4200
aatccttcgt aagagggggg cggacatgct ttggtgtaat gcgaggacat ccgcctcagg    4260
ctactacaaa aagttaggct tcagcgagca gggagagata tttgacacgc cgccagtagg    4320
acctcacatc ctgatgtata aaaggatcac ataactagct agtcagttaa cctagacttg    4380
tccatcttct ggattggcca acttaattaa tgtatgaaat aaaaggatgc acacatagtg    4440
acatgctaat cactataatg tgggcatcaa agttgtgtgt tatgtgtaat tactagttat    4500
ctgaataaaa gagaaagaga tcatccatat ttcttatcct aaatgaatgt cacgtgtctt    4560
tataattctt tgatgaacca gatgcatttc attaaccaaa tccatataca tataaatatt    4620
aatcatatat aattaatatc aattgggtta gcaaaacaaa tctagtctag gtgtgttttg    4680
cgaattcgat atcaagcttt gctctagatc aaactcacat ccaaacataa catggatatc    4740
ttccttacca atcatactaa ttattttggg ttaaatatta atcattattt ttaagatatt    4800
aattaagaaa ttaaagatt ttttaaaaaa atgtataaaa ttatattatt catgattttt    4860
catacatttg attttgataa taaatatatt ttttttaatt tcttaaaaaa tgttgcaaga    4920
cacttattag acatagtctt gttctgttta caaaagcatt catcatttaa tacattaaaa    4980
aatatttaat actaacagta gaatcttctt gtgagtggtg tgggagtagg caacctggca    5040
ttgaaacgag agaaagagag tcagaaccag aagacaaata aaaagtatgc aacaaacaaa    5100
tcaaaatcaa agggcaaagg ctggggttgg ctcaattggt tgctacattc aattttcaac    5160
tcagtcaacg gttgagattc actctgactt ccccaatcta agccgcggat gcaaacggtt    5220
gaatctaacc cacaatccaa tctcgttact tagggctttt ccgtcatta actcacccct    5280 gccacccggt ttccctataa attggaactc aatgctcccc tctaaactcg tatcgcttca    5340
gagttgagac caagacacac tcgttcatat atctctctgc tcttctcttc tcttctacct    5400
ctcaaggtac ttttcttctc cctctaccaa atcctagatt ccgtggttca atttcggatc    5460
ttgcacttct ggtttgcttt gccttgcttt ttcctcaact gggtccatct aggatccatg    5520
tgaaactcta ctcttctttt aatatctgcg gaatacgcgt ttgactttca gatctagtcg    5580
aaatcatttc ataattgcct ttcttctt tagcttatga gaaataaaat cactttttt    5640 ttatttcaaa ataaaccttg ggccttgtgc tgactgagat ggggtttggt gattacagaa    5700
ttttagcgaa ttttgtaatt gtacttgttt gtctgtagtt ttgtttgtt tcttgtttc    5760
```

```
tcatacattc cttaggcttc aattttattc gagtataggt cacaatagga attcaaactt     5820
tgagcagggg aattaatccc ttccttcaaa tccagtttgt ttgtatatat gtttaaaaaa     5880
tgaaactttt gctttaaatt ctattataac ttttttatg gctgaaattt ttgcatgtgt      5940
ctttgctctc tgttgtaaat ttactgttta ggtactaact ctaggcttgt tgtgcagttt     6000
ttgaagtata accatgccac acaacacaat ggcggccacc gcttccagaa ccacccgatt     6060
ctcttcttcc tcttcacacc ccaccttccc caaacgcatt actagatcca ccctccctct     6120
ctctcatcaa accctcacca aacccaacca cgctctcaaa atcaaatgtt ccatctccaa     6180
accccccacg gcggcgccct tcaccaagga agcgccgacc acggagccct tcgtgtcacg     6240
gttcgcctcc ggcgaacctc gcaagggcgc ggacatcctt gtggaggcgc tggagaggca     6300
gggcgtgacg acggtgttcg cgtaccccgg cggtgcgtcg atggagatcc accaggcgct     6360
cacgcgctcc gccgccatcc gcaacgtgct cccgcgccac gagcagggcg gcgtcttcgc     6420
cgccgaaggc tacgcgcgtt cctccggcct ccccggcgtc tgcattgcca cctccggccc     6480
cggcgccacc aacctcgtga gcggcctcgc cgacgcttta atggacagcg tcccagtcgt     6540
cgccatcacc ggccaggtcg cccgccggat gatcggcacc gacgccttcc aagaaacccc     6600
gatcgtggag gtgagcagat ccatcacgaa gcacaactac ctcatcctcg acgtcgacga     6660
catccccgc gtcgtcgccg aggctttctt cgtcgccacc tccggccgcc ccggtccggt      6720
cctcatcgac attcccaaag acgttcagca gcaactcgcc gtgcctaatt gggacgagcc     6780
cgttaacctc cccggttacc tcgccaggct gcccaggccc ccgccgagg cccaattgga      6840
acacattgtc agactcatca tggaggccca aaagcccgtt ctctacgtcg cggtggcag      6900
tttgaattcc agtgctgaat tgaggcgctt tgttgaactc actggtattc ccgttgctag     6960
cactttaatg ggtcttggaa cttttcctat tggtgatgaa tattcccttc agatgctggg     7020
tatgcatggt actgtttatg ctaactatgc tgttgacaat agtgatttgt tgcttgcctt     7080
tggggtaagg tttgatgacc gtgttactgg gaagcttgag gcttttgcta gtagggctaa     7140
gattgttcac attgatattg attctgccga gattgggaag aacaagcagg cgcacgtgtc     7200
ggtttgcgcg gatttgaagt tggccttgaa gggaattaat atgattttgg aggagaaagg     7260
agtggagggt aagtttgatc ttggaggttg gagagaagag attaatgtgc agaaacacaa     7320
gtttccattg ggttacaaga cattccagga cgcgatttct ccgcagcatg ctatcgaggt     7380
tcttgatgag ttgactaatg gagatgctat tgttagtact ggggttgggc agcatcaaat     7440
gtgggctgcg cagttttaca agtacaagag accgaggcag tggttgacct caggggggtct    7500
tggagccatg ggttttggat tgcctgcggc tattggtgct gctgttgcta accctggggc     7560
tgttgtggtt gacattgatg gggatggtag tttcatcatg aatgttcagg agttggccac     7620
tataagagtg gagaatctcc cagttaagat attgttgttg aacaatcagc atttgggtat     7680
ggtggttcag ttgaaggata ggttctacaa gtccaataga gctcacacct atcttggaga     7740
tccgtctagc gagagcgaga tattcccaaa catgctcaag tttgctgatg cttgtgggat     7800
accggcagcg cgagtgacga agaaggaaga gcttagagcg gcaattcaga gaatgttgga     7860
cacccctggc ccctaccttc ttgatgtcat tgtgccccat caggagcatg tgttgccgat     7920
gattcccagt aatggatcct tcaaggatgt gataactgag ggtgatggta gaacgaggta     7980
ctgattgcct agaccaaatg ttccttgatg cttgttttgt acaatatata taagataatg     8040
ctgtcctagt tgcaggattt ggcctgtggt gagcatcata gtctgtagta gttttggtag     8100
caagacattt tattttcctt ttattaaact tactacatgc agtagcatct atctatctct     8160
```

```
gtagtctgat atctcctgtt gtctgtattg tgccgttgga ttttttgctg tagtgagact   8220
gaaaatgatg tgctagtaat aatatttctg ttagaaatct aagtagagaa tctgttgaag   8280
aagtcaaaag ctaatggaat caggttacat attcaatgtt tttcttttt tagcggttgg   8340 tagacgtgta gattcaactt ctcttggagc tcacctaggc aatcagtaaa atgcatattc   8400
cttttttaac ttgccattta tttacttta gtggaaattg tgaccaattt gttcatgtag   8460
aacggatttg gaccattgcg tccacaaaac gtctcttttg ctcgatcttc acaaagcgat   8520
accgaaatcc agagatagtt ttcaaaagtc agaaatggca agttataaa tagtaaaaca   8580 gaatagatgc tgtaatcgac ttcaataaca agtggcatca cgtttctagt tctagaccca   8640
tcagctgggc cggccactag tgagctcggt acccggggc gcgtaatatc atcattagga   8700
agacactgcc catcttgaat aggattttag ctactaaata tgttgatggt ctttatgaaa   8760
aactattaac taggaatatt atgctaccca tatggaaaga agacgctagg gaatagaaaa   8820
gaccatcaaa taaacgaagt caacaccagg tcttccgaag cattaacaat tacctattta   8880
atatgtactc agtccgggtg gatatctcac tacattgacg cagtttgttc aaagacgaac   8940
gccctgaatt atgccatctg cttaggcttt caaatatggt acgctctaat gccaagcctt   9000
atgctggtct tagggtatta tcatcaaatc tttaagccag aggtagttaa atacatcaag   9060
gacaccatag gagtatggca caacgatatt gtcaagatcg catcagatct aataggcaat   9120
aatgaattct tcatgcagcc cgacgtggga acgctcgaaa gcagtggggc ctctgggaca   9180
gggaccagac ctgagtcgct aacatttggg aataagagaa gtagatatac ccaattttt   9240 aactagccaa ggaaggaaag cgggaaaggt ccgatacaaa ggaaagggtt gcgaggctta   9300
acgatttaga atatagctgt tgaggtggca cttgttcccc cggggcgggg gtatatgccc   9360
gtagctttat tctgtcactt ctttcagatc aatgaagttg aaaagttata gagtaaggga   9420
cccttgttta caaagctgtc actccaagaa ctcgaagtca agcatcttcg ggaatatcca   9480
gattagtctt caactagaga aaggatagga atctcctttg cagagttttc ttctcctgct   9540
gatgtagcgg taaagtcaaa agttggatgc cctttttct ttatttaatt aattccgttg   9600
atagagcttt tgagcggatg caagcactag attcttcaac gagtaccaat aataaatgaa   9660 ttaccagac taagagaaga aaacagaaca aaaagattaa gcccagccgc cttcgggaag   9720
acctatcttc gtcgggagga agagccctct ttacaccatt gtgattagaa aaaccgaaa   9780 agtggaccgg cctagtaacc aatagagcgg ggcttgatcc ccactttaaa tctattggat   9840
agagccctca gcccagggca agcgattgaa ttctatttga ttatgggtta ggtggaacct   9900
gaaactagca cttacaaatg agttagcaaa aggaaaaaga caattctcaa atgcgtacaa   9960
gactttcttc cttctttgtt taagaggcca gtctgcgatg gatgctcgtg catgaaaaag  10020
ggctttgatc tattcaccac ttatataata gagccaatct ctgcaggaca agatatctat  10080
tttgtcattg ggaagtaagg cttaagtcga cgaaaaagtt aggaagggg atcatatggc  10140 tagggttgcc ctcggggctc aagggtttag cgatgaagag tgccaagcaa aaggtcaata  10200
ccggtacgcc gatcaaagaa gtccagtggc aaggcccttt cagccaagct agcgtgctga  10260
acagaaagtc gtagagtgat gacagcttct tcttcttgag tcattcgtgt gacaacatca  10320
ggatctcgtc gaaagacctc ctctgcctat ctctcccgca agagaggact cgttatggcg  10380 caccctctttt tagcagtctc gtcaataaga taagattgcc cctcccttct tattgatttg  10440
ataaagggct ttgtccactc cctctcttct tagccgagcg gagtgacggt ttagtttagg  10500
ctttagatgc cactgcgaaa gactctagag atccactctc acagcgtata cgcgacatcc  10560
```

-continued

```
ctatgtatac acaatccttt caagcagcta ggacagctag caagcaagtt atctgttcgc    10620
ggacaagctc tctggatgac aaaaaacatg ctctttcatg cggaaaaaac acggtctttc    10680
gtggaagttg gtcgatttga agtcgcttta tgagtgaaaa tgggtcgatg acgaaaaaga    10740
cggggaaaat gatcaactgt cacattttga tgccagttta gggctaaaat gaactttcat    10800
ccaaaaagac cgagaaaacg ctccactggc aggatccgat cggaaataa                10849

<210> SEQ ID NO 7
<211> LENGTH: 24
<212> TYPE: DNA
<213> ORGANISM: Artificial Sequence
<220> FEATURE:
<223> OTHER INFORMATION: primer

<400> SEQUENCE: 7
ggtcgaatag gctaggttta cgaa                                            24

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
ccaccatgtt gacggatctc t                                               21

<210> SEQ ID NO 9
<211> LENGTH: 18
<212> TYPE: DNA
<213> ORGANISM: Artificial Sequence
<220> FEATURE:
<223> OTHER INFORMATION: primer

<400> SEQUENCE: 9
aagagactaa ggccgctc                                                   18

<210> SEQ ID NO 10
<211> LENGTH: 20
<212> TYPE: DNA
<213> ORGANISM: Artificial Sequence
<220> FEATURE:
<223> OTHER INFORMATION: Junction DNA of event 3560.4.3.5 (10 nt 5'
      genomic/ 10 nt transgene insert)

<400> SEQUENCE: 10
aagagactaa ggccgctcta                                                 20

<210> SEQ ID NO 11
<211> LENGTH: 20
<212> TYPE: DNA
<213> ORGANISM: Artificial Sequence
<220> FEATURE:
<223> OTHER INFORMATION: Junction DNA of event 3560.4.3.5 (10 nt 3'
      genomic/ 10 nt transgene insert)

<400> SEQUENCE: 11
tacccggggg cgcgtaatat                                                 20

<210> SEQ ID NO 12
<211> LENGTH: 40
<212> TYPE: DNA
<213> ORGANISM: Artificial Sequence
<220> FEATURE:
<223> OTHER INFORMATION: Junction DNA of  event 3560.4.3.5 (20 nt 5'
``` genomic/ 20 nt transgene insert)

<400> SEQUENCE: 12
gtttacgaaa aagagactaa ggccgctcta gagatccgtc                    40

<210> SEQ ID NO 13
<211> LENGTH: 40
<212> TYPE: DNA
<213> ORGANISM: Artificial Sequence
<220> FEATURE:
<223> OTHER INFORMATION: Junction DNA of event 3560.4.3.5 (20 nt 3'
      genomic/ 20 nt transgene insert)

<400> SEQUENCE: 13
gtgagctcgg tacccggggg cgcgtaatat catcattagg                    40

<210> SEQ ID NO 14
<211> LENGTH: 8679
<212> TYPE: DNA
<213> ORGANISM: Artificial Sequence
<220> FEATURE:
<223> OTHER INFORMATION: 5' genomic sequence and complete event
      3560.4.3.5 transgene insert

<400> SEQUENCE: 14
agcaattgtt ttgtgcattt ccaaatttca atctgattta ttaaataaaa aaattttaat     60
tcgggttgat tgtaaatcag ctaaagacat tttacagaaa gacgtcaaaa atcttggctc    120
caaacaaatt tttgcaagat ggcaagcaat attaagtgtt tttgattttg acagaatata    180
tcaagggcac tttaaactct ctacctaact atcttacacg tgaattctta tagacaaatt    240
ctcatgccac ctaaggcatc aggcaccccct ctcaggggta gacgaagcac gagtaaagga    300
ttcaagttgg ccctaccaga gccaactatc aaaaagagtt cttccgcatc ctctgggtca    360
tctacccaaa aacctaaaat aaagggtca tcaacccaaa tagtcaccat caaacctgag     420
tcatccactc aggaatcccc aaaaccttca acctcaaaac aaacaaaggc cgactatacc    480
ttctcagtac aacactccag gcccctacaag aaattggtct aaccaaactc ccaaaactcg    540
ccaaaaagac ttgggcagac attgcctcag aatctaatga tgaatttgaa actgatttac    600
aaatcatgat tcaaaactcc aaacaatcca aaacgattgt caatccaaaa ggaaaacaga    660
ccttatccca acaaaagaca ccattaccaa acctactaa cagttatatt tacaaaaata    720
aatttccaac tgttttgtag atggagccaa aattttggga caaaaatccc ttcaaggcta    780
cagccaaggc atttccaccg ggcttccatt tcaaacctat ttccaccaat aaaacaagaa    840
tcttttacga attcatactg atagacacaa actcagtgtc tattaaacac ttcaaagacc    900
caaatgacat aaatttaaac actcattcaa ccatccagat tttaaagttc atacaacctc    960
gacaatgtgg aacaaatata aatcaagcca acaattctt tgtacccttt gatcctatag   1020
gttacactat tgggattatg tagatgcatg gaccaatgta ttctggcatc aaaataacaa   1080
attcaaacat tcttggctta tttatttcaa aactaacacc gtctataatt ttccaaattg   1140
gttcctccaa cggtgggact tttttggacc aaactttgat atctaccccgg agcaagtcca   1200 acaagggttt gatcagttca aaaaaatgtt caattctcag gaatcacgaa tccctgtaga   1260
cctaaaatac ttttccaatt ttgcattgtc gtggatattt tcatggcaat acagatatgg   1320
gaaaactgaa acaacaagc agtttccatc actgcaacat catgcattta tcaagtggtg   1380
gaattagttt gatacatcaa aagcagcacc agatcaagtg agaatctggt ttcaagccca   1440
tccagaattt ttgaaagttg ctaatcctga gacttcttta ttcctcaatc agaagtctca   1500

```
attagctgct tcctttcta gttccaagtc aaaagaaatt ctggcacaaa atctaaaaga    1560
agtcctacag cttctccaac aagaagaaga taaaggctct tcctcaaaga aggaagataa    1620
caattcttca aaagaagatg acgacccttt ctaccaaaat gaaaatgatt gttttggtat    1680
ttctctaaat gatgattaat taaaaaatta catgtactat gtaaatagtt tcggtcacga    1740
aactggcact gtagctacag taaatttttat ggctatttaa ggagttctcg gcccatttgt    1800
gaggtaccct tcaggtagt cagatctcta tttttagaga gagaaactct aggaaacaat    1860
ctttgtaagt ttttctttcg atttcaataa attcaaagtt ttctcttcat atctcttctc    1920
cctcttgacc ggtcctgtgc ggttctgcca tcgcttcagt ttcttctctt ctctcccctt    1980
atcgatattg tgtggctcta ttgccacttc gatttctttt atgttgcttt cattttaatt    2040
tgttttacca ttttctttg atattataat ttctatttaa ctcttggtca tactgcatat    2100
attcataata tattcttaca tcctatctat ccgtttgatc tcttttcact gttatatata    2160
tatatatata tatatatatc gtttaacttc atgttagtaa taagattaga gtaaaaaata    2220
tatatataac gaagttattt taacaaaagg tattttgta aaaaaaaatt atatgctaaa    2280
aaagttttac tatatctaag catgattttt tttaattccc aaaacacgtg taaatatttt    2340
taggaatatt ttgtaaaaaa tcaaacattt tttaattat tcgtataaaa catcaatctt    2400
taagaatcat aatttttaga aatcatgatt tctggatata aaaatacttt ttcttgcagc    2460
caaacgtctt ctaaagccac atgttaatgg gtgtacaaat tataagtttt ttataaacat    2520
atcactttt aaagttaaaa atatcactaa tacgtttcta aatgcatttt ttttagaaat    2580
tataagtttc tagcactcca ttggagttgt atagaactac tactaatcta ctattaataa    2640
caatttatct cctccaaata tttaagtaaa ctgcatattt agagaatgtt ggacagtaaa    2700
gctagccact caatatttag gtgctccccg aaagaggaaa gcaaacaagc caccagcact    2760
tcaatcagta aagctagcca ctcaactcgc tctcttcaaa ttccctttta cattttattt    2820
cagatcctcc acctagccaa gtaggtctca aaaggtttac cccgcatatg cttagtcgcc    2880
gcaagctcca tataggttac tttgcgggct actgaataga atcttcggtg aaaggcgtct    2940
accatatcgg cgcaactatt gatcgagtgc gtgtatacca cgtgaatgcg acacccgaaa    3000
gactagcaga aaagtgcttc agcaacaaac tctcatcgtg agcagtgtct ctgctggcaa    3060
tttcgaaatt actaatatgc tgctctcgag atctccactt ccatcataca accgaaacca    3120
gctaaggaag gagcgatcca taagaatcgc ctcgaatagc cataacctca tctcgccttc    3180
caccgcacca gcaagaggaa accgaattag agctgaaaga atactagagc catcgtagga    3240
gaaccggatt cttgaccgat cgacttttgc ccgaggtcgt taggtcgaat aggctaggtt    3300
tacgaaaaag agactaaggc cgctctagag atccgtcaac atggtggagc acgacactct    3360
cgtctactcc aagaatatca aagatacagt ctcagaagac caaagggcta ttgagacttt    3420
tcaacaaagg gtaatatcgg gaaacctcct cggattccat tgcccagcta tctgtcactt    3480
catcaaaagg acagtagaaa aggaaggtgg cacctacaaa tgccatcatt gcgataaagg    3540
aaaggctatc gttcaagatg cctctgccga cagtggtccc aaagatggac ccccacccac    3600
gaggagcatc gtggaaaaag aagacgttcc aaccacgtct tcaaagcaag tggattgatg    3660
tgatgatcct atgcgtatgg tatgacgtgt gttcaagatg atgacttcaa acctaccta   t 3720
gacgtatggt atgacgtgtg tcgactgatg acttagatcc actcgagcgg ctataaatac    3780
gtacctacgc accctgcgct accatcccta gagctgcagc ttatttttac aacaattacc    3840
aacaacaaca aacaacaaac aacattacaa ttactattta caattacagt cgacccggga    3900
```

```
tccacacgac accatgatag aggtgaaacc gattaacgca gaggatacct atgaactaag    3960
gcatagaata ctcagaccaa accagccgat agaagcgtgt atgtttgaaa gcgatttact    4020
tcgtggtgca tttcacttag gcggctttta caggggcaaa ctgatttcca tagcttcatt    4080
ccaccaggcc gagcactcgg aactccaagg ccagaaacag taccagctcc gaggtatggc    4140
taccttggaa ggttatcgtg agcagaaagc gggatcaact ctagttaaac acgctgaaga    4200
aatccttcgt aagaggggg cggacatgct ttggtgtaat gcgaggacat ccgcctcagg     4260
ctactacaaa aagttaggct tcagcgagca gggagagata tttgacacgc cgccagtagg    4320
acctcacatc ctgatgtata aaaggatcac ataactagct agtcagttaa cctagacttg    4380
tccatcttct ggattggcca acttaattaa tgtatgaaat aaaaggatgc acacatagtg    4440
acatgctaat cactataatg tgggcatcaa agttgtgtgt tatgtgtaat tactagttat    4500
ctgaataaaa gagaaagaga tcatccatat ttcttatcct aaatgaatgt cacgtgtctt    4560
tataattctt tgatgaacca gatgcatttc attaaccaaa tccatataca tataaatatt    4620
aatcatatat aattaatatc aattgggtta gcaaaacaaa tctagtctag gtgtgttttg    4680
cgaattcgat atcaagcttt gctctagatc aaactcacat ccaaacataa catggatatc    4740
ttccttacca atcatactaa ttattttggg ttaaatatta atcattattt ttaagatatt    4800
aattaagaaa ttaaagatt ttttaaaaaa atgtataaaa ttatattatt catgattttt      4860
catacatttg attttgataa taaatatatt ttttttaatt tcttaaaaaa tgttgcaaga    4920
cacttattag acatagtctt gttctgttta caaaagcatt catcatttaa tacattaaaa    4980
aatatttaat actaacagta gaatcttctt gtgagtggtg tgggagtagg caacctggca    5040
ttgaaacgag agaaagagag tcagaaccag aagacaaata aaaagtatgc aacaaacaaa    5100
tcaaaatcaa agggcaaagg ctggggttgg ctcaattggt tgctacattc aattttcaac    5160
tcagtcaacg gttgagattc actctgactt ccccaatcta agccgcggat gcaaacggtt    5220
gaatctaacc cacaatccaa tctcgttact taggggcttt tccgtcatta actcacccct    5280
gccacccggt ttccctataa attggaactc aatgctcccc tctaaactcg tatcgcttca    5340
gagttgagac caagacacac tcgttcatat atctctctgc tcttctcttc tcttctacct    5400
ctcaaggtac ttttcttctc cctctaccaa atcctagatt ccgtggttca atttcggatc    5460
ttgcacttct ggtttgcttt gccttgcttt ttcctcaact gggtccatct aggatccatg    5520
tgaaactcta ctctttcttt aatatctgcg gaatacgcgt ttgactttca gatctagtcg    5580
aaatcatttc ataattgcct ttctttcttt tagcttatga gaaataaaat cactttttt     5640 ttatttcaaa ataaaccttg ggccttgtgc tgactgagat ggggtttggt gattacagaa    5700
ttttagcgaa ttttgtaatt gtacttgttt gtctgtagtt ttgttttgtt ttcttgtttc    5760
tcatacattc cttaggcttc aattttattc gagtataggt cacaatagga attcaaactt    5820
tgagcagggg aattaatccc ttccttcaaa tccagtttgt ttgtatatat gtttaaaaaa    5880
tgaaactttt gctttaaatt ctattataac tttttttatg gctgaaattt tgcatgtgt     5940 ctttgctctc tgttgtaaat ttactgttta ggtactaact ctaggcttgt tgtgcagttt    6000
ttgaagtata accatgccac acaacacaat ggcggccacc gcttccagaa ccacccgatt    6060
ctcttcttcc tcttcacacc ccaccttccc caaacgcatt actagatcca ccctccctct    6120
ctctcatcaa accctcacca aacccaacca cgctctcaaa atcaaatgtt ccatctccaa    6180 acccccacg gcggcgccct tcaccaagga agcgccgacc acggagccct tcgtgtcacg     6240
gttcgcctcc ggcgaacctc gcaagggcgc ggacatcctt gtggaggcgc tggagaggca    6300
```

```
gggcgtgacg acggtgttcg cgtacccegg cggtgcgtcg atggagatcc accaggcgct    6360
cacgcgctcc gccgccatcc gcaacgtgct cccgcgccac gagcagggcg gcgtcttcgc    6420
cgccgaaggc tacgcgcgtt cctccggcct ccccggcgtc tgcattgcca cctccggccc    6480
cggcgccacc aacctcgtga gcggcctcgc cgacgcttta atggacagcg tcccagtcgt    6540
cgccatcacc ggccaggtcg cccgccggat gatcggcacc gacgccttcc aagaaacccc    6600
gatcgtggag gtgagcagat ccatcacgaa gcacaactac ctcatcctcg acgtcgacga    6660 catccccgc gtcgtcgccg aggctttctt cgtcgccacc tccggccgcc ccggtccggt    6720
cctcatcgac attcccaaag acgttcagca gcaactcgcc gtgcctaatt gggacgagcc    6780
cgttaacctc cccggttacc tcgccaggct gcccaggccc ccgccgagg cccaattgga    6840 acacattgtc agactcatca tggaggccca aaagcccgtt ctctacgtcg gcggtggcag    6900
tttgaattcc agtgctgaat tgaggcgctt tgttgaactc actggtattc ccgttgctag    6960
cactttaatg ggtcttggaa cttttcctat tggtgatgaa tattcccttc agatgctggg    7020
tatgcatggt actgtttatg ctaactatgc tgttgacaat agtgatttgt tgcttgcctt    7080
tggggtaagg tttgatgacc gtgttactgg gaagcttgag gcttttgcta gtagggctaa    7140
gattgttcac attgatattg attctgccga gattgggaag aacaagcagg cgcacgtgtc    7200
ggtttgcgcg gatttgaagt tggccttgaa gggaattaat atgattttgg aggagaaagg    7260
agtggagggt aagtttgatc ttggaggttg gagagaagag attaatgtgc agaaacacaa    7320
gtttccattg ggttacaaga cattccagga cgcgatttct ccgcagcatg ctatcgaggt    7380
tcttgatgag ttgactaatg gagatgctat tgttagtact ggggttgggc agcatcaaat    7440
gtgggctgcg cagtttttaca agtacaagag accgaggcag tggttgacct caggggtct    7500 tggagccatg ggttttggat tgcctgcggc tattggtgct gctgttgcta accctggggc    7560
tgttgtggtt gacattgatg gggatggtag tttcatcatg aatgttcagg agttggccac    7620
tataagagtg gagaatctcc cagttaagat attgttgttg aacaatcagc atttgggtat    7680
ggtggttcag ttggaggata ggttctacaa gtccaataga gctcacacct atcttggaga    7740
tccgtctagc gagagcgaga tattcccaaa catgctcaag tttgctgatg cttgtgggat    7800
accggcagcg cgagtgacga agaaggaaga gcttagagcg gcaattcaga gaatgttgga    7860
cacccctggc ccctaccttc ttgatgtcat tgtgccccat caggagcatg tgttgccgat    7920
gattcccagt aatggatcct tcaaggatgt gataactgag ggtgatggta gaacgaggta    7980
ctgattgcct agaccaaatg ttccttgatg cttgttttgt acaatatata taagataatg    8040
ctgtcctagt tgcaggattt ggcctgtggt gagcatcata gtctgtagta gttttggtag    8100
caagacattt tatttttcctt ttatttaact tactacatgc agtagcatct atctatctct    8160
gtagtctgat atctcctgtt gtctgtattg tgccgttgga ttttttgctg tagtgagact    8220
gaaaatgatg tgctagtaat aatatttctg ttagaaatct aagtagagaa tctgttgaag    8280
aagtcaaaag ctaatggaat caggttacat attcaatgtt tttctttttt tagcggttgg    8340
tagacgtgta gattcaactt ctcttggagc tcacctaggc aatcagtaaa atgcatattc    8400 ctttttaac ttgccatttta tttacttttta gtggaaattg tgaccaattt gttcatgtag    8460
aacggatttg gaccattgcg tccacaaaac gtctctttg ctcgatcttc acaaagcgat    8520
accgaaatcc agagatagtt ttcaaaagtc agaaatggca aagttataaa tagtaaaaca    8580
gaatagatgc tgtaatcgac ttcaataaca agtggcatca cgtttctagt tctagaccca    8640
tcagctgggc cggccactag tgagctcggt acccggggg                          8679
```

<210> SEQ ID NO 15
<211> LENGTH: 7532
<212> TYPE: DNA
<213> ORGANISM: Artificial Sequence
<220> FEATURE:
<223> OTHER INFORMATION: 3' genomic sequence and complete transgene
      insert for event 3560.4.3.5

<400> SEQUENCE: 15

| | | | | | |
|---|---|---|---|---|---|
| ggccgctcta | gagatccgtc | aacatggtgg | agcacgacac | tctcgtctac | tccaagaata       60 |
| tcaaagatac | agtctcagaa | gaccaaaggg | ctattgagac | ttttcaacaa | agggtaatat      120 |
| cgggaaacct | cctcggattc | cattgcccag | ctatctgtca | cttcatcaaa | aggacagtag      180 |
| aaaaggaagg | tggcacctac | aaatgccatc | attgcgataa | aggaaaggct | atcgttcaag      240 |
| atgcctctgc | cgacagtggt | cccaaagatg | gacccccacc | cacgaggagc | atcgtggaaa      300 |
| aagaagacgt | tccaaccacg | tcttcaaagc | aagtggattg | atgtgatgat | cctatgcgta      360 |
| tggtatgacg | tgtgttcaag | atgatgactt | caaacctacc | tatgacgtat | ggtatgacgt      420 |
| gtgtcgactg | atgacttaga | tccactcgag | cggctataaa | tacgtaccta | cgcaccctgc      480 |
| gctaccatcc | ctagagctgc | agcttatttt | tacaacaatt | accaacaaca | acaaacaaca      540 |
| aacaacatta | caattactat | ttacaattac | agtcgacccg | ggatccacac | gacaccatga      600 |
| tagaggtgaa | accgattaac | gcagaggata | cctatgaact | aaggcataga | atactcagac      660 |
| caaaccagcc | gatagaagcg | tgtatgtttg | aaagcgattt | acttcgtggt | gcatttcact      720 |
| taggcggctt | ttacagggc | aaactgattt | ccatagcttc | attccaccag | gccgagcact      780 |
| cggaactcca | aggccagaaa | cagtaccagc | tccgaggtat | ggctaccttg | gaaggttatc      840 |
| gtgagcagaa | agcgggatca | actctagtta | aacacgctga | agaaatcctt | cgtaagaggg      900 |
| gggcggacat | gctttggtgt | aatgcgagga | catccgcctc | aggctactac | aaaaagttag      960 |
| gcttcagcga | gcagggagag | atatttgaca | cgccgccagt | aggacctcac | atcctgatgt     1020 |
| ataaaaggat | cacataacta | gctagtcagt | taacctagac | ttgtccatct | tctggattgg     1080 |
| ccaacttaat | taatgtatga | aataaaagga | tgcacacata | gtgacatgct | aatcactata     1140 |
| atgtgggcat | caaagttgtg | tgttatgtgt | aattactagt | tatctgaata | aaagagaaag     1200 |
| agatcatcca | tatttcttat | cctaaatgaa | tgtcacgtgt | ctttataatt | ctttgatgaa     1260 |
| ccagatgcat | ttcattaacc | aaatccatat | acatataaat | attaatcata | tataattaat     1320 |
| atcaattggg | ttagcaaaac | aaatctagtc | taggtgtgtt | ttgcgaattc | gatatcaagc     1380 |
| tttgctctag | atcaaactca | catccaaaca | taacatggat | atcttcctta | ccaatcatac     1440 |
| taattatttt | gggttaaata | ttaatcatta | tttttaagat | attaattaag | aaattaaaag     1500 |
| attttttaaa | aaatgtata | aaattatatt | attcatgatt | tttcatacat | ttgattttga     1560 |
| taataaatat | atttttttta | atttcttaaa | aaatgttgca | agacacttat | tagacatagt     1620 |
| cttgttctgt | ttacaaaagc | attcatcatt | taatacatta | aaaatatttt | aatactaaca     1680 |
| gtagaatctt | cttgtgagtg | gtgtgggagt | aggcaacctg | gcattgaaac | gagagaaaga     1740 |
| gagtcagaac | cagaagacaa | ataaaaagta | tgcaacaaac | aaatcaaaat | caagggcaa     1800 |
| aggctggggt | tggctcaatt | ggttgctaca | ttcaatttc | aactcagtca | acggttgaga     1860 |
| ttcactctga | cttccccaat | ctaagccgcg | gatgcaaacg | gttgaatcta | acccacaatc     1920 |
| caatctcgtt | acttaggggc | ttttccgtca | ttaactcacc | cctgccaccc | ggtttcccta     1980 |
| taaattggaa | ctcaatgctc | ccctctaaac | tcgtatcgct | tcagagttga | gaccaagaca     2040 |
| cactcgttca | tatatctctc | tgctcttctc | ttctcttcta | cctctcaagg | tacttttctt     2100 |

| | | | |
|---|---|---|---|
| ctccctctac | caaatcctag | attccgtggt tcaatttcgg | atcttgcact tctggtttgc | 2160 |
| tttgccttgc | ttttcctca | actgggtcca tctaggatcc | atgtgaaact ctactctttc | 2220 |
| tttaatatct | gcggaatacg | cgtttgactt cagatctag | tcgaaatcat ttcataattg | 2280 |
| cctttctttc | ttttagctta | tgagaaataa aatcactttt | tttttatttc aaaataaacc | 2340 |
| ttgggccttg | tgctgactga | gatggggttt ggtgattaca | gaattttagc gaattttgta | 2400 |
| attgtacttg | tttgtctgta | gttttgtttt gttttcttgt | ttctcataca ttccttaggc | 2460 |
| ttcaattta | ttcgagtata | ggtcacaata ggaattcaaa | ctttgagcag ggaattaat | 2520 |
| cccttcttc | aaatccagtt | tgtttgtata tatgtttaaa | aaatgaaact tttgctttaa | 2580 |
| attctattat | aactttttt | atggctgaaa tttttgcatg | tgtctttgct ctctgttgta | 2640 |
| aatttactgt | ttaggtacta | actctaggct tgttgtgcag | ttttgaagt ataaccatgc | 2700 |
| cacacaacac | aatggcggcc | accgcttcca gaaccacccg | attctcttct tcctcttcac | 2760 |
| accccacctt | ccccaaacgc | attactagat ccaccctccc | tctctctcat caaaccctca | 2820 |
| ccaaacccaa | ccacgctctc | aaaatcaaat gttccatctc | caacccccc acggcggcgc | 2880 |
| ccttcaccaa | ggaagcgccg | accacggagc ccttcgtgtc | acggttcgcc tccggcgaac | 2940 |
| ctcgcaaggg | cgcggacatc | cttgtggagg cgctggagag | gcagggcgtg acgacggtgt | 3000 |
| tcgcgtaccc | cggcggtgcg | tcgatggaga tccaccaggc | gctcacgcgc tccgccgcca | 3060 |
| tccgcaacgt | gctcccgcgc | cacgagcagg gcggcgtctt | cgccgccgaa ggctacgcgc | 3120 |
| gttcctccgg | cctccccggc | gtctgcattg ccacctccgg | ccccggcgcc accaacctcg | 3180 |
| tgagcggcct | cgccgacgct | ttaatggaca gcgtcccagt | cgtcgccatc accggccagg | 3240 |
| tcgcccgccg | gatgatcggc | accgacgcct tccagaaaac | cccgatcgtg gaggtgagca | 3300 |
| gatccatcac | gaagcacaac | tacctcatcc tcgacgtcga | cgacatcccc cgcgtcgtcg | 3360 |
| ccgaggcttt | cttcgtcgcc | acctccggcc gccccggtcc | ggtcctcatc gacattccca | 3420 |
| aagacgttca | gcagcaactc | gccgtgccta attgggacga | gcccgttaac ctccccggtt | 3480 |
| acctcgccag | gctgcccagg | ccccccgccg aggcccaatt | ggaacacatt gtcagactca | 3540 |
| tcatggaggc | ccaaaagccc | gttctctacg tcggcggtgg | cagtttgaat tccagtgctg | 3600 |
| aattgaggcg | ctttgttgaa | ctcactggta ttcccgttgc | tagcacttta atgggtcttg | 3660 |
| gaacttttcc | tattggtgat | gaatattccc ttcagatgct | gggtatgcat ggtactgttt | 3720 |
| atgctaacta | tgctgttgac | aatagtgatt tgttgcttgc | ctttgggta aggttttgatg | 3780 |
| accgtgttac | tgggaagctt | gaggcttttg ctagtagggc | taagattgtt cacattgata | 3840 |
| ttgattctgc | cgagattggg | aagaacaagc aggcgcacgt | gtcggtttgc gcggatttga | 3900 |
| agttggcctt | gaagggaatt | aatatgattt tggaggagaa | aggagtggag ggtaagtttg | 3960 |
| atcttggagg | ttggagagaa | gagattaatg tgcagaaaca | caagtttcca ttgggttaca | 4020 |
| agacattcca | ggacgcgatt | tctccgcagc atgctatcga | ggttcttgat gagttgacta | 4080 |
| atggagatgc | tattgttagt | actggggttg gcagcatca | aatgtgggct gcgcagtttt | 4140 |
| acaagtacaa | gagaccgagg | cagtggttga cctcaggggg | tcttggagcc atgggttttg | 4200 |
| gattgcctgc | ggctattggt | gctgctgttg ctaaccctgg | ggctgttgtg gttgacattg | 4260 |
| atggggatgg | tagtttcatc | atgaatgttc aggagttggc | cactataaga gtggagaatc | 4320 |
| tcccagttaa | gatattgttg | ttgaacaatc agcatttggg | tatggtggtt cagttggagg | 4380 |
| ataggttcta | caagtccaat | agagctcaca cctatcttgg | agatccgtct agcgagagcg | 4440 |
| agatattccc | aaacatgctc | aagtttgctg atgcttgtgg | gataccggca gcgcgagtga | 4500 |

```
cgaagaagga agagcttaga gcggcaattc agagaatgtt ggacacccct ggcccctacc    4560
ttcttgatgt cattgtgccc catcaggagc atgtgttgcc gatgattccc agtaatggat    4620
ccttcaagga tgtgataact gagggtgatg gtagaacgag gtactgattg cctagaccaa    4680
atgttccttg atgcttgttt tgtacaatat atataagata atgctgtcct agttgcagga    4740
tttggcctgt ggtgagcatc atagtctgta gtagttttgg tagcaagaca tttttatttttc   4800 ctttatttta acttactaca tgcagtagca tctatctatc tctgtagtct gatatctcct    4860
gttgtctgta ttgtgccgtt ggattttttg ctgtagtgag actgaaaatg atgtgctagt    4920
aataatattt ctgttagaaa tctaagtaga gaatctgttg aagaagtcaa aagctaatgg    4980
aatcaggtta catattccaat gttttttcttt ttttagcggt tggtagacgt gtagattcaa   5040
cttctcttgg agctcaccta ggcaatcagt aaaatgcata ttccttttttt aacttgccat   5100 ttatttactt ttagtggaaa ttgtgaccaa tttgttcatg tagaacggat ttggaccatt    5160
gcgtccacaa aacgtctctt ttgctcgatc ttcacaaagc gataccgaaa tccagagata    5220
gttttcaaaa gtcagaaatg gcaaagttat aaatagtaaa acagaataga tgctgtaatc    5280
gacttcaata acaagtggca tcacgtttct agttctagac ccatcagctg ggccggccac    5340
tagtgagctc ggtacccggg ggcgcgtaat atcatcatta ggaagacact gcccatcttg    5400
aataggattt tagctactaa atatgttgat ggtcttatg aaaaactatt aactaggaat    5460
attatgctac ccatatggaa agaagacgct aggggaatag aaagaccatc aaataaacga    5520
agtcaacacc aggtcttccg aagcattaac aattacctat ttaatatgta ctcagtccgg   5580
gtggatatct cactacattg acgcagtttg ttcaaagacg aacgccctga attatgccat    5640
ctgcttaggc tttcaaatat ggtacgctct aatgccaagc cttatgctgg tcttagggta    5700
ttatcatcaa atctttaagc cagaggtagt taaatacatc aaggacacca taggagtatg    5760
gcacaacgat attgtcaaga tcgcatcaga tctaataggc aataatgaat tcttcatgca    5820
gcccgacgtg ggaacgctcg aaagcagtgg ggcctctggg acagggacca gacctgagtc    5880
gctaacattt gggaataaga gaagtagata tacccaattt tttaactagc caaggaagga    5940
aagcgggaaa ggtccgatac aaaggaaagg gttgcgaggc ttaacgattt agaatatagc    6000
tgttgaggtg gcacttgttc ccccggggcg ggggtatatg cccgtagctt tattctgtca    6060
cttctttcag atcaatgaag ttgaaaagtt atagagtaag ggaccttgt ttacaaagct    6120 gtcactccaa gaactcgaag tcaagcatct tcgggaatat ccagattagt cttcaactag    6180
agaaaggata ggaatctcct ttgcagagtt ttcttctcct gctgatgtag cggtaaagtc    6240
aaaagttgga tgccctttt tctttatttta attaattccg ttgatagagc ttttgagcgg    6300
atgcaagcac tagattcttc aacgagtacc aataataaat gaattcacca gactaagaga    6360
agaaaacaga acaaaaagat taagcccagc cgccttcggg aagacctatc ttcgtcggga    6420
ggaagagccc tctttacacc attgtgatta gaaaaaaccg aaaagtggac cggcctagta    6480
accaatagag cggggcttga tccccacttt aaatctattg gatagagccc tcagcccagg    6540
gcaagcgatt gaattctatt tgattatggg ttaggtggaa cctgaaacta gcacttacaa    6600
atgagttagc aaaaggaaaa agacaattct caaatgcgta caagactttc ttccttcttt    6660
gtttaagagg ccagtctgcg atggatgctc gtgcatgaaa aagggctttg atctattcac    6720
cacttatata atagagccaa tctctgcagg acaagatatc tattttgtca ttgggaagta    6780
aggcttaagt cgacgaaaaa gttaggaaag gggatcatat ggctagggtt gccctcgggg    6840
ctcaagggtt tagcgatgaa gagtgccaag caaaaggtca ataccggtac gccgatcaaa    6900
```

-continued

```
gaagtccagt ggcaaggccc tttcagccaa gctagcgtgc tgaacagaaa gtcgtagagt      6960
gatgacagct tcttcttctt gagtcattcg tgtgacaaca tcaggatctc gtcgaaagac      7020
ctcctctgcc tatctctccc gcaagagagg actcgttatg gcgcacctct ttttagcagt      7080
ctcgtcaata agataagatt gcccctccct tcttattgat ttgataaagg gctttgtcca      7140
ctccctctct tcttagccga gcggagtgac ggtttagttt aggctttaga tgccactgcg      7200
aaagactcta gagatccact ctcacagcgt atacgcgaca tccctatgta tacacaatcc      7260
tttcaagcag ctaggacagc tagcaagcaa gttatctgtt cgcggacaag ctctctggat      7320
gacaaaaaac atgctctttc atgcggaaaa aacacggtct ttcgtggaag ttggtcgatt      7380
tgaagtcgct ttatgagtga aaatgggtcg atgacgaaaa agacggggaa aatgatcaac      7440
tgtcacattt tgatgccagt ttagggctaa aatgaacttt catccaaaaa gaccgagaaa      7500
acgctccact ggcaggatcc gatcggaaat aa                                    7532

<210> SEQ ID NO 16
<211> LENGTH: 30
<212> TYPE: DNA
<213> ORGANISM: Artificial Sequence
<220> FEATURE:
<223> OTHER INFORMATION: primer

<400> SEQUENCE: 16
tgcccgaggt cgttaggtcg aataggctag                                         30

<210> SEQ ID NO 17
<211> LENGTH: 35
<212> TYPE: DNA
<213> ORGANISM: Artificial Sequence
<220> FEATURE:
<223> OTHER INFORMATION: primer

<400> SEQUENCE: 17
tcctattcaa gatgggcagt gtcttcctaa tgatg                                   35

<210> SEQ ID NO 18
<211> LENGTH: 37
<212> TYPE: DNA
<213> ORGANISM: Artificial Sequence
<220> FEATURE:
<223> OTHER INFORMATION: Taqman probe

<400> SEQUENCE: 18
gataactgag ggtgatggta gaacgaggta ctgattg                                 37

<210> SEQ ID NO 19
<211> LENGTH: 25
<212> TYPE: DNA
<213> ORGANISM: Artificial Sequence
<220> FEATURE:
<223> OTHER INFORMATION: primer

<400> SEQUENCE: 19
tcgatcggtc aagaatccgg ttctc                                              25

<210> SEQ ID NO 20
<211> LENGTH: 35
<212> TYPE: DNA
<213> ORGANISM: Artificial Sequence
<220> FEATURE:
<223> OTHER INFORMATION: primer

<400> SEQUENCE: 20
```

```
caatagccct tggtcttct gagactgtat ctttg                               35

<210> SEQ ID NO 21
<211> LENGTH: 35
<212> TYPE: DNA
<213> ORGANISM: Artificial Sequence
<220> FEATURE:
<223> OTHER INFORMATION: primer

<400> SEQUENCE: 21
gtaatatcat cattaggaag acactgccca tcttg                              35

<210> SEQ ID NO 22
<211> LENGTH: 34
<212> TYPE: DNA
<213> ORGANISM: Artificial Sequence
<220> FEATURE:
<223> OTHER INFORMATION: primer

<400> SEQUENCE: 22
ccatatttga aagcctaagc agatggcata attc                               34

<210> SEQ ID NO 23
<211> LENGTH: 28
<212> TYPE: DNA
<213> ORGANISM: Artificial Sequence
<220> FEATURE:
<223> OTHER INFORMATION: primer

<400> SEQUENCE: 23
ttcagcaaca aactctcatc gtgagcag                                      28

<210> SEQ ID NO 24
<211> LENGTH: 30
<212> TYPE: DNA
<213> ORGANISM: Artificial Sequence
<220> FEATURE:
<223> OTHER INFORMATION: primer 1227

<400> SEQUENCE: 24
tggtcttctg agactgtatc tttgatattc                                    30

<210> SEQ ID NO 25
<211> LENGTH: 30
<212> TYPE: DNA
<213> ORGANISM: Artificial Sequence
<220> FEATURE:
<223> OTHER INFORMATION: primer 1297 (Taqman probe)

<400> SEQUENCE: 25
tgcccgaggt cgttaggtcg aataggctag                                    30

<210> SEQ ID NO 26
<211> LENGTH: 36
<212> TYPE: DNA
<213> ORGANISM: Artificial Sequence
<220> FEATURE:
<223> OTHER INFORMATION: primer 1440

<400> SEQUENCE: 26
tgtgataact gagggtgatg gtagaacgag gtactg                             36

<210> SEQ ID NO 27
<211> LENGTH: 60
<212> TYPE: DNA
<213> ORGANISM: Artificial Sequence
```

```
<220> FEATURE:
<223> OTHER INFORMATION: Junction DNA of event 3560.4.3.5 (30 nt 5'
      genomic/ 30 nt transgene insert)

<400> SEQUENCE: 27
aataggctag gtttacgaaa aagagactaa ggccgctcta gagatccgtc aacatggtgg      60

<210> SEQ ID NO 28
<211> LENGTH: 60
<212> TYPE: DNA
<213> ORGANISM: Artificial Sequence
<220> FEATURE:
<223> OTHER INFORMATION: Junction DNA of event 3560.4.3.5 (30 nt 3'
      genomic/ 30 nt transgene insert)

<400> SEQUENCE: 28
ccggccacta gtgagctcgg tacccggggg cgcgtaatat catcattagg aagacactgc      60

<210> SEQ ID NO 29
<211> LENGTH: 468
<212> TYPE: DNA
<213> ORGANISM: Artificial Sequence
<220> FEATURE:
<223> OTHER INFORMATION: SCP1 promoter probe

<400> SEQUENCE: 29
agatccgtca acatggtgga gcacgacact ctcgtctact ccaagaatat caaagataca      60
gtctcagaag accaaagggc tattgagact tttcaacaaa gggtaatatc gggaaacctc     120
ctcggattcc attgcccagc tatctgtcac ttcatcaaaa ggacagtaga aaaggaaggt     180
ggcacctaca aatgccatca ttgcgataaa ggaaaggcta tcgttcaaga tgcctctgcc     240
gacagtggtc ccaaagatgg acccccaccc acgaggagca tcgtggaaaa agaagacgtt     300
ccaaccacgt cttcaaagca agtggattga tgtgatgatc ctatgcgtat ggtatgacgt     360
gtgttcaaga tgatgacttc aaacctacct atgacgtatg gtatgacgtg tgtcgactga     420
tgacttagat ccactcgagc ggctataaat acgtacctac gcaccctg                 468

<210> SEQ ID NO 30
<211> LENGTH: 416
<212> TYPE: DNA
<213> ORGANISM: Artificial Sequence
<220> FEATURE:
<223> OTHER INFORMATION: glyat4601 probe

<400> SEQUENCE: 30
atgatagagg tgaaaccgat taacgcagag gataccctatg aactaaggca tagaatactc     60
agaccaaacc agccgataga agcgtgtatg tttgaaagcg atttacttcg tggtgcattt    120
cacttaggcg gcttttacag gggcaaactg atttccatag cttcattcca ccaggccgag    180
cactcggaac tccaaggcca gaaacagtac cagctccgag gtatggctac cttggaaggt    240
tatcgtgagc agaaagcggg atcaactcta gttaaacacg ctgaagaaat ccttcgtaag    300
aggggggcgg acatgctttg gtgtaatgcg aggacatccg cctcaggcta ctacaaaaag    360
ttaggcttca gcgagcaggg agagatattt gacacgccgc cagtaggacc tcacat        416

<210> SEQ ID NO 31
<211> LENGTH: 234
<212> TYPE: DNA
<213> ORGANISM: Artificial Sequence
<220> FEATURE:
<223> OTHER INFORMATION: pinII terminator probe

<400> SEQUENCE: 31
```

```
aggatgcaca catagtgaca tgctaatcac tataatgtgg gcatcaaagt tgtgtgttat    60
gtgtaattac tagttatctg aataaaagag aaagagatca tccatatttc ttatcctaaa   120
tgaatgtcac gtgtctttat aattctttga tgaaccagat gcatttcatt aaccaaatcc   180
atatacatat aaatattaat catatataat taatatcaat tgggttagca aaac         234

<210> SEQ ID NO 32
<211> LENGTH: 445
<212> TYPE: DNA
<213> ORGANISM: Artificial Sequence
<220> FEATURE:
<223> OTHER INFORMATION: SAMS probe (5' end)

<400> SEQUENCE: 32
tgtgggagta ggcaacctgg cattgaaacg agagaaagag agtcagaacc agaagacaaa    60
taaaaagtat gcaacaaaca aatcaaaatc aaagggcaaa ggctggggtt ggctcaattg   120
gttgctacat tcaattttca actcagtcaa cggttgagat tcactctgac ttccccaatc   180
taagccgcgg atgcaaacgg ttgaatctaa cccacaatcc aatctcgtta cttaggggct   240
tttccgtcat taactcaccc ctgccacccg gtttccctat aaattggaac tcaatgctcc   300 cctctaaaact cgtatcgctt cagagttgag accaagacac actcgttcat atatctctct   360
gctcttctct tctcttctac ctctcaaggt acttttcttc ccctctacc aaatcctaga    420 ttccgtggtt caatttcgga tcttg                                          445

<210> SEQ ID NO 33
<211> LENGTH: 492
<212> TYPE: DNA
<213> ORGANISM: Artificial Sequence
<220> FEATURE:
<223> OTHER INFORMATION: SAMS probe (3' end)

<400> SEQUENCE: 33
cacttctggt ttgcttttgcc ttgcttttttc ctcaactggg tccatctagg atccatgtga    60
aactctactc tttctttaat atctgcggaa tacgcgtttg actttcagat ctagtcgaaa   120
tcatttcata attgcctttc tttcttttag cttatgagaa ataaaatcac tttttttta    180 tttcaaaata aaccttgggc cttgtgctga ctgagatggg gtttggtgat tacagaattt   240
tagcgaattt tgtaattgta cttgtttgtc tgtagttttg ttttgttttc ttgtttctca   300
tacattcctt aggcttcaat tttattcgag tataggtcac aataggaatt caaactttga   360
gcaggggaat taatcccttc cttcaaatcc agtttgtttg tatatatgtt taaaaaatga   420 aactttgct ttaaattcta ttataacttt ttttatggct gaaattttttg catgtgtctt    480 tgctctctgt tg                                                        492

<210> SEQ ID NO 34
<211> LENGTH: 930
<212> TYPE: DNA
<213> ORGANISM: Artificial Sequence
<220> FEATURE:
<223> OTHER INFORMATION: gm-hra probe (5' end)

<400> SEQUENCE: 34
ccacacaaca caatggcggc caccgcttcc agaaccaccc gattctcttc ttcctcttca    60
caccccacct tccccaaacg cattactaga tccacccctcc ctctctctca tcaaaccctc   120
accaaaccca accacgctct caaaatcaaa tgttccatct ccaaaccccc cacgcggcg    180 cccttcacca aggaagcgcc gaccacggag cccttcgtgt cacggttcgc ctccggcgaa   240
```

```
cctcgcaagg gcgcggacat ccttgtggag gcgctggaga ggcagggcgt gacgacggtg      300
ttcgcgtacc ccggcggtgc gtcgatggag atccaccagg cgctcacgcg ctccgccgcc      360
atccgcaacg tgctcccgcg ccacgagcag ggcggcgtct tcgccgccga aggctacgcg      420
cgttcctccg gcctccccgg cgtctgcatt gccacctccg gccccggcgc caccaacctc      480
gtgagcggcc tcgccgacgc tttaatggac agcgtcccag tcgtcgccat caccggccag      540
gtcgcccgcc ggatgatcgg caccgacgcc ttccaagaaa ccccgatcgt ggaggtgagc      600
agatccatca cgaagcacaa ctacctcatc ctcgacgtcg acgacatccc ccgcgtcgtc      660
gccgaggctt tcttcgtcgc cacctccggc cgccccggtc cggtcctcat cgacattccc      720
aaagacgttc agcagcaact cgccgtgcct aattgggacg agcccgttaa cctccccggt      780
tacctcgcca ggctgcccag gccccccgcc gaggcccaat ggaacacat tgtcagactc      840 atcatggagg cccaaaagcc cgttctctac gtcggcggtg gcagtttgaa ttccagtgct      900
gaattgaggc gctttgttga actcactggt                                       930
```

<210> SEQ ID NO 35
<211> LENGTH: 1030
<212> TYPE: DNA
<213> ORGANISM: Artificial Sequence
<220> FEATURE:
<223> OTHER INFORMATION: gm-hra probe (3' end)

<400> SEQUENCE: 35

```
cgttgctagc actttaatgg gtcttggaac ttttcctatt ggtgatgaat attcccttca       60
gatgctgggt atgcatggta ctgtttatgc taactatgct gttgacaata gtgatttgtt      120
gcttgccttt ggggtaaggt ttgatgaccg tgttactggg aagcttgagg cttttgctag      180
tagggctaag attgttcaca ttgatattga ttctgccgag attgggaaga caagcaggc      240 gcacgtgtcg gtttgcgcgg atttgaagtt ggccttgaag ggaattaata tgattttgga      300
ggagaaagga gtggagggta agtttgatct tggaggttgg agagaagaga ttaatgtgca      360
gaaacacaag tttccattgg gttacaagac attccaggac gcgatttctc cgcagcatgc      420
tatcgaggtt cttgatgagt tgactaatgg agatgctatt gttagtactg gggttgggca      480
gcatcaaatg tgggctgcgc agttttacaa gtacaagaga ccgaggcagt ggttgacctc      540
agggggtctt ggagccatgg gttttggatt gcctgcggct attggtgctg ctgttgctaa      600 ccctgggct gttgtggttg acattgatgg ggatggtagt ttcatcatga atgttcagga      660
gttggccact ataagagtgg agaatctccc agttaagata ttgttgttga acaatcagca      720
tttgggtatg gtggttcagt tggaggatag gttctacaag tccaatagag ctcacaccta      780
tcttggagat ccgtctagcg agagcgagat attcccaaac atgctcaagt tgctgatgc      840 ttgtgggata ccggcagcgc gagtgacgaa gaaggaagag cttagagcgg caattcagag      900
aatgttggac ccctggcc cctaccttct tgatgtcatt gtgccccatc aggagcatgt      960
gttgccgatg attcccagta atggatcctt caaggatgtg ataactgagg gtgatggtag     1020
aacgaggtac                                                            1030
```

<210> SEQ ID NO 36
<211> LENGTH: 649
<212> TYPE: DNA
<213> ORGANISM: Artificial Sequence
<220> FEATURE:
<223> OTHER INFORMATION: gm-als terminator probe

<400> SEQUENCE: 36

```
gcctagacca aatgttcctt gatgcttgtt ttgtacaata tatataagat aatgctgtcc      60
tagttgcagg atttggcctg tggtgagcat catagtctgt agtagttttg gtagcaagac     120
attttatttt ccttttattt aacttactac atgcagtagc atctatctat ctctgtagtc     180
tgatatctcc tgttgtctgt attgtgccgt tggattttt gctgtagtga gactgaaaat      240
gatgtgctag taataatatt tctgttagaa atctaagtag agaatctgtt gaagaagtca     300
aaagctaatg gaatcaggtt acatattcaa tgttttctt tttttagcgg ttggtagacg      360
tgtagattca acttctcttg gagctcacct aggcaatcag taaaatgcat attccttttt     420
taacttgcca tttatttact tttagtggaa attgtgacca atttgttcat gtagaacgga    480
tttggaccat tgcgtccaca aaacgtctct tttgctcgat cttcacaaag cgataccgaa    540
atccagagat agttttcaaa agtcagaaat ggcaaagtta taaatagtaa aacagaatag    600
atgctgtaat cgacttcaat aacaagtggc atcacgtttc tagttctag                 649

<210> SEQ ID NO 37
<211> LENGTH: 26
<212> TYPE: DNA
<213> ORGANISM: Artificial Sequence
<220> FEATURE:
<223> OTHER INFORMATION: primer DP-356-f1

<400> SEQUENCE: 37
gtcgaatagg ctaggtttac gaaaaa                                           26

<210> SEQ ID NO 38
<211> LENGTH: 29
<212> TYPE: DNA
<213> ORGANISM: Artificial Sequence
<220> FEATURE:
<223> OTHER INFORMATION: primer DP-356-r1

<400> SEQUENCE: 38
tttgatattc ttggagtaga cgagagtgt                                        29

<210> SEQ ID NO 39
<211> LENGTH: 30
<212> TYPE: DNA
<213> ORGANISM: Artificial Sequence
<220> FEATURE:
<223> OTHER INFORMATION: Primer DP-356-p (taqman probe)

<400> SEQUENCE: 39
ctctagagat ccgtcaacat ggtggagcac                                       30

<210> SEQ ID NO 40
<211> LENGTH: 35
<212> TYPE: DNA
<213> ORGANISM: Artificial Sequence
<220> FEATURE:
<223> OTHER INFORMATION: Primer 06-0-1610

<400> SEQUENCE: 40
agcaattgtt ttgtgcattt ccaaatttca atctg                                 35

<210> SEQ ID NO 41
<211> LENGTH: 8679
<212> TYPE: DNA
<213> ORGANISM: Artificial Sequence
<220> FEATURE:
<223> OTHER INFORMATION: left border sequence and complete transgene
      insert for event 3560.4.3.5
```

<400> SEQUENCE: 41

```
agcaattgtt ttgtgcattt ccaaatttca atctgattta ttaaataaaa aaattttaat      60
tcgggttgat tgtaaatcag ctaaagacat tttacagaaa gacgtcaaaa atcttggctc     120
caaacaaatt tttgcaagat ggcaagcaat attaagtgtt tttgattttg acagaatata     180
tcaagggcac tttaaactct ctacctaact atcttacacg tgaattctta tagacaaatt     240
ctcatgccac ctaaggcatc aggcacccct ctcaggggta gacgaagcac gagtaaagga     300
ttcaagttgg ccctaccaga gccaactatc aaaaagagtt cttccgcatc ctctgggtca     360
tctacccaaa aacctaaaat aaagggtca tcaacccaaa tagtcaccat caaacctgag     420
tcatccactc aggaatcccc aaaaccttca acctcaaaac aaacaaaggc cgactatacc     480
ttctcagtac aacactccag gccctacaag aaattggtct aaccaaactc ccaaaactcg     540
ccaaaaagac ttgggcagac attgcctcag aatctaatga tgaatttgaa actgatttac     600
aaatcatgat tcaaaactcc aaacaatcca aacgattgt caatccaaaa ggaaaacaga      660
ccttatccca acaaaagaca ccattaccaa aacctactaa cagttatatt tacaaaaata     720
aatttccaac tgttttgtag atggagccaa aattttggga caaaaatccc ttcaaggcta     780
cagccaaggc atttccaccg ggcttccatt tcaaacctat ttccaccaat aaaacaagaa     840
tcttttacga attcatactg atagacacaa actcagtgtc tattaaacac ttcaaagacc     900
caaatgacat aaatttaaac actcattcaa ccatccagat tttaaagttc atacaacctc     960
gacaatgtgg aacaaatata atcaagcca aacaattctt tgtaccctt gatcctatag    1020
gttacactat tgggattatg tagatgcatg gaccaatgta ttctggcatc aaaataacaa    1080
attcaaacat tcttggctta tttatttcaa aactaacacc gtctataatt ttccaaattg    1140
gttcctccaa cggtgggact tttttggacc aaactttgat atctacccgg agcaagtcca    1200
acaagggttt gatcagttca aaaaaatgtt caattctcag gaatcacgaa tccctgtaga    1260
cctaaaatac tttttccaatt ttgcattgtc gtggatattt tcatggcaat acagatatgg    1320
gaaaactgaa aacaacaagc agtttccatc actgcaacat catgcattta tcaagtggtg    1380
gaattagttt gatacatcaa aagcagcacc agatcaagtg agaatctggt ttcaagccca    1440
tccagaattt ttgaaagttg ctaatcctga gacttcttta ttcctcaatc agaagtctca    1500
attagctgct ttccttttcta gttccaagtc aaaagaaatt ctggcacaaa atctaaaaga    1560
agtcctacag cttctccaac aagaagaaga taaaggctct tcctcaaaga aggaagataa    1620
caattcttca aaagaagatg acgaccctt ctaccaaaat gaaaatgatt gttttggtat    1680
ttctctaaat gatgattaat taaaaaatta catgtactat gtaaatagtt tcggtcacga    1740
aactggcact gtagctacag taaattttat ggctatttaa ggagttctcg gcccatttgt    1800
gaggtacctt ttcaggtagt cagatctcta tttttagaga gagaaactct aggaaacaat    1860
ctttgtaagt ttttctttcg atttcaataa attcaaagtt ttctcttcat atctcttctc    1920
cctcttgacc ggtcctgtgc ggttctgcca tcgcttcagt ttcttctctt ctctccctt     1980
atcgatattg tgtggctcta ttgccacttc gatttctttt atgttgcttt cattttaatt    2040
tgttttacca ttttctttg atattataat ttctatttaa ctcttggtca tactgcatat    2100
attcataata tattccttaca tcctatctat ccgtttgatc tcttttcact gttatatata    2160
tatatatata tatatatatc gtttaacttc atgttagtaa taagattaga gtaaaaaata    2220
tatatataac gaagttattt taacaaaagg tatttttgta aaaaaaaatt atatgctaaa    2280
aaagttttac tatatctaag catgattttt tttaattccc aaaacacgtg taaatatttt    2340
```

```
taggaatatt ttgtaaaaaa tcaaacattt ttttaattat tcgtataaaa catcaatctt   2400
taagaatcat aattttaga aatcatgatt tctggatata aaaatacttt ttcttgcagc    2460
caaacgtctt ctaaagccac atgttaatgg gtgtacaaat tataaagttt ttataaacat   2520 atcactttt aaagttaaaa atatcactaa tacgtttcta aatgcatttt ttttagaaat    2580
tataagtttc tagcactcca ttggagttgt atagaactac tactaatcta ctattaataa   2640
caatttatct cctccaaata tttaagtaaa ctgcatattt agagaatgtt ggacagtaaa   2700
gctagccact caatatttag gtgctccccg aaagaggaaa gcaaacaagc caccagcact   2760
tcaatcagta aagctagcca ctcaactcgc tctcttcaaa ttccttttta cattttattt   2820
cagatcctcc acctagccaa gtaggtctca aaaggtttac cccgcatatg cttagtcgcc   2880
gcaagctcca tataggttac tttgcgggct actgaataga atcttcggtg aaaggcgtct   2940
accatatcgg cgcaactatt gatcgagtgc gtgtatacca cgtgaatgcg acacccgaaa   3000
gactagcaga aaagtgcttc agcaacaaac tctcatcgtg agcagtgtct ctgctggcaa   3060
tttcgaaatt actaatatgc tgctctcgag atctccactt ccatcataca accgaaacca   3120
gctaaggaag gagcgatcca taagaatcgc ctcgaatagc cataacctca tctcgccttc   3180
caccgcacca gcaagaggaa accgaattag agctgaaaga atactagagc catcgtagga   3240
gaaccggatt cttgaccgat cgacttttgc ccgaggtcgt taggtcgaat aggctaggtt   3300
tacgaaaaag agactaaggc cgctctagag atccgtcaac atggtggagc acgacactct   3360
cgtctactcc aagaatatca aagatacagt ctcagaagac caaagggcta ttgagacttt   3420
tcaacaaagg gtaatatcgg gaaacctcct cggattccat tgcccagcta tctgtcactt   3480
catcaaaagg acagtagaaa aggaaggtgg cacctacaaa tgccatcatt gcgataaagg   3540
aaaggctatc gttcaagatg cctctgccga cagtggtccc aaagatggac ccccacccac   3600
gaggagcatc gtggaaaaag aagacgttcc aaccacgtct tcaaagcaag tggattgatg   3660
tgatgatcct atgcgtatgg tatgacgtgt gttcaagatg atgacttcaa acctacctat   3720
gacgtatggt atgacgtgtg tcgactgatg acttagatcc actcgagcgg ctataaatac   3780
gtacctacgc accctgcgct accatcccta gagctgcagc ttatttttac aacaattacc   3840
aacaacaaca acaacaaac aacattacaa ttactattta caattacagt cgacccggga   3900
tccacacgac accatgatag aggtgaaacc gattaacgca gaggatacct atgaactaag   3960
gcatagaata ctcagaccaa accagccgat agaagcgtgt atgtttgaaa gcgatttact   4020
tcgtggtgca tttcacttag gcggcttta caggggcaaa ctgatttcca tagcttcatt    4080
ccaccaggcc gagcactcgg aactccaagg ccagaaacag taccagctcc gaggtatggc   4140
taccttggaa ggttatcgtg agcagaaagc gggatcaact ctagttaaac acgctgaaga   4200
aatccttcgt aagagggggg cggacatgct ttggtgtaat gcgaggacat ccgcctcagg   4260
ctactacaaa aagttaggct tcagcgagca gggagagata tttgacacgc cgccagtagg   4320
acctcacatc ctgatgtata aaaggatcac ataactagct agtcagttaa cctagacttg   4380
tccatcttct ggattggcca acttaattaa tgtatgaaat aaaaggatgc acacatagtg   4440
acatgctaat cactataatg tgggcatcaa agttgtgtgt tatgtgtaat tactagttat   4500
ctgaataaaa gagaaagaga tcatccatat ttcttatcct aaatgaatgt cacgtgtctt   4560
tataattctt tgatgaacca gatgcatttc attaaccaaa tccatataca tataaatatt   4620
aatcatatat aattaatatc aattgggtta gcaaaacaaa tctagtctag gtgtgttttg   4680
cgaattcgat atcaagcttt gctctagatc aaactcacat ccaaacataa catggatatc   4740
```

| | | | | | |
|---|---|---|---|---|---|
| ttccttacca | atcatactaa | ttattttggg | ttaaatatta | atcattattt | ttaagatatt | 4800 |
| aattaagaaa | ttaaaagatt | ttttaaaaaa | atgtataaaa | ttatattatt | catgattttt | 4860 |
| catacatttg | attttgataa | taaatatatt | tttttaatt | tcttaaaaaa | tgttgcaaga | 4920 |
| cacttattag | acatagtctt | gttctgttta | caaaagcatt | catcatttaa | tacattaaaa | 4980 |
| aatatttaat | actaacagta | gaatcttctt | gtgagtggtg | tgggagtagg | caacctggca | 5040 |
| ttgaaacgag | agaaagagag | tcagaaccag | aagacaaata | aaaagtatgc | aacaaacaaa | 5100 |
| tcaaaatcaa | agggcaaagg | ctggggttgg | ctcaattggt | tgctacattc | aattttcaac | 5160 |
| tcagtcaacg | gttgagattc | actctgactt | ccccaatcta | agccgcggat | gcaaacggtt | 5220 |
| gaatctaacc | cacaatccaa | tctcgttact | tagggggcttt | tccgtcatta | actcacccct | 5280 |
| gccacccggt | ttccctataa | attggaactc | aatgctcccc | tctaaactcg | tatcgcttca | 5340 |
| gagttgagac | caagacacac | tcgttcatat | atctctctgc | tcttctcttc | tcttctacct | 5400 |
| ctcaaggtac | ttttcttctc | cctctaccaa | atcctagatt | ccgtggttca | atttcggatc | 5460 |
| ttgcacttct | ggtttgcttt | gccttgcttt | ttcctcaact | gggtccatct | aggatccatg | 5520 |
| tgaaactcta | ctcttctttt | aatatctgcg | gaatacgcgt | ttgactttca | gatcagtcg | 5580 |
| aaatcatttc | ataattgcct | ttctttcttt | tagcttatga | gaaataaaat | cacttttttt | 5640 |
| ttatttcaaa | ataaaccttg | ggccttgtgc | tgactgagat | ggggtttggt | gattacagaa | 5700 |
| ttttagcgaa | ttttgtaatt | gtacttgttt | gtctgtagtt | ttgttttgtt | ttcttgtttc | 5760 |
| tcatacattc | cttaggcttc | aattttattc | gagtataggt | cacaatagga | attcaaactt | 5820 |
| tgagcagggg | aattaatccc | ttccttcaaa | tccagtttgt | ttgtatatat | gtttaaaaaa | 5880 |
| tgaaactttt | gctttaaatt | ctattataac | tttttttatg | gctgaaattt | ttgcatgtgt | 5940 |
| ctttgctctc | tgttgtaaat | ttactgttta | ggtactaact | ctaggcttgt | tgtgcagttt | 6000 |
| ttgaagtata | accatgccac | acaacacaat | ggcggccacc | gcttccagaa | ccacccgatt | 6060 |
| ctcttcttcc | tcttcacacc | ccaccttccc | caaacgcatt | actagatcca | ccctccctct | 6120 |
| ctctcatcaa | accctcacca | aacccaacca | cgctctcaaa | atcaaatgtt | ccatctccaa | 6180 |
| acccccacg | gcggcgccct | tcaccaagga | agcgccgacc | acggagccct | tcgtgtcacg | 6240 |
| gttcgcctcc | ggcgaacctc | gcaagggcgc | ggacatcctt | gtggaggcgc | tggagaggca | 6300 |
| gggcgtgacg | acggtgttcg | cgtaccccgg | cggtgcgtcg | atggagatcc | accaggcgct | 6360 |
| cacgcgctcc | gccgccatcc | gcaacgtgct | cccgcgccac | gagcagggcg | gcgtcttcgc | 6420 |
| cgccgaaggc | tacgcgcgtt | cctccggcct | ccccggcgtc | tgcattgcca | cctccggccc | 6480 |
| cggcgccacc | aacctcgtga | gcggcctcgc | cgacgcttta | atggacagcg | tcccagtcgt | 6540 |
| cgccatcacc | ggccaggtcg | cccgccggat | gatcggcacc | gacgccttcc | aagaaacccc | 6600 |
| gatcgtggag | gtgagcagat | ccatcacgaa | gcacaactac | ctcatcctcg | acgtcgacga | 6660 |
| catccccgc | gtcgtcgccg | aggctttctt | cgtcgccacc | tccggccgcc | ccggtccggt | 6720 |
| cctcatcgac | attcccaaag | acgttcagca | gcaactcgcc | gtgcctaatt | gggacgagcc | 6780 |
| cgttaacctc | cccggttacc | tcgccaggct | gcccaggccc | ccgccgagg | cccaattgga | 6840 |
| acacattgtc | agactcatca | tggaggccca | aaagcccgtt | ctctacgtcg | gcggtggcag | 6900 |
| tttgaattcc | agtgctgaat | tgaggcgctt | tgttgaactc | actggtattc | ccgttgctag | 6960 |
| cactttaatg | ggtcttggaa | cttttcctat | tggtgatgaa | tattcccttc | agatgctggg | 7020 |
| tatgcatggt | actgtttatg | ctaactatgc | tgttgacaat | agtgatttgt | tgcttgcctt | 7080 |
| tgggggtaagg | tttgatgacc | gtgttactgg | gaagcttgag | gcttttgcta | gtagggctaa | 7140 |

```
gattgttcac attgatattg attctgccga gattgggaag aacaagcagg cgcacgtgtc     7200
ggtttgcgcg gatttgaagt tggccttgaa gggaattaat atgattttgg aggagaaagg     7260
agtggagggt aagtttgatc ttggaggttg gagagaagag attaatgtgc agaaacacaa     7320
gtttccattg ggttacaaga cattccagga cgcgatttct ccgcagcatg ctatcgaggt     7380
tcttgatgag ttgactaatg gagatgctat tgttagtact ggggttgggc agcatcaaat     7440
gtgggctgcg cagttttaca agtacaagag accgaggcag tggttgacct caggggtct      7500 tggagccatg ggttttggat tgcctgcggc tattggtgct gctgttgcta accctggggc     7560
tgttgtggtt gacattgatg gggatggtag tttcatcatg aatgttcagg agttggccac     7620
tataagagtg gagaatctcc cagttaagat attgttgttg aacaatcagc atttgggtat     7680
ggtggttcag ttggaggata ggttctacaa gtccaataga gctcacacct atcttggaga     7740
tccgtctagc gagagcgaga tattcccaaa catgctcaag tttgctgatg cttgtgggat     7800
accggcagcg cgagtgacga agaaggaaga gcttagagcg gcaattcaga gaatgttgga     7860 caccctggc ccctaccttc ttgatgtcat tgtgccccat caggagcatg tgttgccgat      7920
gattcccagt aatggatcct tcaaggatgt gataactgag ggtgatggta gaacgaggta     7980
ctgattgcct agaccaaatg ttccttgatg cttgttttgt acaatatata aagataatg      8040 ctgtcctagt tgcaggattt ggcctgtggt gagcatcata gtctgtagta gttttggtag     8100
caagacattt tattttcctt ttatttaact tactacatgc agtagcatct atctatctct     8160
gtagtctgat atctcctgtt gtctgtattg tgccgttgga ttttttgctg tagtgagact     8220
gaaaatgatg tgctagtaat aatatttctg ttagaaatct aagtagagaa tctgttgaag     8280
aagtcaaaag ctaatggaat caggttacat attcaatgtt tttcttttt tagcggttgg      8340 tagacgtgta gattcaactt ctcttggagc tcacctaggc aatcagtaaa atgcatattc     8400
cttttttaac ttgccatta tttactttta gtggaaattg tgaccaattt gttcatgtag      8460
aacggatttg gaccattgcg tccacaaaac gtctcttttg ctcgatcttc acaaagcgat     8520
accgaaatcc agagatagtt ttcaaaagtc agaaatggca aagttataaa tagtaaaaca     8580
gaatagatgc tgtaatcgac ttcaataaca agtggcatca cgtttctagt tctagaccca     8640
tcagctgggc cggccactag tgagctcggt acccgggg                             8679
```

<210> SEQ ID NO 42
<211> LENGTH: 7532
<212> TYPE: DNA
<213> ORGANISM: Artificial Sequence
<220> FEATURE:
<223> OTHER INFORMATION: right border sequence and complete transgene
      insert for event 3560.4.3.5

<400> SEQUENCE: 42

```
ggccgctcta gagatccgtc aacatggtgg agcacgacac tctcgtctac tccaagaata      60
tcaaagatac agtctcagaa gaccaaaggg ctattgagac ttttcaacaa agggtaatat     120
cgggaaacct cctcggattc cattgcccag ctatctgtca cttcatcaaa aggacagtag     180
aaaaggaagg tggcacctac aaatgccatc attgcgataa aggaaaggct atcgttcaag     240
atgcctctgc cgacagtggt cccaaagatg gaccccacc cacgaggagc atcgtggaaa      300
aagaagacgt tccaaccacg tcttcaaagc aagtggattg atgtgatgat cctatgcgta     360
tggtatgacg tgtgttcaag atgatgactt caaacctacc tatgacgtat ggtatgacgt     420
gtgtcgacta atgacttaga tccactcgag cggctataaa tacgtaccta cgcaccctgc     480
gctaccatcc ctagagctgc agcttatttt tacaacaatt accaacaaca acaaacaaca     540
```

```
aacaacatta caattactat ttacaattac agtcgacccg ggatccacac gacaccatga      600
tagaggtgaa accgattaac gcagaggata cctatgaact aaggcataga atactcagac      660
caaaccagcc gatagaagcg tgtatgtttg aaagcgattt acttcgtggt gcatttcact      720
taggcggctt ttacaggggc aaactgattt ccatagcttc attccaccag gccgagcact      780
cggaactcca aggccagaaa cagtaccagc tccgaggtat ggctaccttg aaggttatc       840 gtgagcagaa agcgggatca actctagtta aacacgctga agaaatcctt cgtaagaggg      900
gggcggacat gctttggtgt aatgcgagga catccgcctc aggctactac aaaaagttag      960
gcttcagcga gcagggagag atatttgaca cgccgccagt aggacctcac atcctgatgt     1020
ataaaaggat cacataacta gctagtcagt taacctagac ttgtccatct tctggattgg     1080
ccaacttaat taatgtatga aataaaagga tgcacacata gtgacatgct aatcactata     1140
atgtgggcat caaagttgtg tgttatgtgt aattactagt tatctgaata aaagagaaag     1200
agatcatcca tatttcttat cctaaatgaa tgtcacgtgt ctttataatt ctttgatgaa     1260
ccagatgcat ttcattaacc aaatccatat acatataaat attaatcata tataattaat     1320
atcaattggg ttagcaaaac aaatctagtc taggtgtgtt ttgcgaattc gatatcaagc     1380
tttgctctag atcaaactca catccaaaca taacatggat atcttcctta ccaatcatac     1440
taattatttt gggttaaata ttaatcatta ttttttaagat attaattaag aaattaaaag    1500
attttttaaa aaatgtata aaattatatt attcatgatt tttcatacat ttgattttga     1560
taataaatat attttttta atttcttaaa aaatgttgca agacacttat tagacatagt      1620
cttgttctgt ttacaaaagc attcatcatt taatacatta aaaaatattt aatactaaca     1680
gtagaatctt cttgtgagtg gtgtgggagt aggcaacctg gcattgaaac gagagaaaga     1740
gagtcagaac cagaagacaa ataaaaagta tgcaacaaac aaatcaaaat caaagggcaa     1800
aggctggggt tggctcaatt ggttgctaca ttcaattttc aactcagtca acggttgaga     1860
ttcactctga cttccccaat ctaagccgcg gatgcaaacg gttgaatcta acccacaatc     1920
caatctcgtt acttaggggc ttttccgtca ttaactcacc cctgccaccc ggtttcccta     1980
taaattggaa ctcaatgctc ccctctaaac tcgtatcgct tcagagttga gaccaagaca     2040
cactcgttca tatatctctc tgctcttctc ttctcttcta cctctcaagg tacttttctt     2100
ctccctctac caaatcctag attccgtggt tcaatttcgg atcttgcact tctggtttgc     2160
tttgccttgc ttttttcctca actgggtcca tctaggatcc atgtgaaact ctactctttc   2220
tttaatatct gcggaatacg cgtttgactt tcagatctag tcgaaatcat ttcataattg    2280
cctttctttc ttttagctta tgagaaataa aatcacttttt tttttatttc aaaataaacc   2340
ttgggccttg tgctgactga gatggggttt ggtgattaca gaattttagc gaattttgta    2400
attgtacttg tttgtctgta gttttgttt gttttcttgt ttctcataca ttccttaggc    2460 ttcaattta ttcgagtata ggtcacaata ggaattcaaa ctttgagcag gggaattaat    2520 cccttcctc aaatccagtt tgtttgtata tatgttaaa aaatgaaact tttgctttaa    2580
attctattat aactttttt atggctgaaa tttttgcatg tgtctttgct ctctgttgta   2640
aatttactgt ttaggtacta actctaggct tgttgtgcag ttttgaagt ataaccatgc    2700 cacacaacac aatggcggcc accgcttcca gaaccacccg attctcttct tcctcttcac   2760
accccacctt ccccaaacgc attactagat ccaccctccc tctctctcat caaaccctca   2820
ccaaacccaa ccacgctctc aaaatcaaat gttccatctc caaaccccc acggcggcgc    2880 ccttcaccaa ggaagcgccg accacggagc ccttcgtgtc acggttcgcc tccggcgaac   2940
```

```
ctcgcaaggg cgcggacatc cttgtggagg cgctggagag gcagggcgtg acgacggtgt    3000
tcgcgtaccc cggcggtgcg tcgatggaga tccaccaggc gctcacgcgc tccgccgcca    3060
tccgcaacgt gctcccgcgc cacgagcagg gcggcgtctt cgccgccgaa ggctacgcgc    3120
gttcctccgg cctccccggc gtctgcattg ccacctccgg ccccggcgcc accaacctcg    3180
tgagcggcct cgccgacgct taatggaca  gcgtcccagt cgtcgccatc accggccagg    3240
tcgcccgccg gatgatcggc accgacgcct tccaagaaac cccgatcgtg gaggtgagca    3300
gatccatcac gaagcacaac tacctcatcc tcgacgtcga cgacatcccc cgcgtcgtcg    3360
ccgaggcttt cttcgtcgcc acctccggcc gccccggtcc ggtcctcatc gacattccca    3420
aagacgttca gcagcaactc gccgtgccta attgggacga gcccgttaac ctccccggtt    3480
acctcgccag gctgcccagg ccccccgccg aggcccaatt ggaacacatt gtcagactca    3540
tcatggaggc ccaaaagccc gttctctacg tcggcggtgg cagtttgaat tccagtgctg    3600
aattgaggcg ctttgttgaa ctcactggta ttcccgttgc tagcacttta atgggtcttg    3660
gaacttttcc tattggtgat gaatattccc ttcagatgct gggtatgcat ggtactgttt    3720
atgctaacta tgctgttgac aatagtgatt tgttgcttgc cttgggggta aggtttgatg    3780
accgtgttac tgggaagctt gaggcttttg ctagtagggc taagattgtt cacattgata    3840
ttgattctgc cgagattggg aagaacaagc aggcgcacgt gtcggtttgc gcggatttga    3900
agttggcctt gaagggaatt aatatgattt tggaggagaa aggagtggag ggtaagtttg    3960
atcttggagg ttggagagaa gagattaatg tgcagaaaca caagtttcca ttgggttaca    4020
agacattcca ggacgcgatt tctccgcagc atgctatcga ggttcttgat gagttgacta    4080
atggagatgc tattgttagt actggggttg ggcagcatca aatgtgggct gcgcagtttt    4140
acaagtacaa gagaccgagg cagtggttga cctcaggggg tcttggagcc atgggttttg    4200
gattgcctgc ggctattggt gctgctgttg ctaaccctgg ggctgttgtg gttgacattg    4260
atggggatgg tagtttcatc atgaatgttc aggagttggc cactataaga gtggagaatc    4320
tcccagttaa gatattgttg ttgaacaatc agcatttggg tatggtggtt cagttggagg    4380
ataggttcta caagtccaat agagctcaca cctatcttgg agatccgtct agcgagagcg    4440
agatattccc aaacatgctc aagtttgctg atgcttgtgg gataccggca gcgcgagtga    4500
cgaagaagga agagcttaga gcggcaattc agagaatgtt ggacacccct ggcccctacc    4560
ttcttgatgt cattgtgccc catcaggagc atgtgttgcc gatgattccc agtaatggat    4620
ccttcaagga tgtgataact gagggtgatg gtagaacgag gtactgattg cctagaccaa    4680
atgttccttg atgcttgttt tgtacaatat atataagata atgctgtcct agttgcagga    4740
tttggcctgt ggtgagcatc atagtctgta gtagttttgg tagcaagaca tttta ttttc    4800 cttttattta acttactaca tgcagtagca tctatctatc tctgtagtct gatatctcct    4860
gttgtctgta ttgtgccgtt ggattttttg ctgtagtgag actgaaaatg atgtgctagt    4920
aataatattt ctgttagaaa tctaagtaga gaatctgttg aagaagtcaa aagctaatgg    4980
aatcaggtta catattcaat gttttctttt ttttagcggt tggtagacgt gtagattcaa    5040
cttctcttgg agctcaccta ggcaatcagt aaaatgcata ttcctttttt aacttgccat    5100
ttatttactt ttagtggaaa ttgtgaccaa tttgttcatg tagaacggat ttggaccatt    5160
gcgtccacaa aacgtctctt ttgctcgatc ttcacaaagc gataccgaaa tccagagata    5220
gttttcaaaa gtcagaaatg gcaaagttat aaatagtaaa acagaataga tgctgtaatc    5280
gacttcaata acaagtggca tcacgttttct agttctagac ccatcagctg ggccggccac    5340
```

```
tagtgagctc ggtacccggg ggcgcgtaat atcatcatta ggaagacact gcccatcttg   5400
aataggattt tagctactaa atatgttgat ggtctttatg aaaaactatt aactaggaat   5460
attatgctac ccatatggaa agaagacgct aggggaatag aaagaccatc aaataaacga   5520
agtcaacacc aggtcttccg aagcattaac aattacctat ttaatatgta ctcagtccgg   5580
gtggatatct cactacattg acgcagtttg ttcaaagacg aacgccctga attatgccat   5640
ctgcttaggc tttcaaatat ggtacgctct aatgccaagc cttatgctgg tcttagggta   5700
ttatcatcaa atctttaagc cagaggtagt taaatacatc aaggacacca taggagtatg   5760
gcacaacgat attgtcaaga tcgcatcaga tctaataggc aataatgaat tcttcatgca   5820
gcccgacgtg gaacgctcg aaagcagtgg ggcctctggg acagggacca gacctgagtc   5880
gctaacattt gggaataaga aagtagata tacccaattt tttaactagc caaggaagga   5940
aagcgggaaa ggtccgatac aaaggaaagg gttgcgaggc ttaacgattt agaatatagc   6000
tgttgaggtg gcacttgttc ccccggggcg ggggtatatg cccgtagctt tattctgtca   6060
cttctttcag atcaatgaag ttgaaaagtt atagagtaag ggaccttgt ttacaaagct   6120 gtcactccaa gaactcgaag tcaagcatct tcgggaatat ccagattagt cttcaactag   6180
agaaaggata ggaatctcct ttgcagagtt ttcttctcct gctgatgtag cggtaaagtc   6240
aaaagttgga tgcccttttt tctttatttta attaattccg ttgatagagc ttttgagcgg   6300
atgcaagcac tagattcttc aacgagtacc aataataaat gaattcacca gactaagaga   6360
agaaaacaga acaaaaagat taagcccagc cgccttcggg aagacctatc ttcgtcggga   6420
ggaagagccc tctttacacc attgtgatta gaaaaaaccg aaaagtggac cggcctagta   6480
accaatagag cggggcttga tccccacttt aaatctattg gatagagccc tcagcccagg   6540
gcaagcgatt gaattctatt tgattatggg ttaggtggaa cctgaaacta gcacttacaa   6600
atgagttagc aaaaggaaaa agacaattct caaatgcgta caagactttc ttccttcttt   6660
gtttaagagg ccagtctgcg atggatgctc gtgcatgaaa aagggctttg atctattcac   6720
cacttatata atagagccaa tctctgcagg acaagatatc tattttgtca ttgggaagta   6780
aggcttaagt cgacgaaaaa gttaggaaag gggatcatat ggctagggtt gccctcgggg   6840
ctcaagggtt tagcgatgaa gagtgccaag caaaaggtca ataccggtac gccgatcaaa   6900
gaagtccagt ggcaaggccc tttcagccaa gctagcgtgc tgaacagaaa gtcgtagagt   6960
gatgacagct tcttcttctt gagtcattcg tgtgacaaca tcaggatctc gtcgaaagac   7020
ctcctctgcc tatctctccc gcaagagagg actcgttatg gcgcacctct ttttagcagt   7080
ctcgtcaata agataagatt gcccctccct tcttattgat ttgataaagg gctttgtcca   7140
ctccctctct tcttagccga gcggagtgac ggtttagttt aggctttaga tgccactgcg   7200
aaagactcta gagatccact ctcacagcgt atacgcgaca tccctatgta tacacaatcc   7260
tttcaagcag ctaggacagc tagcaagcaa gttatctgtt cgcggacaag ctctctggat   7320
gacaaaaaac atgctctttc atgcggaaaa aacacggtct ttcgtggaag ttggtcgatt   7380
tgaagtcgct ttatgagtga aaatgggtcg atgacgaaaa agacgggaa aatgatcaac   7440 tgtcacattt tgatgccagt ttagggctaa aatgaacttt catccaaaaa gaccgagaaa   7500
acgctccact ggcaggatcc gatcggaaat aa                                 7532

<210> SEQ ID NO 43
<211> LENGTH: 181
<212> TYPE: DNA
<213> ORGANISM: Artificial Sequence
```

```
<220> FEATURE:
<223> OTHER INFORMATION: first 181 nt of the 5' end of the transgene
      insert for event 3560.4.3.5

<400> SEQUENCE: 43
ggccgctcta gagatccgtc aacatggtgg agcacgacac tctcgtctac tccaagaata      60
tcaaagatac agtctcagaa gaccaaaggg ctattgagac ttttcaacaa agggtaatat     120
cgggaaacct cctcggattc cattgcccag ctatctgtca cttcatcaaa aggacagtag     180
a                                                                      181

<210> SEQ ID NO 44
<211> LENGTH: 24
<212> TYPE: DNA
<213> ORGANISM: Artificial Sequence
<220> FEATURE:
<223> OTHER INFORMATION: primer 104312

<400> SEQUENCE: 44
agatccgtca acatggtgga gcac                                              24

<210> SEQ ID NO 45
<211> LENGTH: 26
<212> TYPE: DNA
<213> ORGANISM: Artificial Sequence
<220> FEATURE:
<223> OTHER INFORMATION: primer 104314

<400> SEQUENCE: 45
tgacagatag ctgggcaatg gaatcc                                            26

<210> SEQ ID NO 46
<211> LENGTH: 14
<212> TYPE: DNA
<213> ORGANISM: Artificial Sequence
<220> FEATURE:
<223> OTHER INFORMATION: TaqMan probe 125323

<400> SEQUENCE: 46
tatcgggaaa cctc                                                         14

<210> SEQ ID NO 47
<211> LENGTH: 26
<212> TYPE: DNA
<213> ORGANISM: Artificial Sequence
<220> FEATURE:
<223> OTHER INFORMATION: Primer 109893 (endogenous control)

<400> SEQUENCE: 47
ctttgctgtt tgattgctgg gttgtc                                            26

<210> SEQ ID NO 48
<211> LENGTH: 28
<212> TYPE: DNA
<213> ORGANISM: Artificial Sequence
<220> FEATURE:
<223> OTHER INFORMATION: Primer 109894 (endogenous control)

<400> SEQUENCE: 48
tgtgtggacc cattggcctt tagattat                                          28

<210> SEQ ID NO 49
<211> LENGTH: 16
<212> TYPE: DNA
<213> ORGANISM: Artificial Sequence
<220> FEATURE:
```

```
<223> OTHER INFORMATION: TaqMan Probe 125322 (endogenous control)

<400> SEQUENCE: 49
actctgcagt tgcctt                                                          16

<210> SEQ ID NO 50
<211> LENGTH: 29
<212> TYPE: DNA
<213> ORGANISM: Artificial Sequence
<220> FEATURE:
<223> OTHER INFORMATION: primer 1473

<400> SEQUENCE: 50
ttatttccga tcggatcctg ccagtggag                                             29

<210> SEQ ID NO 51
<211> LENGTH: 23
<212> TYPE: DNA
<213> ORGANISM: Artificial Sequence
<220> FEATURE:
<223> OTHER INFORMATION: primer 1504

<400> SEQUENCE: 51
ccaccatgtt gacggatctc tag                                                  23

<210> SEQ ID NO 52
<211> LENGTH: 23
<212> TYPE: DNA
<213> ORGANISM: Artificial Sequence
<220> FEATURE:
<223> OTHER INFORMATION: primer 1505

<400> SEQUENCE: 52
gcaatggaat ccgaggaggt ttc                                                  23

<210> SEQ ID NO 53
<211> LENGTH: 22
<212> TYPE: DNA
<213> ORGANISM: Artificial Sequence
<220> FEATURE:
<223> OTHER INFORMATION: primer 1506

<400> SEQUENCE: 53
gcaatgatgg catttgtagg tg                                                   22

<210> SEQ ID NO 54
<211> LENGTH: 28
<212> TYPE: DNA
<213> ORGANISM: Artificial Sequence
<220> FEATURE:
<223> OTHER INFORMATION: primer 1549

<400> SEQUENCE: 54
aaactgaagc gatggcagaa ccgcacag                                             28

<210> SEQ ID NO 55
<211> LENGTH: 35
<212> TYPE: DNA
<213> ORGANISM: Artificial Sequence
<220> FEATURE:
<223> OTHER INFORMATION: primer 1550

<400> SEQUENCE: 55
tcgaagtggc aatagagcca cacaatatcg ataag                                     35

<210> SEQ ID NO 56
```

```
<211> LENGTH: 455
<212> TYPE: PRT
<213> ORGANISM: Agrobacterium sp. Cp4

<400> SEQUENCE: 56

Met Ser His Gly Ala Ser Ser Arg Pro Ala Thr Ala Arg Lys Ser Ser
 1               5                  10                  15

Gly Leu Ser Gly Thr Val Arg Ile Pro Gly Asp Lys Ser Ile Ser His
            20                  25                  30

Arg Ser Phe Met Phe Gly Gly Leu Ala Ser Gly Glu Thr Arg Ile Thr
        35                  40                  45

Gly Leu Leu Glu Gly Glu Asp Val Ile Asn Thr Gly Lys Ala Met Gln
    50                  55                  60

Ala Met Gly Ala Arg Ile Arg Lys Glu Gly Asp Thr Trp Ile Ile Asp
65                  70                  75                  80

Gly Val Gly Asn Gly Gly Leu Leu Ala Pro Glu Ala Pro Leu Asp Phe
                85                  90                  95

Gly Asn Ala Ala Thr Gly Cys Arg Leu Thr Met Gly Leu Val Gly Val
            100                 105                 110

Tyr Asp Phe Asp Ser Thr Phe Ile Gly Asp Ala Ser Leu Thr Lys Arg
        115                 120                 125

Pro Met Gly Arg Val Leu Asn Pro Leu Arg Glu Met Gly Val Gln Val
    130                 135                 140

Lys Ser Glu Asp Gly Asp Arg Leu Pro Val Thr Leu Arg Gly Pro Lys
145                 150                 155                 160

Thr Pro Thr Pro Ile Thr Tyr Arg Val Pro Met Ala Ser Ala Gln Val
                165                 170                 175

Lys Ser Ala Val Leu Leu Ala Gly Leu Asn Thr Pro Gly Ile Thr Thr
            180                 185                 190

Val Ile Glu Pro Ile Met Thr Arg Asp His Thr Glu Lys Met Leu Gln
        195                 200                 205

Gly Phe Gly Ala Asn Leu Thr Val Glu Thr Asp Ala Asp Gly Val Arg
    210                 215                 220

Thr Ile Arg Leu Glu Gly Arg Gly Lys Leu Thr Gly Gln Val Ile Asp
225                 230                 235                 240

Val Pro Gly Asp Pro Ser Ser Thr Ala Phe Pro Leu Val Ala Ala Leu
                245                 250                 255

Leu Val Pro Gly Ser Asp Val Thr Ile Leu Asn Val Leu Met Asn Pro
            260                 265                 270

Thr Arg Thr Gly Leu Ile Leu Thr Leu Gln Glu Met Gly Ala Asp Ile
        275                 280                 285

Glu Val Ile Asn Pro Arg Leu Ala Gly Gly Glu Asp Val Ala Asp Leu
    290                 295                 300

Arg Val Arg Ser Ser Thr Leu Lys Gly Val Thr Val Pro Glu Asp Arg
305                 310                 315                 320

Ala Pro Ser Met Ile Asp Glu Tyr Pro Ile Leu Ala Val Ala Ala Ala
                325                 330                 335

Phe Ala Glu Gly Ala Thr Val Met Asn Gly Leu Glu Glu Leu Arg Val
            340                 345                 350

Lys Glu Ser Asp Arg Leu Ser Ala Val Ala Asn Gly Leu Lys Leu Asn
        355                 360                 365

Gly Val Asp Cys Asp Glu Gly Glu Thr Ser Leu Val Val Arg Gly Arg
    370                 375                 380

Pro Asp Gly Lys Gly Leu Gly Asn Ala Ser Gly Ala Ala Val Ala Thr
385                 390                 395                 400
```

```
His Leu Asp His Arg Ile Ala Met Ser Phe Leu Val Met Gly Leu Val
                405             410             415

Ser Glu Asn Pro Val Thr Val Asp Asp Ala Thr Met Ile Ala Thr Ser
            420             425             430

Phe Pro Glu Phe Met Asp Leu Met Ala Gly Leu Gly Ala Lys Ile Glu
            435             440             445

Leu Ser Asp Thr Lys Ala Ala
        450             455
```